US010157263B2

(12) United States Patent
Ortenzi et al.

(10) Patent No.: US 10,157,263 B2
(45) Date of Patent: Dec. 18, 2018

(54) CONTRAST MEDIA INJECTION DATA MANAGEMENT

(71) Applicant: Liebel-Flarsheim Company LLC, Cincinnati, OH (US)

(72) Inventors: Vernon D. Ortenzi, Burlington, KY (US); John Edward Powers, Wildwood, MO (US); Robert J. Ziemba, Cincinnati, OH (US); Rhonda J. Soest, Wildwood, MO (US); Pamela L. Pollard, Dardenne Prairie, MO (US)

(73) Assignee: LIEBEL-FLARSHEIM COMPANY LLC, Cincinnati, OH (US)

( * ) Notice: Subject to any disclaimer, the term of this patent is extended or adjusted under 35 U.S.C. 154(b) by 689 days.

(21) Appl. No.: 14/398,392

(22) PCT Filed: May 7, 2013

(86) PCT No.: PCT/US2013/039808
§ 371 (c)(1),
(2) Date: Oct. 31, 2014

(87) PCT Pub. No.: WO2013/169687
PCT Pub. Date: Nov. 14, 2013

(65) Prior Publication Data
US 2015/0127376 A1 May 7, 2015

Related U.S. Application Data

(60) Provisional application No. 61/644,289, filed on May 8, 2012, provisional application No. 61/726,530, filed on Nov. 14, 2012.

(51) Int. Cl.
*G16H 30/00* (2018.01)
*G06F 19/00* (2018.01)
(Continued)

(52) U.S. Cl.
CPC ......... *G06F 19/3406* (2013.01); *A61M 5/007* (2013.01); *A61M 5/14546* (2013.01);
(Continued)

(58) Field of Classification Search
CPC ........... A61B 8/00; A61B 90/98; H04L 29/06; G06F 17/30; G06Q 10/00; A61M 21/02; G16H 30/00
See application file for complete search history.

(56) References Cited

U.S. PATENT DOCUMENTS 6,287,257 B1 * 9/2001 Matichuk ................. A61B 8/00
600/437
6,339,718 B1 1/2002 Zatezalo et al.
(Continued)

FOREIGN PATENT DOCUMENTS

EP 1965325 A1 9/2008
EP 2000161 A1 12/2008
(Continued)

OTHER PUBLICATIONS

Kim et al., Integration of IEEE 1451 and HL7 Exchanging Information for Patients' Sensor Data, J Med Syst (2010) 34:1033-1041, Published online: Jun. 17, 2009.

*Primary Examiner* — John A Pauls
(74) *Attorney, Agent, or Firm* — Marsh Fischmann & Breyfogle LLP

(57) ABSTRACT

Contrast administration data that relates to operation of a contrast media injector system (602) may be converted from at least one format (e.g., a CAN-compliant format) to at least one other format (e.g., an HL-7-compliant format) by an injection data management module (660) for use by a medical system (600). Data on contrast media prescribed for an imaging operation using an imaging system (690), contrast media data for use in this imaging operation, and data on contrast media actually administered/injected by a con-
(Continued)

trast media injector system (602) for this imaging operation may be stored in a data structure (780) on the injection data management module (660). Patient renal function data may be used to control the dispensing of contrast media from a contrast media/storage/dispensing unit (500), to control the operation of the contrast media injector system (602), or both, and may be stored in the data structure (780) as well.

24 Claims, 64 Drawing Sheets

(51) Int. Cl.
| | | |
|---|---|---|
| *G16H 40/63* | (2018.01) | |
| *A61M 5/00* | (2006.01) | |
| *A61M 5/145* | (2006.01) | |
| *H04L 29/08* | (2006.01) | |
| *G16H 10/60* | (2018.01) | |
| *G16H 50/30* | (2018.01) | |
| *A61M 31/00* | (2006.01) | |

(52) U.S. Cl.
CPC ........... *G06F 19/321* (2013.01); *G16H 10/60* (2018.01); *G16H 40/63* (2018.01); *G16H 50/30* (2018.01); *H04L 67/12* (2013.01); *A61M 31/005* (2013.01); *A61M 2005/14553* (2013.01); *A61M 2205/33* (2013.01); *A61M 2205/35* (2013.01); *A61M 2205/52* (2013.01)

(56) References Cited

U.S. PATENT DOCUMENTS

| | | | |
|---|---|---|---|
| 6,356,780 B1 | 3/2002 | Licato et al. | |
| 6,397,098 B1 | 5/2002 | Uber, III et al. | |
| 6,763,040 B1 * | 7/2004 | Hite | H04L 29/06 370/362 |
| 2004/0024361 A1 | 2/2004 | Fago et al. | |
| 2004/0064041 A1 | 4/2004 | Lazzaro et al. | |
| 2005/0158767 A1 | 7/2005 | Haskell et al. | |
| 2006/0047538 A1 | 3/2006 | Condurso et al. | |
| 2006/0074294 A1 | 4/2006 | Williams, Jr. et al. | |
| 2007/0191690 A1 * | 8/2007 | Hasse | A61B 90/98 600/300 |
| 2007/0238967 A1 | 10/2007 | Sattler et al. | |
| 2007/0255250 A1 | 11/2007 | Moberg et al. | |
| 2008/0147442 A1 | 6/2008 | Warner et al. | |
| 2008/0253634 A1 | 10/2008 | Hay et al. | |
| 2008/0306443 A1 | 12/2008 | Neer et al. | |
| 2009/0069747 A1 | 3/2009 | Neer et al. | |
| 2009/0094058 A1 | 4/2009 | Reiner | |
| 2009/0326370 A1 | 12/2009 | Uber, III et al. | |
| 2010/0036879 A1 * | 2/2010 | Friese | G06F 17/30265 707/812 |
| 2010/0114064 A1 | 5/2010 | Kalafut et al. | |
| 2010/0174181 A1 | 7/2010 | Nemoto | |
| 2010/0217121 A1 | 8/2010 | Nemoto | |
| 2011/0001605 A1 | 1/2011 | Kiani et al. | |
| 2011/0015938 A1 * | 1/2011 | Rabinowitz | G06Q 10/00 705/2 |
| 2012/0157758 A1 * | 6/2012 | Dietz | A61M 21/02 600/28 |
| 2014/0073919 A1 | 3/2014 | Ortenzi et al. | |

FOREIGN PATENT DOCUMENTS

| | | | |
|---|---|---|---|
| JP | 2005-252534 A | 9/2005 | |
| JP | 5227189 B2 | 7/2013 | |
| WO | 2005/076810 A2 | 8/2005 | |
| WO | 2006108026 | 10/2006 | |
| WO | 2008/083313 A2 | 7/2008 | |
| WO | 2008/137375 A2 | 11/2008 | |
| WO | 2010/021952 A1 | 2/2010 | |
| WO | WO 2012/047612 A2 * | 4/2012 | ............ A61M 5/145 |
| WO | 2012/154816 A2 | 11/2012 | |
| WO | 2013009532 | 1/2013 | |

\* cited by examiner

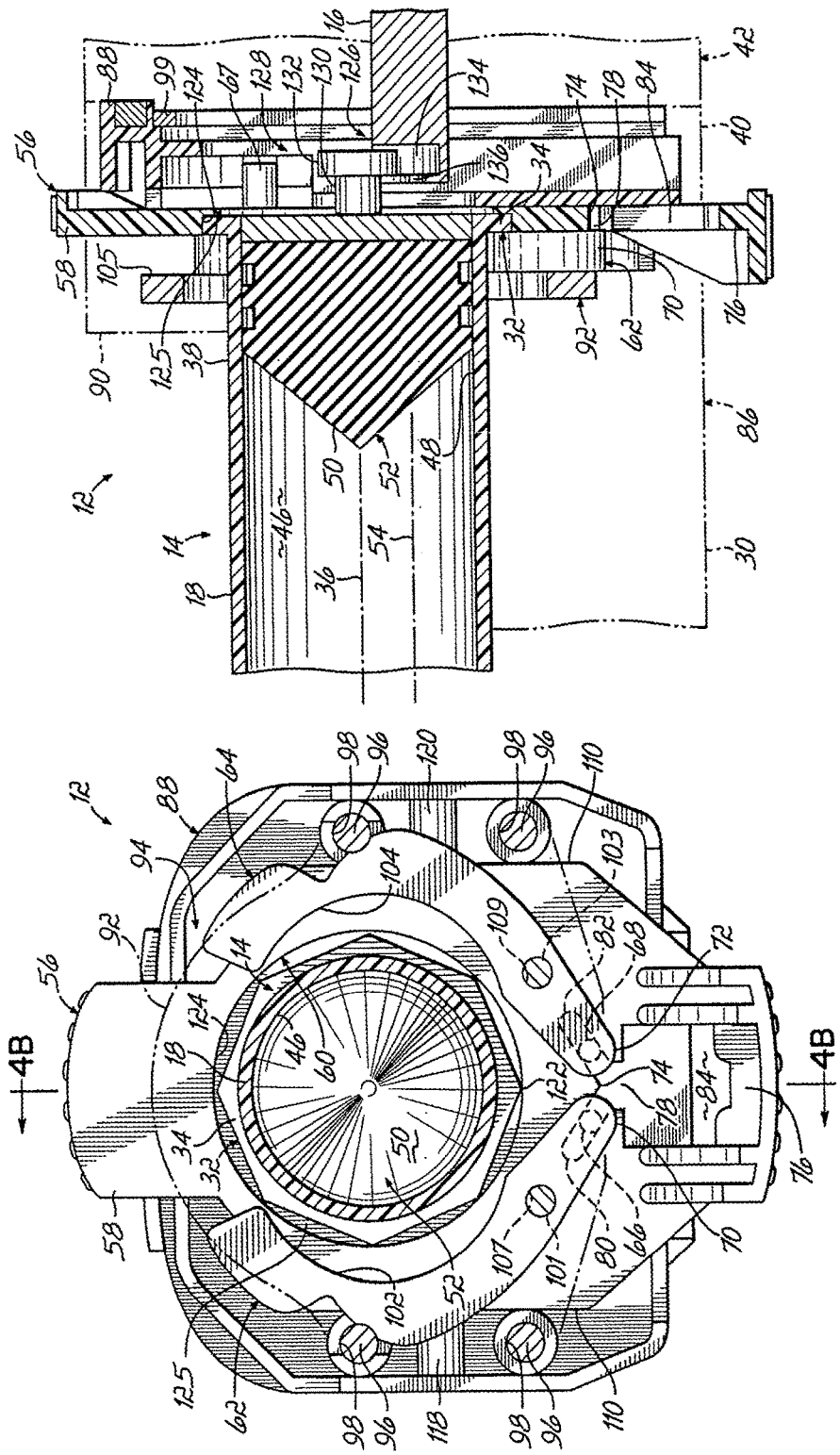

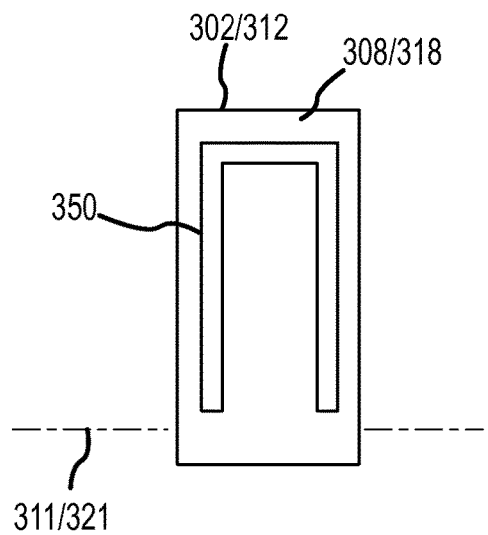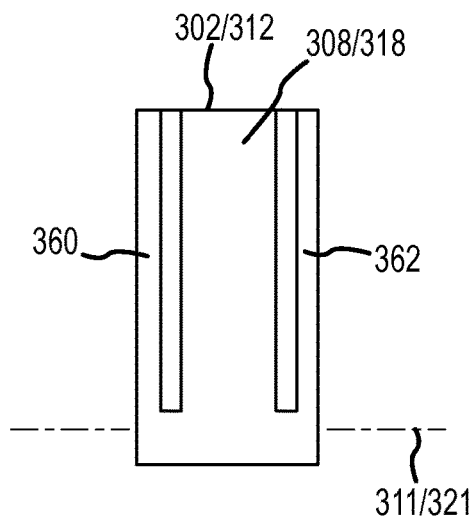
FIG.8A  FIG.8B
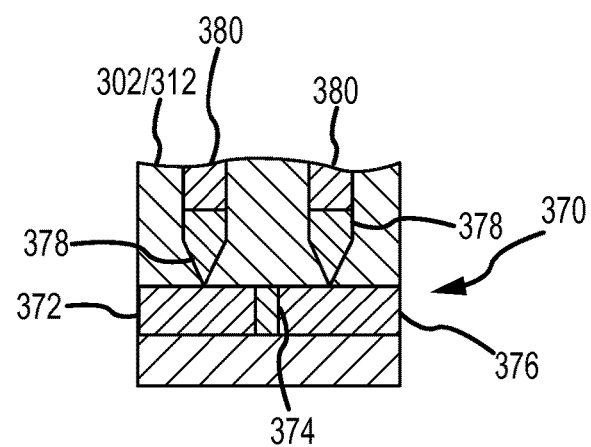
FIG.9

| PROCEDURE DATE 784 | ICD9 CODE 786 | PATIENT ID 788 | PATIENT AGE 790 | PATIENT GENDER 792 | PATIENT WEIGHT (LB) 794 | PATIENT HEIGHT (INCHES) 796 | PATIENT GFR (IF AVAILABLE) 798 | RENAL FUNCTION OVERRIDE RATIONALE 799 |
|---|---|---|---|---|---|---|---|---|
| 1/5/2011 | 722.10 | 4452 | 37 | F | 116 | 70 | 74 | |
| 1/3/2011 | 722.10 | 4785 | 34 | M | 166 | 71 | 63 | |
| 1/2/2011 | 722.52 | 5118 | 31 | F | 102 | 60 | 77 | |
| 1/7/2011 | 715.96-715.97 | 11778 | 52 | F | 103 | 60 | 72 | |
| 1/6/2011 | 729.81 | 11112 | 79 | F | 114 | 67 | 74 | |
| 1/5/2011 | 729.81 | 11445 | 51 | F | 121 | 61 | 73 | |
| 1/2/2011 | 782 | 12111 | 74 | M | 159 | 75 | 79 | |
| 1/2/2011 | 782 | 10779 | 76 | F | 102 | 65 | 61 | |
| 1/2/2011 | 782 | 10446 | 52 | F | 111 | 62 | 66 | |
| 1/3/2011 | 331.9 | 2121 | 39 | F | 89 | 55 | 67 | |
| 1/7/2011 | 39.79 | 3453 | 50 | M | 189 | 70 | 73 | |
| 1/6/2011 | 39.79 | 4119 | 48 | M | 184 | 68 | 69 | |
| 1/5/2011 | 444 | 15108 | 59 | M | 207 | 74 | 59 | |
| 1/5/2011 | 444 | 13110 | 75 | M | 195 | 72 | 72 | |
| 1/4/2011 | 444.81 | 16107 | 56 | M | 281 | 75 | 28 | |
| 1/4/2011 | 444.81 | 12777 | 77 | F | 120 | 68 | 72 | |
| 1/6/2011 | 428 | 10113 | 61 | F | 104 | 69 | 76 | |
| 1/6/2011 | 428 | 9447 | 78 | M | 162 | 70 | 78 | |
| 1/6/2011 | 428 | 9114 | 55 | M | 165 | 73 | 80 | |
| 1/7/2011 | 786.6 | 5784 | 37 | F | 117 | 64 | 76 | |
| 1/6/2011 | 786.6 | 8115 | 70 | F | 116 | 64 | 80 | |
| 1/6/2011 | 786.6 | 7449 | 77 | M | 192 | 68 | 78 | |
| 1/5/2011 | 346.00-346.93 | 789 | 29 | M | 139 | 61 | 61 | |
| 1/3/2011 | 780.4 | 1122 | 19 | F | 160 | 70 | 67 | |

FIG.23A

| PROCEDURE DATE 784 | PATIENT ID 788 | REFERRING PHYSICIAN NAME 800 | REFERRING PHYSICIAN ID 802 | PROCEDURE LOCATION 804 | MODALITY 806 | MEDICAL ORDER ID 808 | PROCEDURE NAME 810 |
|---|---|---|---|---|---|---|---|
| 1/5/2011 | 4452 | DR. JONES | 8394 | MR | MR | IP2218 | LUMBAR |
| 1/3/2011 | 4785 | DR. SMITH | 9384 | MR | MR | IP2218 | LUMBAR |
| 1/2/2011 | 5118 | DR. BROWN | 3892 | MR | MR | IP2218 | LUMBAR |
| 1/7/2011 | 11778 | DR. JONES | 8394 | CT | CT | IP4985 | RUNOFF |
| 1/6/2011 | 11112 | DR. SMITH | 9384 | CT | CT | IP4985 | RUNOFF |
| 1/5/2011 | 11445 | DR. JONES | 8394 | CT | CT | IP4985 | RUNOFF |
| 1/2/2011 | 12111 | DR. DAVIS | 9823 | CT | CT | IP4985 | RUNOFF |
| 1/2/2011 | 10779 | DR. BROWN | 3892 | CT | CT | IP4985 | RUNOFF |
| 1/2/2011 | 10446 | DR. JONES | 8394 | CT | CT | IP4985 | RUNOFF |
| 1/3/2011 | 2121 | DR. RICHARDS | 1234 | OUTPATIENT IMAGING CENTER | CT | OP9836 | HEAD,NECK |
| 1/7/2011 | 3453 | DR. BROWN | 3892 | CATH LAB | ANGIOGRAPHY | IP3445 | CORONARY ANGIOGRAM |
| 1/6/2011 | 4119 | DR. RICHARDS | 1234 | CATH LAB | ANGIOGRAPHY | IP3445 | CORONARY ANGIOGRAM |
| 1/5/2011 | 15108 | DR. JONES | 8394 | CT | CT | IP4665 | CHEST,ABDOMEN,PELVIS |
| 1/5/2011 | 13110 | DR. BROWN | 3892 | CT | CT | IP4665 | CHEST,ABDOMEN,PELVIS |
| 1/4/2011 | 16107 | DR. SMITH | 9384 | CT | CT | IP4665 | CHEST,ABDOMEN,PELVIS |
| 1/4/2011 | 12777 | DR. JONES | 8394 | CT | CT | IP4665 | CHEST,ABDOMEN,PELVIS |
| 1/6/2011 | 10113 | DR. BROWN | 3892 | CT | CT | IP4034 | CARDIAC CTA |
| 1/6/2011 | 9447 | DR. SMITH | 9384 | CT | CT | IP4034 | CARDIAC CTA |
| 1/6/2011 | 9114 | DR. JONES | 8394 | CT | CT | IP4034 | CARDIAC CTA |
| 1/7/2011 | 5784 | DR. JONES | 8394 | MR | MR | IP2256 | BREAST |
| 1/6/2011 | 8115 | DR. RICHARDS | 1234 | MR | MR | IP2356 | BREAST |
| 1/6/2011 | 7449 | DR. DAVIS | 9823 | MR | MR | IP2356 | BREAST |
| 1/5/2011 | 789 | DR. JONES | 8394 | OUTPATIENT IMAGING CENTER | MR | OP8897 | BRAIN |
| 1/3/2011 | 1122 | DR. DAVIS | 9823 | OUTPATIENT IMAGING CENTER | MR | OP8897 | BRAIN |

FIG.23B

| PROCEDURE DATE 784 | PATIENT ID 788 | PRESCRIBED CM VOLUME (mL) 812 | PRESCRIBED CM CONCENTRATION 814 | PRESCRIBED CM FLOW RATE (mL/SEC) 816 | DISPENSED CM VOLUME (mL) 818 | DISPENSED CM CONCENTRATION 820 | DISPENSED DRUG NDC # 822 | DISPENSED DRUG EXPIRATION DATE 824 | ADMINISTERED CM VOLUME (mL) 826 | ADMINISTERED CM CONCENTRATION 828 | ADMINISTERED CM FLOW RATE (mL/SEC) 830 |
|---|---|---|---|---|---|---|---|---|---|---|---|
| 1/5/2011 | 4452 | 30 | 0.5 | 2.5 | 30 | 0.5 | 00019117730 | 11/2/2014 | 30 | 0.5 | 2.5 |
| 1/3/2011 | 4785 | 30 | 0.5 | 2.5 | 30 | 0.5 | 00019117730 | 11/2/2014 | 30 | 0.5 | 2.5 |
| 1/2/2011 | 5118 | 30 | 0.5 | 2.5 | 30 | 0.5 | 00019117730 | 11/2/2014 | 30 | 0.5 | 2.5 |
| 1/7/2011 | 11778 | 125 | 350 | 2.5 | 125 | 350 | 00019133381 | 10/19/2013 | 125 | 300 | 2.5 |
| 1/6/2011 | 11112 | 125 | 350 | 2.5 | 125 | 350 | 00019133381 | 10/19/2013 | 125 | 350 | 2.5 |
| 1/5/2011 | 11445 | 125 | 350 | 2.5 | 125 | 350 | 00019133381 | 10/19/2013 | 125 | 350 | 2.5 |
| 1/2/2011 | 12111 | 125 | 350 | 2.5 | 125 | 350 | 00019133381 | 10/19/2013 | 125 | 350 | 2.5 |
| 1/2/2011 | 10779 | 125 | 350 | 2.5 | 125 | 350 | 00019133381 | 10/19/2013 | 125 | 350 | 2.5 |
| 1/2/2011 | 10446 | 125 | 350 | 2.5 | 125 | 350 | 00019133381 | 10/19/2013 | 125 | 350 | 2.5 |
| 1/3/2011 | 2121 | 75 | 300 | 2.0 | 75 | 300 | 00019133381 | 10/19/2013 | 75 | 300 | 2.0 |
| 1/7/2011 | 3453 | 100 | 350 | N/A | 100 | 350 | 00019133351 | 8/14/2012 | 200 | 350 | N/A |
| 1/6/2011 | 4119 | 100 | 350 | N/A | 100 | 350 | 00019133351 | 8/14/2012 | 168 | 350 | N/A |
| 1/5/2011 | 15108 | 100 | 300 | 2.5 | 100 | 300 | 00019133283 | 9/4/2013 | 100 | 300 | 2.5 |
| 1/5/2011 | 13110 | 100 | 300 | 2.5 | 100 | 300 | 00019133283 | 9/4/2013 | 100 | 300 | 2.5 |
| 1/4/2011 | 16107 | 100 | 300 | 2.5 | 100 | 300 | 00019133283 | 9/4/2013 | 100 | 300 | 2.5 |
| 1/4/2011 | 12777 | 100 | 300 | 4.1 | 100 | 300 | 00019133283 | 9/4/2013 | 100 | 300 | 4.1 |
| 1/6/2011 | 10113 | 125 | 350 | 4.1 | 125 | 350 | 00019133381 | 6/9/2014 | 125 | 350 | 4.1 |
| 1/6/2011 | 9447 | 125 | 350 | 4.1 | 125 | 350 | 00019133381 | 6/9/2014 | 111 | 350 | 4.1 |
| 1/6/2011 | 9114 | 125 | 350 | 2.5 | 125 | 350 | 00019133381 | 6/9/2014 | 125 | 350 | 2.5 |
| 1/7/2011 | 5784 | 20 | 0.5 | 2.5 | 20 | 0.5 | 00019117720 | 3/28/2013 | 20 | 0.5 | 2.5 |
| 1/6/2011 | 8115 | 20 | 0.5 | 2.5 | 20 | 0.5 | 00019117720 | 6/8/2014 | 20 | 0.5 | 2.5 |
| 1/6/2011 | 7449 | 20 | 0.5 | 2.5 | 20 | 0.5 | 00019117720 | 6/8/2014 | 20 | 0.5 | 2.5 |
| 1/5/2011 | 789 | 20 | 0.5 | 2.5 | 20 | 0.5 | 00019117720 | 3/28/2013 | 20 | 0.5 | 2.5 |
| 1/3/2011 | 1122 | 20 | 0.5 | 2.5 | 20 | 0.5 | 00019117720 | 6/8/2014 | 20 | 0.5 | 2.5 |

FIG.23C

| PROCEDURE DATE 784 | PATIENT ID 788 | DISPENSED CM BRAND NAME 831 | DISPENSED CM MANUFACTURER 832 | DISPENSED CM LOT NUMBER 833 | DISPENSED CM MANUFACTURE DATE 834 | DISPENSED CM COMPOSITION 835 | DISPENSED CM PRIMARY FUNCTIONAL INGREDIENT 836 | INJECTOR ID 837 | DCMDTM ID 838 | TIME STAMP 839 |
|---|---|---|---|---|---|---|---|---|---|---|
| 1/5/2011 | 4452 | | | | | | | | | |
| 1/3/2011 | 4785 | | | | | | | | | |
| 1/2/2011 | 5118 | | | | | | | | | |
| 1/7/2011 | 11778 | | | | | | | | | |
| 1/6/2011 | 11112 | | | | | | | | | |
| 1/5/2011 | 11445 | | | | | | | | | |
| 1/2/2011 | 12111 | | | | | | | | | |
| 1/2/2011 | 10779 | | | | | | | | | |
| 1/2/2011 | 10446 | | | | | | | | | |
| 1/3/2011 | 2121 | | | | | | | | | |
| 1/7/2011 | 3453 | | | | | | | | | |
| 1/6/2011 | 4119 | | | | | | | | | |
| 1/5/2011 | 15108 | | | | | | | | | |
| 1/5/2011 | 13110 | | | | | | | | | |
| 1/4/2011 | 16107 | | | | | | | | | |
| 1/4/2011 | 12777 | | | | | | | | | |
| 1/6/2011 | 10113 | | | | | | | | | |
| 1/6/2011 | 9447 | | | | | | | | | |
| 1/6/2011 | 9114 | | | | | | | | | |
| 1/7/2011 | 5784 | | | | | | | | | |
| 1/6/2011 | 8115 | | | | | | | | | |
| 1/6/2011 | 7449 | | | | | | | | | |
| 1/5/2011 | 789 | | | | | | | | | |
| 1/3/2011 | 1122 | | | | | | | | | |

FIG.23D

VIEW RESULTS

PATIENT — 2030

PATIENT ID: 844760
PATIENT NAME: JOE SMITH
PRESCRIPTION NUMBER: PR-19210912
PROCEDURE ID: ABC-192812
PROCEDURE NAME: DVT STUDY
— 2032

SYRINGE

NDC: 844760
DRUG NAME: OPTIRAY 300
VOLUME: 100 ml
CONCENTRATION: 50 mg/dL
— 2034

INJECTOR

CONTRAST VOLUME: 125 ml PROGRAMMED — 2036

| NO. | SIDE | RATE | VOLUME | DELAY |
|---|---|---|---|---|
| 1 | CONTRAST | 5 ml/s | 1 ml | 0 sec |
| 2 | DUAL | 5 ml/s | 1 ml | 0 sec |
| 3 | CONTRAST | 5 ml/s | 1 ml | 0 sec |
| 4 | SALINE | 5 ml/s | 10 ml | 0 sec |
| 5 | CONTRAST | 5 ml/s | 10 ml | 0 sec |
| 6 | SALINE | 5 ml/s | 10 ml | 0 sec |

SALINE VOLUME: 125 ml ACHIEVED @ 11/16/2011 2:31 PM — 2038

| NO. | SIDE | RATE | VOLUME | DELAY |
|---|---|---|---|---|
| 1 | CONTRAST | 5 ml/s | 1 ml | 0 sec |
| 2 | DUAL | 5 ml/s | 1 ml | 0 sec |
| 3 | CONTRAST | 5 ml/s | 1 ml | 0 sec |
| 4 | SALINE | 5 ml/s | 10 ml | 0 sec |
| 5 | CONTRAST | 5 ml/s | 10 ml | 0 sec |
| 6 | SALINE | 5 ml/s | 10 ml | 0 sec |

CONNECTED TO MOTOROLA DUAL BAND BLUETOOTH BARCODE READER

CLOSE

FIG. 40

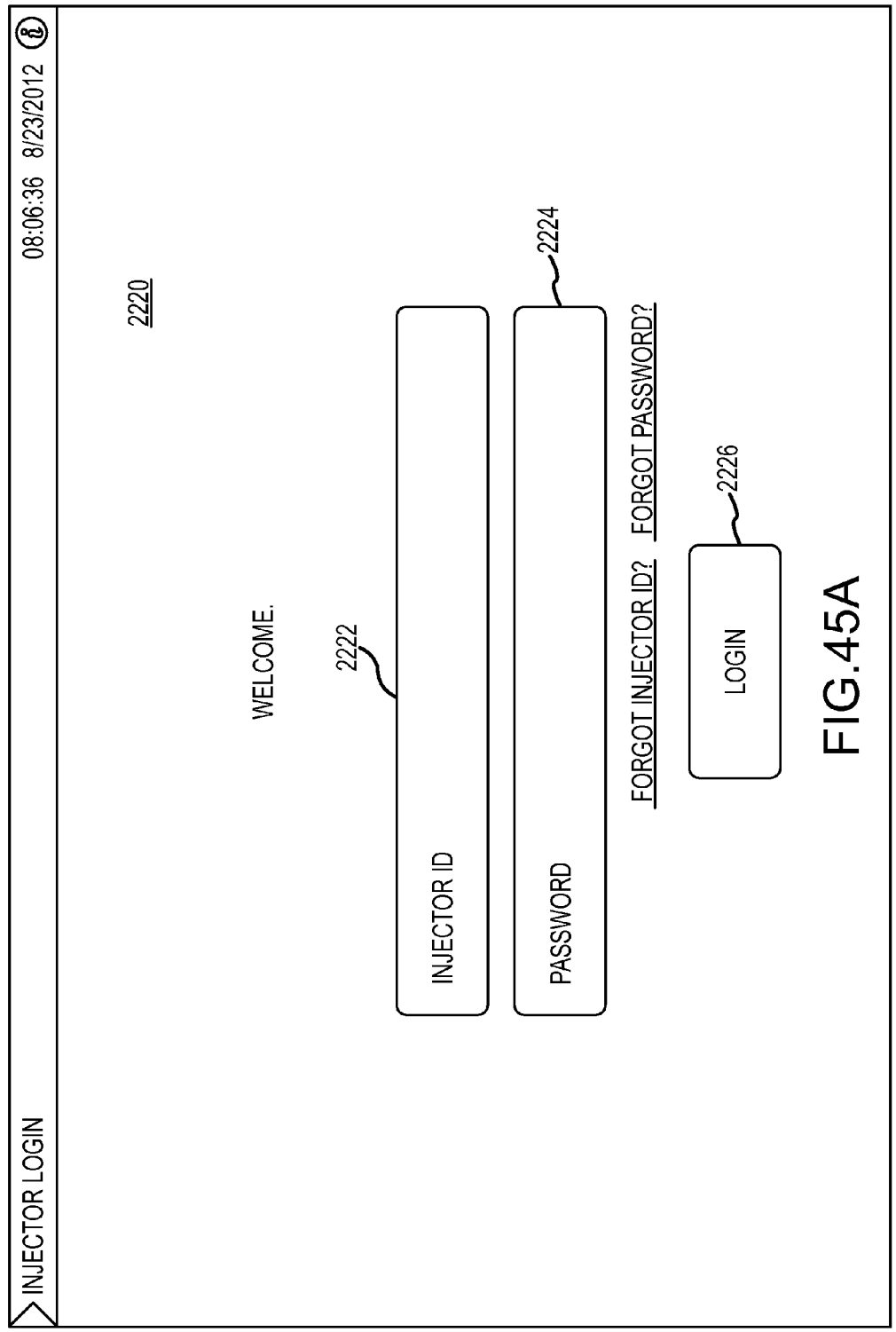

FIG.45B

| LOGOUT | INJECTOR ID: 01 | | 08:06:36 8/23/2012 |
|---|---|---|---|

PATIENT ATTRIBUTES 2279

☑ CONFIRM PATIENT — PATIENT NAME: STEVENSON, MARIA — 2234
PATIENT ID: 1652232265143 — 2236

2270 2272

| ATTRIBUTE | VALUE | THRESHOLD |
|---|---|---|
| PATIENT WEIGHT | 188 | |
| KNOWN PATIENT ALLERGIES | YES | |
| PATIENT GFR | 666666 | |
| IODINE/SEAFOOD ALLERGIES | NO | |
| METFORMIN | 54 | |
| RECENT IODINE LOAD | 10 | 20-80 |
| MYELOMA STATUS | N/A | |
| CURRENT PRESCRIBED MEDICATION | YES | |

FIG. 45E

LOGOUT | INJECTOR ID: 01 08:06:36 8/23/2012

INJECTION DATA
PATIENT NAME: STEVENSON, MARIA
PATIENT ID: 1652232265143

SYRINGE DATA — 2280

| SIDE | NDC (10 DIGITS) | TYPE | NAME | CONCENTRATION | VOLUME | PACKAGE TYPE |
|------|-----------------|----------|---------|---------------|--------|--------------|
| A    | 0019022345      | CONTRAST | OPTIRAY | 320mg/ml      | 100ml  | SYRINGE      |
| B    | 0019034512      | SALINE   | NA      | NA            | 100ml  | BOTTLE       |

INJECTION DATA — 2282

| | INJECT DELAY (SEC) | SCAN DELAY (SEC) | PEAK PRESSURE SETTING (psi) |
|---|---|---|---|
| PROGRAMMED | 5 | 0 | 125 |

| SIDE | PHASE | FLOW (ml/sec) | VOLUME (ml) | PHASE DELAY (sec) |
|------|-------|---------------|-------------|-------------------|
| A    | 1     | 5             | 20          | 12                |
| B    | 2     | 5             | 20          | 12                |
| A    | 3     | 5             | 20          | 12                |
| B    | 4     | 5             | 20          | 12                |
| A    | 5     | 5             | 20          | 12                |
| B    | 6     | 5             | 20          | 12                |

CONTRAST MEDIA INJECTION DATA MANAGEMENT

CROSS-REFERENCE TO RELATED APPLICATIONS

This patent application is a U.S. National Stage of PCT/US2013/039808, filed May 7, 2013, which claims priority to and is a non-provisional patent application of each of the following applications: 1) U.S. Provisional Patent Application Ser. No. 61/644,289, that is entitled "CONTRAST MEDIA INJECTION DATA MANAGEMENT," and that was filed on 8 May 2012; and 2) U.S. Provisional Patent Application Ser. No. 61/726,530, that is entitled "CONTRAST MEDIA INJECTION DATA MANAGEMENT," and that was filed on 14 Nov. 2012. The entire disclosure of each patent application set forth in this Cross-Reference to Related Applications section is hereby incorporated by reference herein.

FIELD OF THE INVENTION

The present invention generally relates to the field of contrast media/agents and, more particularly, to managing contrast media injection/administration data.

BACKGROUND

Various medical procedures require that one or more medical fluids be injected into a patient. For example, medical imaging procedures oftentimes involve the injection of contrast media into a patient, possibly along with saline and/or other fluids. Power injectors may be used for these types of injections.

A power injector generally includes what is commonly referred to as a powerhead. One or more syringes may be mounted to the powerhead in various manners (e.g., detachably; rear-loading; front-Loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

Patient safety is of course of paramount concern when injecting contrast media into a patient. One such safety concern is whether a patient's organs can reasonably tolerate the proposed volume and/or concentration of contrast media (e.g., amount and/or concentration of iodine in at least certain computed tomography contrast medias) to be injected. In this regard, a patient's kidney(s) should be functioning at a level so as to clear the contrast media from the patient's bloodstream within a certain amount of time to avoid undesirable health risks (e.g., damaging the patient's kidney(s) and/or other organs). For example, injections of certain concentrations and volumes of contrast media may adversely impact the health of some patients due to their compromised kidney function.

SUMMARY

A first aspect of the present invention is embodied by a contrast media injector system that includes a powerhead, a syringe, a reader, and a renal function assessment module. The powerhead includes a housing, a motorized drive ram, and a syringe mount (e.g., of any appropriate type, for instance, a removable faceplate or a syringe mount that is fixedly attached to (e.g., integral with) the powerhead (e.g., the housing thereof)). The motorized drive ram of the powerhead is designed to move along an axis, and at least part of the motorized drive ram is located within the housing. The syringe mount of the powerhead is designed to at least substantially immobilize a barrel of the syringe relative to the housing of the powerhead such that the drive ram can move a plunger of the syringe within and relative to the syringe barrel.

The syringe is installed on the powerhead (e.g., using the syringe mount) in the case of the first aspect, and includes a data storage device that stores at least first threshold renal function data. The reader is able to communicate with the syringe data storage device, for instance to retrieve the first threshold renal function data for use by the renal function assessment module. In this regard, the renal function assessment module includes comparative logic that is configured to compare the first threshold renal function data with renal function data on a patient to be imaged.

A number of feature refinements and additional features are applicable to the first aspect of the present invention. These feature refinements and additional features may be used individually or in any combination in relation to the first aspect. As such, each of the following features that will be discussed may be, but are not required to be, used with any other feature or combination of features of the first aspect. The following discussion is separately applicable to the first aspect, up to the start of the discussion of a second aspect of the present invention.

The contrast media injector system may utilize one or more data input devices of any appropriate type (e.g., a user input device). One or more data input devices may be incorporated by the powerhead and/or a remote console of the contrast media injector system. Any remote console of the contrast media injector system may be in communication with the powerhead, may include a remote console display, may include at least one data input device, and/or may be in a different location (e.g., isolated in at least some fashion) from the powerhead of the contrast media injector system. Any data input device incorporated by the contrast media injector system may accommodate the provision of input (e.g., user input) to the contrast media injector system for any appropriate purpose, including programming injection parameters (e.g., to define an injection protocol having one or more phases, each phase including injection parameters such as an amount of fluid to be injected and an injection flow rate, as well as possibly one or more injection delays (sometimes referred to as "holds" and/or "pauses"), each of which can be of finite or infinite duration)). The contrast media injector system could also accommodate data input from one or more external data input devices (i.e., that are not actually part of the contrast media injector system), such as one or more data input devices associated with imaging equipment (e.g., a CT or MR scanner) or other parts of a healthcare facility. A given data input device may be used to provide any appropriate data to the contrast media injector system, for instance renal function data on a patient to be imaged and which may be used by the renal function assessment module as will be discussed below.

One or more data input devices that are available to at least communicate with the contrast media injector system each may be of any appropriate type (e.g., keyboard, touch screen, mouse, joystick, trackball, and/or any combination thereof). Although any appropriate user input may be provided to the contrast media injector system through such a data input device, renal function data of a patient to be imaged may be manually input to the contrast media injector system by a user. The contrast media injector system may include multiple data input devices. In one embodiment, one data input device is associated with a remote console associated with the contrast media injector system (e.g., part of or at least co-located with the remote console in a control room that is separate/isolated from an imaging room having the powerhead and medical imaging equipment), while another data input device is associated with the powerhead (e.g., in the form of a touch screen display that is integrated with the powerhead).

Renal function data on a patient to be imaged in conjunction with operation of the contrast media injector system may be acquired in any appropriate manner and may be communicated to the contrast media injector system in any appropriate manner. Renal function data on a patient to be imaged may be input by a user to the contrast media injector system in any appropriate manner (e.g., manually entering data that is representative of a patient's renal function; in the form of user input). Renal function data on a patient to be imaged may be acquired from one or more data sources that may be in communication or able to communicate with the contrast media injector system, such as a hospital information system (HIS), a radiology information system (RIS), picture archive and communication system (PACS), another system that stores or has access to patient electronic medical records (EMRs), or a renal function testing module.

The renal function assessment module may include (or, in some embodiments, refers to) prompt logic that is configured to issue a prompt for entry of renal function information regarding a patient to be imaged (e.g., manually by a user through an appropriate data input device). The renal function information that is the subject of the prompt may be data that is representative of the renal function of the patient that is to be imaged (e.g., glomerular filtration rate or "GFR", serum creatinine measurement, or any other appropriate renal function indicator). In one embodiment, a first user input is provided to the contrast media injector system in the form of first renal function data of a first patient to be imaged, and the renal function assessment module includes comparative logic that is configured to compare the first renal function data of the first patient with the first threshold renal function data. Both the first renal function data and the first threshold renal function data may be of any appropriate type so long as the data is indicative of patient renal function (e.g., GFR, serum creatinine measurement). For instance, the first renal function data of the first patient may be expressed in terms of a GFR measurement, and the first threshold renal function data to which the first renal function data may be compared may also be in terms of a threshold GFR or an acceptable range of GFR. As another example, the first renal function data of the first patient may be expressed in terms of a serum creatinine measurement, and the first threshold renal function data to which the first renal function data may be compared may also be in terms of a threshold serum creatinine level or an acceptable range of serum creatinine. The first threshold renal function data may be expressed in any appropriate manner (e.g., in the form of a baseline number, such that the first renal function data must be at least as great as the baseline number or, in another embodiment, no greater than the baseline number; in the form of a range, such that the first renal function data must be within this range).

An issued prompt for entry of patient renal function information may be presented on at least one display of the contrast media injector system, for instance on a display associated with (e.g., incorporated by) the powerhead, on a remote console display associated with the contrast media injector system, or both. A data input device may enable a user to manually respond to the noted prompt for renal function information of the patient to be imaged. The prompt may be of any appropriate format, and may request the input of the desired renal function information in any appropriate manner. For instance, the prompt may be in the form of a request for a user to provide/input the renal function information to the contrast media injector system (e.g., for comparison with threshold renal function data). Any data that is representative of a patient's renal function could be manually input through a user input device.

The prompt may simply be in the form of an inquiry directed to determining if the renal function of a patient to be imaged has been determined to be acceptable (e.g., in relation to threshold renal function data). That is, it may be such that a user must simply confirm that the patient's renal function has been checked and has been determined by the user (or other appropriate personnel) to comply with relevant threshold renal function data (e.g., a "yes/no" or "pass/fail" question). In another embodiment, the prompt logic may be configured to issue a prompt (e.g., visually display a prompt to a user) requesting that the user select an answer from a list of displayed answers regarding the patient to be imaged in conjunction with the operation of the contrast media injector system. In yet another embodiment, the prompt logic may be configured to issue a prompt (e.g., visually display a prompt to a user) requesting that the user enter/fill in an empty data field shown on a display of the system with renal function data regarding the patient to be imaged in conjunction with the operation of the contrast media injector system.

In one embodiment, the contrast media injector system may be precluded from being operated to provide a contrast media discharge (e.g., so as to not allow for execution of an injection protocol) based upon the user input provided in relation to the noted prompt. For instance, the contrast media injector system may be configured so that the injector system is precluded from being operated to provide a contrast media discharge (e.g., where at least one syringe plunger is advanced relative to the corresponding syringe barrel by the contrast media injector system) if the patient renal function data that is entered by a user does not comply with the first threshold renal function data. As another example, the contrast media injector system may be configured so that the injector system is precluded from being operated to provide a contrast media discharge if the patient renal function data that is entered by a user does not "pass" an electronic evaluation conducted by the renal function assessment module, which takes the first threshold renal function data stored on the data storage device of the syringe into account when conducting the above-described evaluation. The contrast media injector system may be configured such that the injector system is precluded from being operated to provide a contrast media discharge if the user does not respond to the prompt at all, if the user responds in the negative to a request for verification that the renal function of a patient to be imaged has been determined to be acceptable, or both. The above-referenced preclusions of contrast media injector system operation may include such things as not allowing the injector system to "arm" or be "enabled" to run the programmed injection protocol. Additionally or alternatively, the above-referenced preclusions of contrast media injector system operation may include such things as not allowing the user to initiate (e.g., "run" or "start") the programmed injection protocol (e.g., if the system is allowed to be "armed"/"enabled" prior to an inquiry regarding patient renal function) and/or inject contrast media into the patient manually using one or more hand controls (e.g., buttons) of the injector system.

The renal function assessment module may include one or more processors. In one embodiment, one or more processors of the renal function assessment module are located within and/or incorporated by the powerhead of the contrast media injector system (e.g., one or more processors of the renal function assessment module may be "on board" in relation to the powerhead of the contrast media injector system). In another embodiment, one or more processors of the renal function assessment module are located within and/or incorporated by a remote console associated with the contrast media injector system. At least one processor of the renal function assessment module (e.g., a first processor) may be programmed: 1) to issue a prompt regarding renal function information for a patient to be imaged; 2) to preclude the contrast media injector system from being operated to provide a contrast media discharge (e.g., disallow execution of an injection protocol) if renal function data on a patient to be imaged does not comply with first threshold renal function data (e.g., does not meet or exceed first threshold renal function data); 3) to issue an alarm of any appropriate type or types (e.g., visual, audible) if patient renal function data on a patient to be imaged does not comply with first threshold renal function data (e.g., does not meet or exceed first threshold renal function data); 4) to generate next action instructions as to at least one action to be taken if renal function data on a patient to be imaged does not comply with first threshold renal function data (e.g., does not meet or exceed first threshold renal function data); and/or 5) any combination of two or more of the foregoing.

At least one syringe installed on the powerhead may include contrast media (e.g., CT or MR contrast media), and the first threshold renal function data stored on the data storage device of the syringe may refer to threshold renal function data of the corresponding contrast media in the syringe. Any other appropriate information may be stored on the data storage device of the syringe, for instance the type (e.g., identity, chemical composition, active ingredient) of contrast media within the syringe, the concentration (e.g., iodine content and/or level of another ingredient) of the contrast media within the syringe, the volume of contrast media within the syringe, threshold (e.g., minimum) renal function data for a patient proposed to receive a predefined volume (e.g., 5 ml, 10 ml, 15, ml, 20 ml, 25 ml, 30 ml, 35 ml, 40 ml, 45 ml, 50 ml, 55 ml, 60 ml, 65 ml, 70 ml, 75 ml, 80 ml, 85 ml, 90 ml, 95 ml, 100 ml, 105 ml, 110 ml, 115 ml, 120 ml, 125 ml, 130 ml, 135 ml, 140 ml, 145 ml, 150 ml, any of which may or may not be the entire volume of contrast media within the syringe) or the entire volume of contrast media within the syringe, or any combination thereof.

The reader associated with the contrast media injector system in the case of the first aspect may be of any appropriate type, may be incorporated in any appropriate manner by the contrast media injector system (e.g., on the powerhead, for instance where at least part of this reader may be incorporated by the syringe mount of the powerhead), may be configured to communicate with the syringe data storage device in any appropriate manner (e.g., to read/retrieve data stored on the syringe data storage device), or any combination thereof. In one embodiment, the data storage device of the syringe is in the form of an RF or RFID data tag(s), and the reader is in the form of an electromagnetic device (e.g., an RF antenna) that is configured to electromagnetically read data from (and optionally write data to) the RF data tag(s) on the syringe.

The contrast media injector system may include a data store that includes threshold renal function data for a plurality of contrast media types (e.g., for a plurality of different contrast agents, where the difference between two contrast media types may be in the form of having different concentrations of one or more contrast media constituents). The threshold renal function data for a particular contrast media type may be characterized as "contrast media type-specific threshold renal function data." Although each contrast media type may be associated with a particular threshold renal function, one or more contrast media types could be associated with the same threshold renal function. However, each contrast media type could have a different threshold renal function (e.g., depending on the volume and/or concentration of the contrast media within the syringe). The data store may be of any appropriate configuration for purposes of associating a contrast media type with threshold renal function data, for instance, in the form of a look-up table. In one embodiment, identifying the contrast media type to the contrast media injector system (e.g., through a data input device), and that will be used for an injection (e.g., injected into a patient), results in the corresponding threshold renal function data being automatically retrieved from the data store (e.g., a lookup table) by the contrast media injector system. It should be appreciated that a user could also manually input the first threshold renal function data into the contrast media injector system (e.g., through a user input device for the remote console, for the power injector, or both).

A second aspect of the present invention is embodied by a contrast media injector system that includes a powerhead and a data store. The powerhead includes a housing, a motorized drive ram, and a syringe mount (e.g., of any appropriate type, for instance, a faceplate or a syringe mount that is fixedly attached to (e.g., integral with) the powerhead (e.g., the housing thereof)). The motorized drive ram of the powerhead is designed to move along an axis, and at least part of the motorized drive ram is located within the housing. The syringe mount of the powerhead is designed to at least substantially immobilize a barrel of a syringe relative to the housing of the powerhead such that the drive ram can move a plunger of this syringe within and relative to the syringe barrel. The data store of the injector system includes a plurality of contrast media types and their corresponding threshold renal function.

A number of feature refinements and additional features are applicable to the second aspect of the present invention. These feature refinements and additional features may be used individually or in any combination in relation to the second aspect. As such, each of the following features that will be discussed may be, but are not required to be, used with any other feature or combination of features of the second aspect. The following discussion is applicable to the second aspect, up to the start of the discussion of a third aspect of the present invention. Initially, each feature set forth in relation to the first aspect may be utilized by this second aspect, and vice versa.

The threshold renal function or threshold renal function data for a particular contrast media type (e.g. a minimum patient renal function required/suggested for safe administration of the corresponding contrast media to the patient; a range of acceptable patient renal functions required/suggested for safe administration of the corresponding contrast media to the patient) may be characterized as a "contrast media type-specific threshold renal function." Although each contrast media type may be associated with a particular threshold renal function, one or more contrast media types could be associated with the same threshold renal function (the data store may use relational data storage techniques as desired). However, each contrast media type could have a different threshold renal function. The data store may be of any appropriate configuration for purposes of associating a contrast media type with a threshold renal function, for instance, in the form of a look-up table. In one embodiment, identifying the contrast media type to the contrast media injector system (e.g., through a data input device; through the reader discussed above in relation to the first aspect, which may read data from a data storage device on a syringe that identifies its contrast media type to the contrast media injector system), and that will be used for an injection (e.g., injected into a patient), results in the corresponding threshold renal function being automatically retrieved from the data store (e.g., a lookup table) by the contrast media injector system.

An appropriate computer-readable storage medium may be configured to include the data store utilized by this second aspect. The data store may be incorporated by the contrast media injector system in any appropriate manner. At least part of the data store may reside on the powerhead, on a remote console of the contrast media injector system, on one or more components that are external to the contrast media injector system (e.g., on an imaging system; on a hospital information system (HIS); on a radiology information system (RIS); on a picture archive and communication system (PACS), or any combination thereof).

A third aspect of the present invention is directed to controlling containers of contrast media. Consider the case where there is a supply of a plurality of contrast media containers (e.g., within a contrast media storage/dispensing unit). A renal function check may be undertaken before releasing a particular contrast media container from the supply (e.g., for subsequent use by a contrast media injector system for executing an injection protocol where contrast media from the contrast media container is injected into a patient).

A number of feature refinements and additional features are applicable to the third aspect of the present invention. These feature refinements and additional features may be used individually or in any combination in relation to the third aspect. As such, each of the following features that will be discussed may be, but are not required to be, used with any other feature or combination of features of the third aspect. The following discussion is applicable to the third aspect, up to the start of a discussion of a fourth aspect of the present invention. Initially, the third aspect may be used in conjunction with each of the first and second aspects. Moreover, the third aspect may be implemented in any appropriate manner, including in the form of a contrast media management or dispensing system, as well as in the form of managing the dispensing or release of a contrast media container for subsequent use in an injection procedure or the like.

The third aspect may be implemented in the form of a contrast media management or dispensing system. Such a system may include a contrast media storage/dispensing unit of any appropriate size, shape, configuration, and/or type (e.g., at least generally in the form of a vending machine). This system may store a plurality of contrast media containers of any appropriate type (e.g., in the form of a syringe, bottle, or vial). Each such contrast media container may be in a sealed condition while being stored by the contrast media management system (e.g., such that its contents are isolated from its surrounding environment and/or such that its contents remain sterile), and may remain in this sealed condition when released from the supply. The system may implement a renal function check before allowing a particular contrast media container to be removed from/dispensed by the system. For instance, the system may incorporate a data input device of any appropriate type and in any appropriate manner. Depending upon the data that is provided to the contrast media management system, a contrast media container may or may not be dispensed from or released by the system.

In one implementation of the third aspect, a user may be required to provide input regarding whether or not the renal function of a patient to be imaged has been determined to be sufficient in relation to a particular contrast media type being requested from the supply. A positive response (e.g., a confirmation by a user that the patient's renal function complies with a threshold patient renal function suggested/required to promote safe administration of the contrast media) may allow a container of the desired contrast media to be dispensed or released from the supply. Otherwise, the third aspect may be configured such that a container of the desired contrast media type is not released from the supply (e.g., in the case where the patient's renal function does not meet or exceed a threshold patient renal function suggested/required to promote safe administration of the contrast media).

In another implementation of the third aspect, data regarding renal function of a patient that is to receive the contrast media may be input, as well data regarding the desired contrast media type to be released from the supply. This may entail a user manually entering the relevant data (e.g., inputting data that is representative of the patient's renal function; inputting a patient identifier that allows the patient's most current renal function to be retrieved from one or more data sources (e.g., utilizing a "hospital information system" or HIS); inputting the identification of the desired contrast media type), may entail a user making an appropriate selection from a drop-down menu, or the like. The patient's renal function may be compared with a threshold renal function of the requested contrast media type, and which may be identified to the contrast media storage/dispensing unit in any appropriate manner (e.g., by a user identifying the contrast media type to the unit, and having the unit retrieve the threshold renal function from the data store discussed above; by a user inputting the threshold renal function to the unit through a user input device). In the event that the input patient renal function complies with the threshold renal function of the requested contrast media type (e.g., meets or exceeds this threshold renal function), a container of the desired contrast media type may be released from the supply. Otherwise, the third aspect may be configured such that a container of the desired contrast media type will not be released from the supply.

The plurality of contrast media containers that define the supply for the contrast media management system may be of any appropriate type. In one embodiment, the contrast media management system stores a plurality of prefilled syringes (syringes that have been filled or loaded by a supplier, and that are ultimately transported to an end user or end-use facility; prefilled syringes are not loaded with contrast media by an end user or an end-use facility) that may be released from the contrast media management system only in response to an output from the renal function assessment module. After being released from the contrast media management system (and still in a sealed condition), a given contrast media container may then be used by a contrast media injector system, may be used to inject a patient with contrast media, or both.

Each of the plurality of contrast media containers may include a data storage device of any appropriate type (e.g., an RF tag). Any appropriate information may be stored on any data storage device utilized by any of the contrast media containers. A contrast media type identifier may be stored on a data storage device for a contrast media container, threshold renal function data may be stored on a data storage device for a syringe and that relates to the contrast media within the contrast media container, or the like. The contrast media management system may include a reader of any appropriate type to obtain information from the data storage device of each contrast media container within its supply.

Threshold renal function data associated with contrast media in each contrast media container for the contrast media management system may be retrieved in any appropriate manner. As noted above, threshold renal function data may be retrieved from a data storage device associated with a particular contrast media container. Another option is to retrieve contrast media type data from a data storage device associated with a particular contrast media container, and from this information retrieve corresponding threshold renal function data in any appropriate manner (e.g., via a communication by the contrast media management system with a hospital information system (HIS), with a radiology information system (RIS), with a picture archive and communication system (PACS), with another system housing or having access to electronic medical records (EMRs), or the like; via direct input by a user).

The renal function assessment module may utilize threshold renal function data for a contrast media container of a selected contrast media type to determine whether the contrast media container should be released from its supply. One or more data input devices may be operatively connected with the renal function assessment module. The renal function assessment module may include comparative logic that is configured to compare threshold renal function data with patient renal function data that has been input to the contrast media management system to determine whether the corresponding contrast media container should be released from its supply (e.g., to determine if the renal function data on a patient to be imaged complies with the threshold renal function data of the contrast media to be injected into the patient).

A fourth aspect of the present invention is embodied by a medical imaging system that includes an imaging unit (e.g., CT scanner having an x-ray source, or MRI scanner having a magnet), where the imaging unit includes a renal function assessment module.

A number of feature refinements and additional features are applicable to the fourth aspect of the present invention. These feature refinements and additional features may be used individually or in any combination in relation to the fourth aspect. As such, each of the following features that will be discussed may be, but are not required to be, used with any other feature or combination of features of the fourth aspect.

The imaging system may utilize one or more data input devices of any appropriate type (e.g., a user input device). For instance, one or more data input devices may be incorporated by a remote console of the imaging system. Any remote console of the imaging system may include a remote console display, may include at least one data input device, and/or may be in a different location (e.g., isolated in at least some fashion) from the imaging unit of the imaging system (for instance, outside of an x-ray and/or RF-shielded room that houses the imaging unit). Any data input device incorporated by the imaging system may accommodate the provision of input (e.g., user input) to the imaging system for any appropriate purpose, including programming appropriate imaging parameters. The imaging system could also accommodate data input from one or more external data input devices (i.e., that are not actually part of the imaging system), such as one or more data input devices associated with imaging equipment (e.g., a contrast media injector system), a renal function testing module, or other parts of a healthcare facility (e.g., HIS, RIS, PACS, or any other system housing or having access to patient EMRs). A given data input device may be used to provide any appropriate data to the imaging system, for instance, renal function data on a patient to be imaged and/or threshold renal function data (both of which may be used by the renal function assessment module of the imaging system as will be discussed below).

The renal function assessment module may include (or, in some embodiments, refers to) prompt logic that is configured to issue a prompt for entry of renal function information regarding a patient to be imaged (e.g., manually by a user through an appropriate data input device). The renal function information that is the subject of the prompt may be data that is representative of the renal function of the patient that is to be imaged (e.g., glomerular filtration rate or "GFR", serum creatinine measurement, or any other appropriate renal function indicator). In one embodiment, a first user input is provided to the imaging system in the form of first renal function data of a first patient to be imaged, and the renal function assessment module includes comparative logic that is configured to compare the first renal function data of the first patient with threshold renal function data. Both the first renal function data and the threshold renal function data may be of any appropriate type so long as the data is indicative of patient renal function (e.g., GFR, serum creatinine measurement). The threshold renal function data may be expressed in any appropriate manner (e.g., in the form of a baseline number, such that the first renal function data must be at least as great as the baseline number or, in another embodiment, no greater than the baseline number; in the form of a range, such that the first renal function data must be within this range).

An issued prompt for entry of patient renal function information may be presented on at least one display of the imaging system, for instance, on a display associated with (e.g., incorporated by) a remote console of the imaging system. A data input device may enable a user to manually respond to the noted prompt for renal function information of the patient to be imaged. The prompt may be of any appropriate format, and may request the input of the desired renal function information in any appropriate manner. For instance, the prompt may be in the form of a request for a user to provide/input the renal function information to the imaging system (e.g., for comparison with threshold renal function data). Any data that is representative of a patient's renal function could be manually input through a data input device.

The prompt may simply be in the form of an inquiry directed to determining if the renal function of a patient to be imaged has been determined to be acceptable (e.g., in relation to threshold renal function data). That is, it may be such that a user must simply confirm that the patient's renal function has been checked and has been determined by the user (or other appropriate personnel) to comply with relevant threshold renal function data (e.g., a "yes/no" or "pass/fail" question). In another embodiment, the prompt logic may be configured to issue a prompt (e.g., visually display a prompt to a user) requesting that the user select an answer from a list of displayed answers regarding the patient to be imaged in conjunction with the operation of the imaging system. In yet another embodiment, the prompt logic may be configured to issue a prompt (e.g., visually display a prompt to a user) requesting that the user enter/fill in an empty data field shown on a display of the system with renal function data regarding the patient to be imaged in conjunction with the operation of the imaging system.

The imaging system may be communicatively interconnected with a contrast media injector system (e.g., via an appropriate hardwire interface (e.g., CAN interface) or through an appropriate wireless connection). In such embodiments, the contrast media injector system may be precluded from being operated to provide a contrast media discharge (e.g., so as to not allow for execution of an injection protocol) based upon the user input entered into the imaging system in relation to the noted prompt. For instance, the imaging system may be configured to preclude the injector system from being operated to provide a contrast media discharge (e.g., where at least one syringe plunger is advanced relative to a corresponding syringe barrel by the contrast media injector system) if the patient renal function data that is entered by a user into the imaging system does not comply with the relevant threshold renal function data. As another example, the imaging system may be configured to preclude the injector system from being operated to provide a contrast media discharge if the patient renal function data that is entered by a user does not "pass" an electronic evaluation conducted by the renal function assessment module, which may take threshold renal function data into account when conducting the above-described evaluation. The imaging system may be configured to preclude the injector system from being operated to provide a contrast media discharge if the user of the imaging system does not respond to the prompt at all, if the user of the imaging system responds in the negative to a request for verification that the renal function of a patient to be imaged has been determined to be acceptable, or both. The above-referenced preclusions of contrast media injector system operation initiated by the imaging system may include such things as not allowing the injector system to "arm" or be "enabled" to run a programmed injection protocol. Additionally or alternatively, the above-referenced preclusions of contrast media injector system operation initiated by the imaging system may include such things as not allowing initiation (e.g., "run" or "start") of a programmed injection protocol (e.g., if the injector system is allowed to be "armed"/"enabled" prior to an inquiry regarding patient renal function) and/or inject contrast media into the patient manually using one or more hand controls (e.g., buttons) of the injector system.

The renal function assessment module may include comparative logic that is configured to compare threshold renal function data with renal function data on a patient to be imaged. Renal function data on a patient to be imaged in conjunction with operation of the noted contrast media injector system may be acquired in any appropriate manner and may be communicated to the imaging system in any appropriate manner. Renal function data on a patient to be imaged may be input to the imaging system by a user in any appropriate manner (e.g., manually entering data that is representative of a patient's renal function; in the form of user input). Renal function data on a patient to be imaged may be acquired from one or more data sources that may be in communication or able to communicate with the imaging system, such as a hospital information system (HIS), a radiology information system (RIS), picture archive and communication system (PACS), another system that stores or has access to patient electronic medical records (EMRs), or a renal function testing module.

Threshold renal function data may refer to threshold renal function data of the contrast media to be injected into a patient to be imaged, and may be used by the renal function assessment module to control whether contrast media should be injected into a patient to be imaged. Threshold renal function data may be input to the imaging unit from any appropriate source or combination of sources. Threshold renal function data may be retrieved from a data storage device associated with a syringe to be used in an imaging procedure, and which may then be transmitted to the imaging unit in any appropriate manner. Another option is to retrieve contrast media type data from a data storage device associated with at least one syringe to be used in an imaging procedure, and from this information retrieve corresponding threshold renal function data in any appropriate manner (e.g., via a communication by the imaging system with a hospital information system (HIS), with a radiology information system (RIS), with a picture archive and communication system (PACS), with another system housing or having access to electronic medical records (EMRs), or the like). Threshold renal function information could also be provided to the imaging system via direct user input.

The imaging system may include a database or data store that includes threshold renal function data for a plurality of contrast media types (e.g., for a plurality of different contrast agents, where the difference between two contrast media types may be in the form of having different concentrations of one or more contrast media constituents). The threshold renal function data for a particular contrast media type may be characterized as "contrast media type-specific threshold renal function data." Although each contrast media type may be associated with a particular threshold renal function, one or more contrast media types could be associated with the same threshold renal function. However, each contrast media type could have a different threshold renal function (e.g., depending on the volume and/or concentration of the contrast media within the syringe). The data store may be of any appropriate configuration for purposes of associating a contrast media type with threshold renal function data, for instance, in the form of a look-up table. In one embodiment, identifying the contrast media type to the imaging system (e.g., through a data input device), and that will be used for an injection (e.g., injected into a patient using an interconnected contrast media injector system), results in the corresponding threshold renal function data being automatically retrieved from the data store (e.g., a lookup table) by the imaging system. It should be appreciated that a user could also manually input the threshold renal function data into the imaging system (e.g., through a user input device for the remote console).

At least one syringe may be utilized by the above-noted contrast media injector system, and at least one such syringe may include an appropriate data storage device. Threshold renal function data may be stored on the data storage device of any such syringe and may refer to threshold renal function data for the contrast media contained in the syringe. Any other appropriate information may be stored on the data storage device of the syringe, for instance the type (e.g., identity, chemical composition, active ingredient) of contrast media within the syringe, the concentration (e.g., iodine content and/or level of another ingredient) of the contrast media within the syringe, the volume of contrast media within the syringe, threshold (e.g., minimum) renal function data for a patient proposed to receive a predefined volume (e.g., 5 ml, 10 ml, 15, ml, 20 ml, 25 ml, 30 ml, 35 ml, 40 ml, 45 ml, 50 ml, 55 ml, 60 ml, 65 ml, 70 ml, 75 ml, 80 ml, 85 ml, 90 ml, 95 ml, 100 ml, 105 ml, 110 ml, 115 ml, 120 ml, 125 ml, 130 ml, 135 ml, 140 ml, 145 ml, 150 ml, any of which may or may not be the entire volume of contrast media within the syringe) or the entire volume of contrast media within the syringe, or any combination thereof.

The renal function assessment module utilized by the fourth aspect may include one or more processors. At least one processor of the renal function assessment module (e.g., a first processor) may be programmed: 1) to issue a prompt regarding renal function information for a patient to be imaged; 2) to preclude an interconnected contrast media injector system from being operated to provide a contrast media discharge (e.g., disallow execution of an injection protocol) if renal function data on a patient to be imaged does not comply with threshold renal function data (e.g., does not meet or exceed threshold renal function data); 3) to issue an alarm of any appropriate type or types (e.g., visual, audible) if patient renal function data on a patient to be imaged does not comply with threshold renal function data (e.g., does not meet or exceed threshold renal function data); 4) to generate next action instructions as to at least one action to be taken if renal function data on a patient to be imaged does not comply with threshold renal function data (e.g., does not meet or exceed first threshold renal function data); and/or 5) any combination of two or more of the foregoing.

A fifth aspect of the present invention is embodied by a contrast media injector system that includes a powerhead, a first console (e.g., a remote console), a CAN-compliant injector communication bus, and an injection data management system or module. The powerhead includes a housing, a motorized drive ram, and a syringe mount (e.g., of any appropriate type, for instance, a faceplate). The motorized drive ram of the powerhead is designed to move along an axis, where at least part of the motorized drive ram is located within the housing. The syringe mount of the powerhead is designed to at least substantially immobilize a barrel of the syringe relative to the housing of the powerhead such that the drive ram can move a plunger of the syringe within and relative to the syringe barrel. The first console of the contrast media injector system is in communication with the powerhead, includes a first display, and can be utilized by a user of the contrast media injector system to program injection parameters (e.g., to define an injection protocol having one or more phases, each phase including injection parameters such as an amount of fluid to be injected and an injection flow rate, as well as possibly one or more injection delays (sometimes referred to as "holds" and/or "pauses"), each of which can be of finite or infinite duration). The injection data management module may include a first data conversion unit. This first data conversion unit is operatively interconnected with the CAN-compliant injector communication bus, and is configured to convert CAN-compliant data from the CAN-compliant injector communication bus to HL-7-compliant data (where "HL-7" is "Health Level 7").

A number of feature refinements and additional features are applicable to the fifth aspect of the present invention. These feature refinements and additional features may be used individually or in any combination in relation to the fifth aspect. As such, each of the following features that will be discussed may be, but are not required to be, used with any other feature or combination of features of the fifth aspect. The following discussion is applicable to the fifth aspect, up to the start of the discussion of a sixth aspect of the present invention.

The CAN-compliant data from the CAN-compliant injector communication bus may be of any appropriate CAN version. The HL-7-compliant data may be of any appropriate HL-7 or "Health Level 7" version (e.g., version 1.0, 2.0, or 3.0).

CAN-compliant data from the CAN-compliant injector communication bus may be acquired for conversion by the first data conversion unit in any appropriate manner. This acquired CAN-compliant data may be provided directly to the first data conversion unit for conversion from a CAN-compliant format to an HL-7-compliant format. Another option is for this acquired CAN-compliant data to be provided indirectly to the first data conversion unit (e.g., through a second data conversion unit discussed below) for conversion from a CAN-compliant format to an HL-7-compliant format.

The first data conversion unit may convert CAN-compliant data from the CAN-compliant injector communication bus to HL-7-compliant data in any appropriate manner. This conversion may be characterized as converting a given data object within one standard to the appropriate data object and format in another standard. The first data conversion unit may be incorporated by the contrast media injector system in any appropriate manner to provide the noted conversion function. For instance, the first data conversion unit could be incorporated by an existing subsystem of the contrast media injector system, such as a powerhead, a remote console, or a powerpack. Another option would be for the first data conversion unit to be a completely separate subsystem of the contrast media injector system. For instance, the first data conversion unit could be separate from, but operatively interconnected with, another subsystem of the contrast media injector system such as a powerhead, remote console, or a powerpack. In one embodiment, the first data conversion unit is part of or associated with a single contrast media injector system. In another embodiment, the first data conversion unit is part of or associated with multiple contrast media injector systems. The first data conversion unit may be part of or associated with any appropriate number of contrast media injector systems.

The injection data management system or module may include a second data conversion unit that is operatively interconnected with the CAN-compliant injector communication bus. This second data conversion unit may be configured to convert CAN-compliant data from the CAN-compliant injector communication bus from a first CAN-compliant format (e.g., CAN 2.0A) to a second CAN-compliant format (e.g., CiA 425). The first and second data conversion unit may be characterized as being connected in parallel in one configuration. For instance, the first data conversion unit may convert CAN-compliant data from the noted first CAN-compliant format to HL-7-compliant data, and the second data conversion unit may convert CAN-compliant data from the noted first CAN-compliant format to the second CAN-compliant format (e.g., a "parallel" stream or feed of the same CAN-compliant data from the CAN-compliant injector communication bus could be provided to each of the first data conversion unit and the second data conversion unit, including on a simultaneous basis).

The first and second data conversion units may be characterized as being connected in series in another configuration. For instance, the first data conversion unit may convert CAN-compliant data from the noted second CAN-compliant format (e.g., CiA 425) to HL-7-compliant data. That is, CAN-compliant data (in a first CAN-compliant format) from the CAN-compliant injector communication bus may be transmitted to the second data conversion unit, which may then convert this CAN-compliant data from the first CAN-compliant format (e.g., CAN 2.0A) to the second CAN-compliant format (e.g., CiA 425). CAN-compliant data in the second CAN-compliant format may then be transmitted to the first data conversion module, which may then convert this CAN-compliant data from the second CAN-compliant format to the HL-7-compliant format. In such a case, the CAN-compliant injector communication bus may be characterized as being indirectly interconnected with the first data conversion unit (via the second data conversion unit).

The injection data management module may include a third data conversion unit that is operatively interconnected with the CAN-compliant injector communication bus. This third data conversion unit may be configured to convert CAN-compliant data from the CAN-compliant injector communication bus from a first CAN-compliant format (e.g., CAN 2.0A) to a PACS-compliant format (e.g., DICOM). The first, second, and third data conversion units may be characterized as being connected in parallel in one configuration. For instance, the first data conversion unit may convert CAN-compliant data from the noted first CAN-compliant format to the HL-7-compliant format, the second data conversion unit may convert CAN-compliant data from the noted first CAN-compliant format to the second CAN-compliant format, and the third data conversion unit may convert CAN-compliant data from the noted first CAN-compliant format to a PACS-compliant format (e.g., a "parallel" stream or feed of the same CAN-compliant data from the CAN-compliant injector communication bus could be provided to each of the first, second, and third data conversion units, including on a simultaneous basis).

The second and third data conversion units may be characterized as being connected in series in another configuration (including where the first and third data conversion modules may be characterized as still being connected in parallel). For instance, the third data conversion unit may convert CAN-compliant data from the noted second CAN-compliant format (e.g., CiA 425) to a PACS-compliant format. That is, CAN-compliant data (in a first CAN-compliant format) from the CAN-compliant injector communication bus may be transmitted to the second data conversion unit, which may then convert this CAN-compliant data from the first CAN-compliant format (e.g., CAN 2.0A) to the second CAN-compliant format (e.g., CiA 425). CAN-compliant data in the second CAN-compliant format may then be transmitted to the third data conversion unit, which may then convert this CAN-compliant data from the second CAN-compliant format to a PACS-compliant format. In such a case, the CAN-compliant injector communication bus may be characterized as being indirectly interconnected with the third data conversion unit (via the second data conversion unit).

A medical system may utilize an imaging system and a medical information system, and the injection data management module may be configured to include the above-noted second data conversion unit. The first data conversion unit may be operatively interconnected with the medical information system (e.g., to provide injection-related or contrast administration data from the contrast media injector system to the medical information system in an HL-7-compliant format). The second data conversion unit may be operatively interconnected with the imaging system (e.g., to provide injection-related or contrast administration data from the contrast media injection system to the imaging system, for instance by converting the injection-related or contrast administration data from one CAN-compliant format (e.g., CAN 2.0A) to another CAN-compliant format (e.g., CiA 425)).

The injection data management module may include first and second communication ports. The first communication port may be used to provide converted data from the CAN-compliant injector communication bus to a medical information system operatively interconnected with the injection data management module (e.g., converted data may be output from the first data conversion unit through a first communication port; converted data may be output from the second data conversion unit to the first data conversion unit through one first communication port, and converted data may be output from the first data conversion unit through another first communication port). The second communication port may be used to provide converted data from the CAN-compliant injector communication bus to an imaging system operatively interconnected with the injection data management module.

The first data conversion unit, any second data conversion unit, and any third data conversion unit may be dedicated to a single contrast media injector system. The first data conversion unit, any second data conversion unit, and any third data conversion unit may be collectively part of or associated with any appropriate number of contrast media injector systems.

The contrast media injector system may include a first housing (e.g., a powerpack). The above-noted second data conversion unit may be disposed within this first housing, and there may be a communication link (e.g., a wired communication link, such as an appropriate communication cable) between the first housing and a powerhead of the contrast media injector system. In a first configuration, the first and second data conversion units are each disposed within the noted first housing (e.g., within the powerpack). The first housing in this configuration may include first and second communication ports of any appropriate type (e.g., on an output side of this first housing), where the first communication port is operatively interconnected with the first data conversion unit, and where the second communication port is operatively interconnected with the second data conversion unit (e.g., converted data may be transmitted from the first data conversion unit through the first communication port; converted data may be transmitted from the second data conversion unit through the second communication port). In the case where a contrast media injector system of this first configuration is utilized by the above-noted medical system, the first data conversion unit may be operatively interconnected with the medical information system through the first communication port of this first housing, while the second data conversion unit may be operatively interconnected with the imaging system through the second communication port of this first housing.

In another configuration, the first data conversion unit is not located within the noted first housing (e.g., a powerpack), but which may still contain the second data conversion unit. The first data conversion unit may be a completely separate unit from the first housing. The first housing in this configuration may still utilize first and second communication ports of any appropriate type (e.g., on an output side of the first housing), where each of the first and second communication ports are operatively interconnected with the second data conversion unit (e.g., converted data may be transmitted from the second data conversion unit through each of the first and second communication ports). There may be a communication link of any appropriate type between the first communication port (e.g., on an output side of the first housing) and the first data conversion unit (e.g., a wired communication link, such as an appropriate communication cable). That is, the second data conversion unit may be operatively interconnected with the first data conversion unit through the first communication port. In the case where an injection data management module of this second configuration is utilized by a medical system, the first data conversion unit may be operatively interconnected with the medical information system through the first communication port of the second data conversion unit (as the second data conversion unit is able to transmit converted data to the first data conversion unit through the first communication port, and the first data conversion unit is then able to further convert this data for provision to a medical information system or the like), while the second data conversion unit may be operatively interconnected with the imaging system through the second communication port of the second data conversion unit.

The first and second communication ports of the first housing in the above-noted second configuration may each receive CAN-compliant data from the second data conversion unit in a common CAN-compliant format (e.g., CiA 425). That is, CAN-compliant data that has been converted by the second data conversion unit may be transmitted to an imaging system through the second communication port of the second data conversion unit, and also to the first data conversion unit through the first communication port of the second data conversion unit. The first data conversion unit would then convert this CAN-compliant data to HL-7-compliant data (e.g., for subsequent provision to a medical information system through a first communication port of the first data conversion unit).

The injection data management module may be characterized as including first and second communication nodes. In a first embodiment: 1) the first communication node is operatively interconnected with the CAN-compliant injector communication bus (e.g., directly or indirectly through the above-discussed second data conversion module); 2) only one-way communication is allowed between the CAN-compliant injector communication bus and the second communication node through the first communication node (e.g., CAN-compliant data may be transmitted from the CAN-compliant injector communication bus to the first data conversion unit and then ultimately to a medical information system, but data/commands from the medical information system may not be sent through the first data conversion unit to the CAN-compliant injector communication bus through the first communication node); and 3) the injection data management module accommodates two-way communication through the second communication node. In a second embodiment: 1) the first communication node is operatively interconnected with the CAN-compliant injector communication bus (e.g. directly or indirectly through the above-discussed second data conversion unit); and 2) the injection data management module is of a pull-type data transfer configuration in relation to the second communication node. In a third embodiment: 1) the first communication node is operatively interconnected with the CAN-compliant injector communication bus (e.g. directly or indirectly through the above-discussed second data conversion unit); and 2) the injection data management module is configured to output data to the second communication node only in response to a data request received by the injection data management module through the second communication node. In each of these three embodiments, injection-related or contrast administration data may be sent to the first data conversion unit through the first communication node, the injection data management module may receive a request for injection-related or contrast administration data through the second communication node (e.g., from a hospital information system), and data converted by the first data conversion unit may be made available through the second communication node (e.g., for provision to a hospital information system).

Another embodiment has the injection data management module being configured such that: 1) the first communication node is operatively interconnected with the CAN-compliant injector communication bus (e.g., directly or indirectly through the above-discussed second data conversion unit); and 2) the second communication node is operatively interconnected with a medical information system of any appropriate type (e.g., a hospital information system; an electronic medical records system). The injection data management module may be characterized in this case as being of a push-type configuration—the first data conversion unit may be configured to and/or allow data to be transmitted to the medical information system without first receiving a request for data from the medical information system. Another characterization is that the injection data management module may be configured to transmit data (previously converted by the first data conversion module) to the medical information system on an automated or programmed basis. In each of these instances, injection-related or contrast administration data may be sent to the first data conversion module through the first communication node, the first data conversion unit may then translate this data into an HL-7-compliant format, and the HL-7-compliant data may then ultimately be transmitted from the injection data management module to the medical information system through the second communication node.

The injection data management module may also be of a push/pull configuration. The injection data management module may be configured to accommodate transmission of data to a medical information system in response to receiving a request for data (e.g., a pull-type data transmission). The injection data management module may also be configured to transmit data to a medical information system on an automated or programmed basis (e.g., a push-type data transmission). Yet another option is to allow data to be transmitted from the first data conversion module in response to user input to the contrast media injector system (e.g., manually-initiated).

A sixth aspect of the present invention is embodied by a medical system that includes a contrast media injector system, an imaging system, a first console, a contrast media storage/dispensing unit, a medical information system, and an injection data management system or module. The contrast media injector system and imaging system are operatively interconnected. The first console is operatively interconnected with at least one of the contrast media injector system and the imaging system, and includes both a first display and a first user input device. The contrast media storage/dispensing unit includes a plurality of contrast media containers having contrast media therein, and each such contrast media container incorporates a data storage device (e.g., RF data tag; a bar code). In this regard, the contrast media injector system includes a data reader that is operable to at least read data from a data storage device of a contrast media container having contrast media to be used by the contrast media injector system. The injection data management module includes a first data conversion unit. The injection data management module is disposed between the medical information system and an injector communication bus of the contrast media injector system, and is operatively interconnected with each of the medical information system and injector communication bus.

A seventh aspect of the present invention is embodied by a medical system that includes a contrast media injector system, an imaging system, a first console, a contrast media storage/dispensing unit, at least one renal function assessment module, a medical information system, and an injection data management system or module. The contrast media injector system and imaging system are operatively interconnected. The first console is operatively interconnected with at least one of the contrast media injector system and imaging system, and includes both a first display and a first user input device. The contrast media storage/dispensing unit includes a plurality of contrast media containers having contrast media therein. The injection data management module includes a first data conversion unit. The injection data management module is disposed between the medical information system and an injector communication bus of the contrast media injector system, and is operatively interconnected with each of the medical information system and injector communication bus.

An eighth aspect of the present invention is embodied by a medical system that includes a contrast media injector system, a contrast media data source, an imaging system, a first console, a medical information system, and an injection data management system or module. The contrast media injector system and imaging system are operatively interconnected. The first console is operatively interconnected with at least one of the contrast media injector system and the imaging system, and includes both a first display and a first user input device. The injection data management module is operatively interconnected with each of the contrast media injector system and the medical information system. The injection data management module includes at least one data conversion unit (e.g., a first data conversion unit to convert injection data received from the injector system from a CAN-compliant format to a non-CAN-compliant format). The injection data management module further includes at least one user interface and is configured to display patient data (acquired by the injection data management module from the medical information system), contrast media data (acquired by the injection data management module from the contrast media data source), and contrast media injection data (acquired by the injection data management module from the contrast media injector system).

A ninth aspect of the present invention is embodied by a medical system that includes a contrast media injector system, an imaging system, a first console, a medical information system, and an injection data management system or module. The contrast media injector system and imaging system are operatively interconnected. The first console is operatively interconnected with at least one of the contrast media injector system and the imaging system, and includes both a first display and a first user input device. The injection data management module is operatively interconnected with each of the injector system and the medical information system. The injection data management module includes at least one data conversion unit (e.g., a first data conversion unit to convert injection data received from the injector system from a CAN-compliant format to a non-CAN-compliant format). The injection data management module is configured to store a plurality of injection histories, where each injection history includes patient data, contrast media data, and contrast injection data. The contrast media data and the contrast injection data each pertain to a single, common injection procedure executed on a single, common patient.

A tenth aspect of the present invention is embodied by a medical system that includes a contrast media injector system, an imaging system, a first console, a medical information system, and an injection data management system or module. The contrast media injector system and imaging system are operatively interconnected. The first console is operatively interconnected with at least one of the contrast media injector system and the imaging system, and includes both a first display and a first user input device. The medical information system includes patient data for a plurality of patients, where the patient data for each patient includes a patient ID. The injection data management module is operatively interconnected with each of the injector system and the medical information system. The injection data management module includes at least one data conversion unit (e.g., a first data conversion unit to convert injection data received from the injector system from a CAN-compliant format to a non-CAN-compliant format). The injection data management module is configured to compare a patient ID (retrieved from the medial information system and for a selected patient) with another patient ID that is input to the injection data management module.

An eleventh aspect of the present invention is embodied by a medical system that includes a contrast media injector system, an imaging system, a first console, a medical information system, and an injection data management system or module. The contrast media injector system and imaging system are operatively interconnected. The first console is operatively interconnected with at least one of the contrast media injector system and the imaging system, and includes both a first display and a first user input device. The injection data management module is operatively interconnected with each of the injector system and the medical information system. The injection data management module includes at least one data conversion unit (e.g., a first data conversion unit to convert injection data received from the injector system from a CAN-compliant format to a non-CAN-compliant format). The injection data management module includes a data structure, which in turn includes a patient renal function override rationale field.

A number of feature refinements and additional features are separately applicable to each of above-noted eighth, ninth, tenth, and eleventh aspects of the present invention. These feature refinements and additional features may be used individually or in any combination in relation to each of the above-noted eighth, ninth, tenth, JO and eleventh aspects of the present invention. As such, each of the following features that will be discussed may be, but are not required to be, used with any other feature or combination of features of each of the eighth, ninth, tenth, and eleventh aspects.

The injection data management system or module may include at least one user interface and may be configured to display patient data (acquired by the injection data management module from the medical information system), contrast media data (acquired by the injection data management module from a contrast media data source), and contrast media injection data (acquired by the injection data management module from the contrast media injector system). Representative patient data includes at least one of a patient ID, a patient age, a patient gender, a patient weight, a patient height, a patient GFR, and a patient renal function override rationale (e.g., a rationale for proceeding with a contrast injection, notwithstanding some "deficiency" with a patient's renal function). Contrast media data may include at least one of prescribed contrast media data and dispensed contrast media data, for instance at least one of a prescribed contrast media volume, a prescribed contrast media concentration, a prescribed contrast media flow rate, a dispensed contrast media volume, a dispensed contrast media concentration, a National Drug Code for the dispensed contrast media, a dispensed contrast media brand name, a dispensed contrast media manufacturer, a dispensed contrast media lot number, a dispensed contrast media manufacture date, a dispensed contrast media composition, and a dispensed contrast media primary functional ingredient. Representative contrast media injection data includes at least one of an administered contrast media volume, an administered contrast media concentration, and an administered contrast media flow rate.

The medical system may include a contrast media data source, which may be in the form of a contrast media storage/dispensing unit (e.g., of the type addressed above in relation to the sixth and seventh aspects of the present invention). The contrast media storage/dispensing unit may be operatively interconnected with the injection data management module (e.g., for at least one-way communication therebetween). Contrast media data could be communicated from the contrast media storage/dispensing unit to the injection data management module.

The above-noted contrast media data source may include a data storage device of any appropriate type that is incorporated by a contrast media container of any appropriate type. The data storage device may be in the form of a barcode (e.g., disposed on contrast media syringe), an RE or REID tag (e.g., disposed on contrast media syringe), or the like. The medical system may include a data reader of any appropriate type that is operatively interconnected with the injection data management module. One embodiment has the data reader in the form of a barcode scanner. Another embodiment has the data reader in the form of an RF or any other appropriate electromagnetic reader. The data reader could be a stand-alone component of the medical system, or may be incorporated by another component of the medical system (such as the contrast media injector system, where the data reader could be incorporated into in a syringe mount, or where the data reader could be a separate unit of the contrast media injector system). In any case, the data reader may read contrast media data from the data storage device of the contrast media container, and this contrast media data may be transmitted to the injection data management module (e.g., directly from the data reader; by the data reader providing the contrast media data to the injector system, which may then transmit the contrast media data to the injection data management module).

The injection data management system or module may be configured to store a plurality of injection histories. Each injection history may include patient data, contrast media data, and contrast injection data of the above-described types. Each injection history may pertain to a single injection procedure executed on a single patient.

The injection data management system or module may include a data processing unit or module and a data storage system. The noted injection histories may be stored on the data storage system. The data processing module may be operatively interconnected with the data storage system for facilitating storage of injection histories, for viewing one or more of the stored injection histories, for generating reports regarding one or more of the stored injection histories, for transmitting one or more of the stored injection histories (e.g., to the medical information system), and the like. The data processing module may utilize any appropriate database management software. Injection histories may be accessed in any appropriate manner using any appropriate report writing software.

The injection data management system or module may be configured for storing only a predetermined number of injection histories (e.g., 24 injection histories). In one embodiment, only a predetermined number of the most current injection histories are stored on the injection data management module (e.g., the oldest injection history stored on the injection data management module may be deleted when a new injection history is added to the injection data management module). All injection histories stored on the injection data management module may be transmitted as a batch to the medical information system. The injection data management module may be configured to transmit a predetermined number of injection histories as a batch to the medical information system.

The medical information system may store patient data for a plurality of patients, where the patient data for each patient includes a patient ID. Patient data (including a patient ID) for a selected patient may be retrieved from the medical information system (e.g., a hospital information system; a radiology information system) by the injection data management module. The injection data management module may be configured to compare (e.g., using patient ID validation logic) the retrieved patient ID for the selected patient with another patient ID that is input to the injection data management module.

Patient ID data may be input to the injection data management system or module from two different sources. One patient ID (a patient ID from one source, for instance retrieved from the medical information system) may be compared with another patient ID (a patient ID from a different source) by the injection data management module (e.g., using patient ID validation logic). If the two patient IDs match, the injection data management module may be configured to send a patient ID validation signal to the contrast media injector system, which will allow the contrast injection of the patient to proceed. The contrast media injector system may be required to receive such a patient ID validation signal from the injection data management module in order to be operable to execute a contrast media injection for the associated patient.

Patient ID data may be input to the injection data management system or module in any appropriate manner for purposes of a patient ID validation. For instance, the medical system could include a data reader that is operatively connectable with the injection data management module, and that may retrieve a patient ID from a data storage device for input to the injection data management module. The data reader may be in the form of a barcode scanner. The patient ID may be stored on a barcode, for instance a barcode that is integrated with a wristband worn by the patient. In any case, the injection data management module may be configured to require patient ID data from two different sources, and for there to be a match, before allowing an injection procedure to proceed.

The injection data management system or module may include a data structure (e.g., for storage of a plurality of injection histories in accordance with the foregoing), which in turn may include a patient renal function override rationale field and/or require storage of patient renal function override rationale data for at least certain circumstances. A patient's renal function may be assessed prior to execution of an injection procedure. There may be instances where the patient's renal function does not comply with a renal function threshold, but where a decision is nonetheless made to proceed with the contrast media injection. The injection data management module may store a plurality of standardized patient renal function override rationales. Any of these patient renal function override rationales may be selected (e.g., through a user interface of the injection data management module) for storage as part of an injection history for this particular patient. If a patient's renal function does not comply with a renal function threshold and if a patient renal function override rationale is not input to the injection data management module (e.g., by selecting from a list of patient renal function override rationales stored on the injection data management module), the medical system may be configured to not allow a contrast injection of this patient to proceed.

A number of feature refinements and additional features are separately applicable to each of above-noted sixth, seventh, eighth, ninth, tenth, and eleventh aspects of the present invention. These feature refinements and additional features may be used individually or in any combination in relation to each of the above-noted sixth, seventh, eighth, ninth, tenth, and eleventh aspects of the present invention. As such, each of the following features that will be discussed may be, but are not required to be, used with any other feature or combination of features of each of the sixth, seventh, eighth, ninth, tenth, and elevenths aspects.

One or more data readers may be utilized by the contrast media injector system, and may be incorporated by the contrast media injector system in any appropriate manner (e.g., in a syringe mount; as a separate unit (e.g., a wand) that is detachably connected with another portion of the contrast media injector system). Such a data reader may be used to read data from a data storage device of any appropriate type (e.g., a data tag on a syringe or other contrast media container; a bar code on a patient wristband; a data tag on the badge of medical personnel). The data reader may be in the form of an electromagnetic device, such as an RFID reader.

The first data conversion unit may be incorporated by the medical system in any appropriate manner. The first data conversion unit could be incorporated by the contrast media injector system in any appropriate manner, for instance in accordance with the above-noted fifth aspect. However, the first data conversion unit could be incorporated by the medical system so as to be physically separate from each of the contrast media injector system and the medical information system. The first data conversion unit may be configured to communicate on at least a one-way basis (via the operative connection) with each of the injector system and the medical information system.

The first data conversion unit may be configured to convert data from a first format (e.g., one format) to a second format (e.g., a different format). For instance, the first data conversion unit may receive data in a first format (e.g., directly or indirectly from the contrast media injector system, for instance an injector communication bus), and data transmitted from the first data conversion module may be in a second format (e.g., for receipt by the medical information system). In one embodiment, the first format is CAN-compliant (e.g., CAN 2.0A; CiA 425), and the second format is HL-7-compliant. In this regard, each of the sixth, seventh, eighth, ninth, tenth, and eleventh aspects of the present invention may incorporate the combination of features required by the fifth aspect of the present invention, as well as any of the refinements and additional features discussed above in relation to the fifth aspect.

The injection data management system or module may include a single data conversion unit (e.g., a first data conversion unit). Multiple data conversion units may be utilized by the injection data management module (e.g., a first data conversion unit, along with at least one of a second data conversion unit and a third data conversion unit). A given data conversion unit of the injection data management module may convert data from the contrast media injector system into a different format, for instance into a HL-7-compliant format or into a PACS-compliant format (e.g., DICOM). Data from the contrast media injector system may be in the form of CAN-compliant data. A given data conversion unit of the injection data management module may convert data from the contrast media injector system from one CAN-compliant format into a different CAN-compliant format (e.g., for provision to the imaging system). A given data conversion unit of the injection data management module may convert data, received from the contrast media injector system, from a CAN-compliant format into an HL-7-compliant format or a PACS-compliant format (e.g., DICOM). In the case where multiple data conversion units are utilized by the injection data management module, each data conversion unit may convert data into a different format (e.g., one data conversion unit may convert data into an HL-7-compliant format, and another data conversion unit may convert data into a PACS-compliant format such as DICOM). In one embodiment, the first data conversion module converts data from a CAN-compliant format to a non-CAN-compliant format (e.g., HL-7 or DICOM).

The medical system may include at least one patient renal function assessment module. Such a renal function assessment module may be configured to provide at least one patient renal function check at least at some point in time prior to injecting contrast media into a patient (or administering contrast media to a patient) using the contrast media injector system, where this contrast media may have been provided or dispensed by a contrast media storage/dispensing unit. In one embodiment, a renal function assessment module is incorporated by the contrast media injector system (e.g., a first renal function assessment module). This first renal function assessment module may be configured to provide at least one patient renal function check prior to the contrast media injector system being operated to inject contrast media into a patient (or administer contrast media to a patient). As such, the first aspect of the present invention may be utilized by each of the sixth, seventh, eighth, ninth, tenth, and eleventh aspects. Moreover, the second aspect of the present invention may be utilized by each of the sixth, seventh, eighth, ninth, tenth, and eleventh aspects.

In one embodiment, a renal function assessment module is incorporated by a contrast media storage/dispensing unit (e.g., a second renal function assessment module). This second renal function assessment module may be configured to provide at least one patient renal function check prior to releasing any contrast media container from the contrast media storage/dispensing unit (e.g., for use by the contrast media injector system). As such, the third aspect of the present invention may be utilized by each of the sixth, seventh, eighth, ninth, tenth, and eleventh aspects.

The medical system may include at least one data store. This data store may store a plurality of contrast media types and a corresponding threshold renal function for each contrast media type. As such, the second aspect of the present invention may be utilized by each of the sixth, seventh, eighth, ninth, tenth, and eleventh aspects.

A number of feature refinements and additional features are separately applicable to each of above-noted fifth, sixth, seventh, eighth, ninth, tenth, and eleventh aspects of the present invention. These feature refinements and additional features may be used individually or in any combination in relation to each of the above-noted fifth, sixth, seventh, eighth, ninth, tenth, and eleventh aspects of the present invention. As such, each of the following features that will be discussed may be, but are not required to be, used with any other feature or combination of features of the each of the fifth, sixth, seventh, eighth, ninth, tenth, and eleventh aspects.

Any medical information system described in relation to the fifth, sixth, seventh, eighth, ninth, tenth, and/or eleventh aspects may be of any appropriate type and/or configuration. For instance, such a medical information system could be in the form of a hospital or healthcare information system (HIS), a radiology or radiological information system (RIS), a pharmacy information system (PIS), a hospital management system (HMS), or the like. Each such medical information system may include one more computers, one or more user/data input devices, one or more data storage devices or systems, and the like, and may be arranged and/or distributed in any appropriate manner (e.g., using one or more networks of any appropriate type, such as a local area network, the Internet, a wide area network, or any combination thereof).

Any medical system that utilizes any one or more of the above-noted fifth, sixth, seventh, eighth, ninth, tenth, and/or eleventh aspects of the present invention may utilize a data structure having a plurality of data fields. This data structure may reside on the injection data management module. Data may be stored in any such data structure using any appropriate database management software. Data stored in any such data structure may be accessed in any appropriate manner using any appropriate report writing software.

A group of data fields with data pertaining to a particular injection of a particular patient may be characterized as a record or an injection history in the above-noted data structure. For instance, a medical information system may utilize such a data structure. Representative data fields for this data structure include one or more fields directed to one or more of the following: 1) patient information; 2) physician information; 3) imaging procedure information; 4) prescribed contrast media information (e.g., information on contrast media that has been prescribed for injection or administration to a patient); 5) dispensed contrast media information (e.g., information on contrast media that has been provided or dispensed by the contrast media storage/dispensing unit for subsequent use by the contrast media injector system); 6) administered contrast media information (e.g., information on contrast media that has been injected or administered by the contrast media injector system); 7) the identity of the contrast media injector system used for the injection, the identity of the injection data management module that provided the data, or both; and 8) the time associated with the initiation of an injection procedure, the time associated with the conclusion of an injection procedure, and/or the time associated with the recordation of the data. Data in each of these fields may be linked in any appropriate manner to define a data record for this data structure (e.g., a data record having data for one or more of the above-noted data fields, and where this data record may also be referred to as an injection history as noted).

Prescribed contrast media data (e.g., the contrast media volume that has been prescribed for injection into a patient; the concentration of the contrast media that has been prescribed for injection into a patient; the flow rate(s) that has been prescribed for the injection of contrast media into a patient), dispensed contrast media data (e.g., the contrast media volume that has been dispensed from the contrast media storage/dispensing unit for subsequent injection into a patient; the concentration of the contrast media that has been dispensed from the contrast media storage/dispensing for subsequent injection into a patient), and administered contrast media data (e.g., the contrast media volume that was actually injected into or administered to a patient by the contrast media injector system; the concentration of the contrast media that was actually injected into or administered to a patient by the contrast media injector system; the flow rate(s) that was actually injected into or administered to a patient by the contrast media injector system) may be stored in a data structure of the medical system. Additional data on the contrast media that has been prescribed, dispensed, and/or administered may be stored in the data structure of the medical system, including without limitation the brand name of the contrast media, the manufacturer of the contrast media, the lot number of the contrast media, the expiration date of the contrast media, and the manufacture date for the contrast media. The prescribed contrast media data, dispensed contrast media data, and administered contrast media data described herein may be characterized as injection-related or contrast administration data for purposes of the present invention. The prescribed contrast media data, dispensed contrast media data, and administered contrast media data each may be used for any appropriate purpose. For instance, prescribed contrast media data, dispensed contrast media data, and/or administered contrast media data may be utilized by electronic medical records, inventory tracking systems, medical billing systems, imaging, pharmacy, laboratory, or radiology systems, or the like.

An injection data management system or module may utilize at least one data conversion unit (e.g., the described first data conversion unit). Such an injection data management module may or may not include at least one of a second data conversion unit and a third data conversion unit as described herein. One or more data conversion units of the injection data management module could be disposed in a common housing or in a single unit. One or more data conversion units of the injection data management module could be disposed in a common housing or in a single unit, one or more data conversion units of the injection data management module could each be disposed in a separate housing or unit, or both.

The injection data management system or module may utilize a data processing module or unit. The data processing module could be disposed in a common unit with one or more data conversion units used by the injection data management module (e.g., located within the same outer shell). In this case, one or more processors could be shared by the data processing module and at least one data conversion module that are part of any such common unit, or the data processing module could have a dedicated processor(s) in relation to each such data conversion unit. Each data conversion unit that is disposed within a common unit (e.g. located within the same outer shell) could have a dedicated processor(s), or one or more processors could be shared by multiple data conversion unit that are part of such a common unit. The data processing module could also be disposed in a separate unit in relation to each data conversion unit used by the injection data management module.

One or more processors may be used by the injection data management system or module (e.g., its data processing unit or module) to process requests for contrast administration data received by the injection data management module from one or more medical information systems (e.g., HIS, RIS, an electronic medical records system), to facilitate transmission of data from the injection data management module to one or more medical systems, to store information on the injection data management module, or for any other functionality provided by the injection data management module. One or more processors may also be used by each data conversion unit of the injection data management module to convert data from one format to another. Any appropriate processor architecture may be used in relation to any data processing module and each data conversion unit that may be incorporated by the injection data management module.

The injection data management system or module may include an appropriate data storage system of any appropriate type or types and of any appropriate architecture (e.g., memory of any appropriate type or types; one or more data storage devices) for retaining one or more injection histories. Each injection history may contain various types of data on a particular injection procedure that was undertaken on a particular patient. Multiple injection histories may be stored by the injection data management module. In one embodiment, a predetermined number of the most current injection histories are stored on the injection data management module (e.g., 24 injection histories, or any other appropriate number of multiple injection histories, may be stored by the injection data management module). The injection data management module may use a push-type data transmission configuration, a pull-type data transmission configuration, or a push/pull-type data transmission configuration (e.g., in relation to the first data conversion unit, in relation to any second data conversion unit, and/or in relation to any third data conversion unit). In one embodiment, the data processing module and the data storage system are disposed in a common unit. Converted data from each data conversion unit may be transmitted to the data storage system (whether a given data conversion unit is contained within the same unit as the data processing module and data storage system, or whether a given data conversion unit is in a physically separate unit form the data processing module and data storage system). One or more medical information systems may communicate with the data processing module, including in relation to the transmission of data from the data storage system of the injection data management module to one or more medical information systems.

A user interface (e.g., at least one user input device of any appropriate type, a display, or both) may be operatively interconnected with the injection data management system or module to allow data to be transmitted from the injection data management module in response to user input (e.g., a manual input to the injection data management module by a user). Such a user interface may be used to communicate with the data processing module, the data storage system, each data conversion unit, or any combination thereof. The injection data management module may utilize software for use in converting data from one format to another, storing data on the injection data management module, transmitting data from the injection data management module, processing requests for data, and/or communicating with one or more medical systems (e.g., a medical information system). The injection data management module may include one or more communication ports of any appropriate type, including at least one communication port to allow software updates to be downloaded to/installed on the injection data management module (e.g., an Ethernet port for allowing software updates to be downloaded to the injection data management module from the Internet). The injection data management module could use a separate communication port to communicate with each medical information system of sub-system of a medical system. The injection data management module could have a separate communication port for each data format stored on its data storage system (e.g., a separate communication port for HL-7-compliant data; a separate communication port for PACS-compliant-data; a separate communication port for CAN-compliant data, for instance for communications with an imaging system).

One or more components of the injection data management system or module may have one or more assigned IP addresses. Each component of the injection data management module could have a dedicated IP address or dedicated IP addresses. For instance, the data processing unit or module could have a dedicated IP address or addresses, and each data conversion unit could have a dedicated IP address or addresses. The injection data management module may be accessed locally (e.g., within an internal network through one or more user interfaces of the injection data management module), remotely (e.g., from a computer that is not part of a network including the injection data management module, but that is operatively connectable with the injection data management module), or both in any appropriate manner.

In one embodiment, the above-noted injection data management system or module is used in conjunction with a single contrast media injector system. An injection history in such a case could be configured to include either an appropriate identifier for the contrast media injector system or an appropriate identifier for the injection data management module. In another embodiment, the above-noted injection data management module is used in conjunction with multiple contrast media injector systems. An injection history in such a case could then include both an appropriate identifier for the contrast media injector system that was used for the associated injection, along with an appropriate identifier for the injection data management module that provided the associated injection history.

The contrast media injector system may be used in conjunction with an imaging system. Such an imaging system (e.g., a scanner and a remote console) may use any appropriate imaging technology (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging).

The contrast media injector system may utilize a first console (e.g., a remote console). The first console may be of any appropriate type (e.g., a desktop computer; a laptop computer), and may include one or more displays or monitors, one or more processors, one or more data or user input devices of any appropriate type (e.g., keyboard, mouse, touch screen, joystick, trackball), memory of any appropriate type/configuration, one or more data storage devices of any appropriate type (e.g., a hard drive, flash drive), or any combination thereof. The first console may be located in a different room (e.g., a control room) than a powerhead of the contrast media injector system (e.g., in an imaging room), although the first console could be located in the same room as such a powerhead (e.g., in an imaging room). The first console may be operatively interconnected with only the powerhead, or the remote console could be operatively interconnected with both the powerhead and an imaging system. The first console in this case could be a shared console for the contrast media injector system and the imaging system, the first console could actually be the console for the contrast media injector system (but configured to communicate with and/or control at least certain aspects of the imaging system), or the first console could actually be the console for the imaging system (but configured to communicate with and/or control at least certain aspects of the contrast media injector system).

A twelfth aspect of the present invention is embodied by a medical system that includes a plurality of imaging suites and a plurality of control rooms, where each imaging suite includes an imaging system of any appropriate type. A separate contrast media injector system is associated with each imaging suite, and includes an injection head that is located within its corresponding imaging suite. A given control room may be associated with any appropriate number of imaging suites (e.g., each imaging suite could have a dedicated control room; a given control room could be used by two or more imaging suites).

The medical system of the twelfth aspect further includes an injection data management system having a data management system (DMS) server, along with a separate data translation module and a separate data management system (DMS) console for each contrast media injector system (e.g., each contrast media injector system has a dedicated data translation module/DMS console pair). Each contrast media injector system, a first medical information system of the medical system, each data translation module, each DMS console, and the DMS server are all on the network (e.g., to allow communication between different devices/systems over the network connection).

A number of feature refinements and additional features are applicable to the twelfth aspect of the present invention. These feature refinements and additional features may be used individually or in any combination in relation to the twelfth aspect. As such, each of the following features that will be discussed may be, but are not required to be, used with any other feature or combination of features of the twelfth aspect.

The network for the medical system may include both a local area network and a wide area network. In this case, a plurality of contrast media injector systems and their corresponding data translation module/DMS console pair from the data management system may be on the local area network, while the DMS server may be on the wide area network. The medical system could include a plurality of facilities, where each facility is on its own local area network, and where each facility includes a plurality of contrast media injector systems and a corresponding data translation module/DMS console pair from the data management system. The various local area networks could be interconnected by a wide area network, and again the DMS server could be on such a wide area network.

Each contrast media injector system may include a remote console, along with the noted injection head. The injection head for a given contrast media injector system may be located within its imaging suite, while its corresponding remote console may be located in the control room for this imaging suite. Although the DMS console and data translation module for a given contrast media injector system may be incorporated at any appropriate location, in one embodiment the DMS console for a given contrast media injector system is located in its corresponding control room and the data translation module for this same contrast media injector system is located in its corresponding imaging suite.

The data translation module for each contrast media injector system may include a first data conversion unit that is configured to convert data from one data format to a different data format. For instance, each data translation module may receive injection data from its corresponding contrast media injector system over the network. The first data conversion unit for each contrast media injector system may convert data from a CAN-compliant data format to a non-CAN-compliant format. In one embodiment, this non-CAN-compliant data format is an HL-7-compliant data format. In one embodiment, this non-CAN-compliant data format is a DICOM-compliant data format.

The data translation module for each contrast media injector system may include at least two data conversion units that are each configured to convert data from one data format to a different data format. The first data conversion unit for each contrast media injector system may convert data from a CAN-compliant data format to an HL-7-compliant format. A second data conversion unit of each data translation module may convert data from one CAN-compliant data format to a different CAN-compliant data format. A third data conversion unit of each data translation module may convert data from a CAN-compliant data format to a DICOM-compliant data format.

The data translation module for each contrast media injector system may be configured to send injection data over the network to its corresponding DMS console, where this injection data is first transmitted from the contrast media injector system to its corresponding data translation module over the network. Each data translation module may be configured to send all injection data to its corresponding DMS console after the injection procedure has been completed. Injection data may include programmed injection values, administered or achieved injection values, or both.

The DMS console for each contrast media injector system may be configured to compile a data management system (DMS) patient record that pertains to a single injection procedure on a single patient, where this injection procedure is executed by its corresponding contrast media injector system and injects one or more medical fluids (sequentially, simultaneously, or both) into the patient. Each DMS console may be configured to store a plurality of DMS patient records that are generated from the execution of a corresponding injection procedure on a patient by its corresponding contrast media injector system. Each DMS patient record may include patient data, injection media data (e.g., corresponding with the medical fluid(s) to be injected/actually injected into the patient in conjunction with a given injection procedure, for instance contrast media data, saline media data, or both), and the above-noted injection data.

Patient data for a DMS patient record may be acquired in any appropriate manner. The injection data management system may acquire patient data from a medical information system of the medical system over the network (e.g., HIS and/or RIS). The injection data management system may be configured to retrieve a patient worklist from the network, and patient data may be retrieved from this patient worklist. In one embodiment, each DMS console is configured to retrieve a DICOM worklist (e.g., from a RIS) over the network, and to retrieve patient data from this worklist.

The medical system may include a separate first data reader for each contrast media injector system. Each first data reader may be configured to communicate directly with the data translation module that is associated with the same contrast media injector system. In such a configuration, data acquired by the first data reader would not pass through the corresponding contrast media injector system to reach the corresponding data translation module. The first data reader may be configured to communication with its corresponding data translation module other than via the network. In any case, the first data reader for each contrast media injector system may be used to acquire data regarding the injection procedure to be conducted (or being conducted) on a patient, and to provide the same to the corresponding data translation module.

The first data reader (e.g., a barcode scanner) may be used to acquire patient identification information. A patient data storage device may be associated with a patient (e.g., a barcode that is integrated with a patient wristband worn by the patient), and may include first patient ID data. The first data reader associated with the contrast media injector system that is to be used to perform an injection procedure on such a patient may be configured to read the patient ID data from the patient data storage device, and furthermore may be configured to transmit the acquired first patient ID data to the corresponding data translation module. This first patient ID data may be compared by the injection data management system with second patient ID data acquired from another data source (e.g., from a worklist accessed by the corresponding DMS console), for instance in relation to allowing a DMS patient record to be saved on the corresponding DMS console.

The first data reader for each contrast media injector system may be used to acquire injection media data for inclusion in a DMS patient record to be compiled by and stored on the corresponding DMS console. A first injection media container having a first data storage device may be utilized by the contrast media injector system to conduct an injection procedure on a patient. The above-noted injection media data may be characterized as pertaining to injection media within this first injection media container, and may be stored on the first data storage device for this first injection media container. Injection media data may be read by the first data reader from the first data storage device for the first injection media container, and may be transmitted from the first data reader to the corresponding data translation module. It should be appreciated that such a similar data storage device could be associated with one or more other injection media containers to be used by the contrast media injector system for an injection procedure, and which could be read via the first data reader.

Each contrast media injector system may itself include a second data reader (e.g., the above-noted wand; an RF reader incorporated by a syringe mount of the contrast media injector system). Installing the above-noted first injection media container on a given contrast media injector system may allow its corresponding second data reader to read injection media data from its corresponding first data storage device. This injection media data may then be transmitted from the contrast media injector system to its corresponding data translation module. In one embodiment, the second data reader is in the form of an RF reader, and the first data storage device for the first injection media container is in the form of an RF data tag. It should be appreciated that such a similar data storage device could be associated with one or more other injection media containers to be used by the contrast media injector system for an injection procedure, and which could be read via the second data reader.

The DMS console for each contrast media injector system may be configured to transmit DMS patient records (from storage on the DMS console) to the DMS server over the network. The DMS server may be configured with a DMS patient records database, where a plurality of DMS patient records from each DMS console are stored. DMS patient records may be transmitted from the DMS patient records database of the DMS server to the first medical information system over the network as well, including with the first medical system is in the form of a hospital information system.

A number of feature refinements and additional features are separately applicable to each of above-noted aspects of the present invention. These feature refinements and additional features may be used individually or in any combination in relation to each of the above-noted aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical). Finally, a reference of a feature in conjunction with the phrase "in one embodiment" does not limit the use of the feature to a single embodiment.

Any module, protocol, logic, or the like that may be utilized by any of the various aspects of the present invention may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. Any such module, protocol, logic, or the like may be implemented at any single location or at multiple locations that are interconnected in any appropriate manner (e.g., via any type of network or combination of networks).

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical imaging application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging) and/or any appropriate medical diagnostic and/or therapeutic application (e.g., injection of chemotherapy, pain management, etc.). Any such power injector may be used in conjunction with any component or combination of components, such as an appropriate imaging system (e.g., a CT or MR scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, therapeutic fluid, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injectors syringe plunger drive assembly such that the syringe plunger drive assembly is able to advance the plunger in at least one direction, and possibly in two different, opposite directions.

As used herein, the term "detachably interconnected" describes a relationship between components where the components are interconnected yet retain the ability to be detached from each other where, after detaching, each of the components remains in a usable condition. For example, "a power injector syringe being detachably interconnected with a powerhead" describes a condition where the power injector syringe is currently interconnected to the powerhead in a manner that allows for the power injector syringe to be detached from the powerhead. Furthermore, after such detaching, both the power injector syringe and the powerhead retain the ability to be interconnected (e.g., detachably) with each other (or another component).

BRIEF DESCRIPTION OF THE FIGURES

FIG. 4A is a cutaway view of syringe mount of FIGS. 2B and 2C, particularly showing first and second movable members of the syringe mount in an open position.
FIG. 4B is a cross-sectional view, taken along line 4B-4B of FIG. 4A, and shows a coupling mechanism of a syringe plunger positioned in proximity to a plunger coupling element of a drive ram.
FIG. 8A is a plan view of another RFID antenna layout that may be utilized by the power injector syringe clamp assembly of FIG. 6 (interior surface being illustrated).
FIG. 8B is a plan view of another RFID antenna layout that may be utilized by the power injector syringe clamp assembly of FIG. 6 (interior surface being illustrated).
FIG. 9 is a schematic of an option for providing power to an REID antenna of a power injector syringe clamp assembly, using a pivot pin.

FIGS. 23A-D is one embodiment of a data structure that may be used by a medical system that uses an injection data management system or module having data format conversion capabilities.

FIG. 40 is one embodiment of a results screen that may be used by an injection data management system or module having data format conversion capabilities.

FIG. 45A is one embodiment of a login screen that may be used by an injection data management system or module having data format conversion capabilities.

FIG. 45B is one embodiment of a worklist screen that may be used by an injection data management system or module having data format conversion capabilities.

FIG. 45E is one embodiment of a patient attributes screen that may be used by an injection data management system or module having data format conversion capabilities.

FIG. 45F is one embodiment of a programmed injection data screen that may be used by an injection data management system or module having data format conversion capabilities.

FIG. 45G is one embodiment of an administered injection data screen that may be used by an injection data management system or module having data format conversion capabilities.

FIG. 45H is one embodiment of a cancel injection window that may be used by an injection data management system or module having data format conversion capabilities.

DETAILED DESCRIPTION

Figure 1A:
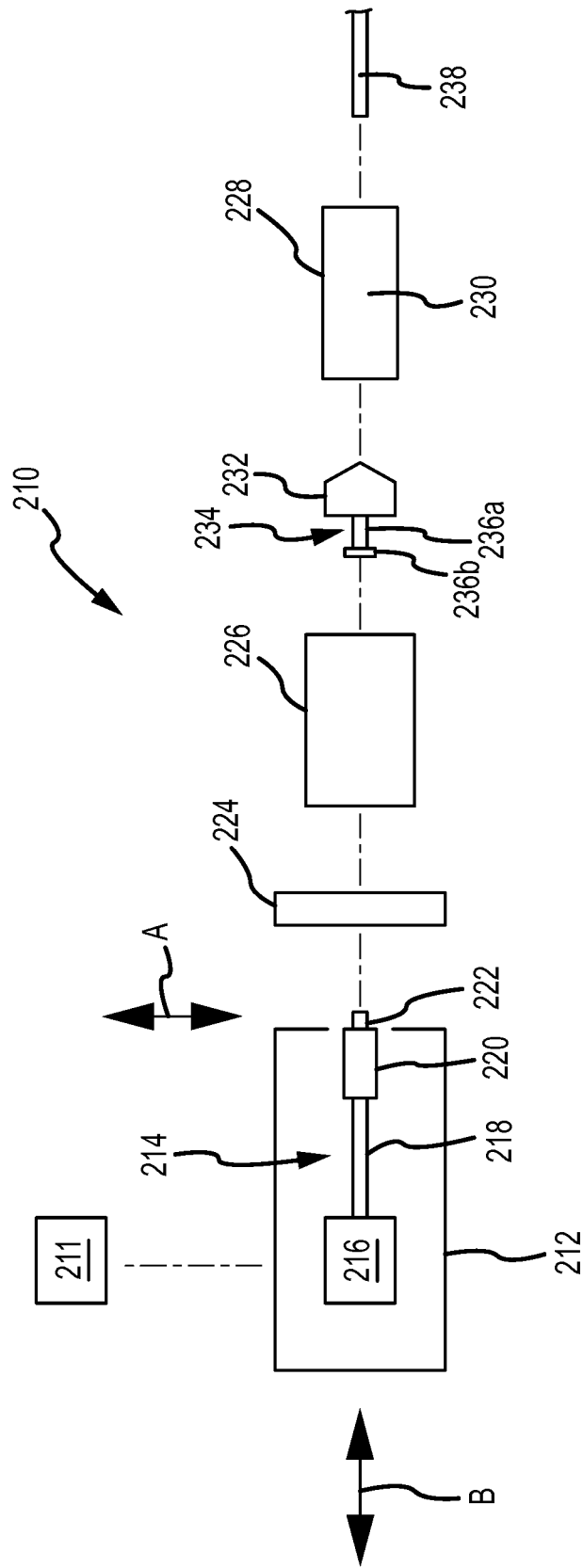
FIG. 1A is a schematic of one embodiment of a power injector.

FIG. 1A presents a schematic of one embodiment of a power injector 210 having a powerhead 212. One or more graphical user interfaces or GUIs 211 may be associated with the powerhead 212. Each GUI 211: 1) may be of any appropriate size, shape, configuration, and/or type; 2) may be operatively interconnected with the powerhead 212 in any appropriate manner; 3) may be disposed at any appropriate location; 4) may be configured to provide one or any combination of the following functions; controlling one or more aspects of the operation of the power injector 210; inputting/editing one or more parameters associated with the operation of the power injector 210; and displaying appropriate information (e.g., associated with the operation of the power injector 210); or 5) any combination of the foregoing. Any appropriate number of GUIs 211 may be utilized. In one embodiment, the power injector 210 includes a GUI 211 that is incorporated by a console that is separate from but which communicates with the powerhead 212. In another embodiment, the power injector 210 includes a GUI 211 that is part of the powerhead 212. In yet another embodiment, the power injector 210 utilizes one GUI 211 on a separate console that communicates with the powerhead 212, and also utilizes another GUI 211 that is on the powerhead 212. Each GUI 211 could provide the same functionality or set of functionalities, or the GUIs 211 may differ in at least some respect in relation to their respective functionalities.

A syringe 228 may be installed on this powerhead 212 and, when installed, may be considered to be part of the power injector 210. Some injection procedures may result in a relatively high pressure being generated within the syringe 228. In this regard, it may be desirable to dispose the syringe 228 within a pressure jacket 226. The pressure jacket 226 is typically associated with the powerhead 212 in a manner that allows the syringe 228 to be disposed therein as a part of or after installing the syringe 228 on the powerhead 212. The same pressure jacket 226 will typically remain associated with the powerhead 212, as various syringes 228 are positioned within and removed from the pressure jacket 226 for multiple injection procedures. The power injector 210 may eliminate the pressure jacket 226 if the power injector 210 is configured/utilized for low-pressure injections and/or if the syringe(s) 228 to be utilized with the power injector 210 is (are) of sufficient durability to withstand high-pressure injections without the additional support provided by a pressure jacket 226. Fluid discharged from the syringe 228 may be directed into a conduit 238 of any appropriate size, shape, configuration, and/or type, which may be fluidly interconnected with the syringe 228 in any appropriate manner, and which may direct fluid to any appropriate location (e.g., to a patient).

The powerhead 212 includes a syringe plunger drive assembly or syringe plunger driver 214 that interacts (e.g., interfaces) with the syringe 228 (e.g., a plunger 232 thereof) to discharge fluid from the syringe 228. This syringe plunger drive assembly 214 includes a drive source 216 (e.g., a motor of any appropriate size, shape, configuration, and/or type, optional gearing, and the like) that powers a drive output 218 (e.g., a rotatable drive screw). A ram 220 may be advanced along an appropriate path (e.g., axial) by the drive output 218. The ram 220 may include a coupler 222 for interacting or interfacing with a corresponding portion of the syringe 228 in a manner that will be discussed below.

The syringe 228 includes a plunger or piston 232 that is movably disposed within a syringe barrel 230 (e.g., for axial reciprocation along an axis coinciding with the double-headed arrow B). The plunger 232 may include a coupler 234. This syringe plunger coupler 234 may interact or interface with the ram coupler 222 to allow the syringe plunger drive assembly 214 to retract the syringe plunger 232 within the syringe barrel 230. The syringe plunger coupler 234 may be in the form of a shaft 236a that extends from a body of the syringe plunger 232, together with a head or button 236b. However, the syringe plunger coupler 234 may be of any appropriate size, shape, configuration, and/or type.

Generally, the syringe plunger drive assembly 214 of the power injector 210 may interact with the syringe plunger 232 of the syringe 228 in any appropriate manner (e.g., by mechanical contact; by an appropriate coupling (mechanical or otherwise)) so as to be able to move or advance the syringe plunger 232 (relative to the syringe barrel 230) in at least one direction (e.g., to discharge fluid from the corresponding syringe 228). That is, although the syringe plunger drive assembly 214 may be capable of bi-directional motion (e.g., via operation of the same drive source 216), the power injector 210 may be configured such that the operation of the syringe plunger drive assembly 214 actually only moves each syringe plunger 232 being used by the power injector 210 in only one direction. However, the syringe plunger drive assembly 214 may be configured to interact with each syringe plunger 232 being used by the power injector 210 so as to be able to move each such syringe plunger 232 in each of two different directions (e.g. in different directions along a common axial path).

Retraction of the syringe plunger 232 may be utilized to accommodate a loading of fluid into the syringe barrel 230 for a subsequent injection or discharge, may be utilized to actually draw fluid into the syringe barrel 230 for a subsequent injection or discharge, or for any other appropriate purpose. Certain configurations may not require that the syringe plunger drive assembly 214 be able to retract the syringe plunger 232, in which case the ram coupler 220 and syringe plunger coupler 234 may not be desired. In this case, the syringe plunger drive assembly 214 may be retracted for purposes of executing another fluid delivery operation (e.g., after another prefilled syringe 228 has been installed). Even when a ram coupler 222 and syringe plunger coupler 232 are utilized, it may be that these components may or may not be coupled when the ram 220 advances the syringe plunger 232 to discharge fluid from the syringe 228 (e.g., the ram 220 may simply "push on" the syringe plunger 234). Any single motion or combination of motions in any appropriate dimension or combination of dimensions may be utilized to dispose the ram coupler 222 and syringe plunger coupler 234 in a coupled state or condition, to dispose the ram coupler 222 and syringe plunger coupler 234 in an uncoupled state or condition, or both.

The syringe 228 may be installed on the powerhead 212 using a syringe mount of any appropriate configuration. For instance, the syringe 228 could be configured to be installed directly on the powerhead 212. A syringe mount may be characterized as a structure that allows a syringe to be installed on the powerhead 212 (e.g., via a detachable connection where a syringe may be attached to and removed from the powerhead 212 without damaging either the syringe or the powerhead 212). Generally, such a syringe mount may be further characterized as at least substantially immobilizing the body or barrel 230 of the syringe 228 such that the drive ram 220 of the injector 210 can move the syringe plunger 232 within and relative to the syringe barrel 230.

In the illustrated embodiment of FIG. 1A, a housing 224 (syringe mount) is appropriately mounted on the powerhead 212 to provide an interface between the syringe 228 and the powerhead 212. This housing 224 may be in the form of an adapter to which one or more configurations of syringes 228 may be installed, and where at least one configuration for a syringe 228 could be installed directly on the powerhead 212 without using any such adapter. The housing 224 may be in the form of a faceplate to which one or more configurations of syringes 228 may be installed. In this case, it may be such that a faceplate is required to install a syringe 228 on the powerhead 212—the syringe 228 could not be installed on the powerhead 212 without the faceplate. When a pressure jacket 226 is being used, it may be installed on the powerhead 212 in the various manners discussed herein in relation to the syringe 228, and the syringe 228 will typically thereafter be installed in the pressure jacket 226.

The housing 224 may be mounted on and remain in a fixed position relative to the powerhead 212 when installing a syringe 228. Another option is to movably interconnect the housing 224 and the powerhead 212 to accommodate installing a syringe 228. For instance, the housing 224 may move within a plane that contains the double-headed arrow A to provide one or more of a coupled state or condition and an un-coupled state or condition between the ram coupler 222 and the syringe plunger coupler 234.

Figure 1B:
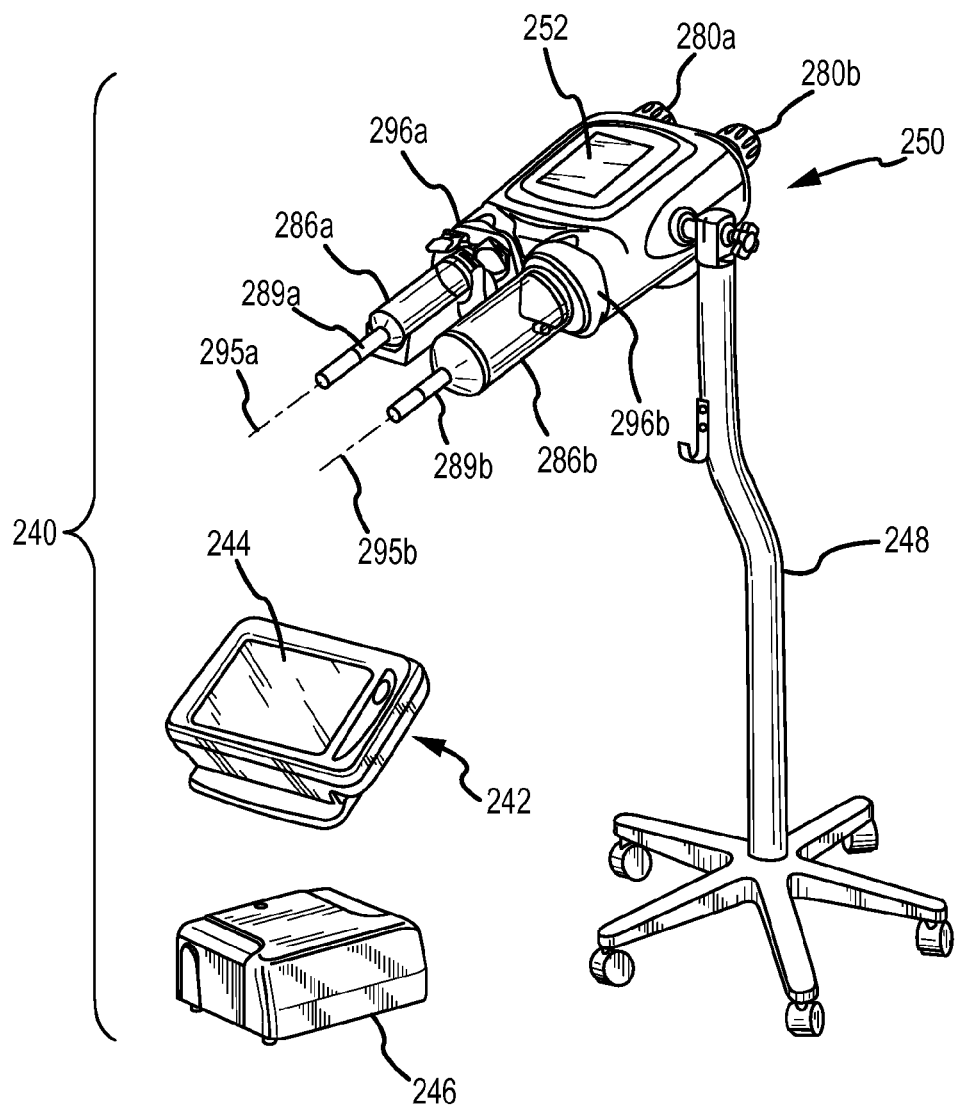
FIG. 1B is a perspective view of one embodiment of a portable stand-mounted, dual-head power injector.

One particular power injector configuration is illustrated in FIG. 1B, is identified by a reference numeral 240, and is at least generally in accordance with the power injector 210 of FIG. 1A. The power injector 240 includes a powerhead 250 (having a housing) that is mounted on a portable stand 248. Two syringes 286a, 286b for the power injector 240 are mounted on the powerhead 250. Fluid may be discharged from the syringes 286a, 286b during operation of the power injector 240.

The portable stand 248 may be of any appropriate size, shape, configuration, and/or type. Wheels, rollers, casters, or the like may be utilized to make the stand 248 portable. The powerhead 250 could be maintained in a fixed position relative to the portable stand 248. However, it may be desirable to allow the position of the powerhead 250 to be adjustable relative to the portable stand 248 in at least some manner. For instance, it may be desirable to have the powerhead 250 in one position relative to the portable stand 248 when loading fluid into one or more of the syringes 286a, 286b, and to have the powerhead 250 in a different position relative to the portable stand 248 for performance of an injection procedure. In this regard, the powerhead 250 may be movably interconnected with the portable stand 248 in any appropriate manner (e.g., such that the powerhead 250 may be pivoted through at least a certain range of motion, and thereafter maintained in a desired position).

It should be appreciated that the powerhead 250 could be supported in any appropriate manner. For instance, instead of being mounted on a portable structure, the powerhead 250 could be interconnected with a support assembly, that in turn is mounted to an appropriate structure (e.g., ceiling, wall, floor). A support assembly for the powerhead 250 may be positionally adjustable in at least some respect (e.g., by having one or more support sections that may be repositioned relative to one or more other support sections), or may be maintained in a fixed position. Moreover, the powerhead 250 may be integrated with any such support assembly so as to either be maintained in a fixed position or so as to be adjustable relative the support assembly.

The powerhead 250 includes a graphical user interface or GUI 252. This GUI 252 may be configured to provide one or more (including any combination) of the following functions: controlling one or more aspects of the operation of the power injector 240; inputting/editing one or more parameters associated with the operation of the power injector 240; and displaying appropriate information (e.g., associated with the operation of the power injector 240). The power injector 240 may include a console 242 and powerpack 246 that each may be in communication with the powerhead 250 in any appropriate manner (e.g., via one or more cables). The console 242 may be placed on a table or mounted on an electronics rack in an examination room or a control room, or at any other appropriate location. The powerpack 246 may be placed on a table or a floor in an examination room or a control room, or at any other appropriate location. The powerpack 246 may include one or more of the following and in any appropriate combination: a power supply for the injector 240; interface circuitry for providing communication between the console 242 and powerhead 250; circuitry for permitting connection of the power injector 240 to remote units such as remote consoles, remote hand or foot control switches, or other original equipment manufacturer (OEM) remote control connections (e.g., to allow for the operation of power injector 240 to be synchronized with the x-ray exposure of an imaging system); and any other appropriate componentry. The console 242 (which may include a touch screen display 244 or any other appropriate display and user input device) may provide one or more of the following functions and in any appropriate combination: allowing an operator to remotely control one or more aspects of the operation of the power injector 240; allowing an operator to enter/edit one or more parameters associated with the operation of the power injector 240; allowing an operator to specify and store programs for automated operation of the power injector 240 (which can later be automatically executed by the power injector 240 upon initiation by the operator); and displaying any appropriate information relation to the power injector 240 and including any aspect of its operation.

Figure 1C:
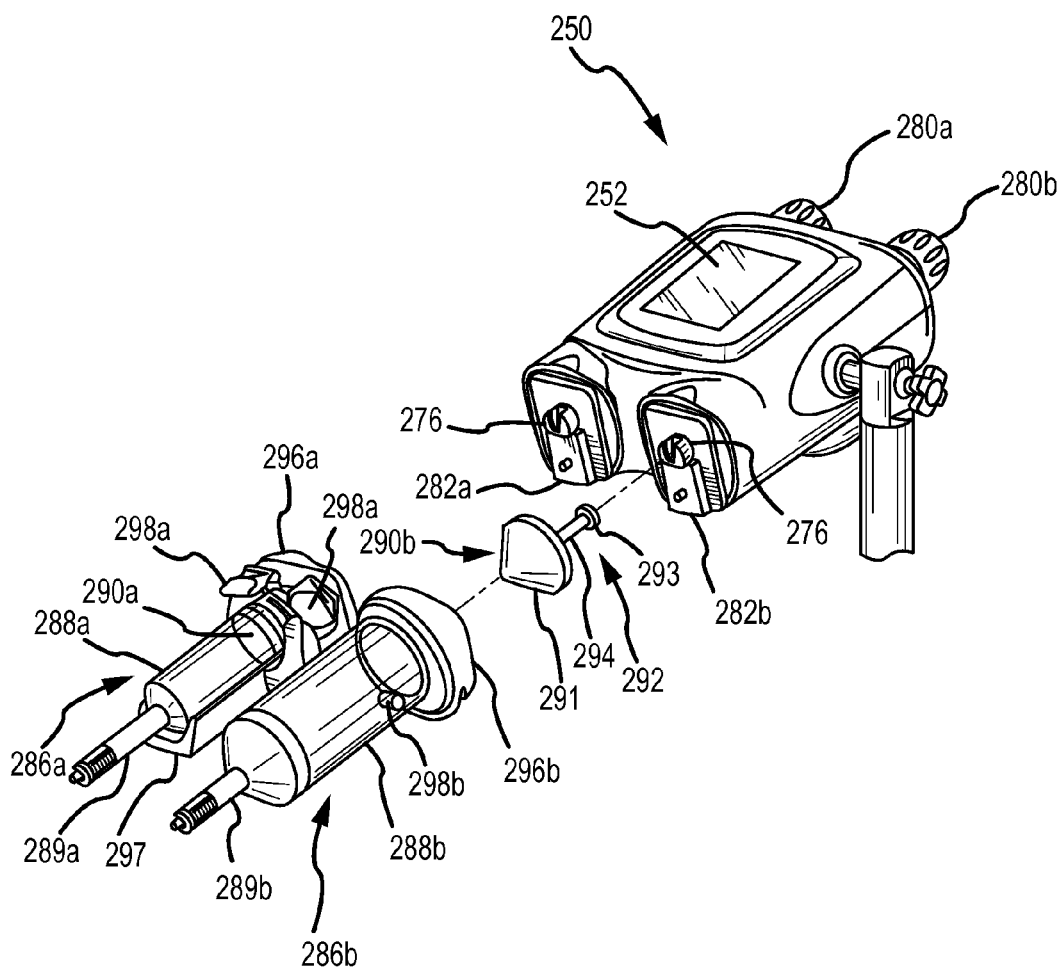
FIG. 1C is an enlarged, partially exploded, perspective view of a powerhead used by the power injector of FIG. 1B.

Various details regarding the integration of the syringes 286a, 286b with the powerhead 250 are presented in FIG. 1C. Each of the syringes 286a, 286b includes the same general components. The syringe 286a includes plunger or piston 290a that is movably disposed within a syringe barrel 288a. Movement of the plunger 290a along an axis 295a (FIG. 1B) via operation of the powerhead 250 will discharge fluid from within a syringe barrel 288a through a nozzle 289a of the syringe 286a. An appropriate conduit (not shown) will typically be fluidly interconnected with the nozzle 289a in any appropriate manner to direct fluid to a desired location (e.g., a patient). Similarly, the syringe 286b includes plunger or piston 290b that is movably disposed within a syringe barrel 288b. Movement of the plunger 290b along an axis 295b (FIG. 1B) via operation of the powerhead 250 will discharge fluid from within the syringe barrel 288b through a nozzle 289b of the syringe 286b. An appropriate conduit (not shown) will typically be fluidly interconnected with the nozzle 289b in any appropriate manner to direct fluid to a desired location (e.g., a patient).

The syringe 286a is interconnected with the powerhead 250 via an intermediate faceplate 296a. This faceplate 296a includes a cradle 297 that supports at least part of the syringe barrel 288a, and which may provide/accommodate any additional functionality or combination of functionalities. For instance, componentry of a data reader may be included in the cradle 297 to facilitate the reading of data from a data storage device associated with the syringe 286a. As another example, the cradle 297 may include a heating mechanism that can be used to warm fluid within the syringe 286a while the syringe 286a is mounted to the powerhead 250. A mounting 282a is disposed on and is fixed relative to the powerhead 250 for interfacing with the faceplate 296a. A ram coupler 276 of a ram 274 (FIG. 1C), which are each part of a syringe plunger drive assembly or syringe plunger driver 256 (FIG. 1D) for the syringe 286a, is positioned in proximity to the faceplate 296a when mounted on the powerhead 250. Details regarding the syringe plunger drive assembly 256 will be discussed in more detail below in relation to FIG. 10. Generally, the ram coupler 276 may be coupled with the syringe plunger 290a of the syringe 286a, and the ram coupler 276 and ram 274 (FIG. 10) may then be moved relative to the powerhead 250 to move the syringe plunger 290a along the axis 295a (FIG. 1B). It may be such that the ram coupler 276 is engaged with, but not actually coupled to, the syringe plunger 290a when moving the syringe plunger 290a to discharge fluid through the nozzle 289a of the syringe 286a.

The faceplate 296a may be moved at least generally within a plane that is orthogonal to the axes 295a, 295b (associated with movement of the syringe plungers 290a, 290b, respectively, and illustrated in FIG. 1B), both to mount the faceplate 296a on and remove the faceplate 296a from its mounting 282a on the powerhead 250. The faceplate 296a may be used to couple the syringe plunger 290a with its corresponding ram coupler 276 on the powerhead 250. In this regard, the faceplate 296a includes a pair of handles 298a. Generally and with the syringe 286a being initially positioned within the faceplate 296a, the handles 298a may be moved to in turn move/translate the syringe 286a at least generally within a plane that is orthogonal to the axes 295a, 295b (associated with movement of the syringe plungers 290a, 290b, respectively, and illustrated in FIG. 1B). Moving the handles 298a to one position moves/translates the syringe 286a (relative to the faceplate 296a) in an at least generally downward direction to couple its syringe plunger 290a with its corresponding ram coupler 276. Moving the handles 298a to another position moves/translates the syringe 286a (relative to the faceplate 296a) in an at least generally upward direction to uncouple its syringe plunger 290a from its corresponding ram coupler 276.

The syringe 286b is interconnected with the powerhead 250 via an intermediate faceplate 296b. A mounting 282b is disposed on and is fixed relative to the powerhead 250 for interfacing with the faceplate 296b. A ram coupler 276 of a ram 274 (FIG. 1D), each of which is part of a syringe plunger drive assembly 256 for the syringe 286b, is positioned in proximity to the faceplate 296b when mounted to the powerhead 250. Details regarding the syringe plunger drive assembly 256 will be discussed in more detail below in relation to FIG. 1D. Generally, the ram coupler 276 may be coupled with the syringe plunger 290b of the syringe 286b, and the ram coupler 276 and ram 274 (FIG. 1D) may be moved relative to the powerhead 250 to move the syringe plunger 290b along the axis 295b (FIG. 1B). It may be such that the ram coupler 276 is engaged with, but not actually coupled to, the syringe plunger 290b when moving the syringe plunger 290b to discharge fluid through the nozzle 289b of the syringe 286b.

The faceplate 296b may be moved at least generally within a plane that is orthogonal to the axes 295a, 295b (associated with movement of the syringe plungers 290a, 290b, respectively, and illustrated in FIG. 1B), both to mount the faceplate 296b on and remove the faceplate 296b from its mounting 282b on the powerhead 250. The faceplate 296b may be used to couple the syringe plunger 290b with its corresponding ram coupler 276 on the powerhead 250. In this regard, the faceplate 296b may include a handle 298b. Generally and with the syringe 286b being initially positioned within the faceplate 296b, the syringe 286b may be rotated along its long axis 295b (FIG. 1B) and relative to the faceplate 296b. This rotation may be realized by moving the handle 298b, by grasping and turning the syringe 286b, or both. This rotation moves/translates both the syringe 286b and the faceplate 296b at least generally within a plane that is orthogonal to the axes 295a, 295b (associated with movement of the syringe plungers 290a, 290b, respectively, and illustrated in FIG. 1B). Rotating the syringe 286b in one direction moves/translates the syringe 286b and faceplate 296b in an at least generally downward direction to couple the syringe plunger 290b with its corresponding ram coupler 276. Rotating the syringe 286b in the opposite direction moves/translates the syringe 286b and faceplate 296b in an at least generally upward direction to uncouple its syringe plunger 290b from its corresponding ram coupler 276.

Each of the faceplates 296a, 296b may be characterized as a syringe mount—a structure that allows a syringe to be installed on the powerhead 250 (e.g., via a detachable connection where a syringe may be attached to and removed from the powerhead 250 without damaging either the syringe or the powerhead 250). Generally, such a syringe mount may be further characterized as at least substantially immobilizing the body or barrel of a syringe such that the drive ram 274 of the injector 240 can move the corresponding syringe plunger within and relative to the corresponding syringe barrel.

As illustrated in FIG. 1C, the syringe plunger 290b includes a plunger body 291 and a syringe plunger coupler 292. This syringe plunger coupler 292 includes a shaft 294 that extends from the plunger body 291, along with a head 293 that is spaced from the plunger body 291. Each of the ram couplers 276 includes a larger slot that is positioned behind a smaller slot on the face of the ram coupler 276. The head 293 of the syringe plunger coupler 292 may be positioned within the larger slot of the ram coupler 276, and the shaft 294 of the syringe plunger coupler 292 may extend through the smaller slot on the face of the ram coupler 276 when the syringe plunger 290b and its corresponding ram coupler 276 are in a coupled state or condition. The syringe plunger 290a may include a similar syringe plunger coupler 292 for interfacing with its corresponding ram coupler 276.

Figure 1D:
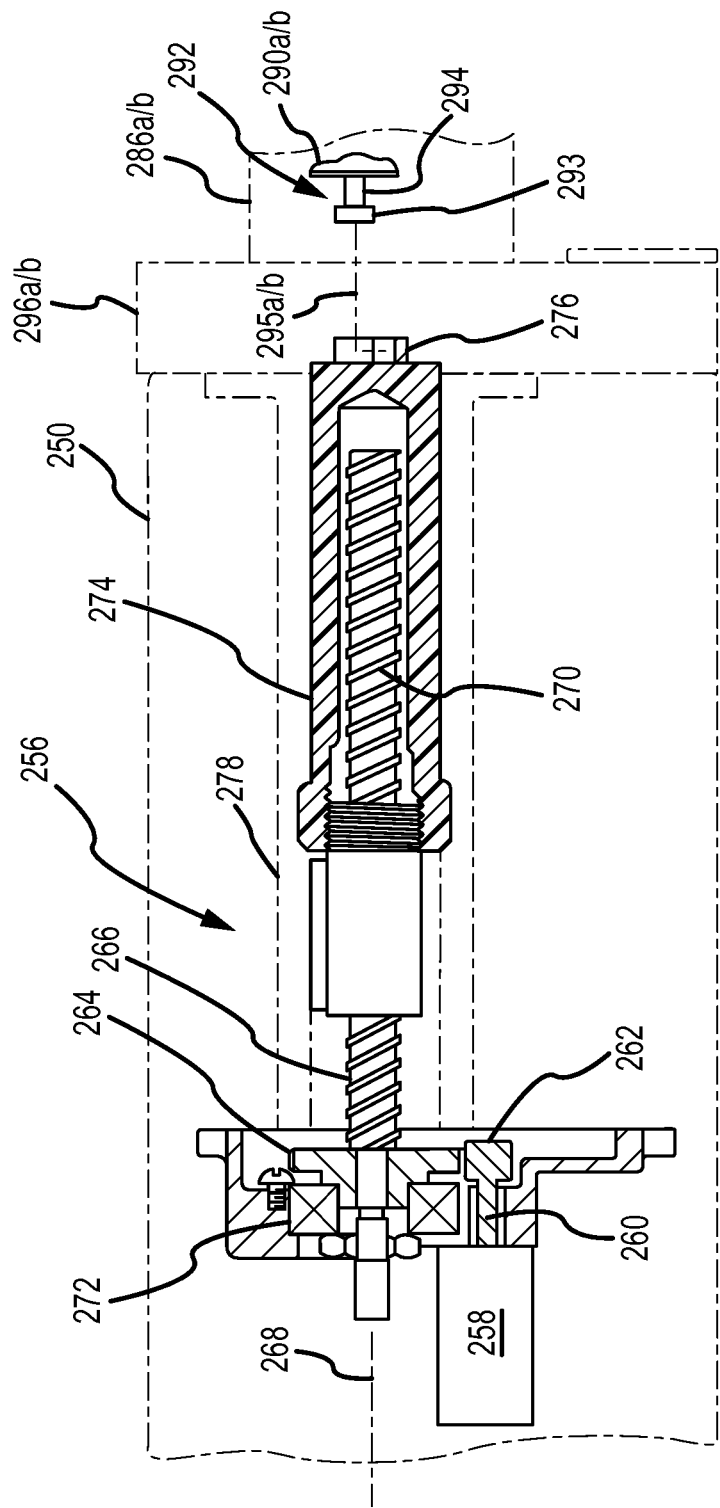
FIG. 1D is a schematic of one embodiment of a syringe plunger drive assembly used by the power injector of FIG. 1B.

The powerhead 250 is utilized to discharge fluid from the syringes 286a, 286b in the case of the power injector 240. That is, the powerhead 250 provides the motive force to discharge fluid from each of the syringes 286a, 286b. One embodiment of what may be characterized as a syringe plunger drive assembly or syringe plunger driver is illustrated in FIG. 1D, is identified by reference numeral 256, and may be utilized by the powerhead 250 to discharge fluid from each of the syringes 286a, 286b. A separate syringe plunger drive assembly 256 may be incorporated into the powerhead 250 for each of the syringes 286a, 286b. In this regard and referring back to FIGS. 1B-C, the powerhead 250 may include hand-operated knobs 280*a* and 280*b* for use in separately controlling each of the syringe plunger drive assemblies 256.

Initially and in relation to the syringe plunger drive assembly 256 of FIG. 1D, each of its individual components may be of any appropriate size, shape, configuration and/or type. At least part of the syringe plunger drive assembly 256 is disposed within the powerhead 250. The syringe plunger drive assembly 256 includes a motor 258, which has an output shaft 260. A drive gear 262 is mounted on and rotates with the output shaft 260 of the motor 258. The drive gear 262 is engaged or is at least engageable with a driven gear 264. This driven gear 264 is mounted on and rotates with a drive screw or shaft 266. The axis about which the drive screw 266 rotates is identified by reference numeral 268. One or more bearings 272 appropriately support the drive screw 266.

A carriage or ram 274 is movably mounted on the drive screw 266. At least part of this ram 274 may be characterized as being disposed within the powerhead 250 (or as being disposed within a housing of the powerhead 250), although part of the ram 274 extends beyond the powerhead 250 on a discharge stroke. Generally, rotation of the drive screw 266 in one direction axially advances the ram 274 along the drive screw 266 (and thereby along axis 268) in the direction of the corresponding syringe 286*a/b* (e.g., a discharge stroke direction), while rotation of the drive screw 266 in the opposite direction axially advances the ram 274 along the drive screw 266 (and thereby along axis 268) away from the corresponding syringe 286*a/b* (e.g., a fluid loading direction). In this regard, the perimeter of at least part of the drive screw 266 includes helical threads 270 that interface with at least part of the ram 274. The ram 274 is movably mounted within an appropriate bushing 278 that does not allow the ram 274 to rotate during a rotation of the drive screw 266. Therefore, the rotation of the drive screw 266 provides for an axial movement of the ram 274 in a direction determined by the rotational direction of the drive screw 266.

The ram 274 includes a coupler 276 that that may be detachably coupled with a syringe plunger coupler 292 of the syringe plunger 290*a/b* of the corresponding syringe 286*a/b*. When the ram coupler 276 and syringe plunger coupler 292 are appropriately coupled, the syringe plunger 290*a/b* moves along with ram 274. FIG. 1D illustrates a configuration where the syringe 286*a/b* may be moved along its corresponding axis 295*a/b* without being coupled to the ram 274. When the syringe 286*a/b* is moved along its corresponding axis 295*a/b* such that the head 293 of its syringe plunger 290*a/b* is aligned with the ram coupler 276, but with the axes 268 still in the offset configuration of FIG. 1D, the syringe 286*a/b* may be translated within a plane that is orthogonal to the axis 268 along which the ram 274 moves. This establishes a coupled engagement between the ram coupler 276 and the syringe plunger coupler 293 in the above-noted manner.

Figure 2A:
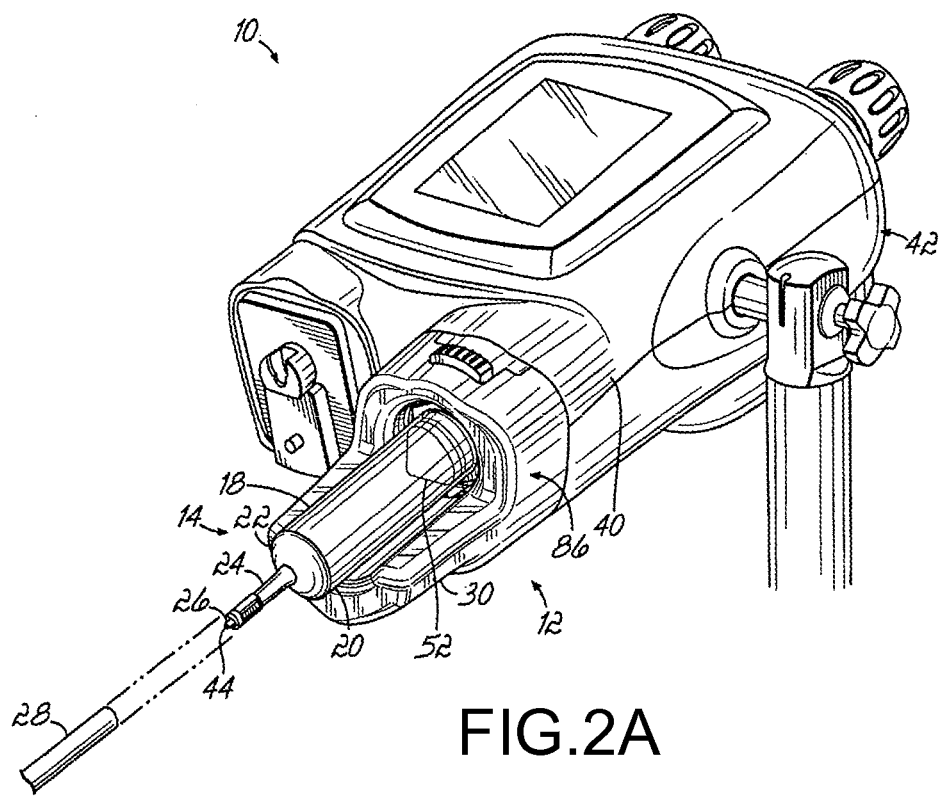
FIG. 2A is a perspective view of an injector head of an injector, having a syringe attached to a forward area thereof.
Figure 2B:
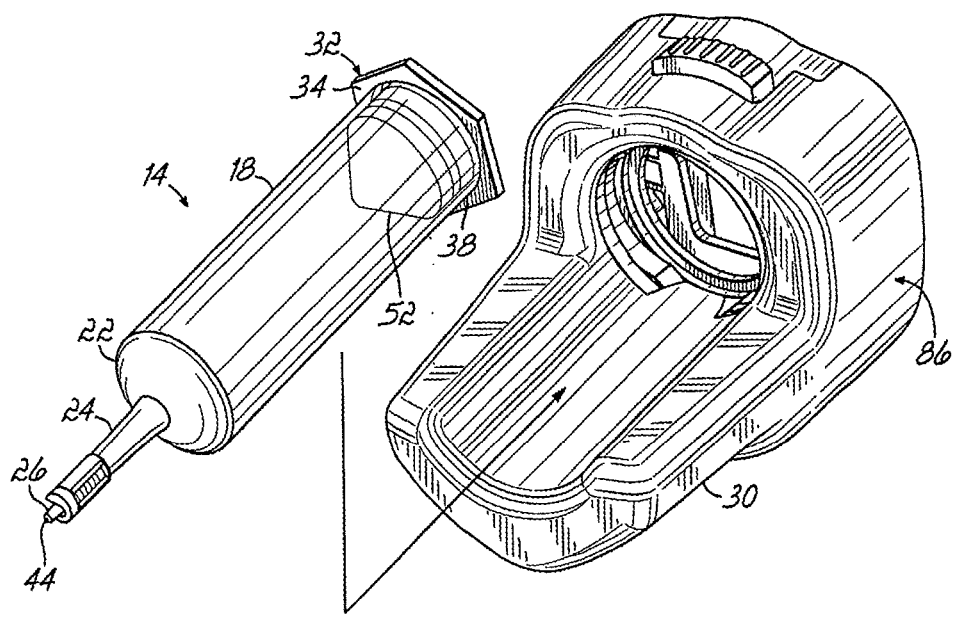
FIG. 2B is a perspective view of one exemplary embodiment of a syringe mount in an assembled condition.
Figure 2C:
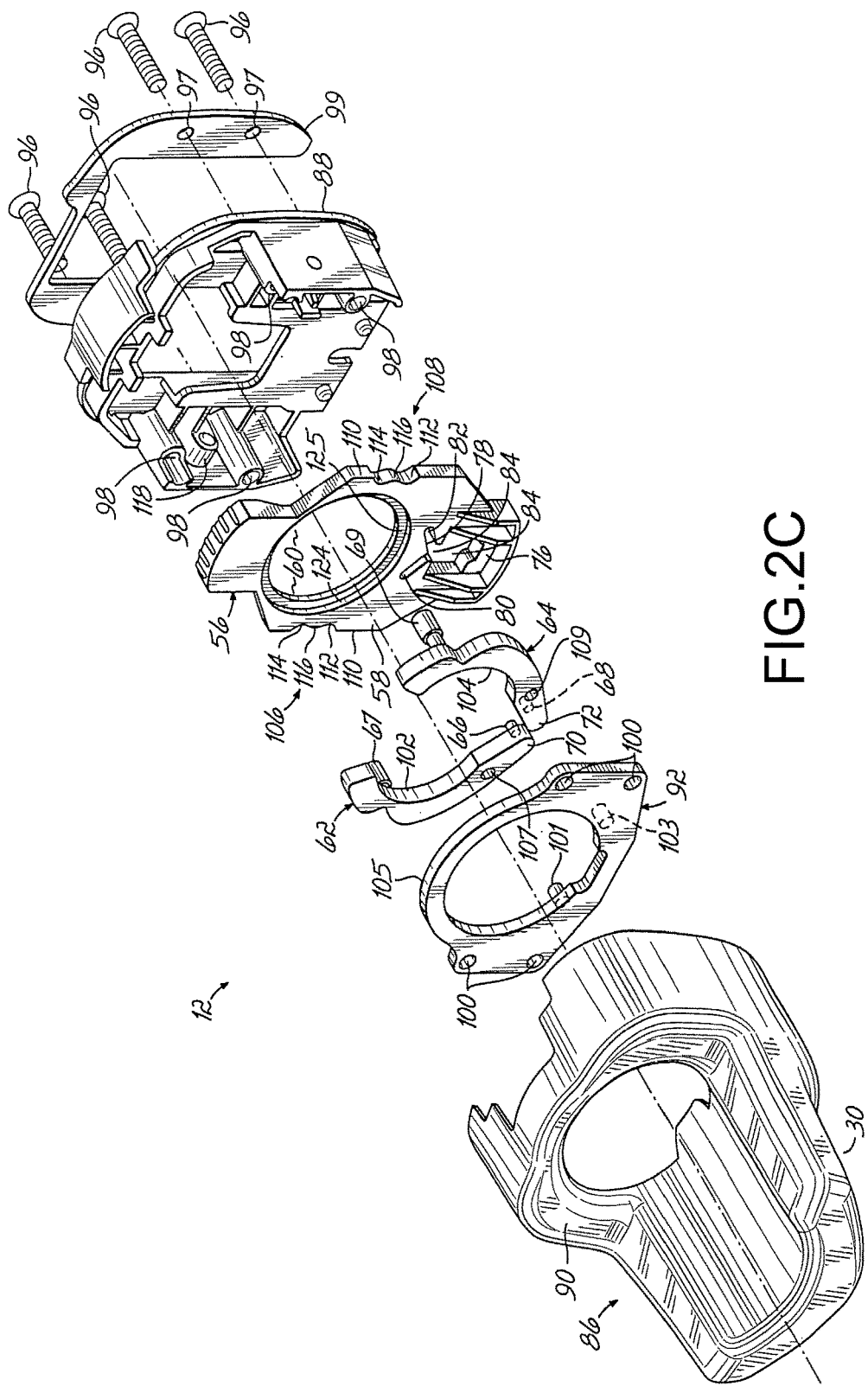
FIG. 2C is an exploded view of the syringe mount of FIG. 2B.
Figure 3B:
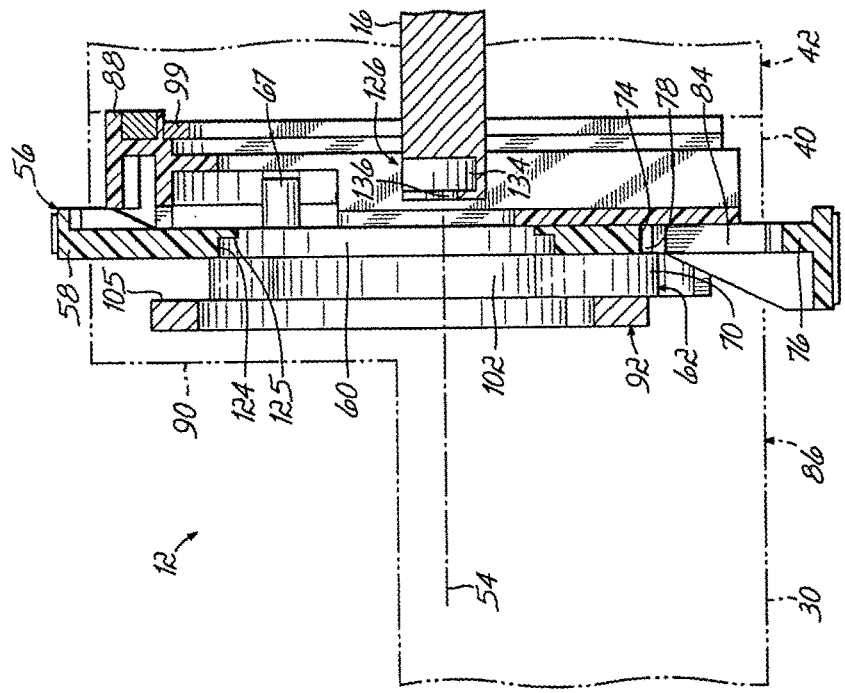
FIG. 3B is a cross-sectional view, taken along line 3B-3B of FIG. 3A.
Figure 3A:
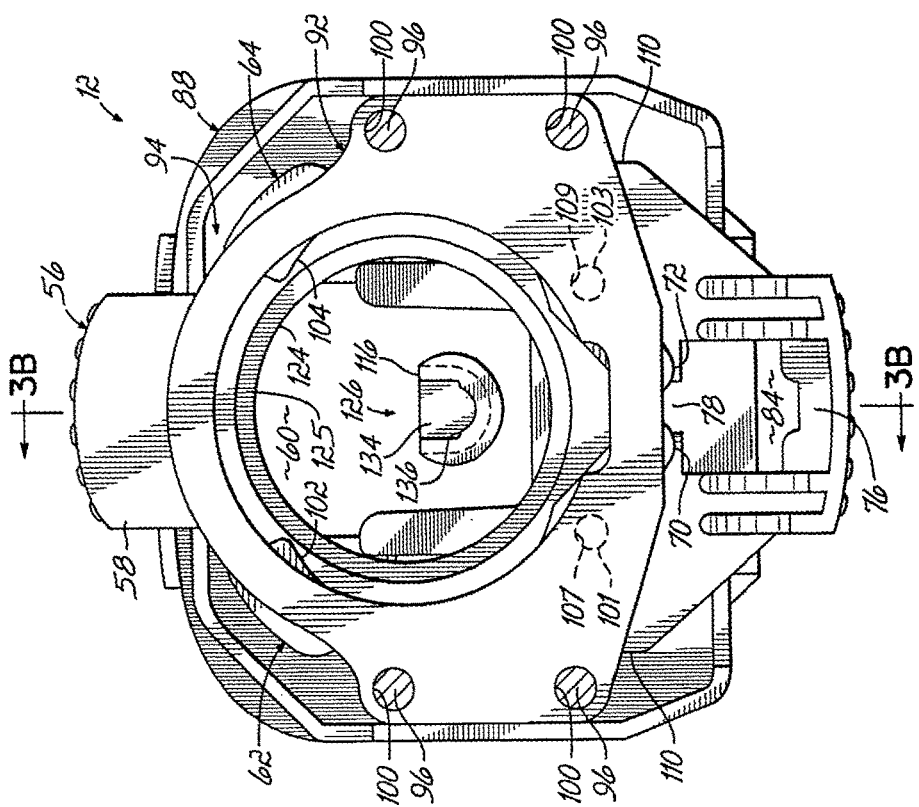
FIG. 3A is a cutaway view of the syringe mount of FIGS. 2B and 2C, particularly showing an actuator of the syringe mount.

Referring now to FIG. 2A, an injector 10 includes a syringe mount 12 to facilitate attachment of a syringe 14 to the injector 10 in alignment with a drive ram 16, in order to provide an injection assembly. The syringe 14 for use with the injector 10 generally includes a body 18 (which may be in the form of an exterior cylindrical barrel), which at its forward end 20, is integral with a conical front wall 22. A neck 24, terminating in a discharge tip 26, generally extends forwardly from and may be integral with the conical front wall 22. The body 18 of the syringe 14 may interface with an interior wall of a pressure jacket (not shown) or a cradle 30 when such a pressure jacket or cradle 30 is present on the injector 10. The syringe 14, as used in conjunction with the injector 10, includes a syringe mating section 32, which may be in the form of a radially outwardly extending flange 34. This flange 34 is positioned in a plane substantially perpendicular to a longitudinal axis 36 of the syringe 14 and may generally be integral with the rearward end 38 of the body 18 of the syringe 14. When the syringe 14 is associated with the injector 10, the flange 34 is positioned into and/or in contact with the syringe mount 12 located on the forward end 40 of a housing 42 of the injector 10. The syringe mating section 32 and syringe mount 12 may be utilized to facilitate operative connection of the syringe 14 to the injector 10, as will be described in greater detail below.

Figure 5B:
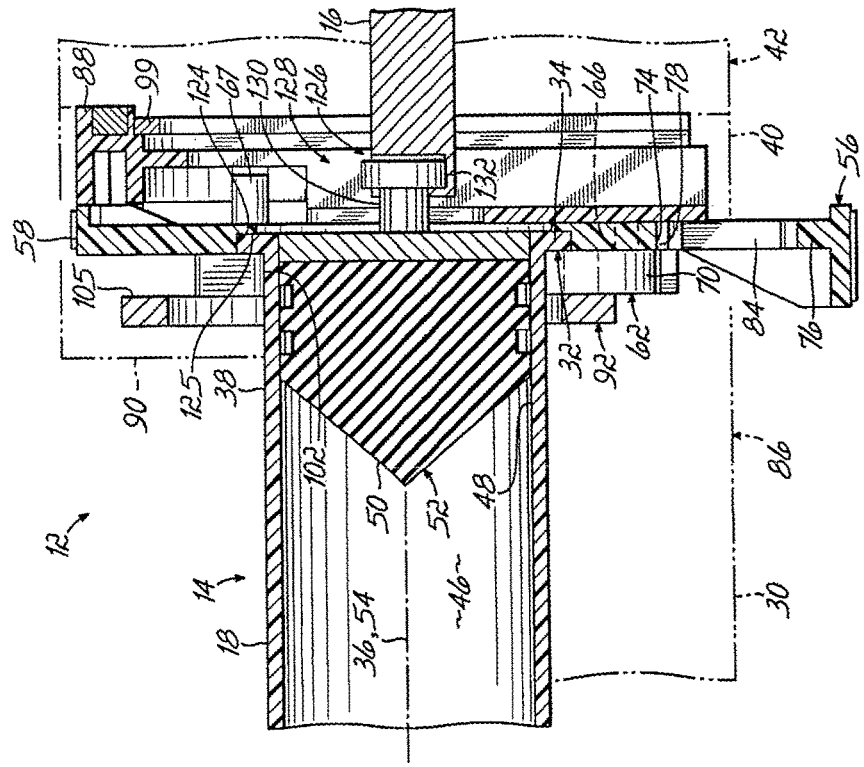
FIG. 5B is a cross-sectional view, taken along line 5B-5B of FIG. 5A, and shows the coupling mechanism on the backside of the syringe plunger engaged with the plunger coupling element of the drive ram.
Figure 5A:
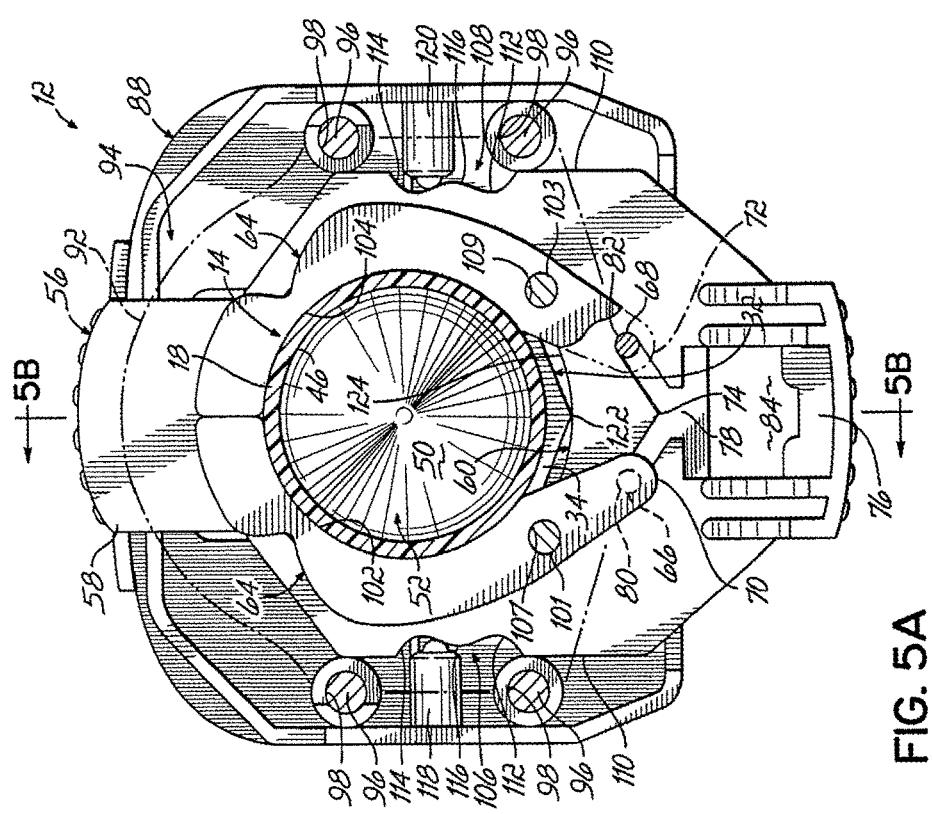
FIG. 5A is a cutaway view of the syringe mount of FIGS. 2B and 2C, particularly showing the first and second movable members in a closed position and engaging a syringe.

Referring now to FIGS. 2A, 4B, and 5B, the discharge tip 26 of the syringe 14 has an orifice 44 defined in its remote end, which may communicate with an internal syringe cavity 46 defined within the neck 24, the conical front wall 22, and the body 18 of the syringe 14. A rearward end 48 of the cavity 46 may be defined by a generally forward facing surface 50 of a syringe plunger 52. In the illustrated embodiment, this forward facing surface 50 is substantially conical. The surface 50 may be of a slope that conforms to the slope of the interior of the conical front wall 22. The syringe plunger 52 may be snugly slidable within the body 18 of the syringe 14 such that the cavity 46 is of variable volume. Tubing 28 may be operatively connected to the discharge tip 26 (e.g., using an appropriate luer fitting) such that fluid can be expressed from the syringe 14 through the tubing 28.

When the syringe 14 is attached to the injector 10, the syringe plunger 52 is preferably located proximal to and in substantial alignment with the drive ram 16 of the injector 10. The drive ram 16 is driven by a motor (not shown) to move in a forward or rearward motion along its longitudinal axis 54 to deploy the drive ram 16, and thus to responsively deploy the syringe plunger 52 in a forward or rearward motion along the longitudinal axis 36 of the syringe 14, to inject fluid into a patient or to fill the syringe 14 with fluid, respectively. For example, one may load a prefilled syringe into the injector 10 and, by deploying the plunger 52 in a forward direction, may thereby expel fluid from the syringe 14. In so doing, the fluid may be injected into the patient. Alternatively, an empty syringe may be loaded into the injector 10 while the syringe plunger 52 may be located at or near its forward-most position. Thereafter, fluid (e.g., contrast media) may be loaded into the syringe 14 by operatively connecting the syringe 14 to a source of fluid and retracting the syringe plunger 52 in a rearward direction in order to draw fluid into the syringe 14. As another alternative, an empty syringe may be loaded into the injector 10 while the syringe plunger 52 may be located at or near its rearward-most position. The plunger 52 of the syringe 14 may thereafter be deployed in a forward direction to expel gas (e.g., air) from the syringe 14 (which is sometimes referred to the art as "initializing" a syringe) in preparation for a subsequent filling procedure. Subsequently, fluid (e.g., contrast media) may be loaded into the syringe 14 by operatively connecting the syringe 14 to a source of fluid and retracting the syringe plunger 52 in a rearward direction in order to draw fluid into the syringe 14.

The injector 10 may be designed to accommodate prefilled syringes or empty syringes of varying volumes. For example, the injector 10 may be adapted to receive 125 ml prefilled syringes (e.g., Ultraject® syringe commercially available from Mallinckrodt Inc. of St. Louis, Mo.). Such syringes may be used for injecting contrast media into a patient. These 125 ml syringes may be prefilled with any of a range of appropriate amounts of fluid, such as 50 ml, 75 ml, 100 ml, 125 ml, or other amount. Additionally, the injector 10 may accommodate an empty syringe of any of a variety of sizes (e.g., 50 ml, 75 ml, 100 ml, 125 ml, 130 ml, 150 ml, 200 ml, etc.).

Referring now to FIGS. 2A-5B, one embodiment of a syringe mount 12 is shown. The syringe mount 12 is a structure that allows the syringe 14 to be installed on the injector 10 (e.g., via a detachable connection where the syringe 14 may be attached to and removed from the injector 10 without damaging either the syringe 14 or the injector 10). Generally, the syringe mount 12 may be further characterized as at least substantially immobilizing the body or barrel 18 of the syringe 14 such that the drive ram 16 of the injector 10 can move the syringe plunger 52 within and relative to the syringe barrel 18.

The syringe mount 12 includes a movable actuator 56 including a wall member 58 defining an orifice 60, and at least a first movable member 62 operatively coupled to the actuator 56 and responsively movable therewith. More specifically, the syringe mount 12 of the illustrated embodiment includes first and second movable members 62, 64 that are operatively coupled to the wall member 58 of the actuator 56. The first and second movable members 62, 64 include first and second pins 66, 68 operatively connected thereto. The first pin 66 is operatively coupled near a first end 70 of the first movable member 62, and the second pin 68 is operatively coupled near a first end 72 of the second movable member 64. The first and second pins 66, 68 are received in at least one slot ID 74 defined in the wall member 58 of the actuator 56, to couple the first and second movable members 62, 64 thereto. The actuator 56 is disposed proximally of the first and second movable members 62, 64. Further, the first and second members 62, 64 may include first and second rods 67, 69 projecting rearwardly therefrom. These first and second rods 67, 69 may confront and move along the outer contour of the wall member 58 of the actuator 56, as the first and second movable members 62, 64 move between open and closed positions.

The slot 74 is defined by the wall member 58 of the actuator 56 at a base portion 76 thereof. The first and second pins 66, 68 are movable (e.g., slidable and optionally rotatable) within the slot 74. Each of the first and second pins 66, 68 can move from a position proximal to the center 78 of the slot 74, to positions near first and second terminal ends 80, 82 of the slot 74. The first and second pins 66, 68 do not both move on one side of the slot 74. Rather, the first pin 66 is adapted to move within one portion of the slot 74, and the second pin 68 is adapted to move within another portion of the slot 74. In particular, in the illustrated embodiment, a base portion 76 of the wall member 58 includes an opening 84 having a top portion thereof in a shape at least generally similar to a "V." The first and second pins 66, 68 are disposed in the "V" portion of this opening 84. When the first and second pins 66, 68 are positioned near the intersection of the two legs of the "V," the first and second movable members 62, 64 are in an open position (see FIG. 4A). When the first and second pins 66, 68 are positioned near the first and second terminal ends 80, 82 of the "V," the first and second movable members 62, 64 are in a closed position (see FIG. 5A). While the slot 74 of the illustrated embodiment is shown and described here as generally having a "V" shape, it will be recognized by those skilled in the art that such a "V" shape is not necessary, and any other shape can be used that allows the first and second movable members 62, 64 to move sufficiently within a slot to operatively connect a syringe to an injector 10. For example, the slot 74 may have a "U" or "C" shape. Those skilled in the art will recognize that more than one slot may be used. For example, two slots forming a "V" shape proximal to the base 76 of the wall member 58 can receive the first and second pins 66, 68 near the point of the "V." Those skilled in the art will recognize that the slots do not necessarily have to be in the shape of a "V."

As can be seen from FIGS. 2A-5B, the actuator 56 and the first and second movable members 62, 64 of the syringe mount 12 are held within a face plate 86 of the housing 42 of the injector 10 (additional views of the face plate may be seen in FIGS. 6-12). Referring particularly to FIG. 2C, the face plate 86 includes a proximal wall portion 88, a distal wall portion 90, a cradle 30 extending distally from the distal wall portion 90, and a coupling plate 92. The first and second movable members 62, 64 are located between the coupling plate 92 and the wall member 58 of the actuator 56, and all three components are then contained within an interior cavity 94 of the face plate 86, formed between the proximal wall portion 88 and distal wall portion 90. The actuator 56 and the first and second movable members 62, 64 are movable within the interior cavity 94. The coupling plate is preferably substantially immobile relative to the proximal and distal wall portions of the face plate 86, as it is preferably fixed to at least one of the proximal and distal wall portions 88, 90. In the illustrated embodiment, this fixing occurs through the use of screws 96, which extend through orifices 97 in a rear plate 99, orifices 98 in the proximal wall portion 88, orifices 100 in the coupling plate 92, and are received in orifices (not shown) in the distal wall portion 90.

The coupling plate 92 includes first and second pivoting shafts 101, 103 projecting from a proximal surface 105 thereof. These first and second pivoting shafts 101, 103 are received in first and second shaft openings 107, 109 defined in the first and second movable members 62, 64, respectively. As such, the first and second movable members 62, 64 are able to exhibit a pivoting motion about the corresponding first and second pivot shafts 101, 103. Stated another way, the first and second movable members 62, 64 are coupled with corresponding the first and second pivoting shafts 101, 103 in a manner such that the movable members 62, 64 can pivot thereabout. The first and second pivoting shafts 101, 103 thus may be said to provide pivot points for the first and second movable members 62, 64.

To initiate loading of the syringe 14 into the syringe mount 12, the flange 34 at the rearward end 38 of the syringe 14 may be passed through an aperture in each of the distal wall portion 90 of the syringe mount 12 and the coupling plate 92 and may be received into the orifice 60 defined in the actuator 56. While the rearward end 38 of the syringe 14 is located in the orifice 60, the syringe 14 may be moved in a first direction substantially perpendicular to the longitudinal axis 54 of the drive ram 16 of the injector 10. Herein, this direction will be referred to as a "downward" direction (as the motion is down relative to the injector 10). However, it will be recognized by those skilled in the art that the motion does not have to be "downward," but that the components of the syringe mount 12 can be configured such that motion in other directions can effect appropriate engagement of the syringe 14 (including, but not limited to, "upward" movement, "side-to-side" movement, or any other appropriate, substantially perpendicular movement such that the longitudinal axis 36 of the syringe 14 is moved into a substantially coaxial relationship with the longitudinal axis 54 of the drive ram 16). This downward motion, in turn, responsively moves the actuator 56 in the downward direction. The motion of the actuator 56 in the downward direction causes each of the first and second pins 66, 68 to move to the corresponding first and second ends 80, 82 of the slot 74 defined in the base portion 76 of the wall member 58. This movement of the pins 66, 68 occurs because the first and second movable members 62, 64 cannot move in the downward direction due to the first and second pivoting shafts 101, 103 of the fixed coupling plate 92 being located within the first and second shaft openings 107, 109 of the first and second movable members 62, 64. Thus, as the actuator 56 moves in the downward direction, the first and second pins 66, 68 move within the slot 74 to the first and second terminal ends 80, 82 thereof. Because the first and second movable members 62, 64 cannot move downwardly, they instead pivot about the pivot points provided by the first and second pivoting shafts 101, 103. In other words, the first and second movable members 62, 64 rotate about the corresponding first and second pivoting shafts 101, 103 at the respective first and second shaft openings 107, 109. As such, the first and second movable members 62, 64 pivot to engage (e.g., substantially, circumferentially envelop) the rearward end 38 of the syringe 14 (see FIG. 5A). Since the flange 34 of the syringe 14 is located within the actuator 56 during this pivoting movement of the movable members 62, 64, the first and second movable members 62, 64 engage the body 18 of the syringe 14 (rather than the flange 34). In embodiments where the movable members 62, 64 are designed such that this engagement with the body 18 of the syringe 14 may be characterized as a substantial enveloping of the body 18, it may be said that this type of engagement allows for greater coverage of the syringe 14 than found in prior syringe mounts, and thus, potentially allows the syringe 14 to withstand greater injection pressures.

In the illustrated embodiment, the first and second movable members 62, 64 are opposite one another and are positioned about the longitudinal axis 54 of the drive ram 16. The first and second movable members 62, 64 each have an arcuate face 102, 104. These arcuate faces 102, 104 are shown as being diametrically opposite one another and located exterior to the body 18 of the syringe 14. When the syringe 14 is properly engaged with the syringe mount 12 of the injector 10, the first and second movable members 62, 64 of the syringe mount 12 are in contact with the side surface of the exterior body 18 of the syringe 14 to hold the syringe 14 in place and in alignment with the drive ram 16 of the injector 10.

In some embodiments, the arcuate faces 102, 104 of the movable members 62, 64 may bear one or more types of engagement enhancing features (e.g., grooves, bumps, indentations, ridges, teeth, combinations thereof, and the like) to improve the ability of the movable members 62, 64 to grip and/or hold the syringe 14. In some embodiments, a grip enhancing coating (e.g., Santoprene® elastomer) may be applied to the arcuate faces 102, 104 of the movable members 62, 64 to facilitate gripping/holding of the syringe 14.

The pivotal movement of the first and second movable members 62, 64 alters the distance between the arcuate faces 102, 104 as they pivot toward and away from one another. In the illustrated embodiment, the first and second movable members 62, 64 are each movable. In some embodiments, it is possible to use a single movable member disposed in spaced relation to an immobile member (e.g., arcuate stop or abutment) toward which the single movable member may be moved.

In some embodiments, first and second movable members 62, 64 are not necessary for appropriate syringe engaging function. In such embodiments, a single gripping member may be used to engage the syringe 14, thereby operatively connecting the syringe 14 to the injector 10. In such embodiments, the single movable member should cover enough of the circumference of the syringe 14, when in contact with the body 18, to hold the syringe 14 against the injector 10. In such embodiments, each arm extending from a center point of the movable member may have a degree of elasticity such that the arms may splay outwardly and inwardly to allow for insertion and/or removal of the syringe 14.

The wall member 58 of the actuator 56 is shown as having a peripheral side surface 110 that includes a first undulating contour 106 and a second undulating contour 108. As shown, the second undulating contour 108 is positioned substantially opposite the first undulating contour 106. Each of these first and second undulating contours 106, 108 includes a first valley 112, a second valley 114, and a ridge 116 disposed therebetween. When positioned within the syringe mount 12 of the injector 10, these first and second undulating contours 106, 108 are confronted by first and second projections 118, 120 (see FIGS. 2C and 5A), which are adapted to ride along the surface of the first and second undulating contours 106, 108 as the actuator 56 is moved between the first and second positions. In the illustrated embodiment, the first and second projections 118, 120 are coupled to the proximal wall portion 88 of the face plate 86, and are spring-biased in a direction toward each of the first and second undulating contours 106, 108. The interaction of the first and second detents 118, 120 and first and second undulating contours 106, 108 assist in maintaining the actuator 56 in either the first or second position until a user desires to move the actuator 56 to either load or unload the syringe 14. In some embodiments, the first and second pins 66, 68 may include bias springs associated with each of the first and second movable members 62, 64. In such embodiments, one end of each of the bias springs may be in contact with its respectively associated movable member, and the opposite end of each bias spring may seat or bear against portions of the housing 42 (or face plate 86) of the injector 10. In some embodiments, at least a portion of these bias springs may be disposed about the pins 66, 68, which form the pivot axes of the first and second movable members 62, 64.

To load a syringe 14 into the injector 10, the syringe 14 is positioned relative to the wall member 58 of the actuator 56 such that the flange 34 at the rearward end 38 of the syringe 14 is received within the orifice 60 of the wall member 58 such that at least one contact point 122 on the periphery of the flange 34 contacts or can be brought into contact with a peripheral surface 124 defining the orifice 60. More specifically, the flange 34, in certain embodiments, may be received by a recess 125 in the actuator 56. The actuator 56 is shown in FIG. 4A as being in the first position, such that the first and second movable members 62, 64 are in the open position. In this first position, the first and second projections 118, 120 are in contact with the first valleys 112 of the corresponding first and second undulating contours 106, 108. The force of the spring bias of the first and second projections 118, 120 at least assists in preventing the wall member 58 of the actuator 56 from moving unassisted to the second position. The drive ram 16 of the injector 10 is preferably positioned such that a plunger coupling mechanism 126 is aligned with a coupling mechanism 128 extending from a rearward face of the syringe plunger 52 (see FIG. 4B).

A user then applies a force to the syringe 14 in a direction substantially perpendicular to, and towards, the longitudinal axis 54 of the drive ram 16. The flange 34 of the syringe 14, contacting the peripheral surface 124 of the wall member 58, is utilized to force the wall member 58 of the actuator 56 to responsively move in a direction substantially perpendicular to the longitudinal axis 54 of the drive ram 16. Enough force is applied to overcome the spring-bias of the first and second projections 118, 120, such that the actuator 56 moves from the first position to the second position. As this occurs, the first and second projections 118, 120 ride along the first and second undulating contours 106, 108 from the first valleys 112, along the ridges 116, and into the second valleys 114. The first and second projections 118, 120 may then be utilized to at least assist in maintaining the wall member 58 in the second position shown in FIG. 5A.

The movement of the wall member 58 from the first position to the second position cooperatively moves the slot 74 of the wall member 58 in a direction substantially perpendicular to the longitudinal axis 54 of the drive ram. And thus, the slot 74 moves relative to the first and second pins 66, 68, thereby causing the first and second pins 66, 68 to move relative to and within the slot 74. More specifically, in the illustrated embodiment, the first and second pins 66, 68 move within the V-shaped slot from a position proximal to the point of the "V," to positions proximal to the terminal ends of each leg of the "V" (from the position shown in FIG. 4A, to the position shown in FIG. 5A). This movement causes a responsive pivotal movement of the first and second movable members 62, 64 from the open position to the closed position such that the rearward end 38 of the syringe 14 is engaged by the first and second movable members 62, 64. In particular, as the actuator 56 moves in the downward direction, the first and second pins 66, 68 move within the slot 74 to the first and second terminal ends 80, 82 thereof. Because the first and second movable members 62, 64 cannot move downwardly, they instead pivot about the pivot points provided by the first and second pivoting shafts 101, 103. In other words, the first and second movable members 62, 64 rotate about the first and second pivoting shafts 101, 103 at the first and second shaft openings 107, 109, respectively.

As the wall member 58 is moved from the first position to the second position, and the syringe 14 moves with the wall member 58 from a position not engaged by the movable members 62, 64 to a position engaged by the movable members 62, 64, the coupling mechanism 128 at the rearward end 38 of the syringe plunger 52 moves from a position not engaged with the plunger coupling mechanism 126 of the drive ram 16 to a position engaged with the plunger coupling mechanism 126 of the drive ram 16. In the illustrated embodiment (see FIGS. 4B and 5B), when the flange 34 of the syringe 14 is aligned with the orifice 60 defined by the wall member 58, the syringe plunger 52 within the syringe 14 is preferably positioned such that the coupling mechanism 128 on the rearward face of the syringe plunger 52 is aligned with the plunger coupling mechanism 126 of the drive ram 16. The coupling mechanism 128 of the illustrated syringe plunger 52 is a projection 128 extending from the rearward face of the syringe plunger 52. This projection 128 may be characterized as exhibiting a "T" shape having a stem portion 130 (parallel to the longitudinal axis 36 of the syringe 14) topped by a cap portion 132 (transverse to the longitudinal axis of the syringe 14). As the wall member 58 is moved from the first position to the second position, the cap portion 132 of the coupling mechanism 128 may be received by the plunger coupling mechanism 126, which in the illustrated embodiment, is a slot 134 formed in the forward end of the drive ram 16.

A slot 134 is defined in the forward end of the drive ram 16 in a shape to receive the coupling mechanism 128 of the syringe 14, and particularly the cap portion 132 thereof. A cross-section of the plunger coupling element 126 is shown as exhibiting a J-shape (having a slot within a hook portion of the "J" configured to receive the cap portion 132), such that when the syringe plunger 52 is engaged with the drive ram 16, the distal end 136 of the "J" shape is positioned distally of a part of the cap portion 132 of the coupling mechanism 128. Thus, when the syringe 14 is initially inserted into the actuator 56 (in the first position), the cap portion 132 of the coupling mechanism 128 is "above" the plunger coupling element 126 of the drive ram 16. However, as the actuator 56 is moved to the second position, the cap portion 132 of the coupling mechanism 128 is moved to be positioned proximally of the distal end 136 of the plunger coupling mechanism 126 of the drive ram 16. Once engaged, an injection procedure may be run, such as by translating the drive ram 16 forward along its longitudinal axis 54 to dispense a fluid, such as contrast media, from the syringe 14. While the slot 134 and extension 128 of the illustrated embodiment have shapes referred to herein as "J" and "T," respectively, it will be recognized by those of skill in the art that any shape that facilitates coupling may be used. Additionally, while the illustrated embodiment depicts first a coupling mechanism 128 and plunger coupling mechanism 126 that result in a passive coupling, those of skill in the art will recognize that coupling mechanisms and plunger coupling mechanisms that result in an active coupling (one which involves some degree of positive gripping) may be used.

As described previously, the syringe mount 12 allows for the syringe 14 to be removed from the face plate 86 and/or forward end 40 of the injector 10, when the drive ram 16 of the injector 10 is at any position. It does not require the drive ram 16 to be returned to a "home" position before detaching the syringe 14 from the injector 10. Thus, during an injection procedure, the translation of the drive ram 16 may be stopped while the drive ram 16 is in an extended position from the front face place 86 of the injector 10. A user can then grip the syringe 14 and move it in an upward direction, thereby overcoming the spring-biased force of the first and second projections 118, 120 to cause the actuator 56 to move from the second position to the first position. As this occurs, the first and second projections 118, 120 ride along the first and second undulating contours 106, 108 from the second valleys 114, over the ridges 116, and into the first valleys 112. Simultaneously, the first and second pins 66, 68 of the first and second movable members 62, 64 will move within the V-shaped slot of the wall member 58 from a position near the terminal ends 80, 82 of the arms of the V to a position near the point of the V. This causes the first and second movable members 62, 64 to pivot from the closed position to the open position by pivoting about the pivot points created by the interaction of the first and second pivoting shafts 101, 103 with the first and second shaft openings 107, 109. Due to the positioning of the flange 34 at the rearward end 38 of the syringe 14 within the orifice 60 of the actuator 56, the actuator 56 allows for enough vertical syringe movement for the T-shaped coupling mechanism on the rearward face of the syringe 14 to clear the slot on the forward end of the drive ram 16, thereby allowing removal of the syringe 14 from the injector 10.

The power injectors 210, 240, and 10 of FIGS. 1A, 18, and 2A, respectively, each may be used for any appropriate application, including without limitation for medical imaging applications where fluid is injected into a subject (e.g., a patient). Representative medical imaging applications for the power injectors 210, 240, 10 include without limitation computed tomography or CT imaging, magnetic resonance imaging or MRI, SPECT imaging, PET imaging, X-ray imaging, angiographic imaging, optical imaging, and ultrasound imaging. The power injectors 210, 240, 10 each could be used alone or in combination with one or more other components. The power injectors 210, 240, 10 each may be operatively interconnected with one or more components, for instance so that information may be conveyed between the power injector 210, 240, 10 and one or more other components (e.g., scan delay information, injection start signal, injection rate).

Any number of syringes may be utilized by each of the power injectors 210, 240, 10, including without limitation single-head configurations (for a single syringe) and dual-head configurations (for two syringes). In the case of a multiple syringe configuration, each power injector 210, 240, 10 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site) while another syringe may discharge into a different conduit (e.g., for provision to a different injection site). Each such syringe utilized by each of the power injectors 210, 240, 10 may include any appropriate fluid, for instance contrast media, a radiopharmaceutical, saline, and any combination thereof. Each such syringe utilized by each of the power injectors 210, 240, 10 may be installed in any appropriate manner (e.g., rear-loading configurations may be utilized; front-loading configurations may be utilized; side-loading configurations may be utilized).

Figure 6:
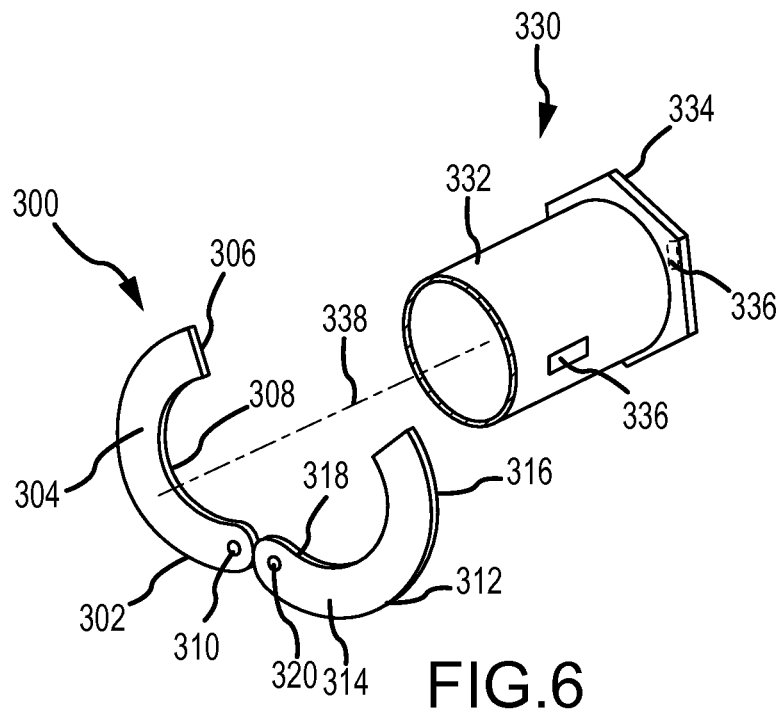
FIG. 6 is a perspective schematic of one embodiment of a power injector syringe clamp assembly that may be used by a power injector syringe mount (e.g., FIGS. 2B and 2C), along with a proximal portion of a representative power injector syringe.

FIG. 6 is a perspective view of one embodiment of a power injector syringe clamp assembly 300, which may be used by the syringe mount 12 of the power injector 10 of FIG. 2A (replacing the movable members 62, 64), as well as any other appropriate power injector. Generally, the clamp assembly 300 may be used to hold or retain a power injector syringe 330 on a powerhead of the corresponding power injector. Although the clamp assembly 300 could exert a compressive force on the power injector syringe 330, such may not be required in all instances. Instead, one or more portions of the clamp assembly 300 could be disposed in closely spaced relation to the power injector syringe 330, one or more portions of the clamp assembly 300 could simply be disposed in interfacing relation with the power injector syringe 330, or both. The clamp assembly 300 includes at least one RFID antenna for communicating with one or more RFID tags 336 on the power injector syringe 330 (e.g., to read data from one or more RFID tags 336; to write data to one or more RFID tags 336). Any appropriate number of RFID antennas may be utilized by the clamp assembly 300, with each RFID antenna being of any appropriate size, shape, configuration, and/or type (e.g., of any appropriate layout or pattern). Any appropriate way of providing power to an RFID antenna of the clamp assembly 300 may be utilized. Any appropriate way of incorporating one or more RFID antennas with the clamp assembly 300 may be utilized (e.g., separately mounting one or more RFID antennas to the clamp assembly 300; integrating one or more RFID antennas into the structure of the clamp assembly 300; and including any combination thereof).

Figure 7:
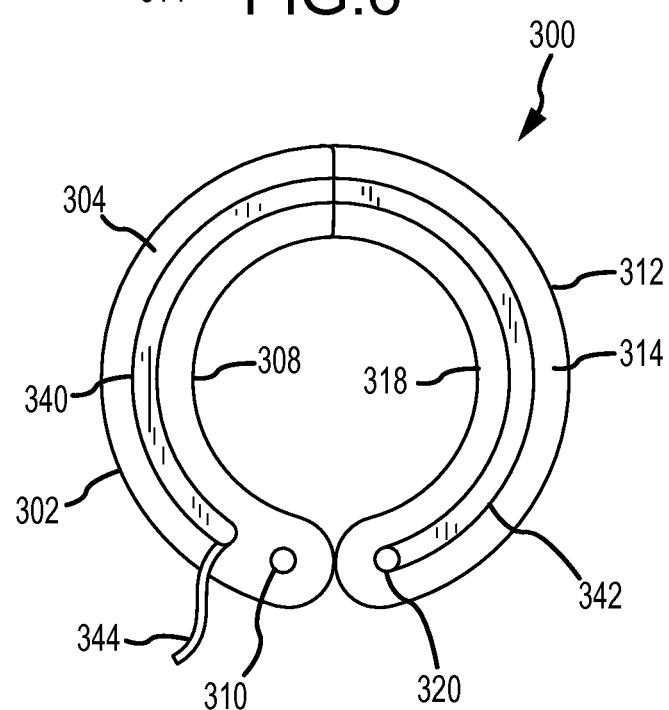
FIG. 7 is a plan view of one RFID antenna layout that may be utilized by the power injector syringe clamp assembly of FIG. 6 (end surfaces being illustrated).

Various integrations of an RFID antenna by the clamp assembly 300 will be discussed below in relation to FIGS. 7-10. Referring first to FIG. 7, there the clamp assembly 300 includes a first clamp member 302 and a second clamp member 312. The first clamp member 302 and the second clamp member 312 may be characterized as being disposed in opposing relation. In the illustrated embodiment, each clamp member 302, 312 is disposed outwardly from different portions of the syringe barrel 332 of the power injector syringe 330, but at the same location along the length dimension of the power injector syringe 330 (the length dimension coinciding with an axis 338). The first clamp member 302 includes oppositely disposed end surfaces 304, 306, along with an inner or interior surface 308. The end surface 306 would project toward or face a flange 334 of the power injector syringe 330 when positioned within the clamp assembly 300 and with the clamp assembly 300 being in a closed configuration (a representative closed configuration being shown in FIG. 7). That is, the syringe flange 334 would be disposed behind the clamp assembly 300 in the view shown in FIG. 6. The inner surface 308 would project toward or face the barrel 332 of the power injector syringe 330 when positioned within the clamp assembly 300 and with the clamp assembly 300 being in its closed configuration. A first pivot pin 310 pivotally interconnects the first clamp member 302 with the powerhead of the power injector that is incorporating the clamp assembly 300.

The second clamp member 312 includes oppositely disposed end surfaces 314, 316, along with an inner or interior surface 318. The end surface 316 would project toward or face the syringe flange 334 of the power injector syringe 330 when positioned within the clamp assembly 300 and with the clamp assembly 300 being in a closed configuration. That is, the syringe flange 334 would be disposed behind the clamp assembly 300 in the view shown in FIG. 6. The inner surface 318 would project toward or face the barrel 332 of the power injector syringe 330 when positioned within the clamp assembly 300 and with the clamp assembly 300 being in its closed configuration. A second pivot pin 320 pivotally interconnects the first clamp member 312 with the powerhead of the power injector that is incorporating the clamp assembly 300.

The flange 334 of the power injector syringe 330 may be characterized as being located at or on a proximal end of the power injector syringe 330 (e.g., an oppositely disposed distal end of the power injector syringe 330 may accommodate a fluid discharge from the power injector syringe 330; the flange 334 being located similarly to the flange 34 of the syringe 14 shown in FIG. 2A). At least one RFID tag 336 is disposed on the power injector syringe 330. Each RFID tag 336 may be of any appropriate size, shape, configuration, and/or type, may be fabricated in any appropriate manner, may be encoded with any appropriate information, and may be disposed at any appropriate location on the power injector syringe 330. Any appropriate number of RFID tags 336 may be disposed on the power injector syringe 330, and multiple RFID tags 336 may be disposed in any appropriate arrangement. One or more RFID tags 336 could be disposed on the syringe barrel 332, one or more RFID tags 336 could be disposed on the flange 334 of the power injector syringe 330, or both.

The illustrated embodiment of the clamp assembly 300 allows each of the first clamp member 302 and the second clamp member 312 to move between at least two general positions to define open and closed configurations for the clamp assembly 300. Each of the first clamp member 302 and the second clamp member 312 may be moved along any appropriate path or combination of paths to define open and closed configurations for the clamp assembly 300. Any appropriate way of actuating the clamp assembly 300 into each of its open and closed configurations may be utilized. In one embodiment, a single actuator of any appropriate size, shape, configuration, and/or type (e.g., actuator 56) simultaneously pivots the first clamp member 302 and the second clamp member 312 about their respective pivot pins 310, 320. It should be appreciated that separate actuators could be provided for each of the first clamp member 302 and the second clamp member 312. It should be appreciated that one of the first clamp member 302 and the second clamp member 312 could actually be maintained in a stationary or fixed position (at least relative to the other clamp member 302, 312), while the other is moved in any appropriate manner to provide the open and closed configurations for the clamp assembly 300 (not shown).

FIG. 7 illustrates one option for integrating at least one RFID antenna with the clamp assembly 300. A first RFID antenna section 340 is disposed on the end surface 304 of the first clamp member 302 (end surface 306 being another option—not shown), while a second RFID antenna section 342 is disposed on the end surface 314 of the second clamp member 312 (end surface 316 being another option—not shown). The first RFID antenna section 340 and the second RFID antenna section 342 each could be autonomous or independently operable (e.g., fully functional) RFID antennas. Alternatively, the first RFID antenna section 340 and the second REID antenna section 342 may collectively define a single RFID antenna (at least when the clamp assembly 300 is in the closed configuration shown in FIG. 7). Any appropriate layout may be utilized for each of the first RFID antenna section 340 and the second RFID antenna section 342.

Two options for providing power to an RFID antenna integrated with the clamp assembly 300 are illustrated by FIG. 7. Power to the REID antenna section 340 is provided by a flex connector 344 of any appropriate size, shape, configuration, and/or type. Power to the second RFID antenna section 342 is provided though the second pivot pin 320, which would therefore be formed from an electrically conductive material or combination of materials.

Another layout for an RFID antenna is illustrated in FIG. 8A. Here an REID antenna section 350 is disposed on an inner surface 308/318 of the first/second clamp member 302/312 (the surface of the clamp member 302/312 that projects toward or faces the syringe barrel 332 when the power injector syringe 330 is positioned within the clamp assembly 300). Although the first/second pivot pins 310/320 are not shown in FIG. 8A, the first/second pivot axis 311/321 is shown in FIG. 8A (the axis 311/321 about which the respective first/second clamp member 302/312 moves). The RFID antenna section 350 functions itself as an RFID antenna in the illustrated embodiment, although it could be configured to collectively define an RFID antenna with another RFID antenna section on the other clamp member 302/312 of the clamp assembly 300 (not shown).

FIG. 8B shows another possible layout for an RFID antenna on the power injector syringe clamp assembly 300 of FIG. 6. Here a first RFID antenna section 360 and a second RFID antenna section 362 are each disposed on an inner surface 308/318 of the first/second clamp member 302/312 (the surface of the clamp member 302/312 that projects toward or faces the syringe barrel 332 when the power injector syringe 330 is positioned within the clamp assembly 300). Although the first/second pivot pins 310/320 are not shown in FIG. 8B, the first/second pivot axis 311/321 is shown in FIG. 8B (the axis 311/321 about which the respective first/second clamp member 302/312 moves). The RFID antenna sections 360, 362 could each function as an RFID antenna in the illustrated embodiment. Each RFID antenna section 360, 362 could collectively define an RFID antenna with another RFID antenna section on the other clamp member 302/312 of the clamp assembly 300 (such that the clamp assembly 300 would include two, separate RFID antennas). Finally, each RFD antenna section 360, 362 could be part of a single RFID antenna for the clamp assembly 300, including where one or more RFID antenna sections are disposed on the other clamp member 302/312.

Two ways of providing electrical power to an RFID antenna on the clamp assembly 300 were discussed above in relation to FIG. 7. Additional options are presented in FIGS. 9 and 10. In FIG. 9, a pivot pin 370 is configured to provide separate electrical connections to the pair of spaced RFID antenna sections 360, 362 shown in FIG. 8B. The pivot pin 370 for the clamp member 302/312 includes a first conductive section 372 and a second conductive section 376 that are separated by an intermediate insulator section 374. A pair of movable and electrically conductive pins 378 are spaced from each other and biased into contact with the pivot pin 370 in any appropriate manner (e.g., using a spring or the like—not shown). One conductive pin 378 engages the first conductive section 372 of the pivot pin 370, while the other conductive than 378 engages the second conductive section 376 of the pivot pin 370. Each conductive pin 378 is in electrical contact with its own conductor 380, at least when the conductive pins 378 are in contact with the pivot pin 370. One conductor 380 extends to or is otherwise in electrical communication with the first RFID antenna section 360, while the other conductor 380 extends to or is otherwise in electrical communication with the second RFID section 362 (see FIG. 8B).

Figure 10:
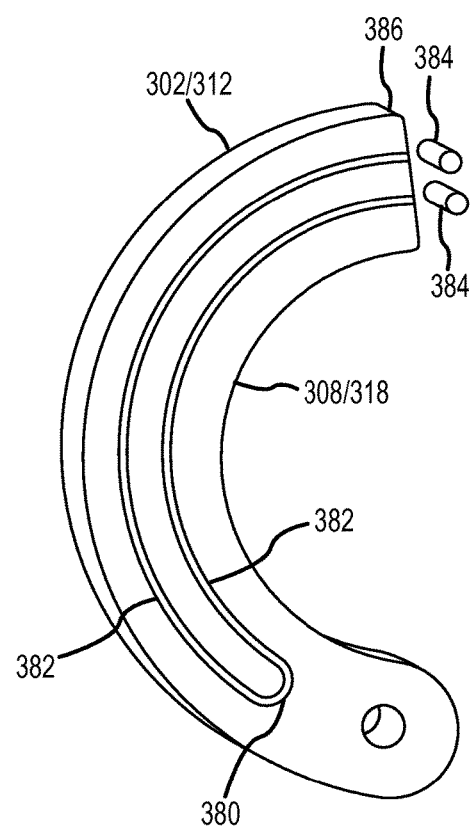
FIG. 10 is a schematic view of another RFID antenna layout that may be utilized by the power injector syringe clamp assembly of FIG. 6, along with another option for providing power to an RFID antenna.

The first/second clamp member 302/312 shown in FIG. 10 includes an RFID antenna section 380, which in turn includes a pair of legs 382 that are spaced from each other. Each leg 382 extends to an edge 386 of the clamp member 302/312, and is aligned with its own electrical contact 384 (e.g., mounted on a powerhead). When the clamp member 302/312 is moved to dispose the clamp assembly 300 into its closed configuration, each leg 382 is brought into electrical contact with its corresponding electrical contact 384. The other clamp member 302/312 could have a similar pair of electrical contacts 384, or the other clamp member 302/312 could also be brought into contact with the electrical contacts 384 shown in FIG. 10.

A power injector syringe clamp assembly of any appropriate size, shape, configuration and/or type (e.g., including any appropriate number of clamp members, including utilizing a single clamp member and where multiple clamp members are utilized and disposed in any appropriate arrangement) may include at least one RFID antenna in accordance with the foregoing. In one embodiment, one or more RFID antennas are incorporated by a power injector syringe clamp assembly in a manner such that relative positioning requirements between this clamp assembly and an installed power injector syringe are reduced. It may be desirable for each RFID tag on an installed power injector syringe to be readable by one or more RFID antennas of the power injector syringe clamp assembly, regardless of its position within the power injector syringe clamp assembly.

One or more clamp members of the power injector syringe clamp assembly may include an RFID antenna in accordance with the foregoing. A given RFID antenna may be incorporated with a single clamp member, or may be incorporated with multiple clamp members. Although each clamp member of the power injector syringe clamp assembly could include an RFID antenna, it may be such that one or more clamp members will not have any RFID antenna included therewith in the case of a multi-clamp member configuration (at least one clamp member, however, will still include at least one RFID antenna in such an instance).

The various power injector syringe clamp assemblies described herein may be utilized by any appropriate power injector and may be integrated in any appropriate manner. In one embodiment, the syringe clamp assembly is mounted on a powerhead of the power injector. In another embodiment, the syringe clamp assembly is incorporated into the structure of a faceplate that in turn may be detachably mounted (e.g., by hand or without any tools) to a powerhead of a power injector. In yet another embodiment, the syringe clamp assembly is incorporated into the structure of an adapter that in turn is mounted to a powerhead of a power injector.

Figure 11:
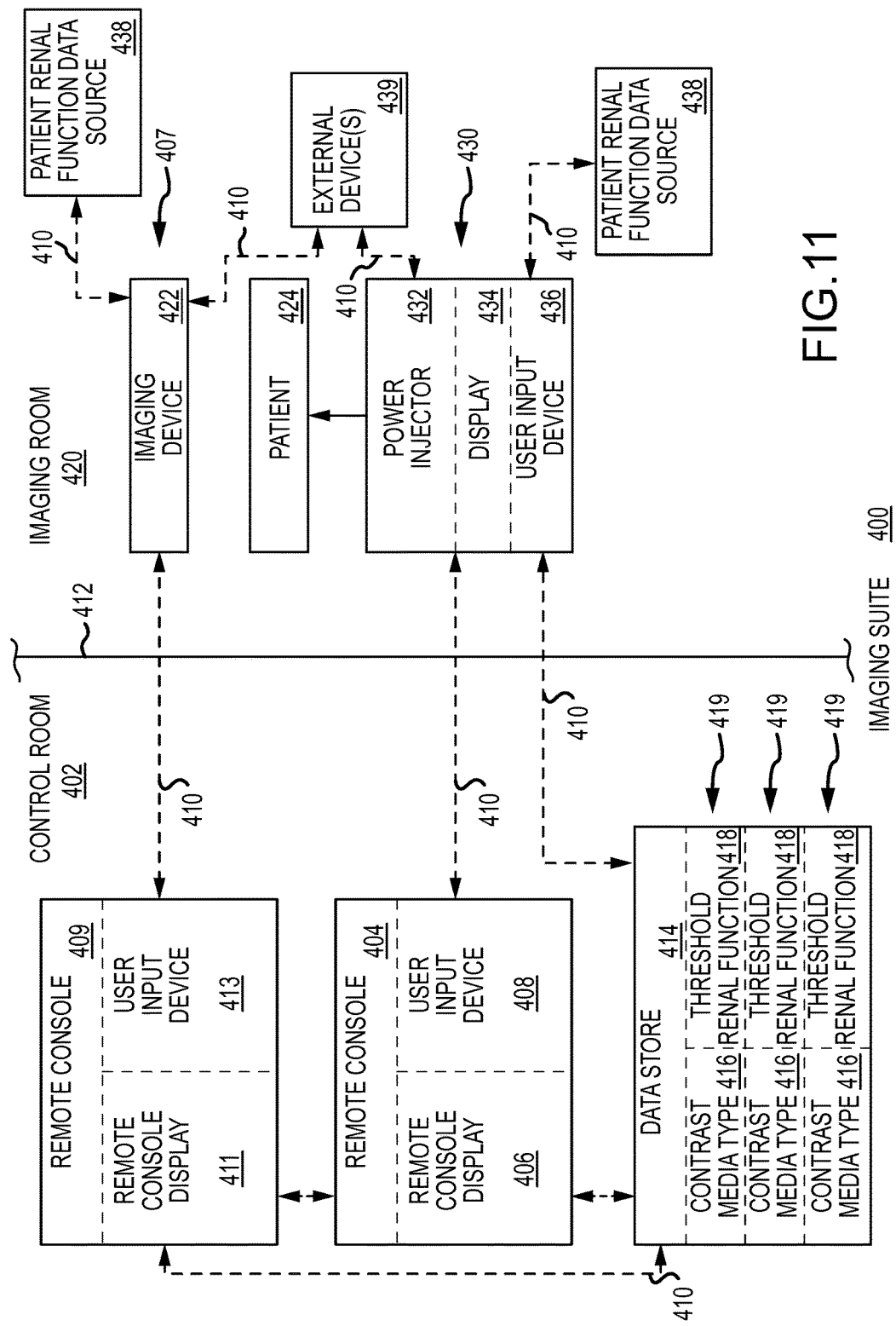
FIG. 11 is a schematic of one embodiment of an imaging suite that incorporates patient renal function assessment functionality.

FIG. 11 presents one embodiment of an imaging suite 400 that includes a contrast media injector system 430, a medical imaging system 407, a data store 414, and at least one patient renal function data source 438. One or more external devices 439 may communicate with the injector system 430 and/or the medical imaging system 407. A given device 439 may be characterized as being "external" if it is not actually part of a particular system 430 and/or 407. One or more external devices 439 could also communicate with the data store 414 and/or one or more patient renal function data sources 438. Representative external devices 439 include without limitation a hospital information system (HIS), a radiology information system (RIS), a picture archive and communication system (PACS), a patient electronic medical records (EMRs) system, or the like.

The data store 414 may be operatively connected with the contrast media injector system 430 and/or the medical imaging system 407 by a communication link 410 of any appropriate type. The data store 414 could be incorporated by the contrast media injector system 430 and/or could be incorporated by the medical imaging system 407. A patient renal function data source 438 may be operatively connected with the contrast media injector system 430 and/or the medical imaging system 407 by a communication link 410 of any appropriate type.

The medical imaging system 407 includes a remote console 409 and an imaging unit or device 422. The contrast media injector system 430 in turn includes a power injector 432 and a remote console 404. The power injector 432 may be of any appropriate configuration, for example, in the form of the power injectors 10 and 210 addressed above. The imaging device 422 may be of any appropriate size, shape, configuration, and/or type, and its image-acquisition functionality may utilize any appropriate technology or combination of technologies. In the illustrated embodiment, the imaging suite 400 includes a control room 402 and an imaging room 420 that are separated by an appropriate barrier 412. This separation may not be required in all instances. In some embodiments, this barrier may include radiation (e.g., alpha, beta and/or gamma) shielding, RF shielding, and/or any other type of material that may reduce the likelihood of undesired conditions that could hinder image acquisition.

The remote console 404 (e.g., a computer) of the contrast media injector system 430 may be located in the control room 402. Components of the remote console 404 include a remote console display 406 and at least one data or user input device 408. Each user input device 408 of the injector system 430 may be of any appropriate type, for instance, in the form of a keyboard, mouse, touch screen, joystick, trackball, or the like. The remote console 404 is operatively interconnected with the power injector 432 by a communication link 410 of any appropriate type. Generally, a user may program injection parameters for the power injector 432 (e.g., define an injection protocol, for instance one or more phases and where each phase includes injection parameters such as a volume of contrast media to be injected and an injection flow rate, along with possibly one or more injection delays (e.g., a hold or a pause)) through the user input device 408 of the remote console 404. Any appropriate data may be entered through the user input device 408.

Similarly, the remote console 409 (e.g., a computer) of the medical imaging system 407 may be located in the control room 402. Components of the remote console 409 may include a remote console display 411 and at least one data or user input device 413. Each user input device 413 of the medical imaging system 407 may be of any appropriate type, for instance, in the form of a keyboard, mouse, touch screen, joystick, trackball, or the like. The remote console 409 of the imaging system 407 is operatively interconnected with the imaging device 422 by a communication link 410 of any appropriate type. Generally, a user may program imaging parameters for the imaging device 422 and/or control (e.g., initiate and/or terminate) imaging procedures by way of the user input device 413 of the remote console 409. Any appropriate data may be entered through the user input device 413.

The medical imaging system 407 (e.g., the remote console 409 thereof) may be operatively connected with the contrast media injector system 430 (e.g., the remote console 404 thereof). In the case where the imaging system 407 is indeed operatively connected with the injector system 430, some embodiments allow for a user to program injection parameters and/or control (e.g., initiate and/or terminate) injection procedures for the power injector 432 through the user input device 413 of the imaging system's remote console 409 in addition to the performing the programming and/or control functionalities herein-described with regard to the imaging device 422. In some embodiments of the imaging suite 400, the injector system 430 and the medical imaging system 407 may only include a single, shared remote console (not shown) from which a user may perform any of the herein-described program and/or control operations for both the imaging device 422 and the power injector 432.

The power injector 432 is operatively connected with the remote console 404, may be operatively connected with one or both of the data store 414 and the imaging device 422, and is fluidly connectable with a patient 424 (e.g., such that the power injector 432 may inject contrast media into the patient 424). The power injector 432 may include a display 434 and at least one data or user input device 436 of any appropriate type (e.g., a keyboard, mouse, touch screen, joystick, trackball, or the like). Any appropriate data may be entered through the user input device 436.

The data store 414 may be of any appropriate configuration and may be incorporated by an appropriate computer-readable storage medium. The data store 414 could be a stand-alone component, may be incorporated by the contrast media injector system 430 in any appropriate manner (e.g., as part of the remote console 404, as part of the power injector 432, by a stand-alone storage device, or any combination thereof), and/or may be incorporated by the medical imaging system 407 in any appropriate manner (e.g., as part of the remote console 411, by a stand-alone storage device, or any combination thereof).

The data store 414 includes a plurality of contrast media types 416 and a corresponding threshold renal function 418 for each contrast media type 416. Herein, a "contrast media type" may be defined at least in part by the concentration of one or more constituents (e.g., active ingredients) of the contrast media. As another example, a "contrast media type" may be defined at least in part by the total amount of a particular constituent (e.g., active ingredient) found within the total volume of contrast media in the syringe or found within a predefined reference volume of contrast media in the syringe (e.g., "x" mg of iodine per 1 ml of contrast media). Yet another example of a "contrast media type" may refer to the commercial names/identities for contrast media, each of which corresponds with desired data (e.g., threshold (e.g., minimum acceptable) renal function for a proposed receipt thereof, which may or may not be associated with certain concentration and/or volume restrictions/guidelines for approved dosing).

The threshold renal function 418 may be of any appropriate type so long as it is indicative of patient renal function (e.g., GFR, serum creatinine measurement). For instance, the threshold renal function 418 may be in terms of a threshold GFR or an acceptable range of GFR. As another example, the threshold renal function 418 may be in terms of a threshold serum creatinine level or an acceptable range of serum creatinine. The threshold renal function 418 may be expressed in any appropriate manner (e.g., in the form of a baseline number, such that a patient renal function must be at least as great as the baseline number or, in another embodiment, no greater than the baseline number; in the form of a range, such that patient renal function data must be within this range). The threshold renal function 418 may be characterized as a minimum patient renal function required/suggested for safe administration of the corresponding contrast media to the patient 424, may be characterized as a range of acceptable patient renal functions required/suggested for safe administration of the corresponding contrast media to the patient 424, or both.

With regard to the data store 414: 1) any way of identifying the contrast media type 416 may be utilized; 2) any way of expressing or characterizing a threshold renal function 418 may be utilized (e.g., a baseline number; a range); and 3) any way of associating a given contrast media type 416 with a threshold renal function 418 may be utilized. Although each contrast media type 416 could have a different threshold renal function 418, two or more of the contrast media types 416 could have the same threshold renal function 418.

A given contrast media type 416 and its corresponding threshold renal function 418 may be characterized as defining a record 419 within the data store 414 (e.g., a lookup table configuration). Although only three records 419 are illustrated for the data store 414 in FIG. 11, any appropriate number of records 419 may be contained within the data store 414. Moreover, data may be stored in any appropriate manner within the data store 414 (e.g., in the form of a relational database, wherein a given threshold renal function 419 may be stored in relation to multiple contrast media types 416). Further, this data store 414 may be located in any appropriate location throughout a healthcare facility including, but not limited to: 1) within the injector system 430; 2) within the imaging system 407; 3) within a stand-alone information storage system; 4) within a hospital information system (HIS); within a radiology information system (RIS); or 5) within a picture archive and communication system (PACS).

The patient renal function data source 438 may be characterized as being part of, operatively connected with or connectable to, and/or communicable with the contrast media injector system 430 and/or the medical imaging system 407. Each of the contrast media injector system 430 and the medical imaging system 407 could have a dedicated patient renal function data source 438, or the contrast media injector system 430 and the medical imaging system 407 could communicate with the same patient renal function data source 438. It may also be that only one of the contrast media injector system 430 and the medical imaging system 407 communicates with a patient renal function data source.

The patient renal function data source 438 may include data of any appropriate type on the renal function of a patient that is to be imaged using the contrast media injector system 430 and the imaging system 407. Patient renal function data within a given patient renal function data source 438 may be of any appropriate type so long as the data is indicative of patient renal function (e.g., GFR, serum creatinine measurement). For instance, patient renal function data may be expressed in terms of a GFR measurement. As another example, patient renal function data may be expressed in terms of a serum creatinine measurement.

The patient renal function data source 438 may be in the form of user input provided to the contrast media injector system 430 through the user input device 436 for the power injector 432, through the user input device 408 for the remote console 404, through a data or user input device for the imaging system 407, or otherwise. The patient renal function data source 438 could also be in the form of a hospital information system (HIS), a radiology information system (RIS), a picture archive and communication system (PACS), a renal function testing module (e.g., a representative device of this type being described in U.S. Patent Application Publication No. 2006/0074294 to Williams et al., published Apr. 6, 2006), or the like. A given patient renal function data source 438 may include any one or more of the foregoing. Patient renal function data from any of these "external" components may communicate with the contrast media injector system 430 and/or the imaging system 407 in any appropriate manner to make patient renal function information available to the contrast media injector system 430 and/or the imaging system 407 (e.g., the patient renal function data source 438 need not be input to the contrast media injector system 430 through the user input device 436 of the power injector 432).

Figure 12:
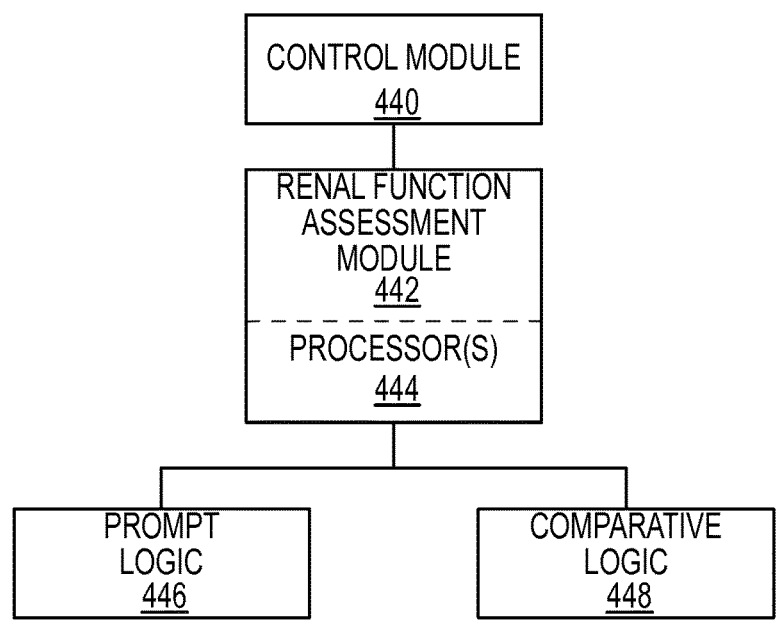
FIG. 12 is a schematic of one embodiment of a control module that incorporates renal function assessment functionality and that may be used by one or more components of the imaging suite of FIG. 11.

One embodiment of a control module is illustrated in FIG. 12, may be utilized by the injector system 430 and/or the imaging system 407, and is identified by reference numeral 440. The control module 440 may be utilized in relation to the power injector 432 and/or the imaging device 422 shown in FIG. 11. All or any portion of the control module 440 may be incorporated by the remote console 404 of the contrast media injector system 430, by the power injector 432, by the remote console 409 of the imaging system 407, by the imaging device 422, or by any combination thereof. Generally, the control module 440 includes a renal function assessment module 442. This renal function assessment module 442 may include one or more processors 444. The processor(s) 444 of the renal function assessment module 442 may be programmed or otherwise configured in accordance with at least one of prompt logic 446 and comparative logic 448 (e.g., programmed to execute the protocols 450 and 480 that are addressed below). Generally, the prompt logic 446 may be used by the contrast media injector system 430 and/or the imaging system 407 to issue (e.g., visually display) a prompt for a user to manually input renal function information for the patient 424 to the contrast media injector system 430 and/or imaging system 407, and the comparative logic 448 may be used by the contrast media injector system 430 and/or imaging system 407 to assess the renal function of the patient 424 to determine whether or not an injection for this patient 424 should proceed (e.g., whether the power injector 432 should allow itself to be operated so as to provide a contrast media discharge). In the case where the imaging system 407 is operatively connected with the injector system 430, or where the imaging system 407 and the injector system 430 share a common remote console, the prompt logic 446 may be used by the injector system 430 and/or the imaging system 407 to issue (e.g., visually display) a prompt for a user to manually input renal function information for the patient 424 to the injector system 430 and/or the imaging system 407, and the comparative logic 448 may be used by the injector system 430 and/or imaging system 407 to assess the renal function of the patient 424 to determine whether or not an injection should proceed in relation to this patient 424.

Figure 13:
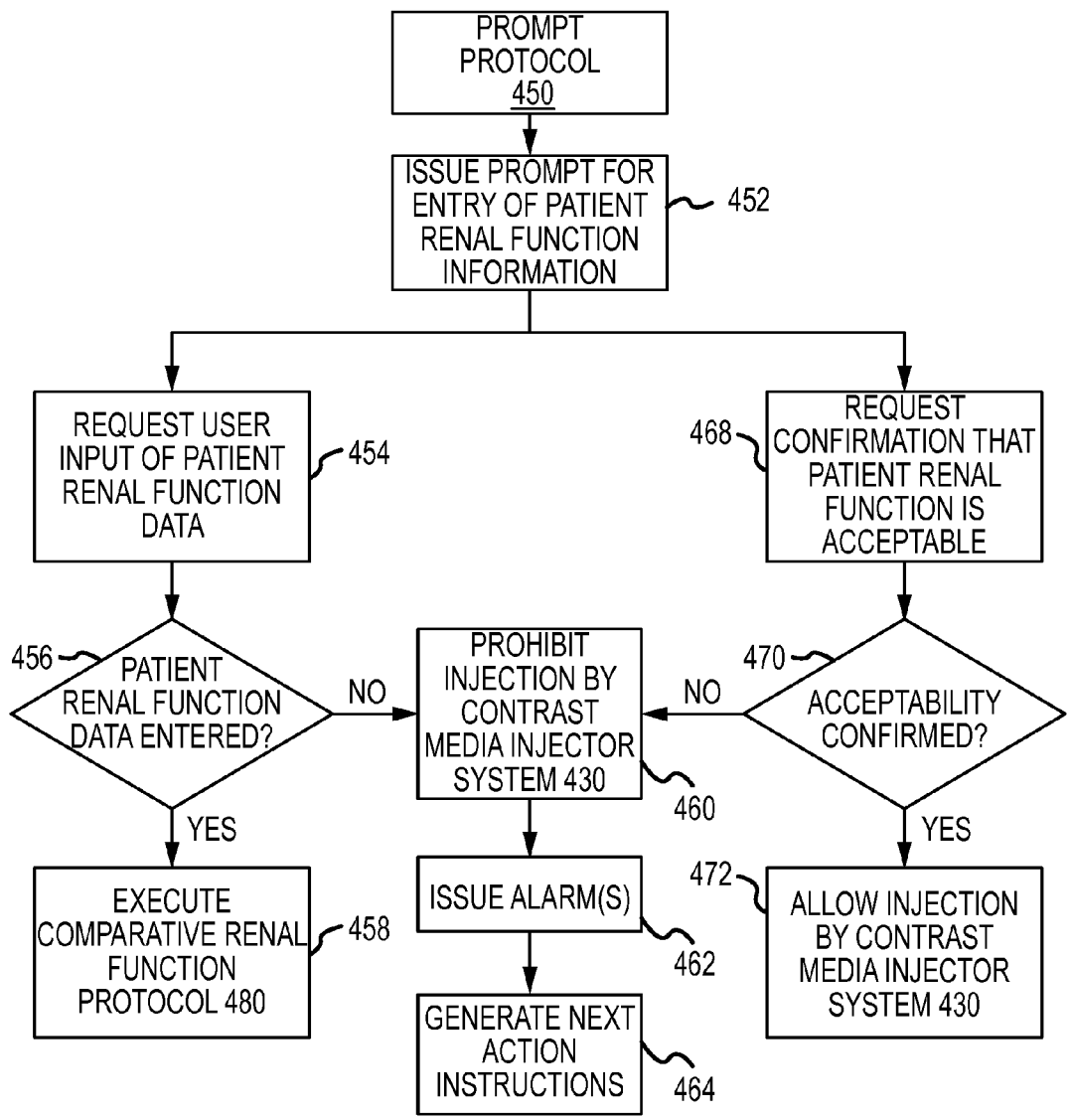
FIG. 13 is a schematic of one embodiment of a protocol that may be used by a renal function assessment module of the control module of FIG. 12.

One embodiment of a protocol that may be used by the prompt logic 446 of the renal function assessment module 442 (FIG. 12) is shown in FIG. 13 and is identified by reference numeral 450. Generally, the protocol 450 is directed to issuing a prompt (e.g., a message on at least one of the displays 406, 411, 434) for a user to manually input renal function information for the patient 424 to be imaged. Step 452 of the protocol 450 is directed to issuing a prompt for the entry of patient real function information (e.g., data that is representative of or that otherwise relates to the renal function of the patient 424). This prompt may be presented on the injector system's remote console display 406, on the power injector display 434, on a display (not shown) of the imaging device 422, on the imaging system's remote console display 411, on a display of a single, commonly shared remote console, or any combination thereof, and may be presented in any appropriate manner (e.g., in the form of a message or request for entry of the noted information).

Figure 14:
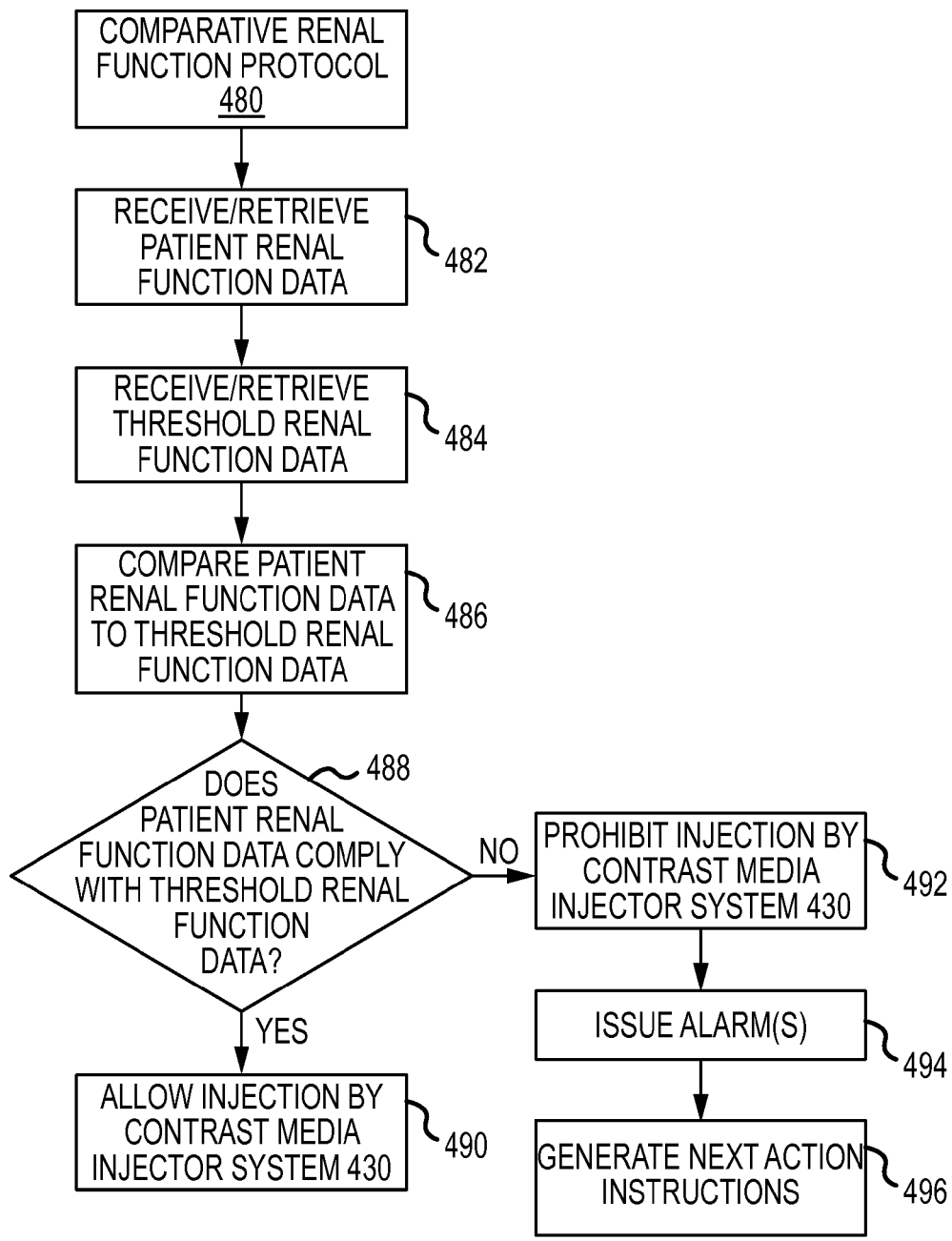
FIG. 14 is a schematic of another embodiment of a protocol that may be used by the renal function assessment module of the control module of FIG. 12.

Different types of prompts are embodied by step 452. The prompt of step 452 may be a request for user input of patient renal function data (e.g., any data that is representative of the renal function of the patient 424), and as noted by step 454 of the prompt protocol 450 of FIG. 13. User input for purposes of step 456 may be provided (e.g., manually input) through a user input device 408 of the remote console 404, through a user input device 436 of the power injector 432, through a data or user input device (not shown) of the imaging device 422, through a user input device 413 of the remote console 409 that is associated with the imaging device 422 and that is located in the control room 402, or any combination thereof. If patient renal function data is entered, step 456 allows the protocol 450 to proceed to step 458, which is directed to comparing this user input to threshold renal function data (e.g., through execution of a protocol 480 that is illustrated in FIG. 14 and that will be addressed in more detail below). Otherwise, the protocol 450 instead proceeds from step 456 to step 460, which will also be addressed in more detail below.

Another form for the prompt associated with step 452 of the protocol 450 of FIG. 13 is addressed by step 468. The prompt may be in the form of a request for confirmation that a user/operator of the contrast media injector system 430 and/or or imaging system 407 has determined that the renal function of the patient 424 is acceptable for proceeding with an injection of a certain contrast media (step 468). User input for purposes of step 468 may be provided (e.g., manually input) through the user input device 408 of the injector system's remote console 404, through a user input device 436 of the power injector 432, through a data or user input device (not shown) of the imaging device 422, through a user input device 413 of the imaging system's remote console 409, through a user input device (not shown) of a single, commonly shared remote console, or any combination thereof. If the renal function assessment module 442 receives positive confirmation that the renal function of the patient 424 is acceptable to proceed with an injection of contrast media (step 470), the protocol 450 proceeds to step 472. Otherwise, the protocol 450 proceeds from step 470 to step 460.

Step 460 of the protocol 450 of FIG. 13 is reached when a patient renal function check has failed in at least some respect. For example, step 460 may be reached as a result of the user failing to enter the patient's renal function data (e.g., for purposes of step 456). As another example, step 460 may be reached as a result of the user failing to input a required confirmation that the patient's renal function data has been checked and/or meets or exceeds a particular minimum renal function requirement from step 470. Because of this renal function check failure, the proposed injection of the patient 424 by the contrast media injector system 430 is not allowed to proceed, which is shown in step 460 of the protocol 450. This injection prohibition of step 460 may be implemented in any appropriate manner. For instance, it may be implemented by activating a lock-out function incorporated by the contrast media injector system 430, by not allowing the contrast media injector system 430 to "arm" or to be "enabled" to run a programmed injection protocol, by not allowing a user/operator to initiate (e.g., "run" or "start") a programmed injection protocol, by not allowing a user/operator to inject contrast media into the patient 424 manually (e.g., using one or more hand controls (e.g., buttons, levers) of the contrast media injector system 430, or any combination thereof.

One or more additional functionalities may be employed in response to the failure of a renal function check. Step 462 of the protocol 450 is directed to issuing one or more alarms. Each alarm may be of any appropriate type (e.g., audible, visual). Step 464 is directed to generating next action instructions. These instructions could be presented on the injector system's remote console display 406, on the power injector display 434, on a display (not shown) of the imaging device 422, on the imaging system's remote console display 411, on a display of a single, commonly shared remote console, or any combination thereof. These instructions could be programmed into the contrast media injector system 430 and/or the medical imaging system 407, and could provide guidance to an operator as to how to deal with the failure of a renal function check. Any one or more of steps 460, 462, and 464 could be executed in response to the failure of a renal function check and in any appropriate order, including where two or more of these steps are executed simultaneously.

One embodiment of a protocol that may be used by the comparative logic 448 of the renal function assessment module 442 (FIG. 12) is shown in FIG. 14 and is identified by reference numeral 480. Generally, the protocol 480 is directed to assessing the renal function of the patient 424 to determine whether or not an injection should proceed (e.g., whether the contrast media injector system 430 should be operated so as to provide a contrast media discharge). Step 482 of the protocol 480 is directed to receiving or retrieving information (e.g., through at least one of the user input devices 408, 413, 436) in the form of renal function data for the patient 424. This renal function data may be any type of data that is representative of the renal function of the patient 424 (e.g., information that quantifies the renal function of the patient 424 in at least some respect), and may be received/retrieved in any appropriate manner.

Threshold renal function data is received or retrieved pursuant to step 484 of the protocol 480. This threshold renal function data may be any type of data that represents a threshold for the renal function that should exist in order for the patient 424 to receive an injection from the contrast media injector system 430 (e.g., an injection of a particular type of contrast media). The threshold renal function data may be received/retrieved in any appropriate manner. A user could look up the threshold renal function data from any appropriate source/sources and manually input the same into the contrast media injector system 430 and/or imaging system 407 (e.g., through at least one of the user input devices 408, 413, 436). A user could search the data store 414 (e.g., by manually entering a contrast media type 416 into the contrast media injector system 430 (or select the same from a listing provided by the system 430) through at least one of the user input devices 408, 413, 436 to identify a relevant threshold renal function 418. This relevant threshold renal function 418 could be retrieved in any appropriate manner by the contrast media injector system 430 and/or imaging system 407 pursuant to step 484 (e.g., by a user "clicking" on the threshold renal function 418 identified from the search of the data store 414; by the contrast media injector system 430 and/or imaging system 407 automatically retrieving the relevant threshold renal function 418 from the information provided by the user on the contrast media type 416).

Yet another option for purposes of step 484 of the protocol 480 of FIG. 14 would be for the contrast media injector system 430 and/or imaging system 407 to automatically retrieve the threshold renal function data for step 484, for instance, by the contrast media injector system 430 reading a data tag or the like on a syringe installed on the power injector 432 (e.g., by the power injector 432 incorporating an appropriate electromagnetic device and by such a syringe including an RF/RFID tag (more generally, a data storage device of any appropriate type) that at least identifies the contrast media type 416 within the syringe (e.g., including a volume of fluid within the syringe and/or a concentration of one or more constituents of the contrast media), all in accordance with the discussion presented above regarding the embodiment of FIG. 6). The threshold renal function data could be stored on such a data tag on the syringe, and then read by the electromagnetic device of the power injector 432 (more generally, a "reader") for purposes of step 484. The threshold renal function data could also be retrieved by storing the contrast media type 416 on such a data tag on the syringe, which could then be read by the electromagnetic device of the power injector 432 for purposes of step 484. The identification of the contrast media type 416 within the syringe could then be used to search the data store 414 to identify the corresponding threshold renal function 418 for purposes of step 484 of the protocol 480.

The patient renal function data (step 482) is compared with the threshold renal function data (step 484) pursuant to step 486 of the protocol 480. This comparison may be undertaken in any appropriate manner (e.g., by one or more processors 444 of the renal function assessment module 442 of FIG. 12). Step 488 of the comparative renal function protocol 480 of FIG. 14 is directed to determining if the patient renal function data (step 482) complies with the threshold renal function data (step 484). For instance, a determination may be made as to whether the patient renal function data (step 482) meets or exceeds the threshold renal function data (step 484). In any case, if the patient renal function data (step 482) complies with the threshold renal function data (step 484), the protocol 480 proceeds to step 490, which is directed to allowing the injection of the patient 424 by the contrast media injector system 430 to proceed. If the patient renal function data (step 482) does not comply with the threshold renal function data (step 484), the protocol 480 instead proceeds to step 492.

Step 492 of the protocol 480 of FIG. 14 is reached when a renal function check has failed in at least some respect. In this regard, the injection of the patient 424 by the contrast media injector system 430 is not allowed to proceed through execution of step 492 of the protocol 480. This may be implemented in any appropriate manner, for instance in accordance with step 460 of the prompt protocol 450 discussed above in relation to FIG. 13.

One or more additional functionalities may be employed in response to the failure of a renal function check. Step 494 of the protocol 480 is directed to issuing one or more alarms. Each alarm may be of any appropriate type (e.g., audible, visual). Step 496 is directed to generating next action instructions. These instructions could be presented on the injector system's remote console display 406, on the power injector display 434, on a display (not shown) of the imaging device 422, on the imaging system's remote console display 411, on a display of a single, commonly shared remote console, or any combination thereof. These instructions could be programmed into the contrast media injector system 430 and/or the medical imaging system 407, and could provide guidance to an operator as to how to deal with the failure of a renal function check. Any one or more of steps 492, 494, and 496 could be executed in response to the failure of a renal function check and in any appropriate order, including where two or more of these steps are executed simultaneously.

Figure 15:
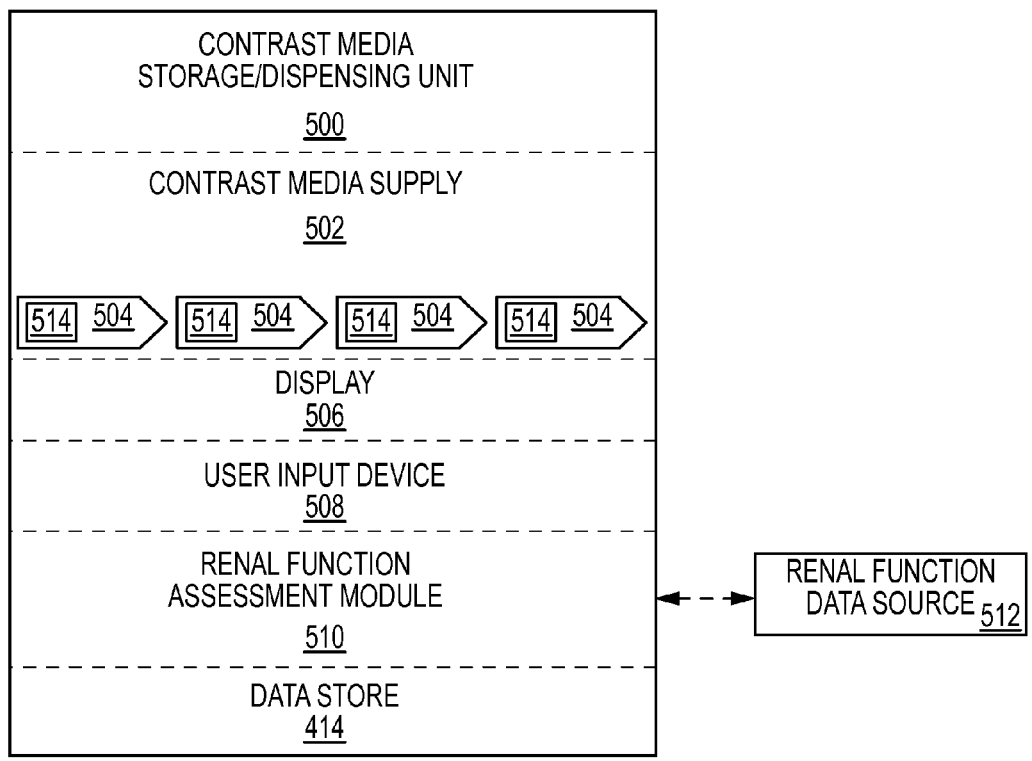
FIG. 15 is a schematic of one embodiment of a contrast media storage/dispensing unit that incorporates renal function assessment functionality.

One embodiment of a contrast media storage/dispensing unit is illustrated in FIG. 15 and is identified by reference numeral 500. The contrast media storage/dispensing unit 500 may be utilized in conjunction with the imaging suite 400 discussed above in relation to FIGS. 11-14. However, the contrast media storage/dispensing unit 500 may also be implemented independently of such an imaging suite 400. Generally, the contrast media storage/dispensing unit 500 is directed to providing a renal function check prior to releasing contrast media for use in conjunction with an injection of a patient (e.g., prior to providing contrast media to a technician for use in a proposed injection procedure for a given patient).

The contrast media storage/dispensing unit 500 may be characterized as including or being in the form of a supply 502 of discrete quantities of contrast media. These discrete quantities of contrast media may be retained within a plurality of contrast media containers 504 that are of any appropriate type (e.g., syringes, vials, bags), that collectively define the contrast media supply 502, and that may be stored in any appropriate manner by/within the contrast media storage/dispensing unit 500. Multiple containers 504 of one or more contrast media types may be included within the contrast media supply 502. In one embodiment, at least some of the contrast media containers 504 being stored within the contrast media storage/dispensing unit 500 are in the form of a "prefilled syringe." "Prefilled syringes" are syringes that are loaded with contrast media or other medical fluids at a manufacturing facility prior to transporting the same to an end-use facility such as a hospital, clinic, or the like. Although all of the contrast media containers 504 being stored within the contrast media storage/dispensing unit 500 may be of a common type and/or may be of a common size/configuration, such may not be the case in all instances.

The contrast media containers 504 are in a sealed condition or state both when stored in the contrast media storage/dispensing unit 500, as well as when/after being released from the contrast media storage/dispensing unit 500. Being in a "sealed condition" encompasses that a given contrast media container 504 is not currently in a configuration to inject contrast media into a patient 424. Being in a "sealed condition" also encompasses that a given contrast media container 504 is usable in a patient injection procedure only after being released from the contrast media storage/dispensing unit 500. Each of the contrast media containers 504 may be characterized as being adapted for use with a medical fluid delivery system, such as the contrast media injector system 430. After being released from the contrast media storage/dispensing unit 500, a given contrast media container 504 may need to be appropriately interconnected with a medical fluid delivery system (e.g., contrast media injector system 430) prior to being able to inject contrast media into a patient 424.

Each of the contrast media containers 504 may include a data storage device 514 of any appropriate type (e.g., an RF or RFD tag). Any appropriate information may be stored on the data storage device 514 of each contrast media container 504. Representative data that may be stored on a given data storage device 514 includes without limitation a contrast media type identifier (where a "contrast media type" may: 1) be defined at least in part by the concentration of one or more constituents (e.g., active ingredients) of the contrast media; 2) be defined at least in part by the total amount of a particular constituent (e.g., active ingredient) found within the total volume of contrast media in the corresponding container 504 or found within a predefined reference volume of contrast media in the corresponding container 504 (e.g., "x" mg of iodine per 1 ml of contrast media); 3) refer to the commercial names/identities for contrast media), threshold renal function data (e.g., threshold (e.g., minimum acceptable) renal function, which may or may not be associated with certain concentration and/or volume restrictions/guidelines for approved dosing), and the like.

Other components of the contrast media storage/dispensing unit 500 include a renal function assessment module 510 (e.g., at least generally in accordance with the renal function assessment module 442 of the control module 440 of FIG. 12, and thereby including one or more processors that may be programmed to undertake the protocols 520 and 540 that are addressed below) and at least one data or user input device 508 (in accordance with the user input devices 408, 413, 436 discussed above in relation to the imaging suite 400 of FIG. 11). The contrast media storage/dispensing unit 500 may also include one or more displays 506, as well as the data store 414 discussed above in relation to the imaging suite 400 of FIG. 11. Renal function information may also be made available to the contrast media storage/dispensing unit 500 (e.g., to the renal function assessment module 510) through a renal function data source 512 (e.g., HIS, RIS, PACS, injector system 430, imaging system 407, or a patient electronic medical records system).

Figure 16:
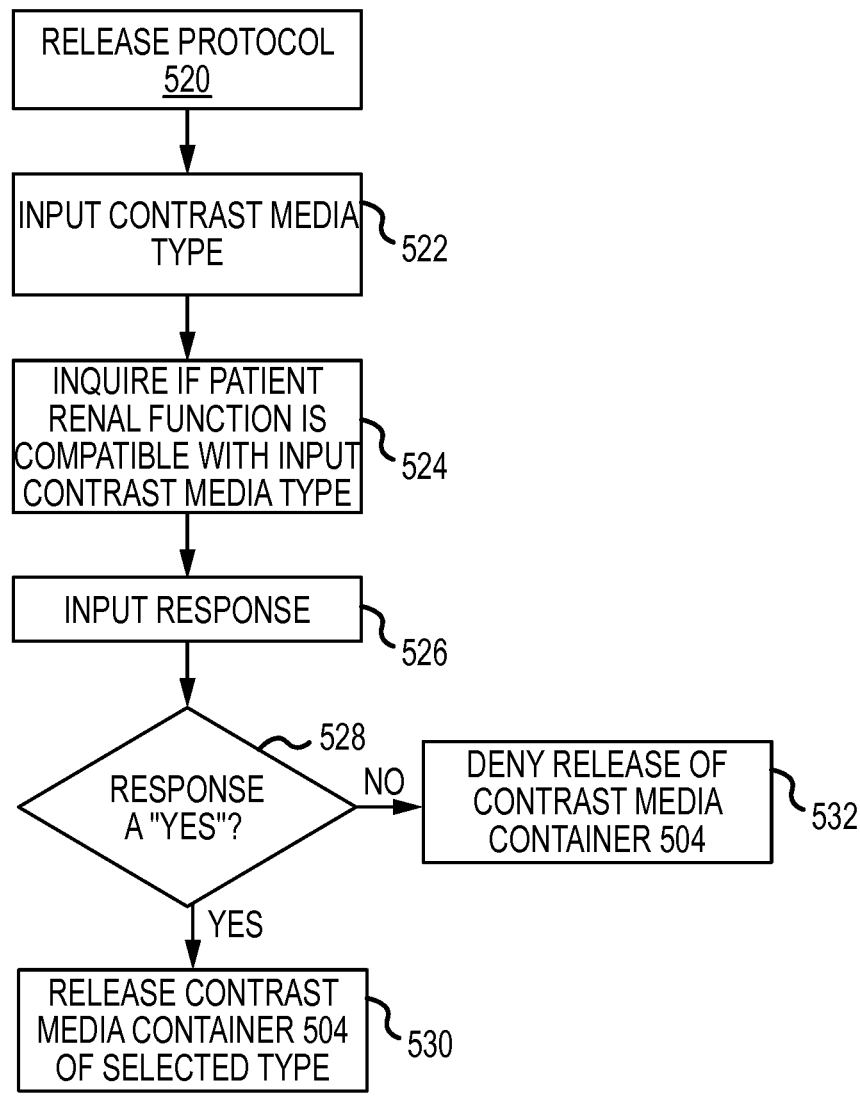
FIG. 16 is one embodiment of a protocol that may be used by the contrast media storage/dispensing unit of FIG. 15 for purposes of determining whether a contrast media container should be released from the unit.

FIG. 16 illustrates one embodiment of a release protocol 520 that may be incorporated by the renal function assessment module 510 for the contrast media storage/dispensing unit 500 for purposes of determining whether a contrast media container 504 should be released/dispensed by contrast media storage/dispensing unit 500. Step 522 of the protocol 520 is directed to inputting (entering or selecting) or acquiring the contrast media type (e.g., which may include one or more of brand name, active ingredient, concentration, and volume) that is desired to be retrieved from the contrast media storage/dispensing unit 500. The input associated with step 522 may be provided in any appropriate manner, such as through the user input device 508 of the contrast media storage/dispensing unit 500.

Step 524 of the release protocol 520 of FIG. 16 is directed to questioning/inquiring whether the patient renal function has been determined to be compatible with the contrast media type that was input pursuant to step 522. This may be presented on the display 506 of the contrast media storage/dispensing unit 500. User input may be provided through step 526 of the protocol 520 (e.g., through the user input device 508). If the user input was an affirmative response (e.g., a "yes"), the protocol 520 proceeds from step 528 to step 530. Step 530 is directed to releasing a contrast media container 504 from the contrast media supply 502 in accordance with the contrast media type identified through step 522. If no user input is provided pursuant to step 526, or if the user input was a negative response (e.g., a "no"), the contrast media storage/dispensing unit 500 will not release a contrast media container 504 from the contrast media supply 502 (e.g., pursuant to step 532 of the release protocol 520).

One or more additional functionalities may be employed in response to the contrast media release/dispensing denial of step 532. For example, next action instructions may be generated. These instructions could be presented on the storage/dispensing unit's display 506. These instructions could be programmed into the contrast media storage/dispensing unit 500, and could provide guidance to a technician as to how to deal with the failure of a renal function check.

Figure 17:
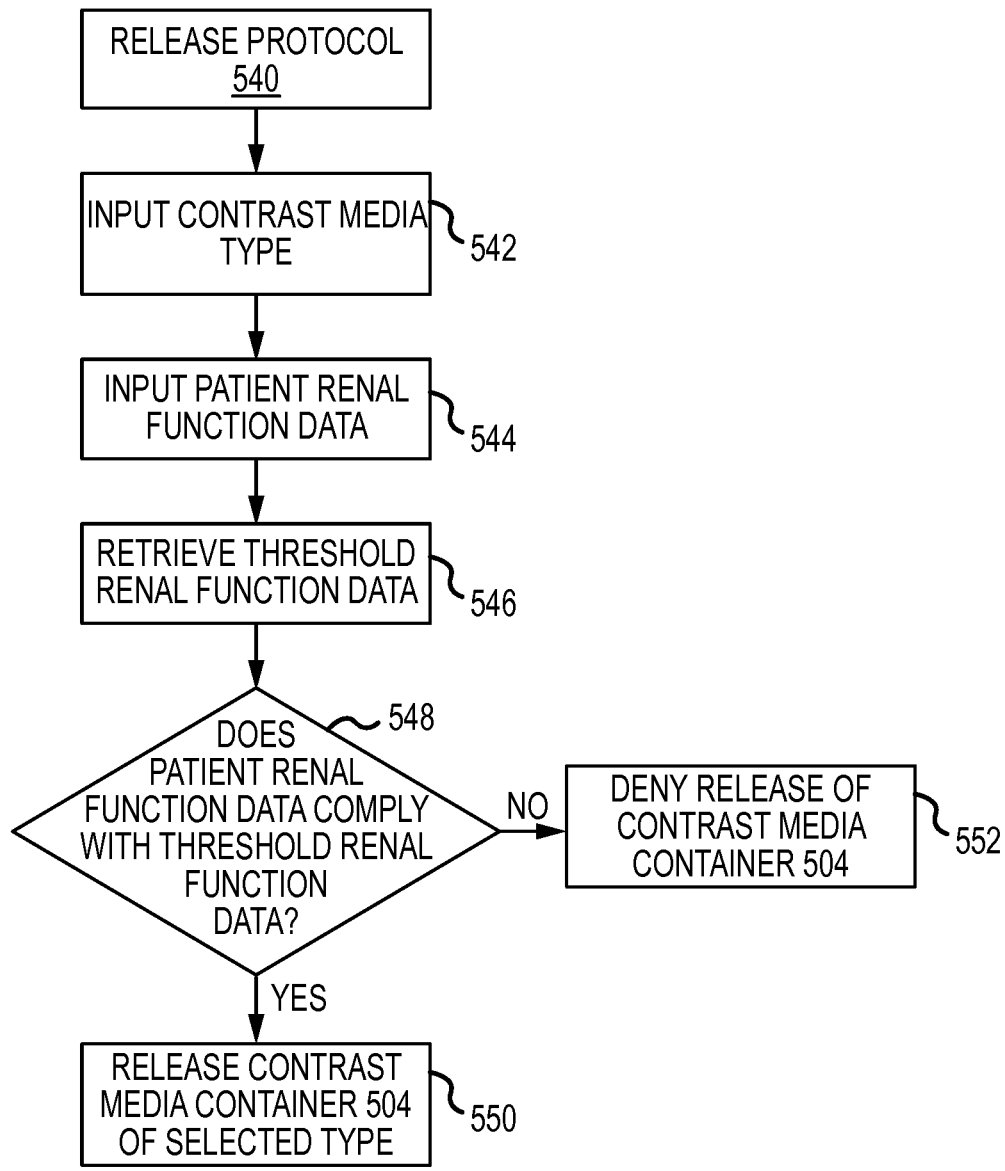
FIG. 17 is another embodiment of a protocol that may be used by the contrast media storage/dispensing unit of FIG. 15 for purposes of determining whether a contrast media container should be released from the unit.

FIG. 17 illustrates another embodiment of a release protocol 540 that may be incorporated by the renal function assessment module 510 for the contrast media storage/dispensing unit 500 for purposes of determining whether a contrast media container 504 should be released/dispensed by contrast media storage/dispensing unit 500. Step 542 of the protocol 540 is directed to inputting or acquiring the contrast media type that is desired to be retrieved from the contrast media storage/dispensing unit 500. The input associated with step 542 may be provided in any appropriate manner, such as through the user input device 508 of the contrast media storage/dispensing unit 500.

Step 544 of the release protocol 540 of FIG. 17 is directed to providing input to the contrast media storage/dispensing unit 500 regarding patient renal function data of the above-described type. This may be undertaken in any appropriate manner. One option is for patient renal function data (e.g., GFR, serum creatinine measurement) to be manually input by a user through the user input device 508 of the contrast media storage/dispensing unit 500. Another option would be for the contrast media storage/dispensing unit 500 to including a listing of renal function data, and for a user to manually select the relevant patient renal function data from such a listing through the user input device 508. Yet another option could be for the contrast media storage/dispensing unit 500 to be operatively connected with (e.g., in communication with) one or more renal function data sources 512 (e.g., HIS, RIS, PACS, injector system 430, imaging system 407, a patient electronic medical records system), and to retrieve the patient renal function data for step 544 from such a renal function data source 512. For instance, a user could input an appropriate patient identifier to the contrast media storage/dispensing unit 500 through the user input device 508, and the contrast media storage/dispensing unit 500 could then retrieve the patient renal function data for step 544 from one or more renal function data sources 512. As an alternative to a user manually entering the patient renal function data, that data could be retrieved from a renal function data source 512 by the unit 500 in response to an electronic read device (not shown) of the unit 500 identifying the patient by way of reading an appropriate data source (e.g., bar code or RFID tag presented to the unit 500 by a technician). In other embodiments, the patient's renal function data could be stored on an appropriate data source (e.g., bar code or RFID tag) and could be input into the unit 500 simply by a technician exposing that data source to an electronic read device (not shown) of the unit 500.

Threshold renal function data is retrieved pursuant to step 546 of the release protocol 540 of FIG. 17. This threshold renal function data may be any type of data that represents a threshold for the renal function that should exist in order for the patient to receive an injection of a particular type of contrast media (e.g., from the contrast media injector system 430). The threshold renal function data may be retrieved in any appropriate manner. A user could look up the threshold renal function data from any appropriate source/sources and manually input the same into the contrast media storage/dispensing unit 500 (e.g., through the user input device 508). A user could search the data store 414 (e.g., by manually entering a contrast media type into the contrast media storage/dispensing unit 500 through the user input device 508) to identify a relevant threshold renal function 418 (e.g., see FIG. 11 regarding the data store 414). This relevant threshold renal function 418 could be retrieved in any appropriate manner by the contrast media storage/dispensing unit 500 pursuant to step 546 (e.g., by a user "clicking" on the threshold renal function 418 identified from the search of the data store 414; by the contrast media storage/dispensing unit 500 automatically retrieving the relevant threshold renal function 418 from the information provided by the user on the contrast media type 416—utilizing the data store 414).

Step 548 of the release protocol 540 is directed to determining if the patient renal function data (step 544) complies with the threshold renal function data (step 546). This determination/comparison may be undertaken in any appropriate manner (e.g., by one or more processors of the renal function assessment module 510). For instance, a determination may be made as to whether the patient renal function data (step 544) meets or exceeds the threshold renal function data (step 546). In any case, if the patient renal function data (step 544) complies with the threshold renal function data (step 546), the protocol 540 proceeds to step 550, and which is directed to releasing a contrast media container 504 from the contrast media supply 502 in accordance with the contrast media type provided through step 542. If the patient renal function data (step 544) does not comply with the threshold renal function data (step 546), the contrast media storage/dispensing unit 500 will not release a contrast media container 504 from the contrast media supply 502 (e.g., pursuant to step 552 of the release protocol 540).

Any of the modules, protocols, logic, or the like addressed in relation to the renal function checks for the embodiments of FIGS. 11-17 may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. These modules, protocols, logic, or the like may be implemented at any single location or at multiple locations that are interconnected in any appropriate manner (e.g., via any type of network).

Figure 18A:
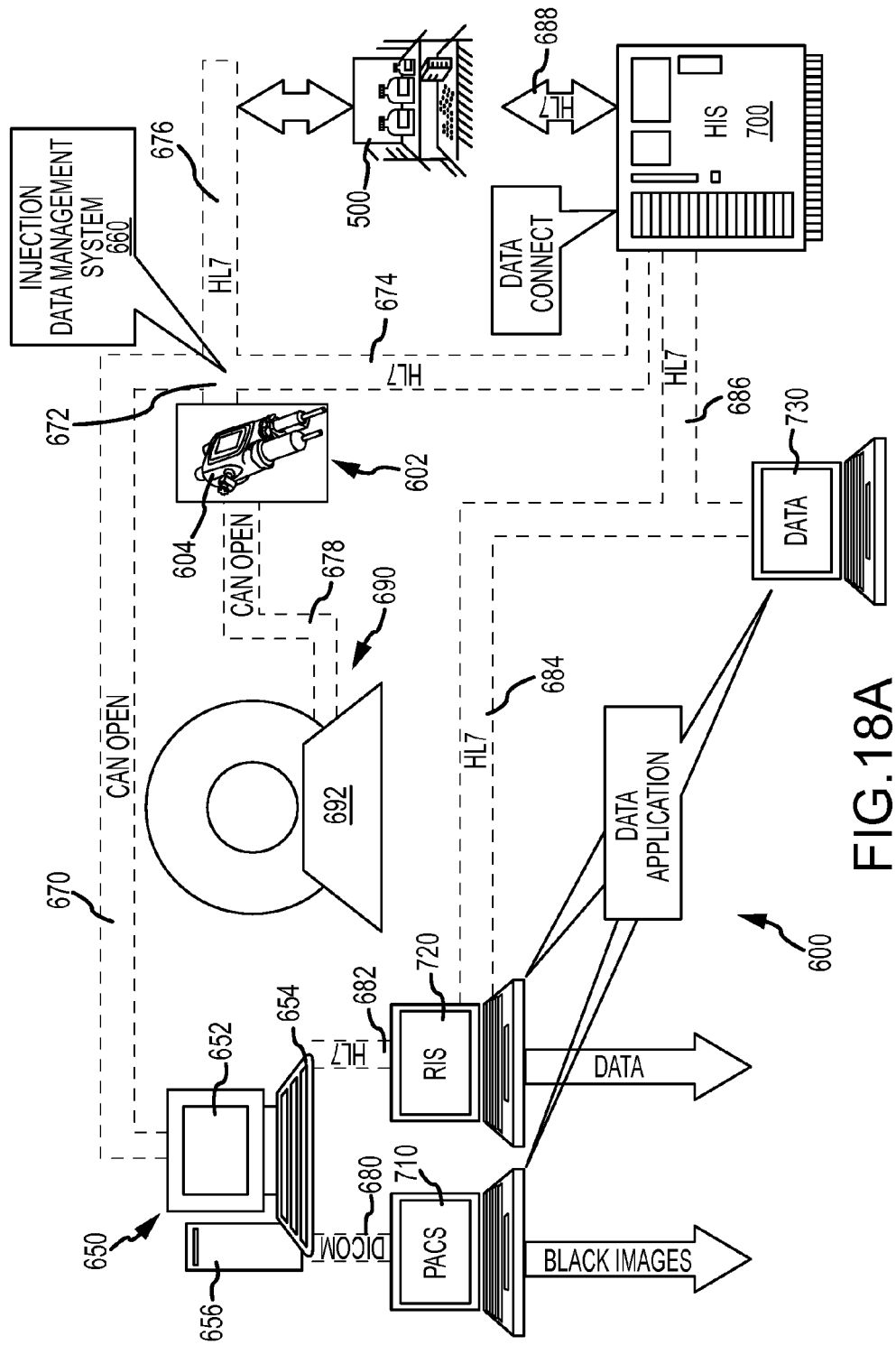
FIG. 18A is one embodiment of a medical system having an injection data management system or module with data format conversion or translation capabilities.

One embodiment of a medical system is illustrated in FIG. 18A and is identified by reference numeral 600. The medical system 600 includes a contrast media injector system 602, an injection data management system or module 660 (or more generally a data management system or module 660), an imaging system 690, a contrast media storage/dispensing unit 500 (discussed above in relation to FIG. 15), a hospital information system or HIS 700, a picture archiving and communications system or PACS 710, and a radiology/radiological information system or RIS 720. Multiple contrast media injector systems 602 and multiple imaging systems 690 could be part of the same medical system 600. Multiple contrast media storage/dispensing units 500 could be utilized as well.

The imaging system 690 may be in accordance with the imaging system 407 discussed above in relation to FIG. 11. In this regard, the imaging system 690 may include an imaging device or unit 692, as well as a remote console (not shown in FIG. 18A). The imaging device 692 may utilize any appropriate imaging technology or combination of imaging technologies.

The HIS 700 may be characterized as a computer system that is configured to manage information that relates to one or more aspects of hospital operations. This computer system may utilize any appropriate architecture or combination of architectures. The HIS 700 may utilize any appropriate combination of hardware and/or software that is distributed in any appropriate arrangement and that is operatively interconnected in any appropriate manner (e.g., any appropriate communication link or combination of communication links, including utilizing one or more networks of any appropriate type). The HIS 700 may utilize one or more servers, one or more processors integrated in any appropriate processing architecture, one or more workstations (e.g., desktop computers; laptop computers; terminals in the form of a display and keyboard), or the like that are in communication over one or more networks of any appropriate type (e.g., a local area network; a wide area network; the Internet; a private network).

A data storage system of any appropriate type may be used by the HIS 700 to store data that relates to one or more aspects of hospital operations (e.g., any appropriate data storage architecture of computer-readable storage medium). Any appropriate data structure or combination of data structures may be utilized by the HIS 700. Representative data that may be stored by the HIS 700 includes medical/patient information (e.g., electronic patient medical records), administrative information, and financial information. Data may be stored by the HIS 700 on a computer-readable storage medium and in any appropriate form. Data may be stored in one or more databases of the HIS 700, and data stored by the HIS 700 may be linked as desired/required and in any appropriate manner.

The HIS 700 may be characterized as including the one or more subsystems, along with their corresponding data. Representative subsystems of the HIS 700 may include without limitation PACS 710; RIS 720; a Clinical Information System (CIS); a Laboratory Information System (LIS); a Pharmacy Information System (PIS); a Nursing Information System (NIS); and a Financial Information System (FIS).

The PACS 710 may be characterized as a computer system (e.g., combination of hardware and software) that provides for storage, retrieval, management, access to, presentation, and distribution of medical images of any appropriate type (e.g., magnetic resonance, computed tomography, ultrasound, positron emission tomography, etc). Image files may be stored by the PACS 710 on any appropriate computer-readable storage medium (e.g., in the form of one or more digital files). Non-image data may be stored by the PACS 710.

The PACS 710 may utilize one or more servers that each have one or more image databases, and that may be accessed in any appropriate manner (e.g., through a local area network, through a wide area network, over the Internet or any other public network). The above-noted imaging system 690 may be characterized as being part of the PACS 710. Other components of the PACS 710 may include without limitation a network for distribution and exchange of patient information, one or more workstations (e.g., a terminal and keyboard; a desktop computer; a laptop computer), and a data storage system (e.g., computer readable storage medium) for the storage and retrieval of images and related documentation.

The RIS 720 may be characterized as a computer system (e.g., combination of hardware and software) that provides for storage, review, manipulation, and distribution of patient radiological data and imagery. Patient radiological data and imagery may be stored by the RIS 720 on any appropriate data storage system (e.g., computer-readable storage medium). The RIS 720 may incorporate patient management functionality (e.g., tracking patient workflow within a radiology department; storing, retrieving, and viewing image data and related documentation), scheduling functionality, patient tracking functionality (e.g., providing access to the entirety of a patient's radiology history), reporting functionality, image tracking functionality, and billing functionality (e.g., financial recordkeeping, electronic payment, claim submission).

The contrast media injector system 602 may be in the form of a power injector (e.g., power injector 210 discussed above in relation to FIG. 1A; power injector 240 discussed above in relation to FIGS. 1B-D; power injector 10 discussed above in relation to FIGS. 2A-5B; contrast media injector system 430 discussed above in relation to FIG. 11). In accordance with the foregoing embodiments, the contrast media injector system 602 includes an injection head or powerhead 604, and what is commonly referred to as a remote console 650 (more generally a first console 650). In one embodiment, the powerhead 604 is located in one location (e.g., imaging room 420 in FIG. 11), while the remote console 650 is located in another location (e.g., control room 402 in FIG. 11). However, the powerhead 604 and remote console 650 could be co-located (e.g., within an imaging room 420, shown in FIG. 11).

The remote console 650 for the contrast media injector system 602 may include at least one display 652, at least one user or data input device 654, and possibly a processing system 656 (e.g., a CPU; one or more processors). The discussion presented above with regard to the remote console 404 of the contrast media injector system 430 of FIG. 11 is equally applicable to the remote console 650 used by the medical system 600 of FIG. 18A. The remote console 650 may be a designated part of the contrast media injector system 602, and may be configured to only communicate with at least one other portion of the contrast media injector system 602 (e.g., the powerhead 604, for instance through the injection data management module 660 (e.g., which may be incorporated at least in part by a powerpack). Another option is for the remote console 650 to be a designated part of the contrast media injector system 602, but where it may be configured to communicate with both the imaging system 690 and at least one other portion of the contrast media injector system 602 (e.g., the powerhead 604, for instance through the injection data management module 660). Yet another option is for the remote console 650 to be a shared unit between the contrast media injector system 602 and the imaging system 690. The remote console 650 could be a designated part of the imaging system 690, but where it may be configured to communicate with both the imaging device 692 and the contrast media injector system 602 (e.g., the powerhead 604, for instance through the injection data management module 660).

The contrast media injector system 602 of FIG. 18A may include at least part of the injection data management system 660 (e.g., a data conversion or translation module 664, discussed below in relation to FIGS. 18B and 18C). As will be discussed in more detail below, the injection data management system 660 may be configured to convert or translate data from at least one format into at least one other format. Generally, the injection data management system 660 at least in part provides for or accommodates communication between the contrast media injector system 602 and various other components of the medical system 600 (which may be referred to as sub-systems of the medical system 600). Any architecture may be used for these handling these communications. In the illustrated embodiment, the injection data management system 660 is not part of the powerhead 604, but is able to communicate with the powerhead 604 over a communication link 672 of any appropriate type (e.g., a wired connection; an appropriate data cable; wirelessly). In one embodiment, a single injection data management system 660 is used with a single contrast media injector system 602. In another embodiment, a single injection data management system 660 may be used with any appropriate number of contrast media injector systems 602 (e.g., a single injection data management system 660 could be associated with multiple contrast media injector systems 602, for instance as shown in FIG. 18C).

The remote console 650 of the contrast media injector system 602 may communicate with the powerhead 604 over a communication link 670 of any appropriate type (e.g., a wired connection; an appropriate data cable; wirelessly), for instance through the injection data management system 660 (e.g., a data conversion module 664; a conversion or translation of a data format for data transmitted between the powerhead 604 and the remote console 650 may not be required). Communications between the remote console 650 and the powerhead 604 may utilize a first CAN-compliant format (where CAN stands for "Controller Area Network"). In one embodiment, data is transmitted over the communication link 670 is in accordance with a CAN 2.0A standard.

The contrast media injector system 602 may communicate with the imaging system 690 over a communication link 678 of any appropriate type (e.g., a wired connection; an appropriate data cable; wirelessly). Communications between the contrast media injector system 602 and the imaging system 690 may be directed through the injection data management system 660 (e.g., a data conversion module 664). The contrast media injector system 602 may utilize one CAN-compliant format (e.g., CAN 2.0A), while the imaging system 690 may utilize another CAN-compliant format (e.g., CiA 425). Contrast administration data from the contrast media injector system 602 may be converted from one format to another format by the injection data management system 660 for transmission to the imaging system 690. In one embodiment, the medical system 600 is configured such that there may be two-way communications between the contrast media injector system 602 and the imaging system 690 through the injection data management system 660 (e.g., such that the injection data management system 660 can provide both a CAN 2.0A to CiA 425 conversion, as well as a CiA 425 to CAN 2.0A conversion, for instance through a data conversion module 664). However, the medical system 600 could be configured such that there may only be one-way communications between the contrast media injector system 602 and the imaging system 690 (in either direction).

The contrast media injector system 602 may communicate with the HIS 700 over a communication link 674 of any appropriate type (e.g., a wired connection; an appropriate data cable; wirelessly). Communications between the contrast media injector system 602 and the HIS 700 may be directed through the injection data management system 660 (e.g., a data conversion module 664). The contrast media injector system 602 may utilize one CAN-compliant format (e.g., CAN 2.0A), while the HIS 700 may utilize an HL-7-compliant format. Contrast administration data from the contrast media injector system 602 may be converted from one format to another format by the injection data management system 660 (e.g., a data conversion module 664) for transmission to the HIS 700 (e.g., CAN 2.0A to HL-7). In one embodiment, the medical system 600 is configured such that there is only one-way communication between the powerhead 604 of contrast media injector system 602 and the HIS 700 (e.g., from the powerhead 604 to the HIS 700, through the injection data management system 660, for instance through a data conversion module 664).

The contrast media injector system 602 may communicate with the contrast media storage/dispensing unit 500 (e.g., CMSDU 500) over a communication link 676 of any appropriate type (e.g., a wired connection; an appropriate data cable; wirelessly). Communications between the contrast media injector system 602 and the contrast media storage/dispensing unit 500 may be directed through the injection data management system 660 (e.g., a data conversion module 664). The contrast media injector system 602 may utilize one CAN-compliant format (e.g., CAN 2.0A), while the contrast media storage/dispensing unit 500 may utilize an HL-7-compliant format. Contrast administration data from the contrast media injector system 602 may be converted from one format to another by the injection data management system 660 (e.g., a data conversion module 664) for transmission to the contrast media storage/dispensing unit 500 (e.g., CAN 2.0A to HL-7).

The contrast media injector system 602 may communicate with the PACS 710 over a communication link 680 of any appropriate type (e.g., a wired connection; an appropriate data cable; wirelessly). Communications between the contrast media injector system 602 and the PACS 710 may be directed through the injection data management system 660 (e.g., FIGS. 19 and 20), for instance through a data conversion module 664. The communication link 680 may extend from the injection data management system 660 to the PACS 710 (e.g., the communication link 680 need not extend through the remote console 650). The contrast media injector system 602 may utilize one CAN-compliant format (e.g., CAN 2.0A), while PACS 710 may utilize a DICOM ("Digital imaging and Communications in Medicine") format. Contrast administration data from the contrast media injector system 602 may be converted from one format to another format by the injection data management system 660 (e.g., a data conversion module 664) for transmission to the PACS 710 (e.g., CAN 2.0A to DICOM).

The contrast media injector system 602 may communicate with the RIS 720 over a communication link 682 of any appropriate type (e.g., a wired connection; an appropriate data cable; wirelessly). Communications between the contrast media injector system 602 and the RIS 720 may be directed through the injection data management system 660 (e.g., FIGS. 19 and 20), for instance through a data conversion module 664. The communication link 682 may extend from the injection data management system 660 to the RIS 720 (e.g., the communication link 682 need not extend through the remote console 650). The contrast media injector system 602 may utilize one CAN-compliant format (e.g., CAN 2.0A), while the RIS 720 may utilize an HL-7-compliant format and/or a DICOM-compliant format. Contrast administration data from the contrast media injector system 602 may be converted from one format to another format by the injection data management system 660 (e.g., a data conversion module 664) for transmission to the RIS 720 (e.g., CAN 2.0A to HL-7; CAN 2.0A to DICOM).

The medical system 600 accommodates other communications. As shown in FIG. 18A, the contrast media storage/dispensing unit 500 may communicate with the HIS 700 over a communication link 688 of any appropriate type (e.g., a wired connection; an appropriate data cable; wirelessly). Communications between the contrast media storage/dispensing unit 500 and the HIS 700 may utilize an HL-7-compliant format. The medical system 600 may include one or more workstations 730 (e.g., a desktop computer, a laptop). In the illustrated embodiment, a workstation 730 is able to communicate with the RIS 720 over a communication link 684 of any appropriate type (e.g., a wired connection; an appropriate data cable; wirelessly), and is also able to communicate with the HIS 700 over a communication link 686 of any appropriate type (e.g., a wired connection; an appropriate data cable; wirelessly).

As noted, the communication architecture between the injection data management system 660 and the various sub-systems of the medical system 600 (more generally the communication architecture of the medical system 600) may be of any appropriate configuration. The injection data management system 660 could directly communicate with one or more of these sub-systems (e.g., HIS 700; PACS 710; RIS 720; CMSDU 500), the injection data management system 660 could indirectly communicate with one or more of these sub-systems, or both. For instance, the communication architecture could be such that data in one format (e.g., HL-7) could be directed from the injection data management system 660 to one of these sub-systems (e.g., HIS 700), and this sub-system, could then direct this data to other subsystems that require data of the same format (e.g., the communication architecture could provide for an indirect communication between the injection data management system 660 and one or more sub-systems of the medical system 600).

The injection data management system 660 used by or associated with the contrast media injector system 602 may be characterized as providing a communication interface between at least part of the contrast media injector system 602 (e.g., its powerhead 604) and at least one other medical system, where this medical system(s) requires that data be transmitted from the injection data management module 660 in something other than a CAN-compliant format (e.g., HL-7-compliant data; DICOM-compliant data).

Figure 18B:
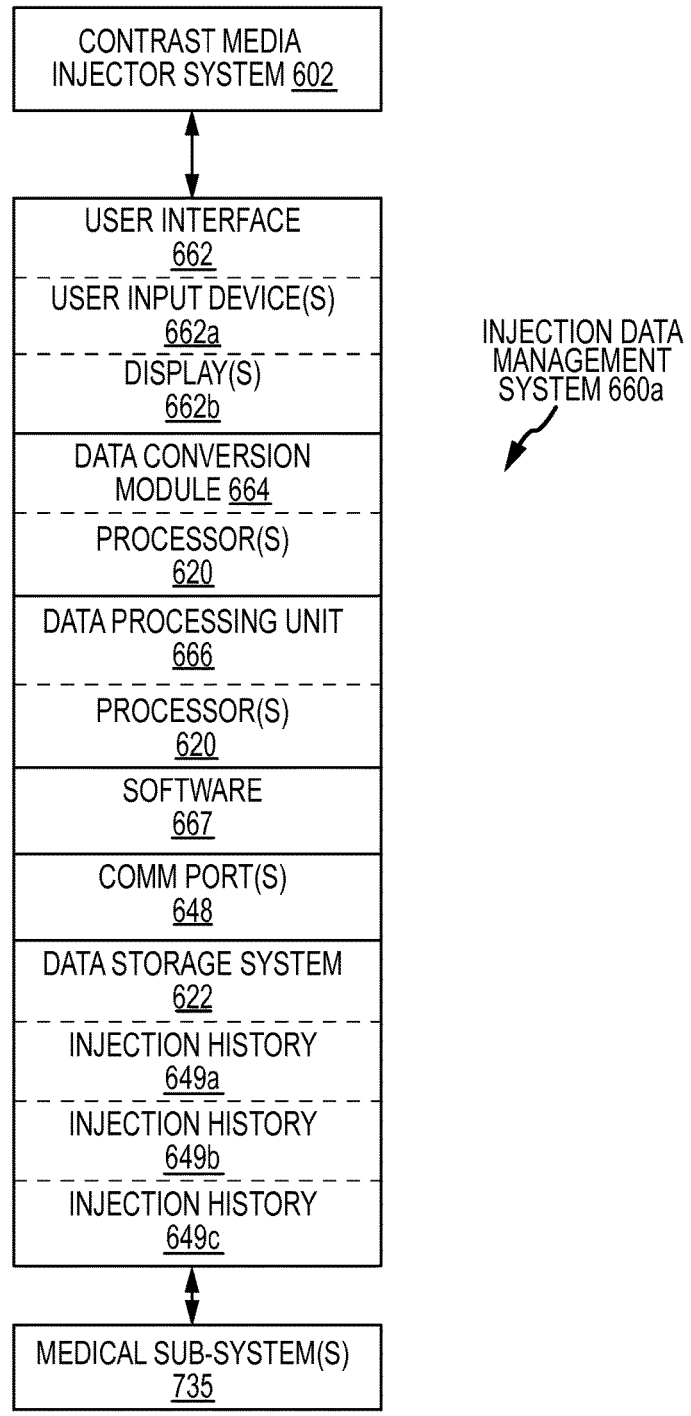
FIG. 18B is a schematic of a representative embodiment for an injection data management system or module having data format conversion capabilities.
Figure 18C:
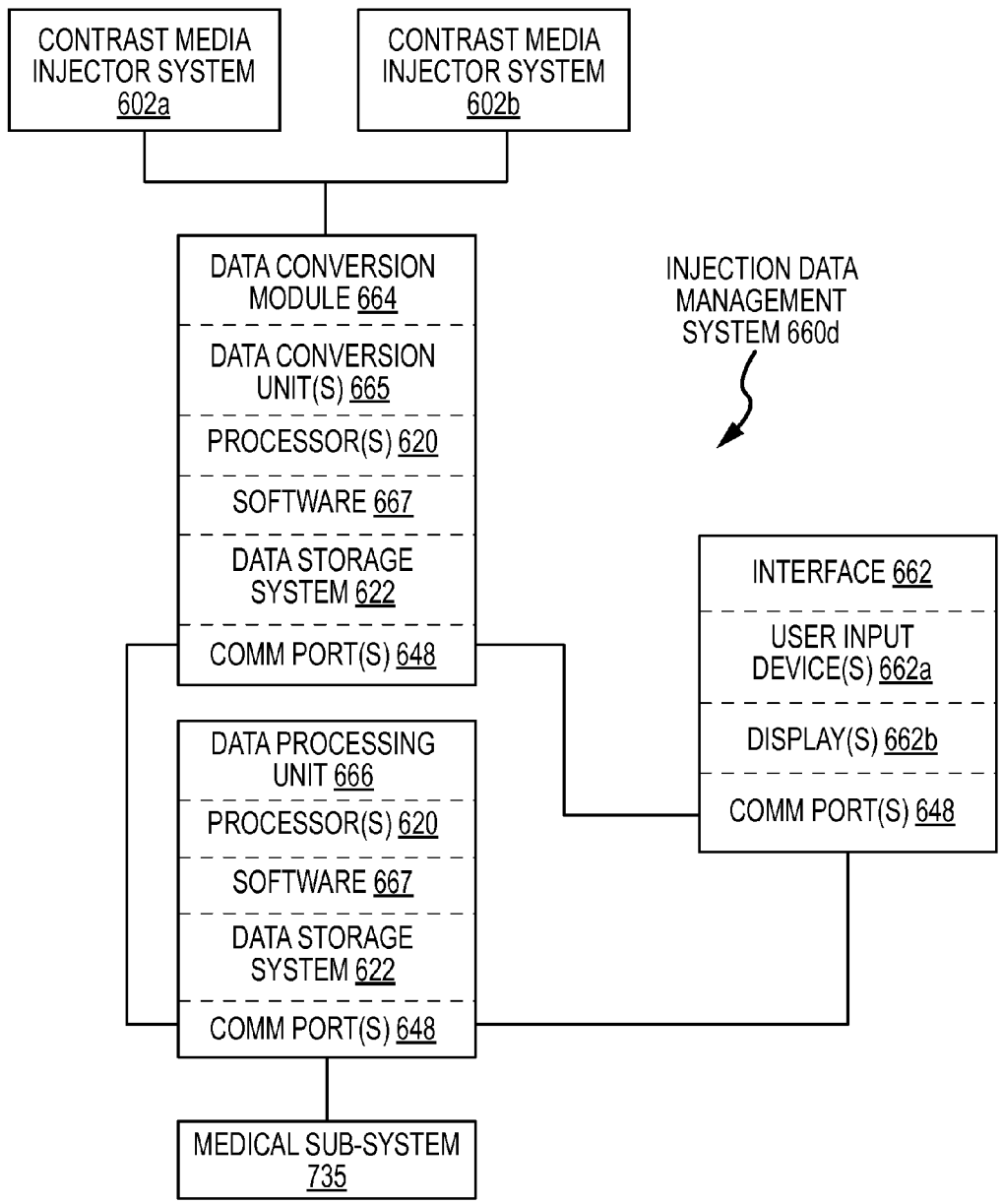
FIG. 18C is a schematic of a representative embodiment for an injection data management system or module having data format conversion capabilities.

FIG. 18B presents a schematic of one embodiment of the injection data management system 660 from the medical system 600 of FIG. 18A, and that is identified by reference numeral 660a. The injection data management system or module 660a may be implemented in any appropriate architecture (e.g., the injection data management system 660a could be an autonomous unit in relation to the remainder of the medical system 600; one or more parts of the injection data management system 660a could be incorporated by one or more of the sub-systems of the medical system 600). In the FIG. 18B configuration, the injection data management system 660a provides an interface between a contrast media injector system 602 (e.g., its powerhead 604) and at least one medical sub-system 735 that requires data to be in something other than in a CAN-compliant format (e.g., HL-7-compliant data; DICOM-compliant data). Each medical sub-system 735 in communication with the injection data management system 660a may be of any appropriate type, for instance the HIS 700, the RIS 720, or the PACS 710 discussed above, or any other electronic medical records system(s) (e.g., a medical data or information system). The medical sub-system 735 could also be in the form of the contrast media storage/dispensing unit 500 described in relation to FIG. 18A.

The injection data management system 660a may include a user interface 662 of any appropriate type. This user interface 662 may include one or more user input devices 662a of any appropriate type (e.g., a keyboard, a touch-screen, a graphical user interface), one or more displays 662b of any appropriate type, or both. The injection data management system 660a may use a data conversion or translation module 664 having one or more data conversion or translation units (e.g., the data translation module 664 may include multiple data conversion units, including in accordance with the architectures illustrated in FIGS. 19 and 20 which each have three data conversion units), and with each data conversion unit converting data (e.g., received from the contrast media injector system 602) from one CAN-compliant format to a different format. At least one data conversion unit for the data conversion module 664 of the injection data management system 660a may be configured to convert data (e.g., received from the contrast media injector system 602) from a CAN-compliant format to a non-CAN-compliant format (e.g., an HL-7-compliant format; a MOM-compliant format). Any data conversion function provided by the injection data management system 660a may utilize one or more processors 620 of any appropriate type and disposed in any appropriate architecture (e.g., each data conversion unit of the data conversion module 664 may use one or more processors 620).

The injection data management system 660a may use a data processing module or unit 666. The data processing unit 666 and each data conversion unit of the data conversion module 664 may be arranged in any appropriate architecture (e.g., each data conversion unit of the data conversion module 664 and the data processing unit 666 could be part of a common unit (e.g., located within the same outer shell); one or more data conversion units of the data conversion module 664 may be disposed in a common unit (e.g., located within the same outer shell), one or more data conversion units of the data conversion module 664 may each be disposed in a separate unit, or both; the data processing unit 666 could be disposed in a separate unit from each of the data conversion units of the data conversion module 664; the data processing unit 666 and at least one data conversion unit of the data conversion module 664 could be disposed in a common unit (e.g., located within the same outer shell), and one or more data conversion units of the data conversion module 664 could be disposed in one or more separate units).

One or more processors 620 may be used by the data processing unit 666 in relation to: processing requests for contrast administration data received by the injection data management system 660a from one or more medical sub-systems 735; transmitting data from the injection data management system 660a to one or more medical sub-systems 735 (e.g., in response to a request for data from one or more medical system 735; in an automated or programmed manner; other than in response to a request for data from one or more medical system 735; at the initiation of the contrast media injector system 602 itself and/or the injection data management system 660a itself); storing information on the injection data management system 660a (e.g., within its data storage system 622, discussed below); or any combination thereof. Multiple processors 620 may be arranged in any appropriate processing architecture for purposes of the injection data management system 660a.

One or more processors 620 could be shared between the data processing unit 666 and one or more data conversion units of the data conversion module 664, including when the data processing unit 666 and one or more data conversion units of the data conversion module 664 are disposed in a common unit (e.g., located within the same outer shell). The data processing unit 666 could have one or more dedicated processors 620, one or more data conversion units of the data conversion module 664 could have one or more dedicated processors 620, or both. A configuration could be utilized where each processor 620 used by the data processing unit 666 is unavailable for use by any one or more data conversion units of the data conversion module 664 of the injection data management system 660a. One or more data conversion units of the data conversion module 664 of the injection data management system 660a could share one or more processors 620, one or more data conversion units of the data conversion module 664 of the injection data management system 660a could have one or more dedicated processors 620, or both. Any appropriate processor architecture could be used in relation to the injection data management system 660a in relation to the data processing module 666 and each data conversion unit of the data conversion module 664.

Software 667 of any appropriate type/format may be used by the injection data management system 660a to translate data from one format to another, to receive input from one or more medical sub-systems 735, to transmit data to one or more medical sub-systems 735, to store data on the injection data management system 660a, and/or in relation to any other functionality of the injection data management system 660a. Updates to the software 667 may be downloaded to the injection data management system 660a through one or more communication ports 648 of any appropriate type (e.g., the injection data management system 660a may include a communication port 648 in the form of an Ethernet port that would allow software updates to be downloaded to the injection data management system 660a over the Internet).

The injection data management system 660a may utilize a data storage system 622 of any appropriate type (e.g., hard drive, solid state memory, flash memory, non-volatile ram, any appropriate memory). The data storage system 622 may be arranged in any appropriate data storage architecture. Generally, contrast administration data may be transmitted to the injection data management system 660a and stored on its data storage system 622. The contrast administration data that is provided to the injection data management system 660a may be of any appropriate type (e.g., predefined) and may be provided to the injection data management system 660a on any appropriate basis (e.g., on a real-time basis; intermittently; on a batch-type basis, for instance at the end of a programmed injection). In one embodiment, an injection history 649 includes data relating to a particular injection of a particular patient (e.g., the execution of an injection protocol or a programmed injection by the contrast media injector system 602 for a particular patient).

Multiple injection histories 649 may be stored by the injection data management system 660*a*. Any appropriate number of multiple injection histories 649 (injection histories 649*a*, 649*b*, and 649*c* being shown for the illustrated embodiment) may be stored on the injection data management system 660*a*. In one embodiment, a predetermined number of the most recent injection histories 649 (e.g., the most recent 24 injection histories 649, although any appropriate number of injection histories 649 may be stored on the injection data management system 660*a* at a given time) may be stored by the injection data management system 660*a*. A single injection history 649 could be communicated to one or more medical sub-systems 735 from the injection data management system 660*a*. Multiple injection histories 649 could be collectively sent to one or more medical sub-systems 735 from the injection data management system 660*a*. Any appropriate number of multiple injection histories 649 (and any appropriate manner of selecting multiple injection histories 649) may be sent in any appropriate manner to one or more medical sub-systems 735 through the injection data management system 660*a*. In one embodiment, a batch of multiple injection histories 649 are sent to one or more medical sub-systems 735 from the injection data management system 660*a*.

The injection data management system 660*a* may have its own user interface 662 in accordance with FIG. 18B. One or more of the remote console 650 (for a contrast media injector system 602), one or more workstations 730, any user interface incorporated by or otherwise associated with the contrast media injector system 602 (e.g., a keyboard or touchscreen display on the powerhead 604), and/or any other user interface of the medical system 600 could provide a user interface/input function for the injection data management system 660*a*. More than one user interface could be used for providing user input to the injection data management system 660*a* (e.g., a user interface 662 incorporated by the injection data management system 660*a*, along with one or more of the above-noted types of devices). User input to the injection data management system 660*a* could also be provided entirely through an external device that is operatively connected with the injection data management system 660*a*, but that is actually part of another sub-system 735 of the medical system 600.

Any appropriate architecture may be used by the injection data management system 660*a*. All of the functionality of the injection data management system 660*a* could be incorporated into a single physical unit. A distributed architecture could be used for the injection data management system 660*a* as well. For instance, the data conversion functionality could be provided by one or more separate units, and the data processing/data storage/user interface functionalities could be provided by a separate unit that is operatively connected with one or more data conversion units. Such a representative configuration is illustrated in FIG. 18C in the form of an injection data management module or system 660*d*. Although the injection data management system 660*d* is shown in relation to servicing multiple contrast media injector systems 602 (e.g., contrast media injector system 602*a* and contrast media injector system 602*b*), the injection data management system 660*d* could be dedicated to a single contrast media injector system 602. In any case, the injection data management system 660*d* includes at least one data conversion or translation module 664 (which in turn has one or more data conversion or translation units 665), a separate data processing unit 666, and at least one user interface 662 (that can communicate with both the data conversion module 664 and the data processing unit 666). Each data conversion module 664 could be dedicated to a single contrast media injector system 602. A single data conversion module 664 could be dedicated to any appropriate number of multiple contrast media injector systems 602 as shown in FIG. 18C. In any case, data may be transmitted between each data conversion module 664 and the data processing unit 666 (e.g., using corresponding communication ports 648). A user interface 662 may communicate with the data processing unit 666 and at least one data conversion module 664, and may be incorporated in any appropriate manner (e.g., separate from each of the data processing unit 666 and each data conversion module 664; as part of the data processing unit 666).

Figure 19:
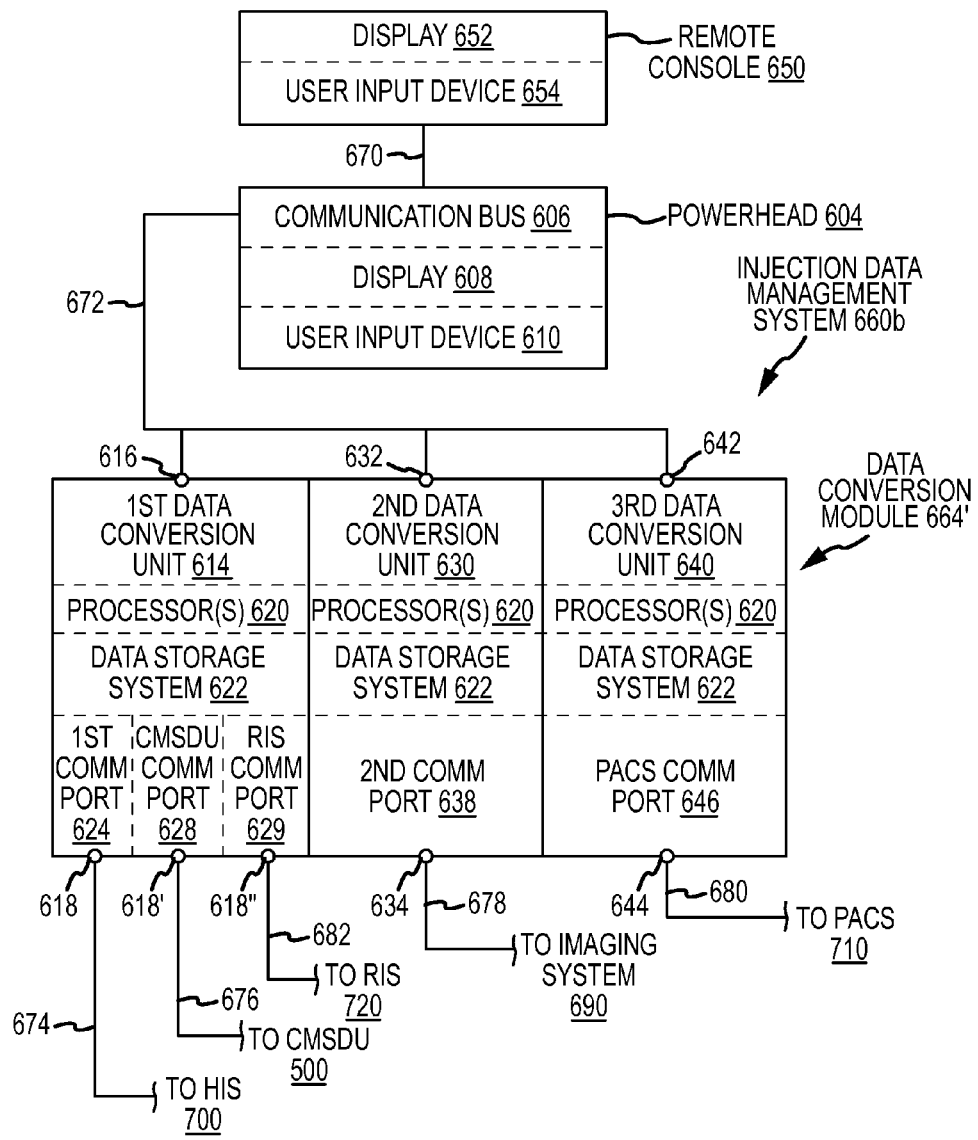
FIG. 19 is a functional schematic of an embodiment of a data translation or conversion module having multiple data conversion units.
Figure 20:
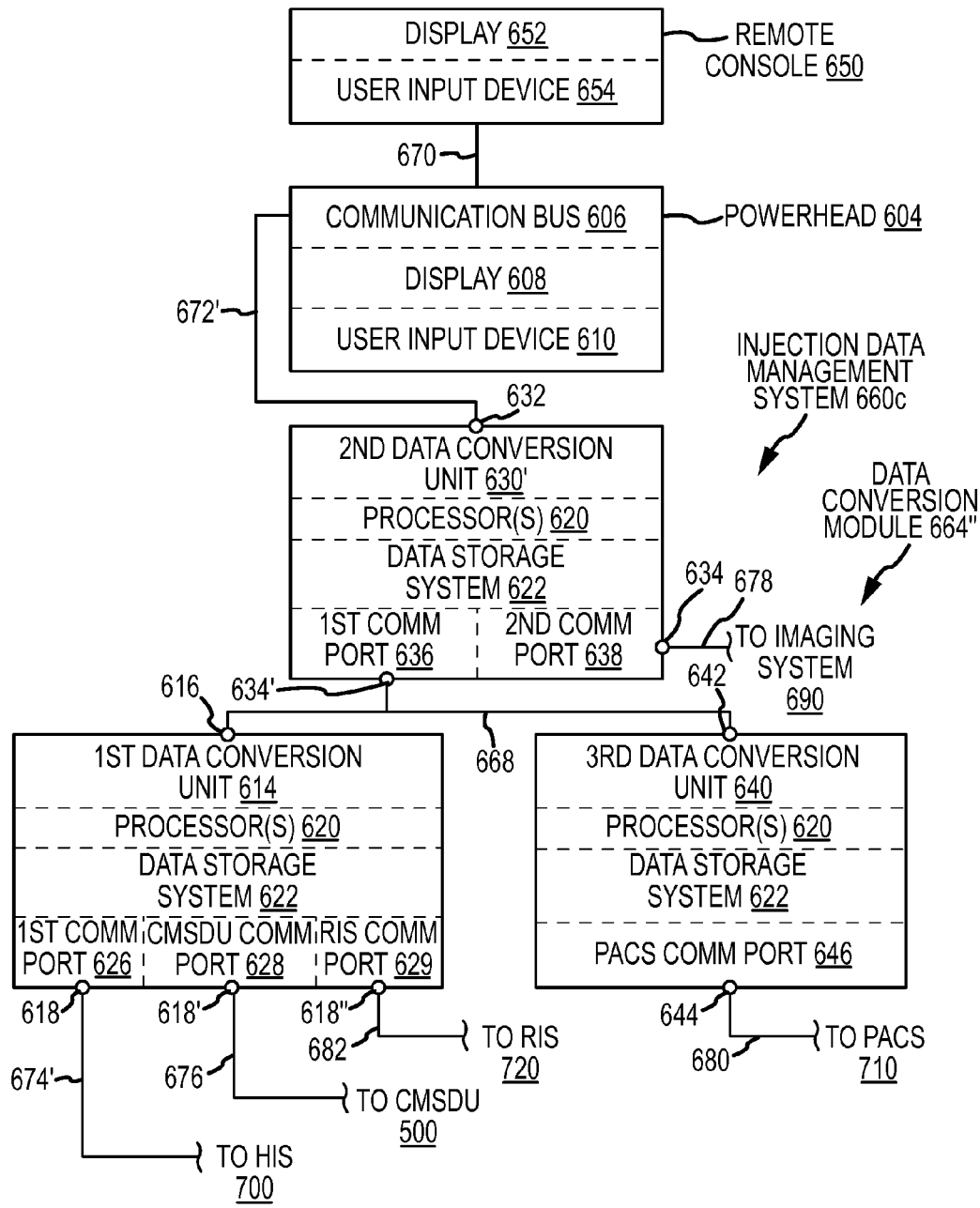
FIG. 20 is a functional schematic of an embodiment of a data translation or conversion module having multiple data conversion units.

Each data conversion module 664 of the injection data management system 660*d* may include multiple data conversion units 665, including in accordance with the architectures illustrated in FIGS. 19 and 20 that each include three data conversion or translation units. In one embodiment, the injection data management system 660*d* includes a single data processing unit 666, a single data conversion module 664 (each data conversion module 664 servicing multiple contrast media injector systems 602), and at least one user interface 662. In one embodiment, the injection data management system 660*d* includes a single data processing unit 666, a single data conversion module 664 that is dedicated to a single contrast media injector system 602, and at least one user interface 662. In one embodiment, the injection data management system 660*d* includes a single data processing unit 666, a plurality of data translation modules 664 (each data translation module 664 being dedicated to a single contrast media injector system 602), and at least one user interface 662 for each data conversion module 664 (including where a given data conversion module 664 has a dedicated user interface 662 that can also communicate with the data processing unit 666).

FIG. 19 presents a functional schematic or block diagram of one configuration for at least part of the injection data management system 660 for the medical system 600 of FIG. 18A (e.g., a data conversion module 664'), and that is identified by reference numeral 660*b* in FIG. 19. Initially, the injection data management system 660*b* may incorporate any one or more of the features of the injection data management system 660*a* discussed above in relation to FIG. 18B. In accordance with the foregoing, the injection head or powerhead 604 of the contrast media injector system 602 may include a display 608 and at least one user input device 610 (e.g., a keyboard; configuring the display 608 to have touch screen functionality).

The contrast media injector system 602 may utilize what may be characterized as an injector communication bus 606 for transmitting data throughout the contrast media injector system 602. The injector communication bus 606 may utilize a first CAN-compliant format for data communications, such as a CAN 2.0A. Although the injector communication bus 606 is shown as being located within the powerhead 604, the injector communication bus 606 may extend throughout the contrast media injector system 602. For instance, the communication link 670 between the remote console 650 and the powerhead 604, as well as the communication link 672 between the powerhead 604 and the injection data management system 660*b*, may be considered as part of the injector communication bus 606 as well.

The illustrated portion of the injection data management system 660*b* of the FIG. 19 embodiment (e.g., a data conversion or translation module 664') may be in the form of or as a component of a variation of the powerpack 246 discussed above in relation to the power injector 240 of FIG. 1B (e.g., by its inclusion of a first data conversion or translation unit 614 and a third data conversion or translation unit 640). At least part of the injection data management system 660*b* may be integrated other than through the powerpack 246 (e.g., part or the entirety of the injection data management system 660*b* could be separate from the powerpack 246). A data conversion module 664' in the form of a single/common unit could also be physically separate from the powerpack 246 of the type discussed above in relation to the power injector 240 of FIG. 1B. A distributed architecture could also be used by the data conversion module 664' (e.g., the data conversion module 664' may be implemented using two or more units that are physically separate from one another, but that are operatively connected in the manner shown in FIG. 19). The injection data management system 660*b* may use any appropriate architecture. In any case, the powerhead 604 of the contrast media injector system 602 communicates with the data conversion module 664' of the injection data management system 660*b* over the noted communication link 672.

In the illustrated embodiment, the data conversion module 664' includes three different data conversion or translation units. Any appropriate number of data conversion units may be utilized by the data conversion module 664'. The data conversion module 664' includes a first data conversion or translation unit 614 that is operatively interconnected with the injector communication bus 606 of the contrast media injector system 602 (e.g., via the communication link 672, which may actually be part of the injector communication bus 606). Generally, the first data conversion unit 614 converts contrast administration data from a first CAN-compliant format (e.g., CAN 2.0A) into an HL-7-compliant format (e.g., for provision to the HIS 700 or any other medical sub-system 735 that requires data in an HL-7 compliant format). This may be undertaken in any appropriate manner.

The first data conversion unit 614 may utilize one or more processors 620 of any appropriate type. One or more processors 620 may be used for the data conversion provided by the first data conversion unit 614. One or more processors 620 may be used by the injection data management system 660*b* to process requests for contrast administration data received by the injection data management system 660*b* from the HIS 700 or any other medical sub-system 735. Multiple processors 620 may be arranged in any appropriate processing architecture for purposes of the first data conversion unit 614.

The first data conversion unit 614 may utilize the data storage system 622 of the injection data management system 660*b*, which again may be of any appropriate type/configuration (e.g., hard drive, solid state memory, flash memory, non-volatile ram). The data storage system 622 may be arranged in any appropriate data storage architecture and may be distributed in any appropriate fashion. Generally, contrast administration data may be transmitted to the first data conversion unit 614 and stored on the data storage system 622 of the injection data management system 660*b* (including "on-board" the data conversion module 664', for instance in accordance with the data conversion module 664 illustrated in FIG. 18C). The contrast administration data that is provided to the first data conversion unit 614 may be of any appropriate type (e.g., predefined) and may be provided to the first data conversion unit 614 on any appropriate basis (e.g., on a real-time basis; intermittently; on a batch-type basis, for instance at the end of a programmed injection).

The data conversion module 664' may be characterized as including a first communication port 624, a CMSDU communication port 628, and a RIS communication port 629. The first communication port 624 of the data conversion module 664' is operatively interconnected with the HIS 700 through the communication link 674. The CMSDU communication port 628 of the data conversion module 664' is operatively interconnected with the contrast media storage/dispensing unit 500 through the communication link 676. The RIS communication port 629 of the data conversion module 664' is operatively interconnected with the RIS 720 through the communication link 682. The data conversion module 664' could have a single communication port for outputting data in an HL-7-compliant format in accordance with the foregoing (and which could be directed to one or more medical sub-systems 735 that require data in an HL-7-compliant format).

The data conversion module 664' may be characterized as including a first communication node 616 associated with the injector communication bus 606, a second communication node 618 associated with the first communication port 624, a communication node 618' associated with the CMSDU communication port 628, and a communication node 618" associated with the RIS communication port 629. In the illustrated embodiment, the HIS 700 is able to send communications (e.g., a request for contrast administration data) to the data conversion module 664' through the second communication node 618 and the first communication port 624. In one embodiment, the data conversion module 664' is configured so as to not allow communications from the HIS 700 to proceed past the first communication node 616 to the injector communication bus 606 of the contrast media injector system 602. The first communication port 624 of the data conversion module 664' may therefore be characterized as being of a pull-type configuration (e.g., contrast administration data may be "pulled" from the injection data management system 660*b* by the HIS 700). Stated another way, the injection data management system 660*b* may be configured to transmit contrast administration data to the HIS 700 only in response to a request for contrast administration data submitted by the HIS 700 to the injection data management system 660*b*—the contrast media injector system 602 does not automatically "push" contrast administration data to the HIS 700, through the data conversion module 664', in this type of configuration. One or more processors 620 of the injection data management system 660*b* may receive such a request for contrast administration data from the HIS 700, may retrieve the relevant contrast administration data from the data storage system 622 of the injection data management system 660*b*, and may transmit (or allow the transmission of) the retrieved contrast administration data to the HIS 700 through the first communication port 624 of the data conversion module 664' and communication link 674. In other embodiments, the injection data management system 660*b* may allow for two-way communication between the contrast media injector system 602 and the HIS 700.

In one embodiment, the injection data management system 660*b* is configured to send communications to the HIS 700 without first requiring a request or prompt from the HIS 700. In this regard, the first communication port 624 of the data conversion module 664' may be characterized as being of a push-type configuration (e.g., contrast administration data may be "pushed" from the injection data management module 660*b* to the HIS 700 on any appropriate basis). Stated another way, the injection data management module 660*b* may be configured to transmit contrast administration data to the HIS 700 without first requiring a request for contrast administration data from the HIS 700 (e.g., the contrast media injector system 602 may be configured to automatically "push" contrast administration data to the HIS 700, through the data conversion module 664',). The contrast media injector system 602 may be configured to transmit contrast administration data to the HIS 700, through the data conversion module 664', on an automated or programmed basis, in response to user input provided to the injection data management system 660*b*, or both. The injection data management system 660*b* may also be configured for push/pull communications in relation to the HIS 700—the injection data management system 660*b* may transmit data to the HIS 700 in response to a request from the HIS 700, and the injection data management system 660*b* may also be configured to transmit data to the HIS 700 on a programmed or automated basis.

The injection data management system 660*b* includes a second data conversion or translation unit 630 that is operatively interconnected with the injector communication bus 606 of the contrast media injector system 602 (e.g., via the communication link 672, which may actually be part of the injector communication bus 606). Generally, the second data conversion unit 630 converts contrast administration data between a first CAN-compliant format (e.g., CAN 2.0A; associated with the injector communication bus 606 of the contrast media injector system 602) and a second CAN-compliant format (e.g., CiA 425; associated with the imaging system 690). This may be undertaken in any appropriate manner. The second data conversion unit 630 may be configured to provide for a conversion of commands that may be sent between the powerhead 604/remote console 650 of the contrast media injector system 602 and the imaging system 690.

The second data conversion unit 630 may utilize one or more processors 620 of any appropriate type. One or more processors 620 may be used for the data conversion provided by the second data conversion unit 630. One or more processors 620 may be used to process requests for data (e.g., contrast administration data) received by the injection data management system 660*b* from the imaging system 690 (or any other medical sub-system 735 that requires data in the format provided by the second data conversion unit 630). Multiple processors 620 may be arranged in any appropriate processing architecture for purposes of the second data conversion unit 630.

The second data conversion unit 630 may utilize the data storage system 622 of the injection data management system 660*b*. The data storage system 622 may be arranged in any appropriate data storage architecture and may be distributed in any appropriate fashion. Generally, data may be transmitted to the second data conversion unit 630 and stored on the data storage system 622 of the injection data management system 660*b* for use in conjunction with communications between the contrast media injector system 602 and the imaging system 690 or any other medical sub-system 735 (including "on-board" the data conversion module 664', for instance in accordance with the data conversion module 664 illustrated in FIG. 18C).

The data conversion module 664' may be characterized as including a second communication port 638. The second communication port 638 of the data conversion module 664' is operatively interconnected with the imaging system 690 through the communication link 678. The data conversion module 664' may be characterized as including a first communication node 632 associated with the injector communication bus 606, and a second communication node 634 associated with the second communication port 638. In one embodiment, the injection data management system 660*b* is configured to allow two-way communications between the contrast media injector system 602 and the imaging system 690. For example, communications may be sent by the imaging system 690 to the contrast media injector system 602 (e.g., the powerhead 604 thereof) through the injection data management system 660*b* (where the communication is converted from one CAN-compliant format (e.g., CiA 425) to another CAN-compliant format (e.g., CAN 2.0A)) and communication link 672. Similarly, communications may be sent from the contrast media injector system 602 (e.g., the powerhead 604 thereof) to the imaging system 690 through the communication link 672, second data conversion unit 630 (where the communication is converted from one CAN-compliant format (e.g., CAN 2.0A) to another CAN-compliant format (e.g., CiA 425)) and communication link 678. It should be appreciated that the second data conversion unit 630 could provide data to any other medical sub-system 735 that requires data in the format provided by the second data conversion unit 630.

The injection data management system 660*b* may include a third data conversion or translation unit 640 that is operatively interconnected with the injector communication bus 606 of the contrast media injector system 602 (e.g., via the communication link 672, which may actually be part of the injector communication bus 606). Generally, the third data conversion unit 640 converts data (e.g., contrast administration data) from a first CAN-compliant format (e.g., CAN 2.0A; associated with the injector communication bus 606 of the contrast media injector system 602) to a PACS-compliant and/or a DICOM-compliant forma. This may be undertaken in any appropriate manner. It should be appreciated that the third data conversion unit 640 could provide data to any medical sub-system 735 that requires data in the format provided by the third data conversion unit 640.

The third data conversion unit 640 may utilize one or more processors 620 of any appropriate type. One or more processors 620 may be used for the data conversion provided by the third data conversion unit 640. One or more processors 620 may be used by the injection data management system 660*b* to process requests for contrast administration data received by the injection data management system 660*b* from the PACS 710 or any other medical sub-system 735. Multiple processors 620 may be arranged in any appropriate processing architecture for purposes of the third data conversion unit 640.

The third data conversion unit 640 may utilize the data storage system 622 of the injection data management unit 660*b*. The data storage system 622 may be arranged in any appropriate data storage architecture and may be distributed in any appropriate fashion. Generally, data may be transmitted to the third data conversion unit 640 and stored on the data storage system 622 for use in conjunction with communications between the contrast media injector system 602 and the PACS 710 or any other medical sub-system 735 (including "on-board" the data conversion module 664', for instance in accordance with the data conversion module 664 illustrated in FIG. 18C).

The data conversion module 664' may be characterized as including a PACS communication port 646. The PACS communication port 646 of the data conversion module 664' is operatively interconnected with the PACS 710 through the communication link 680. The data conversion module 664' may be characterized as including a first communication node 642 associated with the injector communication bus 606, and a second communication node 644 associated with the PACS communication port 646. In one embodiment, the injection data management system 660b is configured to allow two-way communications between the contrast media injector system 602 and the PACS 710. For example, communications may be sent by the PACS 710 to the contrast media injector system 602 (e.g., the powerhead 604 thereof) through the data conversion module 664' (where the communication is converted from a PACS-compliant format (e.g., DICOM) to a CAN-compliant format (e.g., CAN 2.0A)) and communication link 680. Similarly, communications may be sent from the contrast media injector system 602 (e.g., the powerhead 604 thereof) to the PACS 710 through the communication link 672, third data conversion unit 640 (where the communication is converted from a CAN-compliant format (e.g., CAN 2.0A) to a PACS-compliant format (e.g., DICOM)) and communication link 680.

The injection data management system 660b may be of a "pull-type" configuration, as described herein, for communicating with the PACS 710 (e.g., where the injection data management system 660b transmits data to the PACS 710 only in response to a request from the PACS 710). The injection data management system 660b may be of a "push-type" configuration, as described herein, for communicating with the PACS 710 (e.g., where the injection data management system 660b transmits data to the PACS 710 other than in response to a request from the PACS 710; where the contrast media injector system 602 and/or the injection data management system 660b are configured to transmit data to the PACS 710 on an automated or programmed basis). The injection data management system 660b may be of a "push/pull-type" configuration, as described herein, for communicating with the PACS 710. Data from the injection data management system 660b may also be transmitted in response to user input to the injection data management system 660b.

The first data conversion unit 614, second data conversion unit 630, and third data conversion unit 640 may be characterized as being interconnected in parallel (as opposed to being in series) in the FIG. 19 configuration. Communications from the injector communication bus 606 may be simultaneously directed to each of the first data conversion unit 614, second data conversion unit 630, and third data conversion unit 640. The first data conversion unit 614, second data conversion unit 630, and third data conversion unit 640 may be characterized as being part of a common structure or as being disposed within a common housing. The first data conversion unit 614, the second data conversion unit 630, and the third data conversion unit 640 may be incorporated by the injection data management system 660b in a single/common unit or may be distributed in any appropriate manner (e.g., in two or more units that are physically separate from one another). Again, each of the first data conversion unit 614, second data conversion unit 630, and third data conversion unit 640 may provide data to one or more medical sub-systems 735 that require data of the type provided by the first data conversion unit 614, second data conversion unit 630, and third data conversion unit 640.

FIG. 20 presents a functional schematic or block diagram of another configuration for the injection data management system 660 for use with the contrast media injector system 602 of the medical system 600 of FIG. 18A (e.g., a data conversion or translation module 664"), and that is identified by reference numeral 660c in FIG. 20. Corresponding components between the embodiments of FIGS. 19 and 20 are identified by the same reference numeral. Those corresponding components that differ in at least some respect are identified by a "single prime" or "double prime" designation in FIG. 20.

The injection data management system 660c of FIG. 20 (more specifically its data conversion module 664") utilizes each of the above-discussed first data conversion unit 614 and third data conversion unit 640, along with a modified second data conversion unit 630'. Moreover, the injection data management system 660c of FIG. 20 utilizes a different arrangement of these components. Generally, the second data conversion unit 630' is connected in series with the first data conversion unit 614, and is also connected in series with the third data conversion unit 640. As in the case of the FIG. 19 embodiment, the first data conversion unit 614 and third data conversion unit 640 of the injection data management system 660c may be connected in parallel and as illustrated in FIG. 20.

The first data conversion unit 614, the second data conversion unit 630', and the third data conversion unit 640 may be incorporated by the injection data management system 660c in a single/common unit. For instance, the data conversion module 664" may be in the form of or as a component of a variation of the powerpack 246 discussed above in relation to the power injector 240 of FIG. 1B (e.g., by its inclusion of a first data conversion unit 614 and a third data conversion unit 640). A data conversion module 664" in the form of a single/common unit could also be physically separate from the powerpack 246 of the type discussed above in relation to the power injector 240 of FIG. 1B. A distributed architecture could also be used by the data conversion module 664" (e.g., the data conversion module 664" may be implemented using two or more units that are physically separate from one another, but that are operatively connected in the manner shown in FIG. 20). Any appropriate architecture may be used by the injection data management system 660c. The injection data management system 660c may also incorporate any one or more of the features of the injection data management system 660a discussed above in relation to FIG. 18B.

The second data conversion unit 630' converts contrast administration data between a first CAN-compliant format (e.g., CAN 2.0A; associated with the injector communication bus 606 of the contrast media injector system 602) and a second CAN-compliant format (e.g., CiA 425; associated with the imaging system 690). This data conversion may be undertaken in any appropriate manner. However, in the FIG. 20 configuration, the injector communication bus 606 only communicates directly with the second data conversion unit 630' (and therefore the communication link 672' between the injection data management system 660c and the powerhead 604 uses the noted "single prime" designation—the communication link 672' does not extend directly to either the first data conversion unit 614 or the third data conversion unit 640 in the FIG. 20 configuration).

The contrast media injector system 602 and imaging system 690 continue to communicate through the second data conversion unit 630' in the manner discussed above for the FIG. 19 embodiment. However, in order to allow the injector communication bus 606 to also communicate with each of the first data conversion unit 614 and the third data conversion unit 640, the second data conversion unit 630' includes a first communication port 636 and a communication link 668. A second communication node 634' may be characterized as being associated with the first communication port 636 of the second data conversion unit 630'.

The configuration and functionality of each of the first data conversion unit 614 and the third data conversion unit 640 in the FIG. 20 embodiment remains in accordance with the FIG. 19 embodiment. However, contrast administration data may be transmitted from the injector communication bus 606 through the first communication port 636 of the injector data management system 660c (where a conversion from one CAN-compliant format to another CAN-compliant format occurs), and then may be transmitted over the communication link 668 to one or both of the first data conversion unit 614 and the third data conversion unit 640 in the FIG. 20 configuration (where further conversions are undertaken in accordance with the foregoing).

Figure 21:
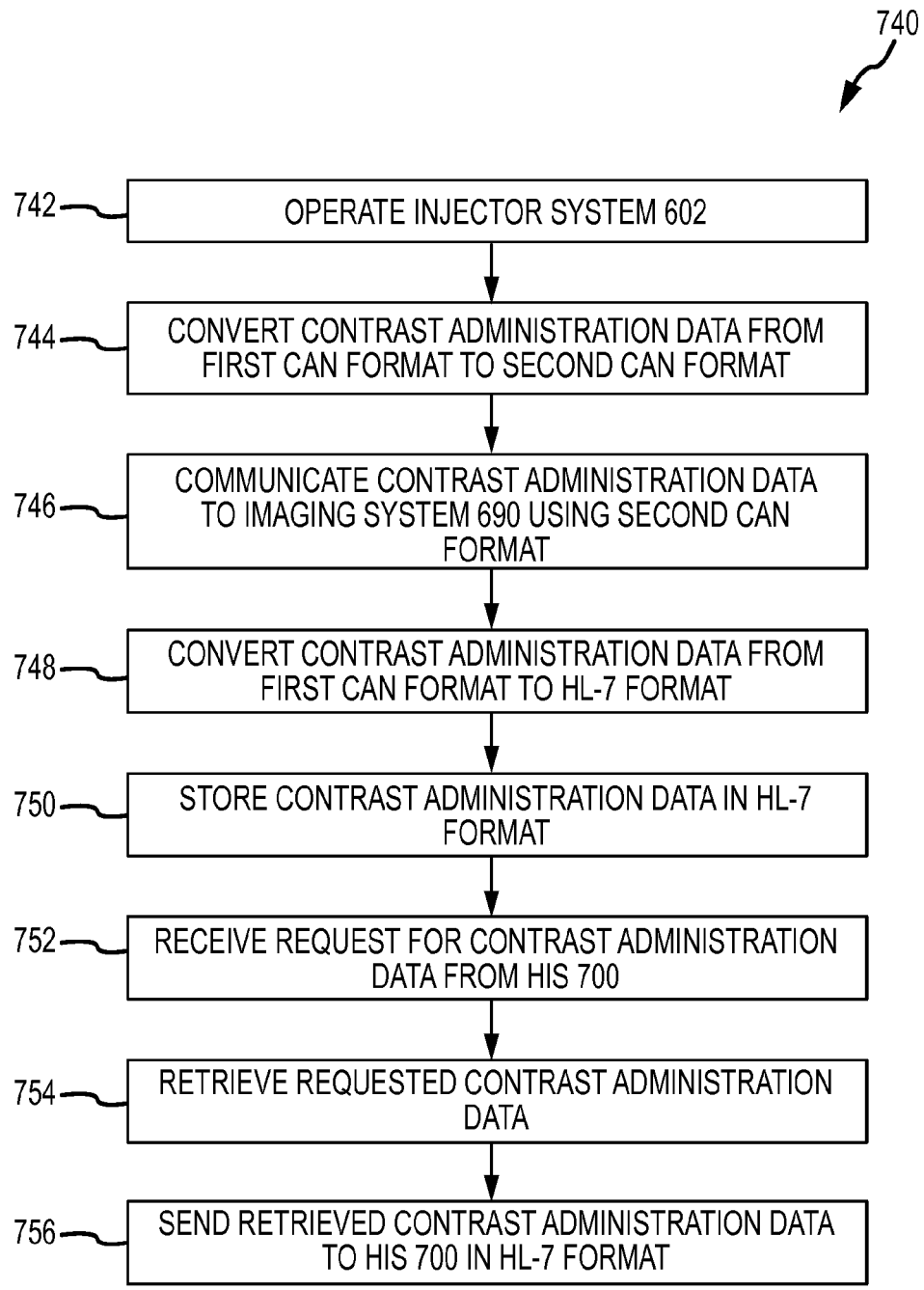
FIG. 21 is one embodiment of a data management protocol for the injection data management system of FIG. 19.

One embodiment of a data management protocol 740 is presented in FIG. 21, and may be utilized by the injection data management system 660b of FIG. 19. The contrast media injector system 602 may be operated (step 742), for instance to execute a programmed injection where contrast media is injected into or administered to a patient (e.g., on at least somewhat of an automated basis) by the contrast media injector system 602. Contrast administration data (e.g., data that relates in at least some manner to the execution of step 742) may be converted from a first CAN-compliant format (e.g., CAN 2.0A) to a second CAN-compliant format (e.g., CiA 425) in accordance with step 744 (e.g., using the second data conversion unit 630 of FIG. 19). This converted data (step 744) may be sent or transmitted to the imaging system 690 (e.g., via the communication link 678; to any other medical sub-system 735) at any appropriate time and in any appropriate manner (step 746).

Contrast administration data (e.g., data on or pertaining to the contrast media that is used in the execution of step 742, for instance contrast-related data stored or to be stored in a data record 782 of a data structure 780, as discussed below in relation to FIGS. 23A-D, such as one or more of the manufacturer, manufacturing date, lot number, NDC code, composition, concentration, main functional ingredient(s), and expiration date of the contrast media that was/is to be used in the execution of step 742; contrast media volumes dispensed and/or administered in relation to the execution of step 742; the flow rate(s) used in the administration of the contrast media) may be converted from the noted first CAN-compliant format to an HL-7-compliant format pursuant to step 748 of the data management protocol 740 (e.g., using the first data conversion unit 614 of FIG. 19). The conversions associated with steps 744 (e.g., CAN 2.0A to CiA 425) and 748 (e.g., CAN 2.0A to HL-7) may be executed in any appropriate order, including simultaneously or where the execution of these steps at least partially overlap. The converted data from step 748 (HL-7-compliant format) may be stored by the injection data management system 660b in the HL-7-compliant format and in accordance with step 750 (e.g., stored by the data storage system 622 of the injection data management system 660b).

The injection data management system 660b may receive a request for contrast administration data from the HIS 700 or any other medical sub-system 735 (step 752) in the execution of the data management protocol 740. One or more processors 620 of the injection data management system 660b may assess this request. The requested contrast administration data (step 752, which has already been converted from a CAN-compliant format to an HL-7-compliant format) may be retrieved pursuant to step 754 (e.g., from the data storage system 622 of the injection data management system 660b using one or more one or more processors 620). The retrieved contrast administration data (step 754) may then be sent or transmitted to the HIS 700 (or any other medical sub-system 735) pursuant to step 756 (e.g., via communication link 674). In a "push-type" configuration for the injection data management system 660b, step 752 of the protocol 740 may not be required. It should be appreciated that step 748 of the protocol 740 could be directed to converting CAN-compliant data into PACS-compliant data or DICOM-compliant data, and that this data could be transmitted from the injection data management system 660b (e.g., to PACS 710 or any other medical sub-system 735) pursuant to step 756.

Figure 22:
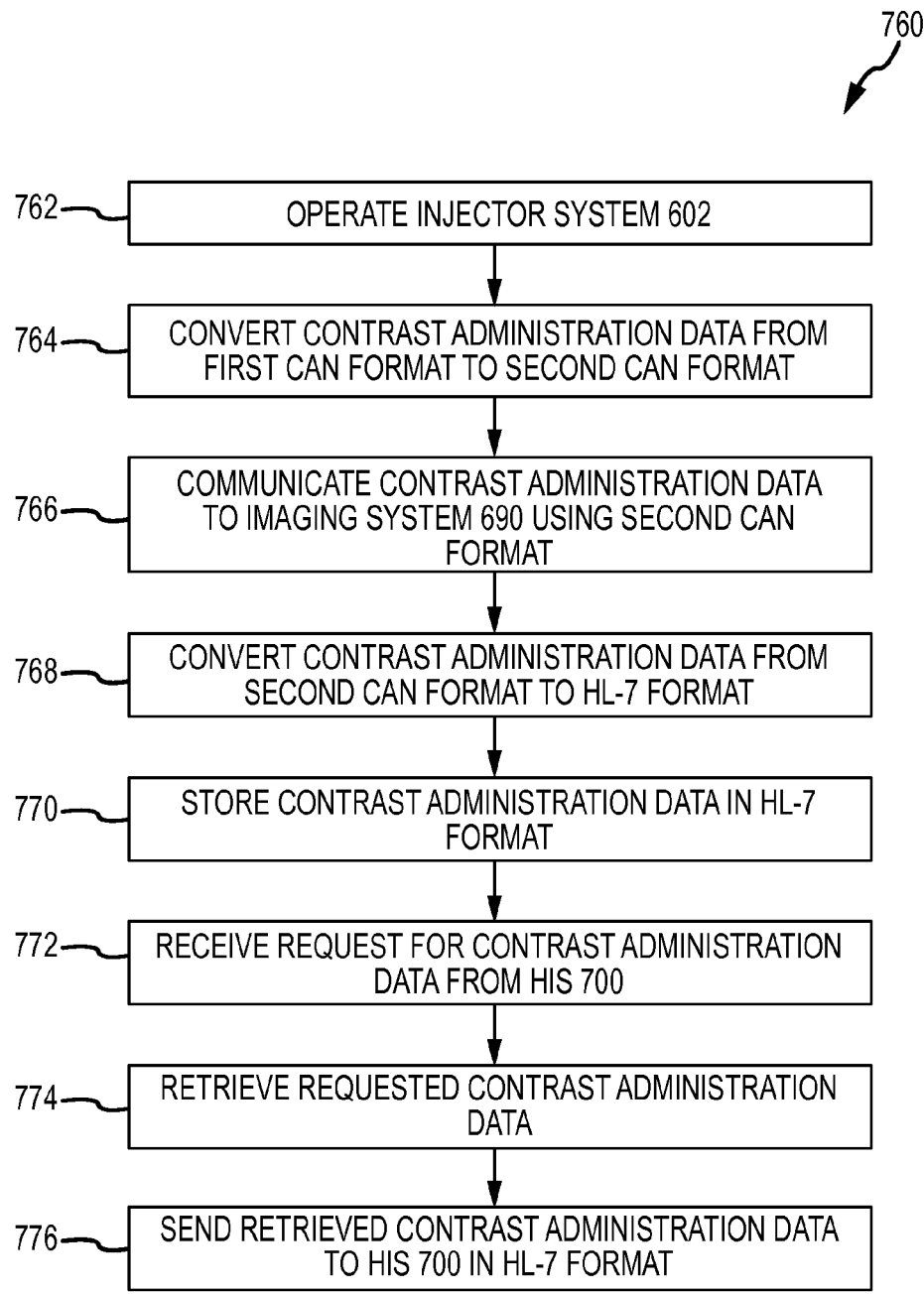
FIG. 22 is one embodiment of a data management protocol for the injection data management system of FIG. 20.

One embodiment of a data management protocol 760 is presented in FIG. 22, and may be utilized by the injection data management system 660c of FIG. 20. The contrast media injector system 602 may be operated (step 762), for instance to execute a programmed injection where contrast media is injected into or administered to a patient (e.g., on at least somewhat of an automated basis) by the contrast media injector system 602. Contrast administration data (e.g., data that relates in at least some manner to the execution of step 762) may be converted from a first CAN-compliant format (e.g., CAN 2.0A) to a second CAN-compliant format (e.g., CiA 425) in accordance with step 764 (e.g., using the second data conversion unit 630' of FIG. 20). This converted data (step 764) may be sent or transmitted to the imaging system 690 or any other medical sub-system 735 (e.g., via the communication link 678) at any appropriate time and in any appropriate manner (step 766).

Contrast administration data (e.g., data that relates in at least some manner to the execution of step 762) may be converted from the noted second CAN-compliant format to an HL-7-compliant format pursuant to step 768 of the data management protocol 760 (e.g., by transmitting CAN-compliant data from second data conversion unit 630' to the first data conversion unit 614, where the first data conversion unit 614 converts this CAN-compliant data to HL-7-compliant data). The conversions associated with steps 764 (e.g., CAN 2.0A to CiA 425) and 748 (e.g., CiA 425 to HL-7) are executed in series in the case of the data management protocol 760, with step 764 needing to be executed prior to step 768. The converted data from step 768 (HL-7-compliant format) may be stored by the injection data management system 660c in the HL-7-compliant format and in accordance with step 770 (e.g., stored by the data storage system 622 of the injection data management system 660c).

The injection data management system 660c may receive a request for contrast administration data from the HIS 700 or any other medical sub-system 735 (step 772) in the execution of the data management protocol 760. One or more processors 620 of the injection data management system 660c may assess this request. The requested contrast administration data (step 772, which has already been converted from a CAN-compliant format to an HL-7-compliant format) may be retrieved pursuant to step 774 (e.g., from the data storage system 622 of the injection data management system 660c, using one or more one or more processors 620 of the injection data management system 660c). The retrieved contrast administration data (step 774) may then be sent or transmitted to the HIS 700 or any other medical sub-system 735 pursuant to step 776 (e.g., via communication link 674). In a "push-type" configuration for the injection data management system 660c, step 772 of the protocol 760 may not be required. It should be appreciated that step 768 of the protocol 760 could be directed to converting CAN-compliant data into PACS-compliant data or DICOM-compliant data, and that this data could be transmitted from the injection data management system 660c (e.g., to PACS 710 or any other medical sub-system 735) pursuant to step 776.

The medical system 600 of FIG. 18A may store various data relating to imaging and/or contrast media injection/administration operations. One embodiment of a data structure for storing data regarding the medical system 600 is presented in FIGS. 23A-D and is identified by reference numeral 780. The data structure 780 includes a plurality of data records 782 (24 in the illustrated embodiment). Any appropriate number of records 782 may be stored in the data structure 780. Each record 782 may also be referred to as an individual injection history 649 (e.g., discussed above in relation to FIG. 18B) or as an individual DMS patient record 2420 (discussed below in relation to FIGS. 41B and 41C). Data may be stored in the data structure 780 using any appropriate database management software. Data stored in the data structure 780 may be accessed in any appropriate manner using any appropriate report writing software. In one embodiment, the data structure 780 is incorporated by any of the injection data management systems addressed herein.

The following fields may be used to define a given data record 782 of the data structure 780, and data in these various fields may be linked in any appropriate manner to define the corresponding data record 782: a procedure date field 784 (e.g., the date of a particular imaging operation (using the imaging system 690) where contrast media was administered to the patient (using the contrast media injector system 602)); an ICD9 code field 786 (e.g., a particular code in the International Classification of Diseases); a patient ID field 788 (e.g., any appropriate way of identifying the patient for the corresponding imaging operation); a patient age field 790 (e.g., a number that identifies the age of the patient for the corresponding imaging operation); a patient gender field 792 (e.g., any appropriate way of identifying the gender of the patient for the corresponding imaging operation); a patient weight field 794 (e.g., a number that identifies the weight of the patient for the corresponding imaging operation); a patient height field 796 (e.g., a number(s) that identifies the height of the patient for the corresponding imaging operation); a patient GFR field 798 (e.g., a number that identifies the glomerular filtration rate, estimated glomerular filtration rate, or the like (e.g., some other metric that is representative of kidney or renal function) of the patient for the corresponding imaging operation); a renal function override rationale field 799 (e.g., the rationale for proceeding with a contrast injection when the patient's renal function did not comply with a renal function threshold); a referring physician name field 800 (e.g., the name of the referring physician for the corresponding imaging operation); a referring physician ID field 802 (e.g., a number or code that identifies the referring physician for the corresponding imaging operation); a procedure location field 804 (e.g., a name, room/suite number, or code that identifies a particular location for the corresponding imaging operation); a modality field 806 (e.g., a name, number, or code that identifies the type of imaging technology that was used for the corresponding imaging operation); a medical order ID field 808 (e.g., a name, number, or code that is associated with a particular medical order for the corresponding imaging operation); a procedure name field 810 (e.g., a name, number, or code that identifies the patient region that was imaged by the corresponding imaging operation); a prescribed contrast media volume field 812 (e.g., a number that identifies the volume of contrast media that was prescribed (e.g., by an attending physician) for use during the corresponding imaging operation); a prescribed contrast media concentration field 814 (e.g., a number that identifies the concentration of contrast media that was prescribed (e.g., by the attending physician) for use during the corresponding imaging operation); a prescribed contrast media flow rate field 816 (e.g., a number that identifies the flow rate of contrast media that was prescribed (e.g., by the attending physician) for use during the corresponding imaging operation); a dispensed contrast media volume field 818 (e.g., a number that identifies the volume of contrast media that was dispensed by the contrast media storage/dispensing unit 500 for use during the corresponding imaging operation); a dispensed contrast media concentration field 820 (e.g., a number that identifies the concentration of contrast media that was dispensed by the contrast media storage/dispensing unit 500 for use during the corresponding imaging operation); a dispensed drug NDC field 822 (e.g., the National Drug Code for the contrast media that was dispensed by the contrast media storage/dispensing unit 500 for use during the corresponding imaging operation); a dispensed drug expiration date field 824 (e.g., a date that identifies the expiration date of the drug that was dispensed by the contrast media storage/dispensing unit 500 for use during the corresponding imaging operation); an administered contrast media volume field 826 (e.g., a number that identifies the volume of contrast media that was administered (injected) by the contrast media injector system 602 for the corresponding imaging operation); an administered contrast media concentration field 828 (e.g., a number that identifies the concentration of contrast media that was administered (injected) by the contrast media injector system 602 during the corresponding imaging operation); an administered contrast media flow rate field 830 (e.g., a number that identifies the flow rate of contrast media that was administered (injected) by the contrast media injector system 602 during the corresponding imaging operation); a dispensed contrast media brand name field 831 (e.g., any way of identifying the brand name of the contrast media that was dispensed by the contrast media storage/dispensing unit 500 for use during the corresponding imaging operation); a dispensed contrast media manufacturer field 832 (e.g., any way of identifying the manufacturer of the contrast media that was dispensed by the contrast media storage/dispensing unit 500 for use during the corresponding imaging operation); a dispensed contrast media lot number field 833 (e.g., any way of identifying the lot number of the contrast media that was dispensed by the contrast media storage/dispensing unit 500 for use during the corresponding imaging operation); a dispensed contrast media manufacture date field 834 (e.g., any way of identifying the manufacturing date of the contrast media that was dispensed by the contrast media storage/dispensing unit 500 for use during the corresponding imaging operation); a dispensed contrast media composition field 835 (e.g., any way of identifying the composition of the contrast media that was dispensed by the contrast media storage/dispensing unit 500 for use during the corresponding imaging operation); a dispensed contrast media primary functional ingredient field 836 (e.g., any way of identifying the primary functional ingredient (e.g., gadolinium, iodine, etc) of the contrast media that was dispensed by the contrast media storage/dispensing unit 500 for use during the corresponding imaging operation); an injector ID field 837 (e.g., any appropriate way of identifying the particular contrast media injector system 602 or powerhead 604 that was used in the injection); and data conversion/translation module or DCM/TM ID field 838 (e.g., any appropriate way of identifying the particular data conversion/translation module associated with and/or on which the injection history 649 may be originally stored). In the event that a given injection data management system 660 is specific to a single contrast media injector system 602 or powerhead 604 (e.g., where the injection data management module 660 is associated with a single contrast media injector system 602), only one of the injector ID field 837 or DCM/DTM ID field 838 may be needed. In the event that a given injection data management system 660 is used by multiple contrast media injector systems 602, it may be desirable to use both the injector ID field 837 and the DCM/DTM ID field 838.

Figure 24:
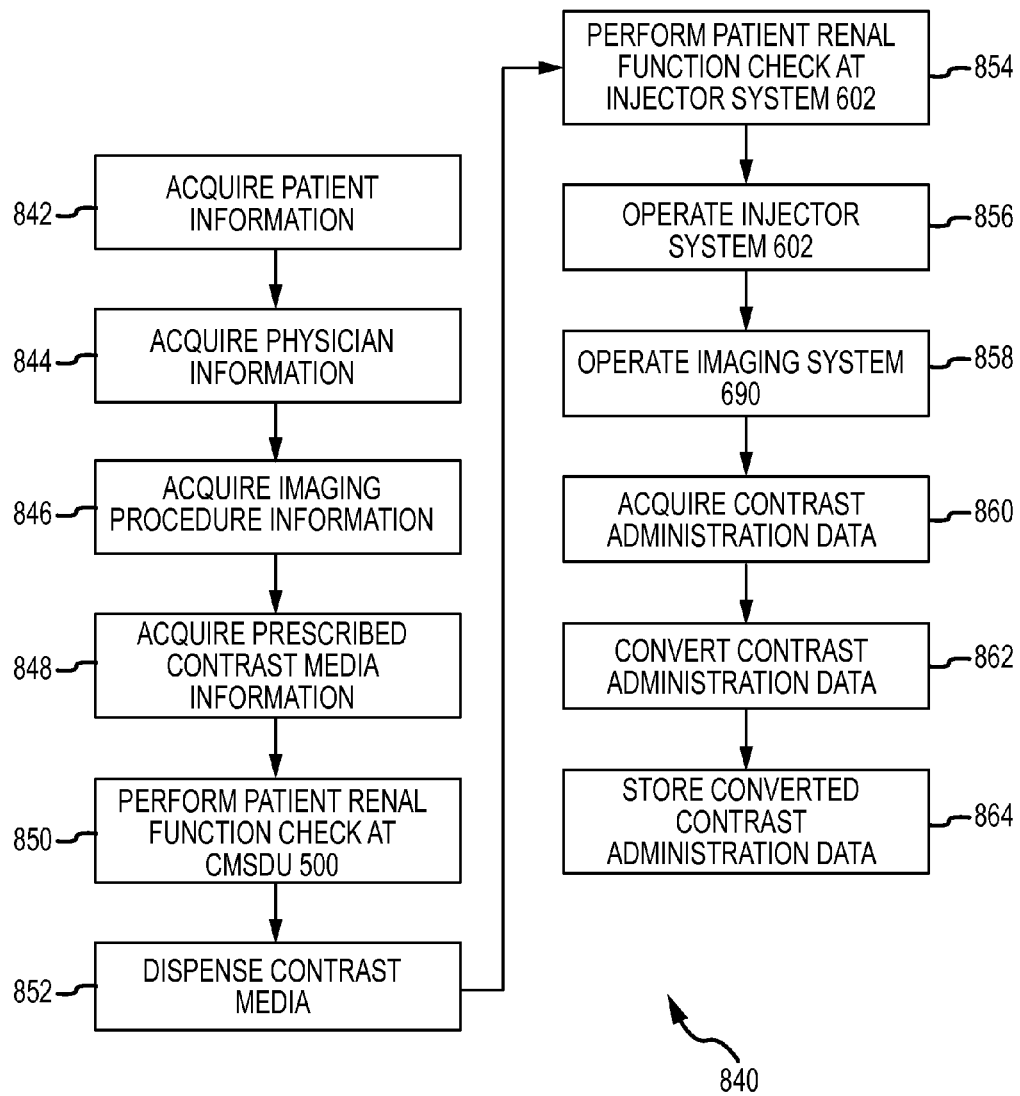
FIG. 24 is one embodiment of an imaging protocol that may be executed by a medical system that uses an injection data management system or module having data format conversion capabilities.

One embodiment of an imaging protocol 840 is presented in FIG. 24, and may be used by the medical system 600 of FIG. 18A. Patient information may be acquired pursuant to step 842 (e.g., for fields 786-798 of the data structure 780). Physician information may be acquired pursuant to step 844 (e.g., for fields 800, 802 of the data structure 780). Imaging procedure information may be acquired pursuant to step 846 (e.g., for fields 804-810 of the data structure 780). Prescribed contrast media information may be acquired pursuant to step 848. Information for each of steps 842, 844, 846, and 848 may be acquired in any appropriate order (e.g., any sequence and/or simultaneous acquisition of information from two or more steps) and in any appropriate manner, for instance from the HIS 700, via input to the medical system 600 in any appropriate manner (e.g., using the remote console 650 or a workstation 730; reading the information from a data storage device; from RIS 720; from PACS 710; from any other data system within the hospital).

A patient renal function check of some type may be undertaken at the contrast media storage/dispensing unit 500 pursuant to step 850 of the imaging protocol 840. The patient renal function check of step 850 may be in the form of the contrast medical storage/dispensing unit 500 requiring that a confirmation be entered through a user input device 508 of the unit 500, where this confirmation is that patient renal function has been checked. The patient renal function check of step 850 may be in the form of the contrast medical storage/dispensing unit 500 requiring that the patient's renal function be input to the unit 500 in any appropriate manner (e.g., through a user input device 508 of the unit 500; entry of patient information such that patent renal function data may be retrieved from the HIS 700). The patient renal function that is input to the contrast media storage/dispensing unit 500 may be compared with the threshold renal function of the contrast media to be dispensed from the contrast media storage/dispensing unit 500. If the patient renal function information that has been input to the contrast media storage/dispensing unit 500 complies with the threshold renal function of the contrast media to be dispensed from the contrast media storage/dispensing unit 500, the unit 500 may dispense the contrast media (step 852; e.g., in the form of a contrast media container 504 being provided for use by the contrast media injector system 602 to inject/administer contrast media to a patient).

A patient renal function check of some type may also or alternatively be undertaken at the contrast media injector system 602 pursuant to step 854 of the imaging protocol 840. The patient renal function check of step 854 may be in the form of the contrast media injector system 602 requiring that a confirmation be entered through a user input device (e.g., via user input device 654 of the remote console 650; via user input device 610 on the powerhead 604), where this confirmation is that patient renal function has been checked. The patient renal function check of step 854 may be in the form of the contrast media injector system 602 requiring that the patient's renal function be input to the injector system 602 in any appropriate manner (e.g., via user input device 654 of the remote console 650; via user input device 610 on the powerhead 604; via entry of patient information such that patent renal function data may be retrieved from the HIS 700). The patient renal function that is input to the contrast media injector system 602 may be compared with the threshold renal function of the contrast media to be administered from the contrast media injector system 602. Any appropriate way of inputting the threshold renal function data to the contrast media injector system 602 may be utilized (e.g., a user may be required to input the threshold renal function to the contrast media injector system 602 though a user input device of the injector system 602; the threshold renal function could be retrieved by the injector system 602 from the corresponding contrast media container 504 provided by the contrast media storage/dispensing unit 500; the threshold renal function would be retrieved from the HIS 700). If the patient renal function information that has been input to the contrast media injector system 602 complies with the threshold renal function of the contrast media to be administered (injected) by the contrast media injector system 602, the injector system 602 may be operated pursuant to step 856 to administer/inject contrast media into the patient (e.g., via execution of a programmed injection).

The injector system 602 (step 856) and imaging system 690 (step 858) may be operated in any appropriate manner to acquire a desired image/images of the patient undergoing the imaging procedure. Step 860 of the imaging protocol 840 is directed to acquiring contrast administration data (e.g., relating at least in some manner to the operation of the contrast media injector system 602). At least some of the contrast administration data may be converted from one format to another format pursuant to step 862 of the imaging protocol 840 (e.g., in accordance with FIGS. 19-22 above), and this converted contrast administration data may be stored pursuant to step 864 of the imaging protocol 840 (e.g., in the data structure 780). This converted contrast administration data may be used in any appropriate manner, for instance for electronic records purposes; for inventory tracking purposes; for billing purposes; for use by or in relation to laboratory information systems; medication and procedure error tracking; quality controls; contrast media usage reporting; documentation of drug dispense and administration; documentation of patient exposure to radiation and/or iodine; patient outcomes analyses; departmental reporting; and contrast usage analysis and reporting.

Figure 25:
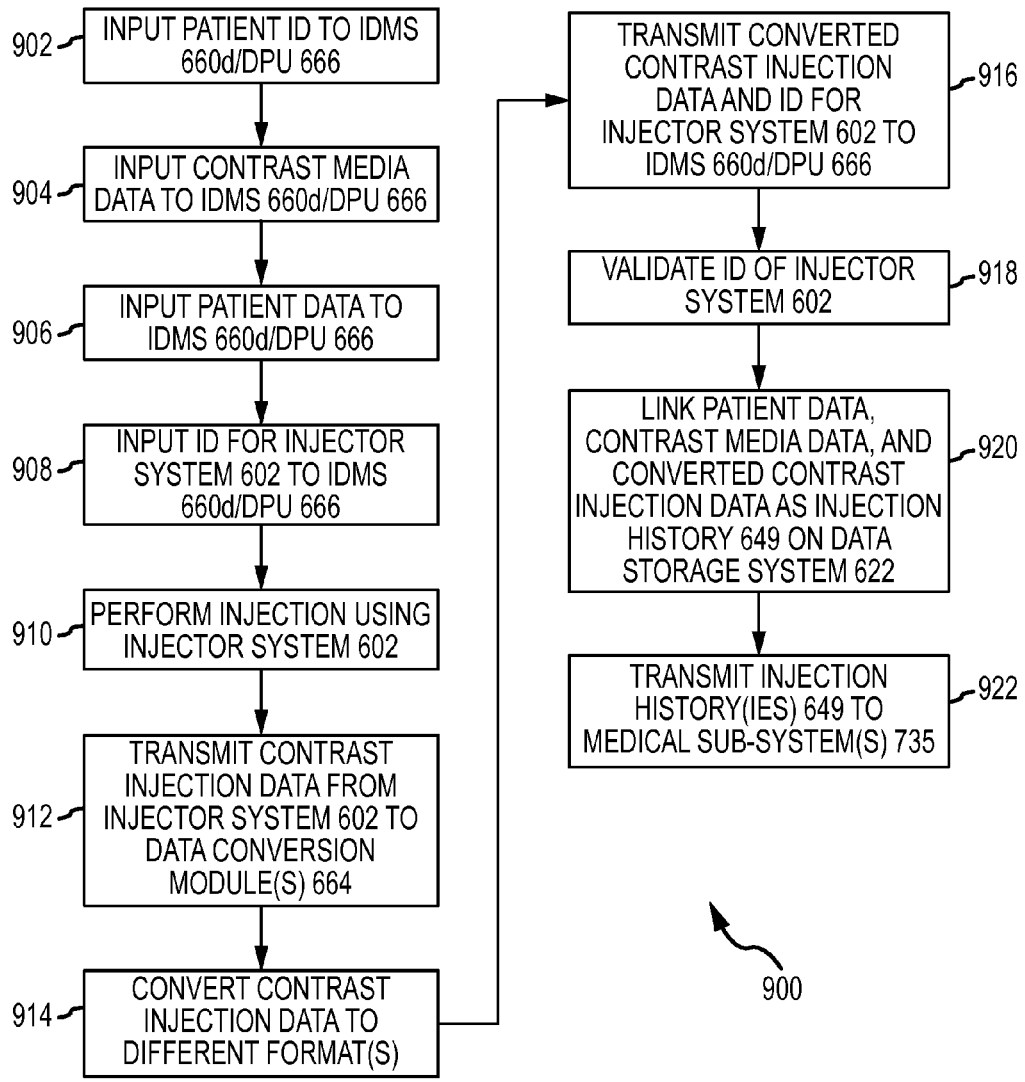
FIG. 25 is one embodiment of a data management protocol that may be used by an injection data management system or module having data format conversion capabilities.

FIG. 25 presents one embodiment of a data management protocol that may be used by an injection data management system as described herein, and that is identified by reference numeral 900 in FIG. 25. Although the data management protocol 900 will be described in relation to the injection data management system 660d of FIG. 18C, the data management protocol 900 may be used by any of the injection data management systems (e.g., 660, 660a, 660b, and 660c) described herein.

A patient ID (e.g., for patient ID field 788 of data structure 780 discussed above in relation to FIGS. 23A-D) may be input to the injection data management system 660d (e.g., the data processing unit 666) pursuant to step 902 of the data management protocol 900 of FIG. 25. The patient ID could be provided to the injection data management system 660d in any appropriate manner for purposes of step 902, including through a user interface 662, through a bar code scanner 694 that will discussed below in relation to FIG. 27, through any other appropriate data reader, or the like.

Contrast media data (e.g., for fields 818-824 and fields 831-836 of data structure 780 discussed above in relation to FIGS. 23A-D) may be input to the injection data management system 660*d* (e.g., the data processing unit 666) pursuant to step 904 of the data management protocol 900 of FIG. 25. Contrast media data may be provided to the injection data management system 660*d* in any appropriate manner for purposes of step 904, including by retrieving such contrast media data from contrast media storage/dispensing unit 500 (e.g., via a communication link of any appropriate type between the injection data management system 660*d* and the contrast media storage/dispensing unit 500), by reading a data storage device 613 on a syringe 612 that will be used in the injection procedure (as will discussed in more detail below in relation to FIG. 27; e.g., using a barcode scanner 694; using a data reader that is part of the injector system 602, for instance a data reader (e.g., an RFID antenna) incorporated in a syringe mount of the injector system 602 (e.g., FIGS. 8A-10), a separate unit (e.g., a wand) that is detachably connected with another portion of the contrast media injector system 602, or both), or the like. The patient ID provided pursuant to step 902 could also be used by the injection data management system 660*d* to retrieve contrast media data from another medical sub-system 735 is operatively interconnected with the injection data management system 660*d* (e.g., HIS 700).

Patient data (e.g., for fields 784-810 of data structure 780 discussed above in relation to FIGS. 23A-D) may be input to the injection data management system 660*d* (e.g., the data processing unit 666) pursuant to step 906 of the data management protocol 900 of FIG. 25. Patient data may be provided to the injection data management system 660*d* in any appropriate manner for purposes of step 906. For instance, the patient ID provided pursuant to step 902 may be used by the injection data management system 660*d* to retrieve patient data from a medical sub-system 735 that is operatively interconnected with the injection data management system 660*d* (e.g., the HIS 700), and which would then transmit this data back to the injection data management system 660*d*.

The ID of the contrast media injector system 602 that will be used in the injection procedure may be input to the injection data management system 660*d* (e.g., the data processing unit 666) pursuant to step 908 of the data management protocol 900 of FIG. 25. The ID of the injector system 602 may be provided to the injection data management system 660*d* in any appropriate manner for purposes of step 908. A user could manually input an ID for the injector system 602 through a user interface 662 of the injection data management system 660*d*. A data storage device of any appropriate type on the injector system 602 (e.g., a data tag) could be read and transmitted to the injection data management system 660*d*. The ID of the injector system 602 could also be automatically tagged to data (e.g., contrast injection data, including programmed/prescribed contrast injection data and administered/achieved contrast injection data) that is transmitted from the injector system 602 to the injection data management system 660*d*. If a single injector system 602 is used by a given data conversion module 664 of the injection data management system 660*d*, the ID for the injector system 602 could be in the form of an ID associated with this data conversion module 664 (which could then be automatically tagged to data received from the injector system 602).

A patient is injected with contrast media using the contrast media injector system 602 in accordance with step 910 of the data management protocol 900 of FIG. 25 (e.g., via execution of an injection protocol as described herein). Contrast injection data may be transmitted from the injector system 602 to one or more data conversion units of a data conversion module 664 of the injection data management system 660*d* pursuant to step 912. This contrast injection data may be programmed/prescribed contrast injection data (e.g., for fields 812-816 of data structure 780 discussed above in relation to FIGS. 23A-D), administered/achieved contrast injection data (e.g., for fields 826-830 of data structure 780 discussed above in relation to FIGS. 23A-D), or both.

Contrast injection data that is provided to a given data conversion unit of the data conversion module 664 is converted from one format (e.g., a CAN-compliant format) to another format (e.g., a non-CAN-compliant format, such as HL-7 or DICOM) pursuant to step 914 of the data management protocol 900 of FIG. 25, and in accordance with the foregoing. The converted contrast injection data may be transmitted from the injector system 602 to the injection data management system 660*d* (e.g., data processing unit 666) pursuant to step 916 of the protocol 900.

Step 918 may be used by the data management protocol 900 of FIG. 25, and is directed to validating an ID of the injector system 602 (from step 908). When contrast media for an injection procedure is retrieved from the contrast media storage/dispensing unit 500 (e.g., in the form of a contrast media container 504, such as a syringe with the desired contrast media), it may be a prerequisite to input the ID of the injector system 602 to be used in the injection to the contrast media storage/dispensing unit 500 (alone or in combination with the patient ID), the ID for the injector system 602 ID could be stored on a data storage device 514 attached to the associated contrast media container 504, or both. The ID for the injector system 602 associated with step 908 may be transmitted to the injection data management system 660*d* (e.g., data processing unit 666) pursuant to step 908 and/or step 916. This injector system 602 ID (step 908) may be compared with the ID of the injector system 602 associated with the contrast media used in the injection for purposes of step 918. If these IDs match, the protocol 900 may proceed to step 920. Otherwise, the protocol 900 could be configured address any mismatch of injector system 602 IDs.

Patient data (e.g., for fields 784-810 of data structure 780 discussed above in relation to FIGS. 23A-D), contrast media data (e.g., for fields 818-824 and fields 831-836 of data structure 780 discussed above in relation to FIGS. 23A-D), contrast injection data (e.g., programmed/prescribed contrast injection data, such as for fields 812-816 of data structure 780 discussed above in relation to FIGS. 23A-D; administered/achieved contrast injection data, such as for fields 826-830 of data structure 780 discussed above in relation to FIGS. 23A-D) may be linked together in any appropriate manner and stored on the data storage system 622 of the injection data management system 660*d* as an injection history 649 pursuant to step 920 of the data management protocol 900 of FIG. 25.

One or more injection histories 649 stored on the injection data management system 660*d* (e.g., on its data storage system 622) may be transmitted to one or more medical sub-systems 735 (e.g., HIS 700; RIS 720; PACS 710) pursuant to step 922 of the data management protocol 900 of FIG. 25. As discussed above, one or more injection histories 649 may be "pulled" from the injection data management system 660*d* by one or more medical sub-systems 735, one or more injection histories 649 may be "pushed" from the injection data management system 660*d* to one or more medical sub-systems 735, or both. In one embodiment, multiple injection histories 649 are simultaneously transmitted from the injection data management system 660d to one or more medical sub-systems 735 for purposes of step 922 of the protocol 900.

Figure 26:
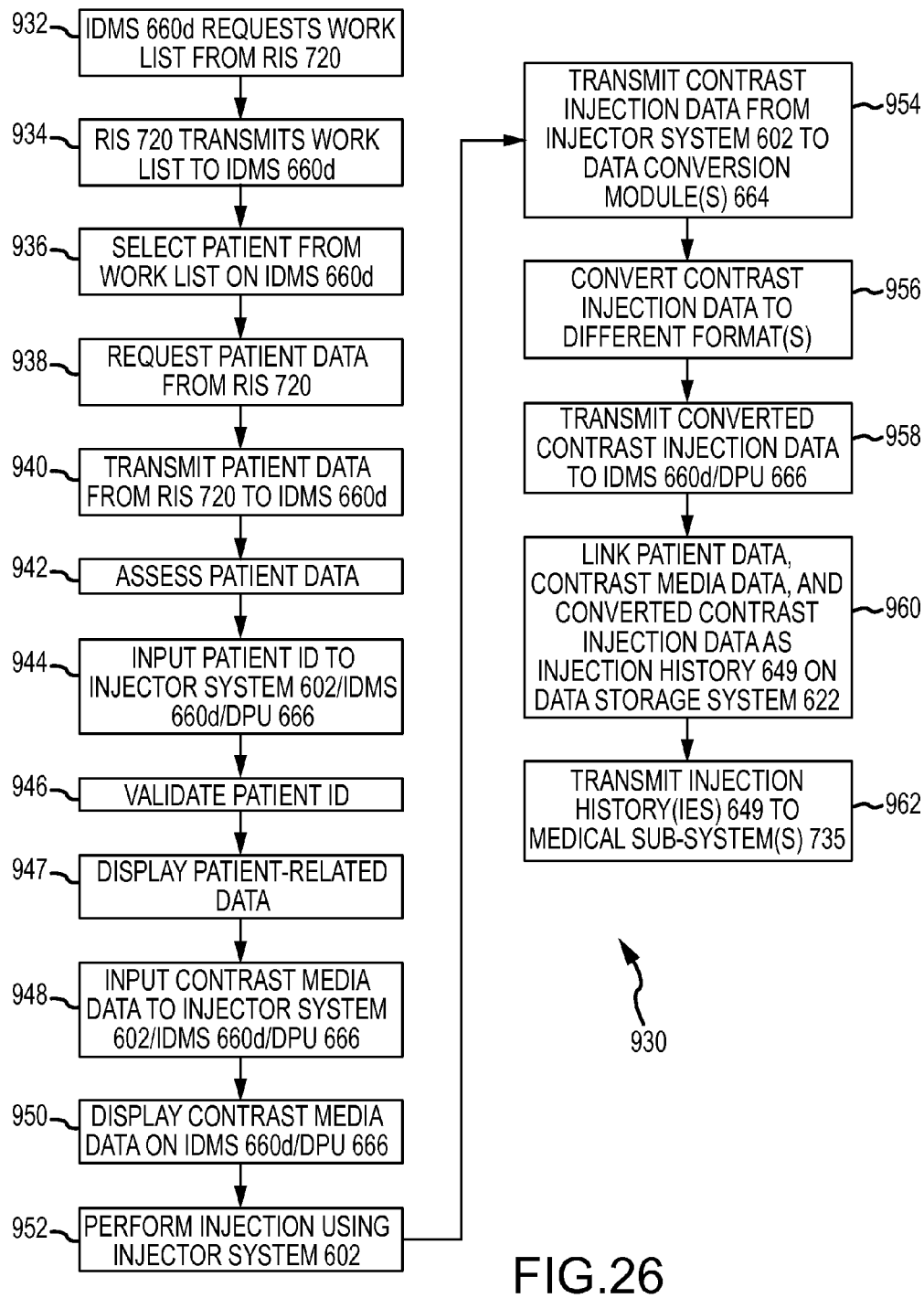
FIG. 26 is another embodiment of a data management protocol that may be used by an injection data management system or module having data format conversion capabilities.

FIG. 26 presents one embodiment of a data management protocol that may be used by an injection data management system as described herein, and that is identified by reference numeral 930 in FIG. 26. Although the data management protocol 930 will be described in relation to the injection data management system 660d of FIG. 18C, the data management protocol 930 may be used by any of the injection data management systems (e.g., 660, 660a, 660b, and 660c) described herein.

Step 932 of the data management protocol 930 of FIG. 26 is directed to the injection data management system 660d (e.g., data processing unit 666) requesting a worklist from the RIS 720. The worklist from the RIS 720 contains a list of patients that are scheduled for an injection procedure over a given time period (e.g., for a given day). The RIS 720 may transmit the requested worklist to the injection data management system 660d (e.g., data processing unit 666) pursuant to step 934. A patient may be selected from the worklist that is now stored on the injection data management system 660d (e.g., through a user interface 662 of the data processing unit 666). Patient data (e.g., for fields 784-810 of data structure 780 discussed above in relation to FIGS. 23A-D) for the selected patient (step 936) may be requested from the RIS 720 by the injection data management system 660d pursuant to step 938. This patient data may be transmitted from the RIS 722 to the injection data management system 660d (e.g., data processing unit 666) pursuant to step 940.

Steps 932-940 of the data management protocol 930 of FIG. 26 are generally directed to acquiring patient data (e.g., for fields 784-810 of data structure 780 discussed above in relation to FIGS. 23A-D) for the injection data management system 660d. Patient data may be acquired in any appropriate manner for purposes of the data management protocol 930, including in accordance with steps 902 and 906 of the data management protocol 900 discussed above in relation to FIG. 25.

The patient data provided to the injection data management system 660d may be assessed pursuant to step 942 of the data management protocol 930 of FIG. 26. For instance, step 942 may be directed to a renal function assessment in accordance with the foregoing. This assessment is also addressed in more detail below in relation to FIG. 33. Any appropriate assessment of patient data may be undertaken pursuant to step 942, for instance to assess patient allergies in relation to a contrast media injection, medication(s) being taken by the patient in relation to a contrast media injection, and the like.

A patient ID may be input to the injector system 602 and/or to the injection data management system 660d pursuant to step 944 of the data management protocol 930 of FIG. 26 (e.g., in accordance with step 902 of the data management protocol 900 of FIG. 25). The patient ID may be validated pursuant to step 946. For instance, the patient ID that is input to the injection data management module 660 (step 944) may be compared with the patient ID that is included with the patient data provided through step 940. In one embodiment, the contrast media injector system 602 will be unable to execute an injection for a patient if the patient ID is not validated pursuant to step 946 of the data management protocol 930.

Patient-related data of any appropriate type may be displayed on the injection data management system 660d (e.g., on a display 662b of the data processing unit 666) pursuant to step 947 of the data management protocol 930 of FIG. 26. Patient data for/from fields 784-810 of data structure 780 discussed above in relation to FIGS. 23A-D may be displayed pursuant to step 947. Historical contrast media injection data for the patient could be displayed pursuant to step 947. The data display associated with step 947 could present information from and/or relating to the assessment of step 942 (e.g., patient allergy information; medication(s) being taken by the patient; myeloma status information).

Contrast media data (e.g., for fields 818-824 and fields 831-836 of data structure 780 discussed above in relation to FIGS. 23A-D) may be input to the injection data management system 660d (e.g., the data processing unit 666) pursuant to step 948 of the data management protocol 930 of FIG. 26. Contrast media data may be provided to the injection data management system 660d in any appropriate manner for purposes of step 948, including by retrieving such contrast media data from contrast media storage/dispensing unit 500, by reading a data storage device 613 on a syringe 612 that will be used in the injection procedure (as will discussed in more detail below in relation to FIG. 27; e.g., using a bar code scanner 694; using a data reader that is part of the injector system 602, for instance a data reader (e.g., an RFID antenna) incorporated in a syringe mount of the injector system 602 (e.g., FIGS. 8A-10), a separate unit (e.g., a wand) that is detachably connected with another portion of the contrast media injector system 602, or both), or the like. This contrast media data may be displayed on the injection data management system 660d (e.g., on a display 662b of the data processing unit 666) pursuant to step 950.

It should be appreciated that data may be acquired pursuant to the data management protocol 930 of FIG. 26 in any appropriate manner. Data for the data management protocol 930 may be acquired in any appropriate order. Contrast media data for a particular contrast media injection of a particular patient could be acquired prior to actually acquiring at least some of the patient data. The assessment of patient data pursuant to step 942 may also be executed at any appropriate time prior to the contrast media injection associated with step 952, and could also utilize contrast media data from step 948. Steps 942, 946, 947, and 950 (and any related steps) could also be utilized by the data management protocol 900 of FIG. 25.

A patient is injected with contrast media using the contrast media injector system 602 in accordance with step 952 of the data management protocol 930 of FIG. 26. Contrast injection data is transmitted from the injector system 602 to one or more data conversion units of the data conversion module 664 of the injection data management system 660d pursuant to step 954. This contrast injection data may be programmed/prescribed contrast injection data (e.g., for fields 812-816 of data structure 780 discussed above in relation to FIGS. 23A-D), administered/achieved contrast injection data (e.g., for fields 826-830 of data structure 780 discussed above in relation to FIGS. 23A-D), or both.

Contrast injection data that is provided to a given data conversion unit of the data conversion module 664 is converted from one format (e.g., a CAN-compliant format) to another format (e.g., a non-CAN-compliant format, such as HL-7 or DICOM) pursuant to step 956 of the data management protocol 930 of FIG. 26, and in accordance with the foregoing. The converted contrast injection data may be transmitted to the injection data management system 660d (e.g., data processing unit 666) pursuant to step 958 of the protocol 930.

Patient data (e.g., for fields 784-810 of data structure 780 discussed above in relation to FIGS. 23A-D), contrast media data (e.g., for fields 818-824 and fields 831-836 of data structure 780 discussed above in relation to FIGS. 23A-D), contrast injection data (e.g., programmed/prescribed contrast injection data, such as for fields 812-816 of data structure 780 discussed above in relation to FIGS. 23A-D; administered/achieved contrast injection data, such as for fields 826-830 of data structure 780 discussed above in relation to FIGS. 23A-D) may be linked together in any appropriate manner and stored on the data storage system 622 of the injection data management system 660d as an injection history 649 pursuant to step 960 of the data management protocol 930 of FIG. 26.

One or more injection histories 649 stored on the injection data management system 660d (e.g., on its data storage system 622) may be transmitted to one or more medical sub-systems 735 (e.g., HIS 700; RIS 720; PACS 710) pursuant to step 962 of the data management protocol 930 of FIG. 26. As discussed above, one or more injection histories 649 may be "pulled" from the injection data management system 660d by one or more medical sub-systems 735, one or more injection histories 649 may be "pushed" from the injection data management system 660d to one or more medical sub-system 735, or both. In one embodiment, multiple injection histories 649 are simultaneously transmitted from the injection data management system 660d to one or more medical sub-systems 735 for purposes of step 922 of the protocol 930.

Figure 27:
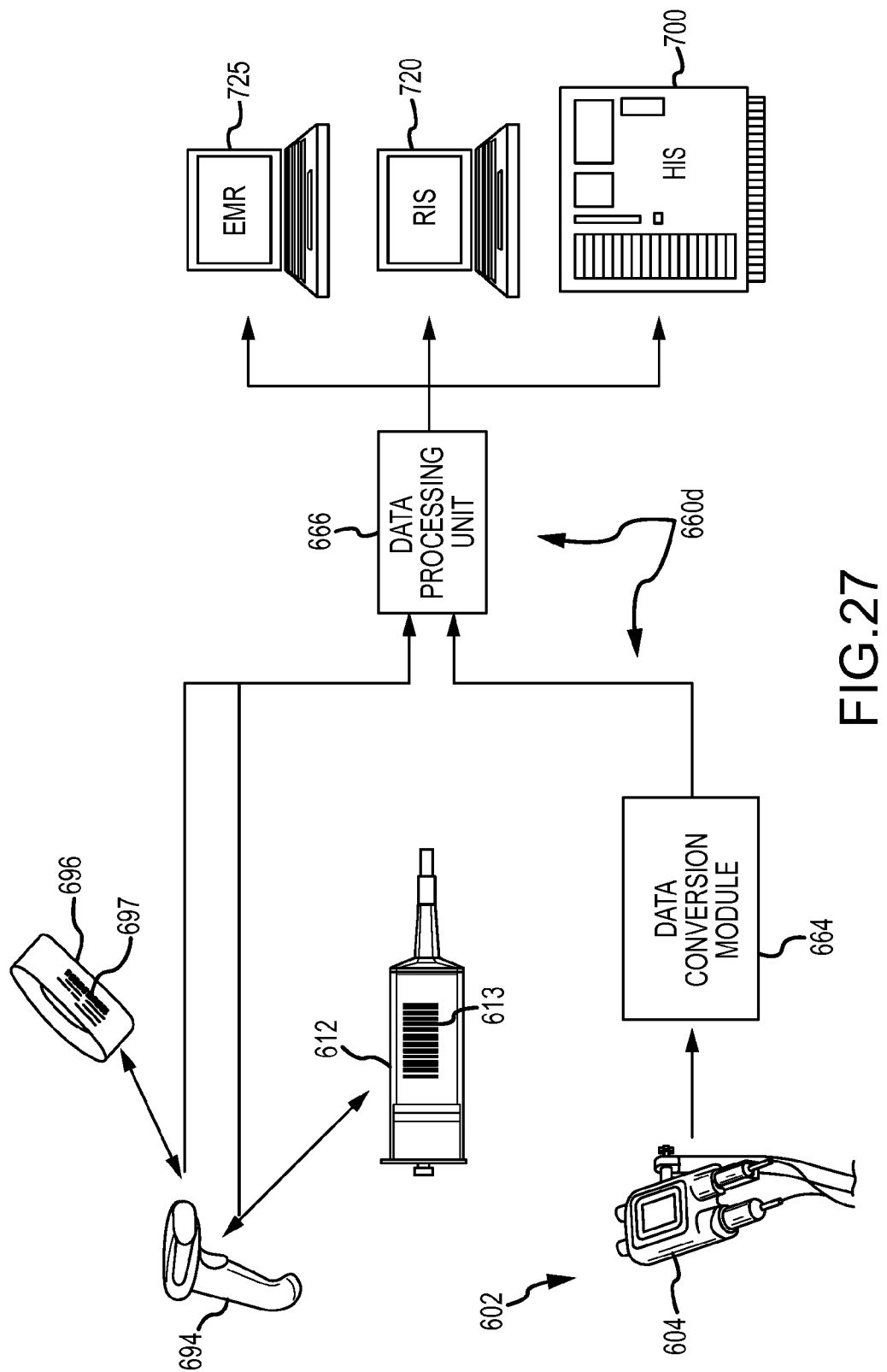
FIG. 27 is a schematic of an implementation of the injection data management system or module of FIG. 18C.

FIG. 27 illustrates an implementation of the injection data management system 660d of FIG. 18C, and which may be used in relation to the data management protocol 900 of FIG. 25 and/or the data management protocol 930 of FIG. 26. Three representative medical sub-systems 735 are illustrated in FIG. 27, namely the HIS 700, the RIS 720, and an electronic medical records system 725.

The patient ID (e.g., for step 902 of the data management protocol 900 of FIG. 25; for step 944 of the data management protocol 930 of FIG. 26) may be acquired by using a barcode scanner 694 to read a data storage device 697 (e.g., a barcode) on a wristband 696 attached to or worn by the patient. Any appropriate data reader could be used to read patient ID information stored on any appropriate data storage device associated with the patient (e.g., on a wristband, on a badge). The barcode scanner 694 may be operatively interconnected with the data processing unit 666 of the injection data management system 660d in any appropriate manner (e.g., using any appropriate communication link), and may transmit data on the patient ID in any appropriate manner and on any appropriate basis to the injection data management system 660d. The barcode scanner 694 could also be operatively interconnected with the contrast media injector system 602 to provide data on the patient ID to the contrast media injector system 602, which could then transmit the patient ID to the injection data management system 660d at an appropriate time and in any appropriate manner.

Contrast media data (e.g., for fields 818-824 and fields 831-836 of data structure 780 discussed above in relation to FIGS. 23A-D) may be stored on a data storage device 613 (e.g., a barcode separately attached to this syringe 612; an RFID tag separately attached to this syringe 612) that is incorporated by a syringe 612 in any appropriate. The barcode scanner 694 may be used to read the contrast media data from the data storage device 613. Any appropriate data reader could be used to read contrast media data stored on the data storage device 613 of the syringe 612 (e.g., an RF data reader). As noted above, the barcode scanner 694 may be operatively interconnected with the data processing unit 666 of the injection data management module 660d in any appropriate manner (e.g., using any appropriate communication link), and may transmit contrast media data in any appropriate manner and on any appropriate basis to the injection data management module 660d. The barcode scanner 694 could also be operatively interconnected with the contrast media injector system 602 to provide contrast media data to the contrast media injector system 602, which could then transmit contrast media data to the injection data management system 660d at an appropriate time and in any appropriate manner.

The injection data management systems described herein (e.g., 660, 660a, 660b, 660c, and 660d) may utilize various screens or user interface screens that may be presented on one or more of displays 662b of one or more user interfaces 662 (e.g., a screen being an output presented on a display(s) 662b of an injection data management system), for instance to facilitate execution of one or more of the data management protocols 900, 930 of FIGS. 25 and 26, respectively. FIGS. 28-40 present representative screens of this type. Although these figures will be described in relation to the injection data management system 660d, they are applicable to and/or may be adapted for the other injection data management systems described herein as well (e.g., 660, 660a, 660b, and 660c).

Figure 28:
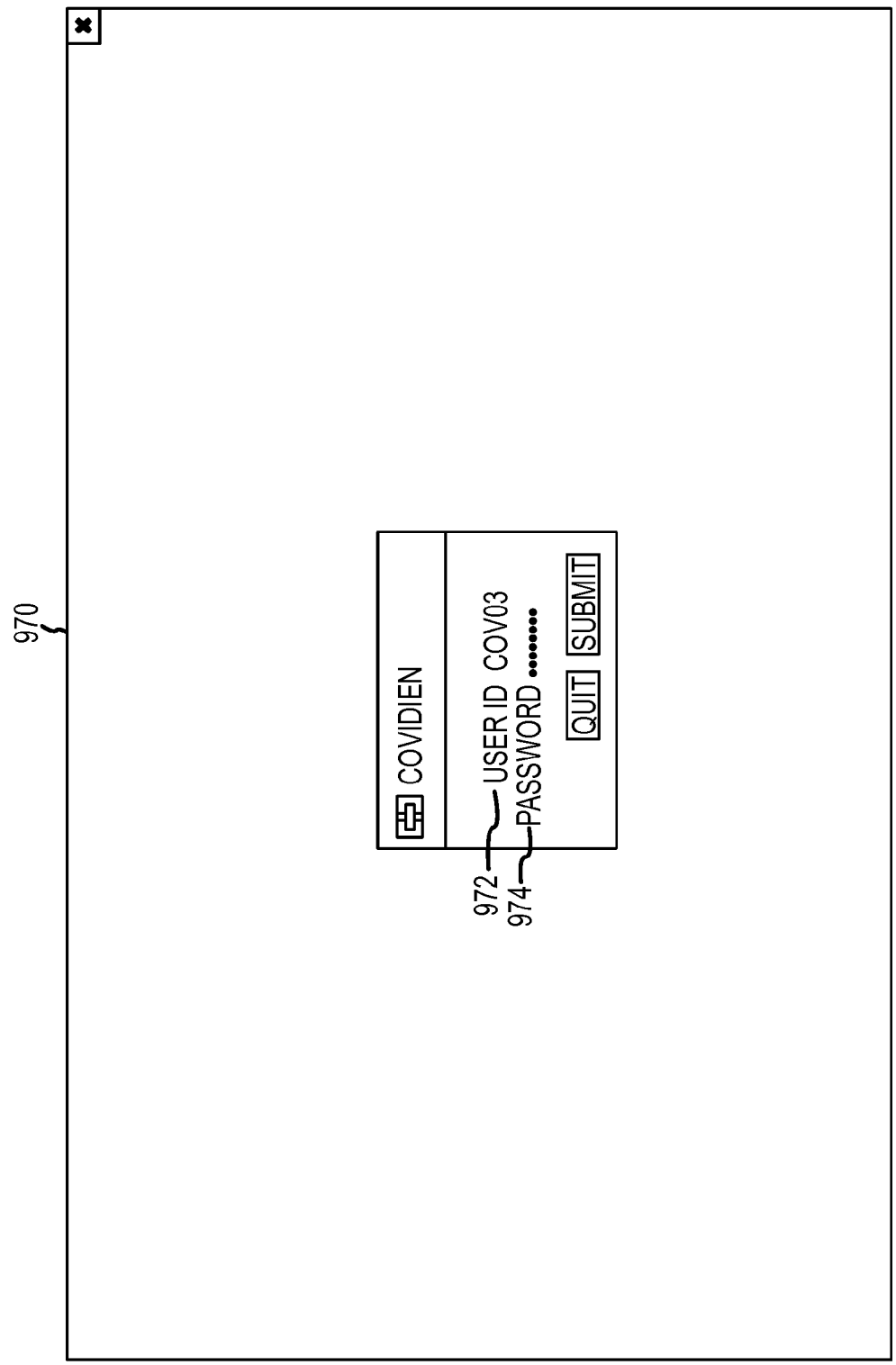
FIG. 28 is one embodiment of a login screen that may be used by an injection data management system or module having data format conversion capabilities.

FIG. 28 presents one embodiment of a login screen 974 for the injection data management system 660d. A user may be required to provide a user ID to a user ID field or prompt 972, a password to a password field or prompt 974, or both, in order to gain access to the functionality of the injection data management system 660d.

Figure 29:
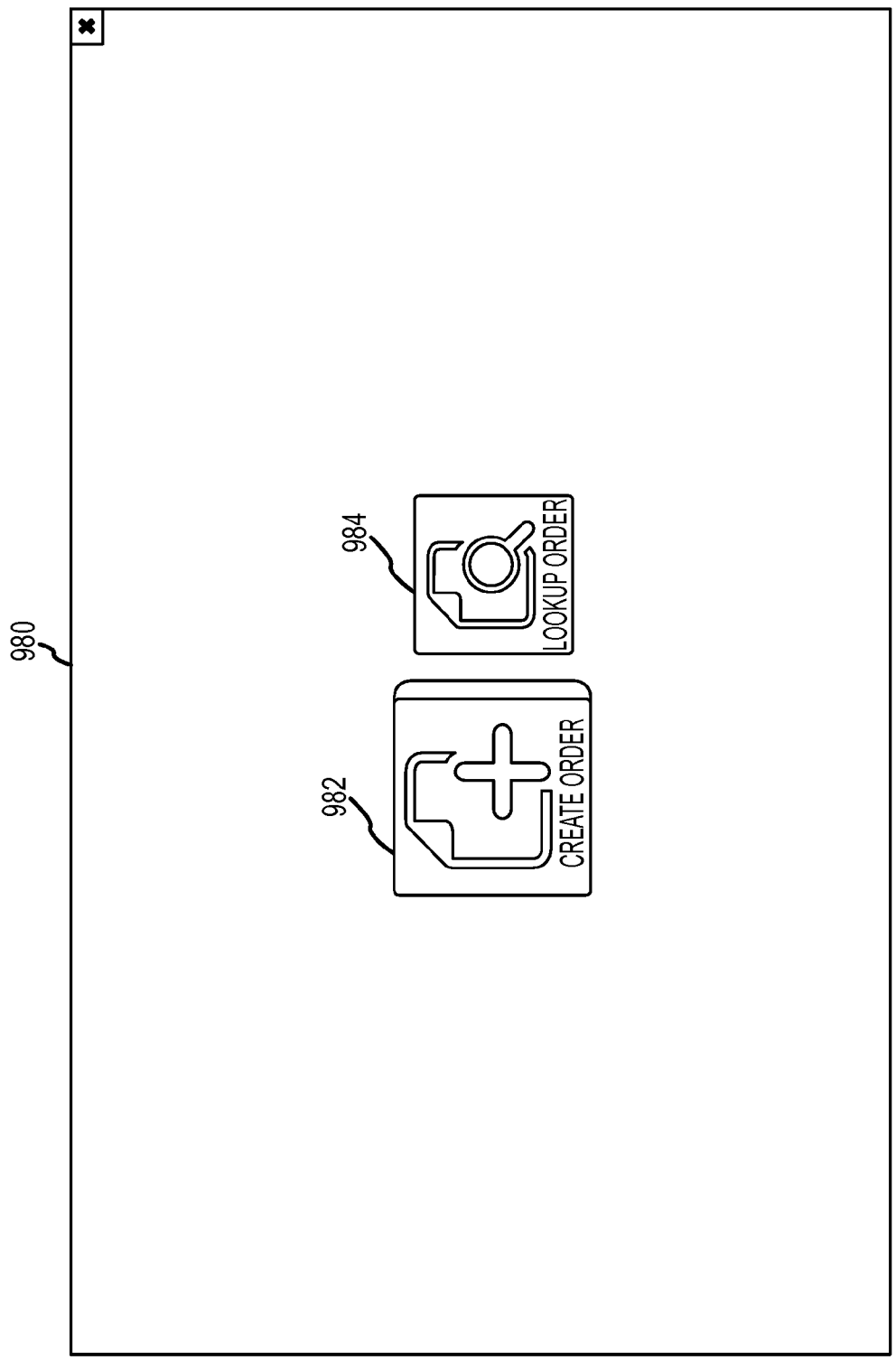
FIG. 29 is one embodiment of a main screen that may be used by an injection data management system or module having data format conversion capabilities.

FIG. 29 presents one embodiment of a main or home screen 980 for the injection data management system 660d. The main screen 984 includes both a create order button 982 and a lookup order button 984. A user may activate the create order button 982 to initiate the input of patient data (e.g., for fields 784-810 of data structure 780 discussed above in relation to FIGS. 23A-D) to the injection data management system 660d. A user may activate the lookup order button 984 to initiate communication between the injection data management system 660d and, for instance, the RIS 720 for purposes of the execution of one or more of steps 932-940 of the data management protocol 930 of FIG. 26 (e.g., to retrieve a worklist from the RIS 720; to access a worklist on the injection data management system 660d that has already been retrieved from the MS 720 by the injection data management system 660d).

Figure 30:
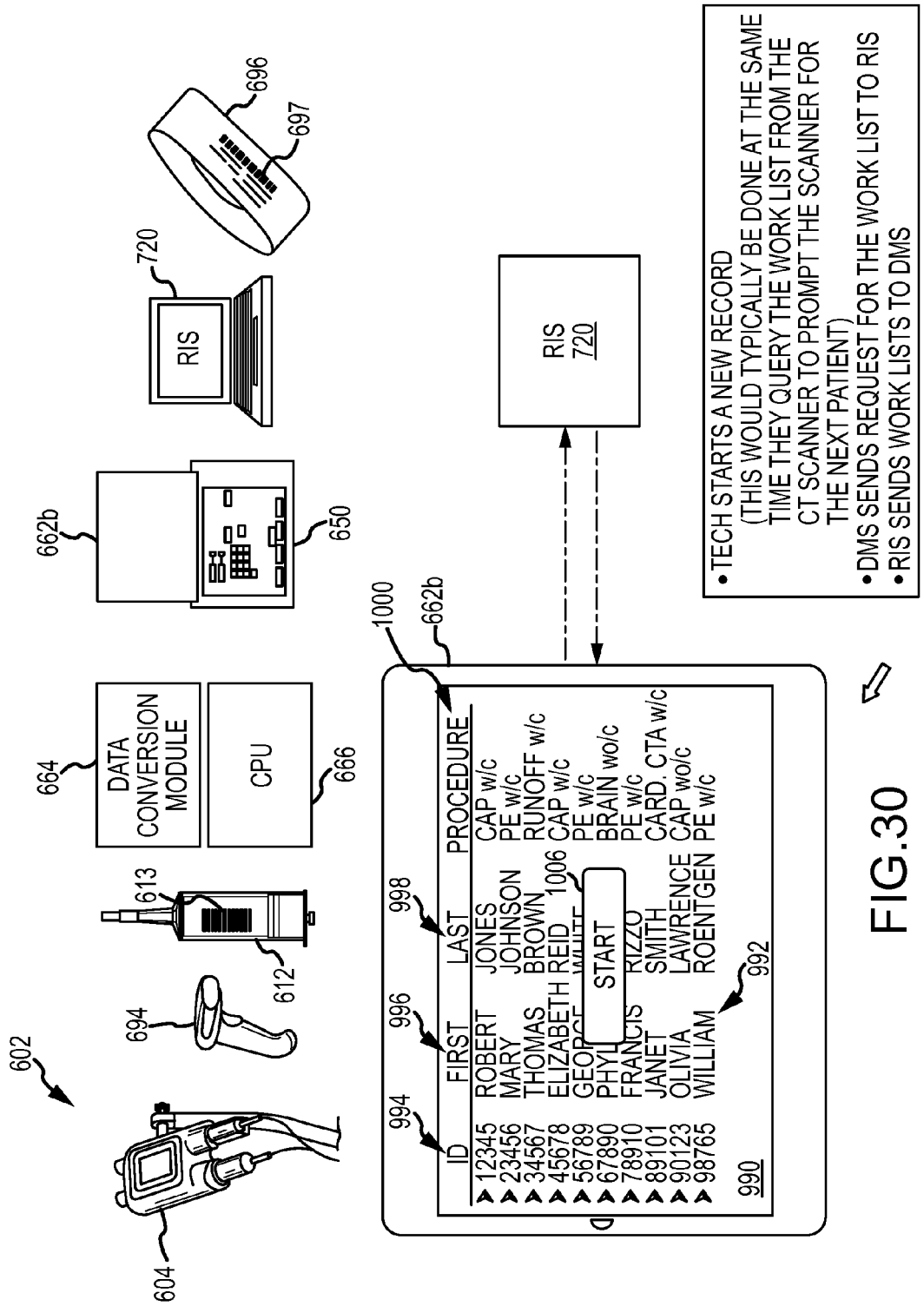
FIG. 30 is one embodiment of a worklist screen that may be used by an injection data management system or module having data format conversion capabilities.

FIG. 30 presents one embodiment of a worklist screen 990 for the injection data management system 660d. A worklist 992 is presented on the worklist screen 990 (e.g., relating to steps 932-936 of the data management protocol 930 of FIG. 26). Each entry in the worklist 992 includes a patient ID 994, a patient first name 996, a patient last name 998, and a procedure name 1000 (e.g., the nature of the associated imaging operation where "w/c" means "with contrast, and where "wo/c" means without contrast). A start button 1006 may be activated to start a new record or injection history 649 (e.g., FIG. 18B) for the data structure 780 (e.g. FIGS. 23A-D), which again may be stored on the data storage system 622 of the injection data management system 660d. Activating the start button 1006 may present the "create new record" screen 1040 that is discussed below in relation to FIG. 34.

Figure 31:
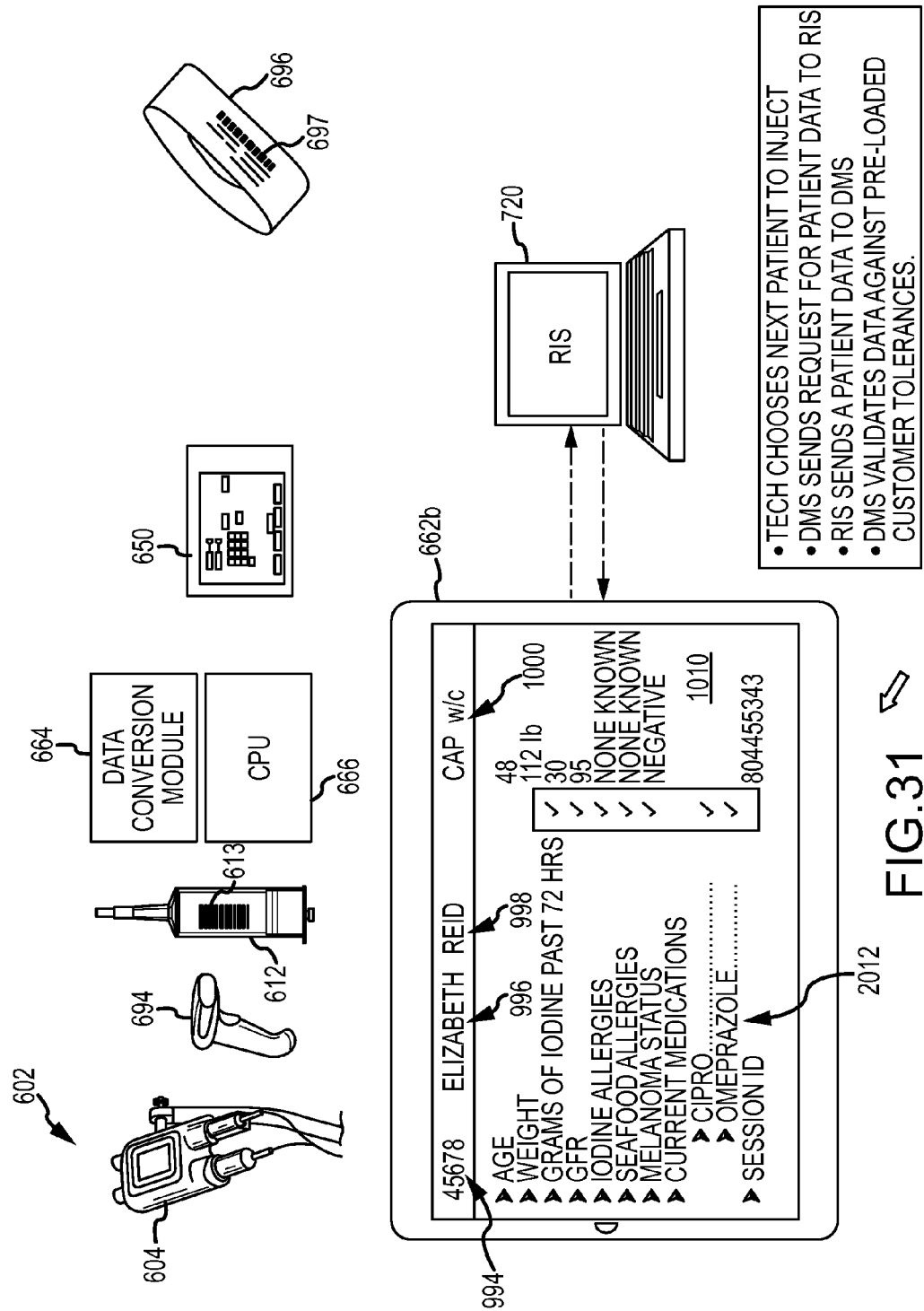
FIG. 31 is one embodiment of a patient data screen that may be used by an injection data management system or module having data format conversion capabilities.

FIG. 31 presents one embodiment of a patient data screen 1010 for the injection data management system 660d. The patient ID 994, patient first name 996, patient last name 998, and procedure name 1000 may be displayed on the patient data screen 1010. Patient data 2012 may also be presented on the patient data screen 1010 (e.g., relating to steps 938 and 940 of the data management protocol 930 of FIG. 26; data for one or more of fields 784-810 of data structure 780 discussed above in relation to FIGS. 23A-D). A validation indicator 2020 (e.g., a "checkmark") may be displayed next to patient data 2012 where a determination has been made that the corresponding patient data is appropriate and/or acceptable for the given patient in relation to the upcoming injection procedure.

Figure 32:
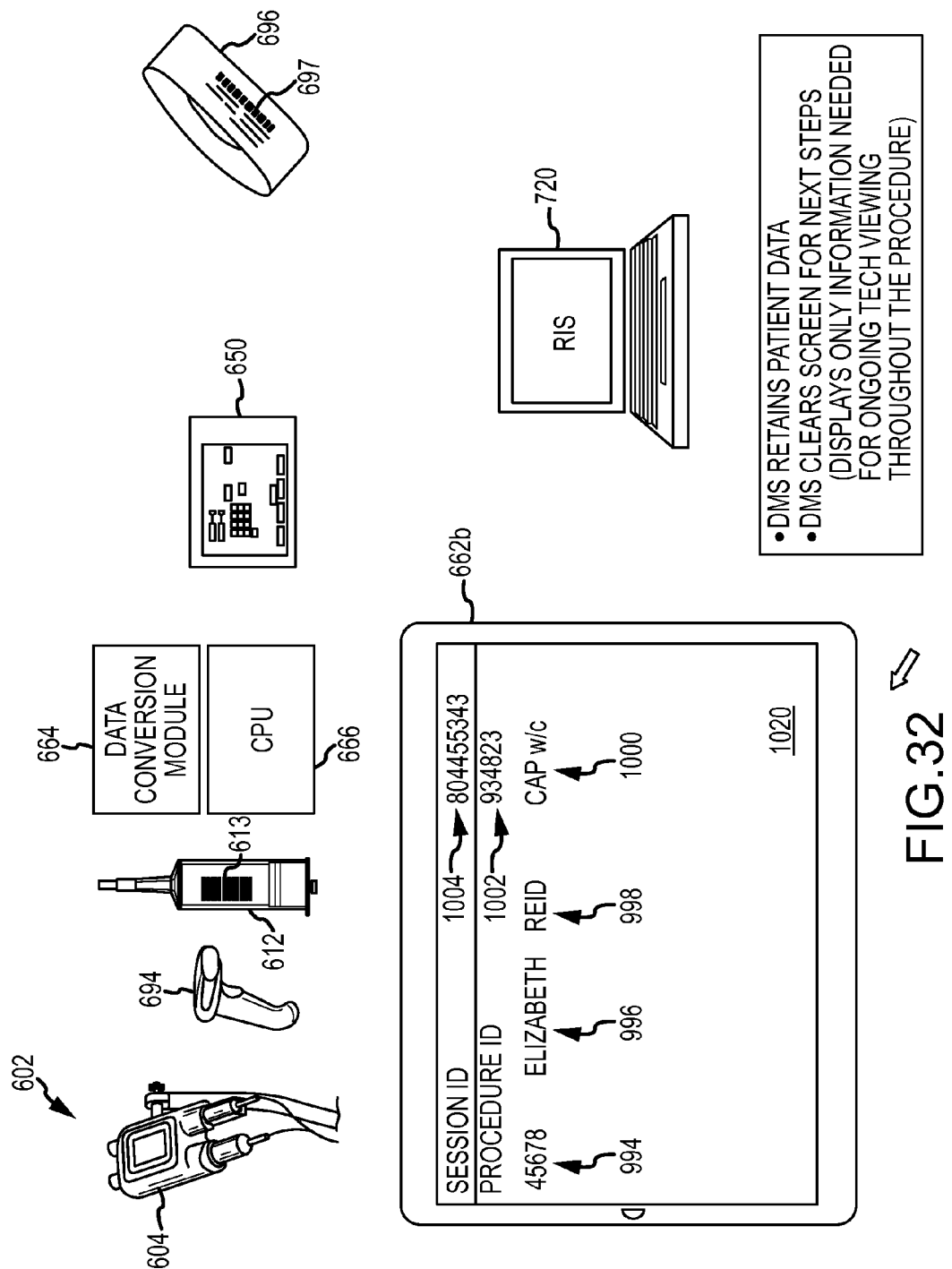
FIG. 32 is one embodiment of a clear patient data screen that may be used by an injection data management system or module having data format conversion capabilities.

FIG. 32 presents one embodiment of a clear patient data screen 1020 for the injection data management system 660*d*. The patient ID 994, patient first name 996, patient last name 998, and procedure name 1000 may continue to be displayed on the clear patient data screen 1020. However, the injection data management system 660*d* removes at least some of the patient data 2012 (FIG. 31) for purposes of the clear patient data screen 1020 (e.g., to facilitate execution of subsequent steps in relation to the injection data management module 660*d*). Patient data 2012 that is removed from the screen, however, is retained in the data storage system 622 of the injection data management system 660*d*. A session ID 1004 and procedure ID 1002 may also be presented on the clear patient data screen 1020.

Figure 33:
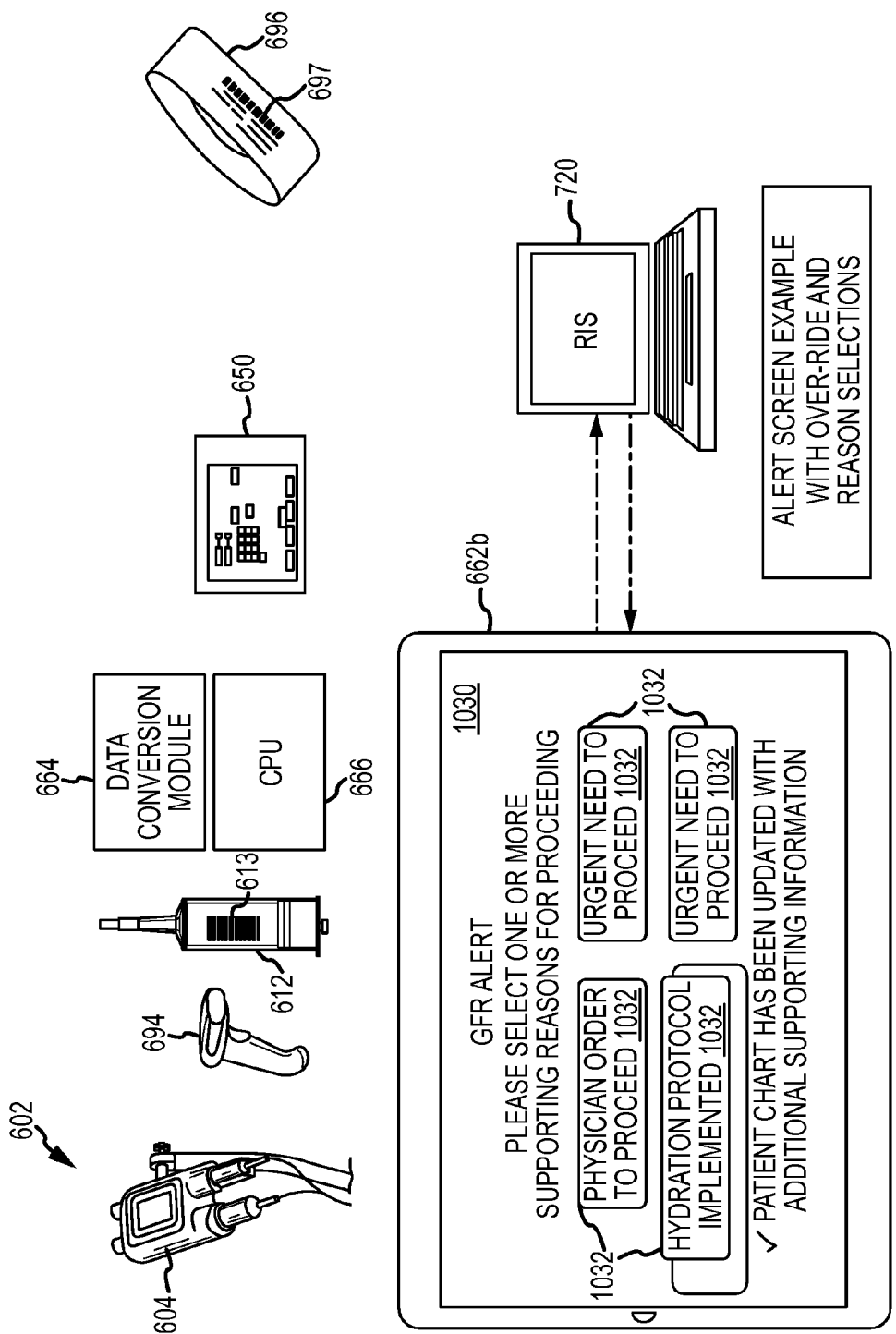
FIG. 33 as one embodiment of a GFR alert screen that may be used by an injection data management system or module having data format conversion capabilities.
Figure 34:
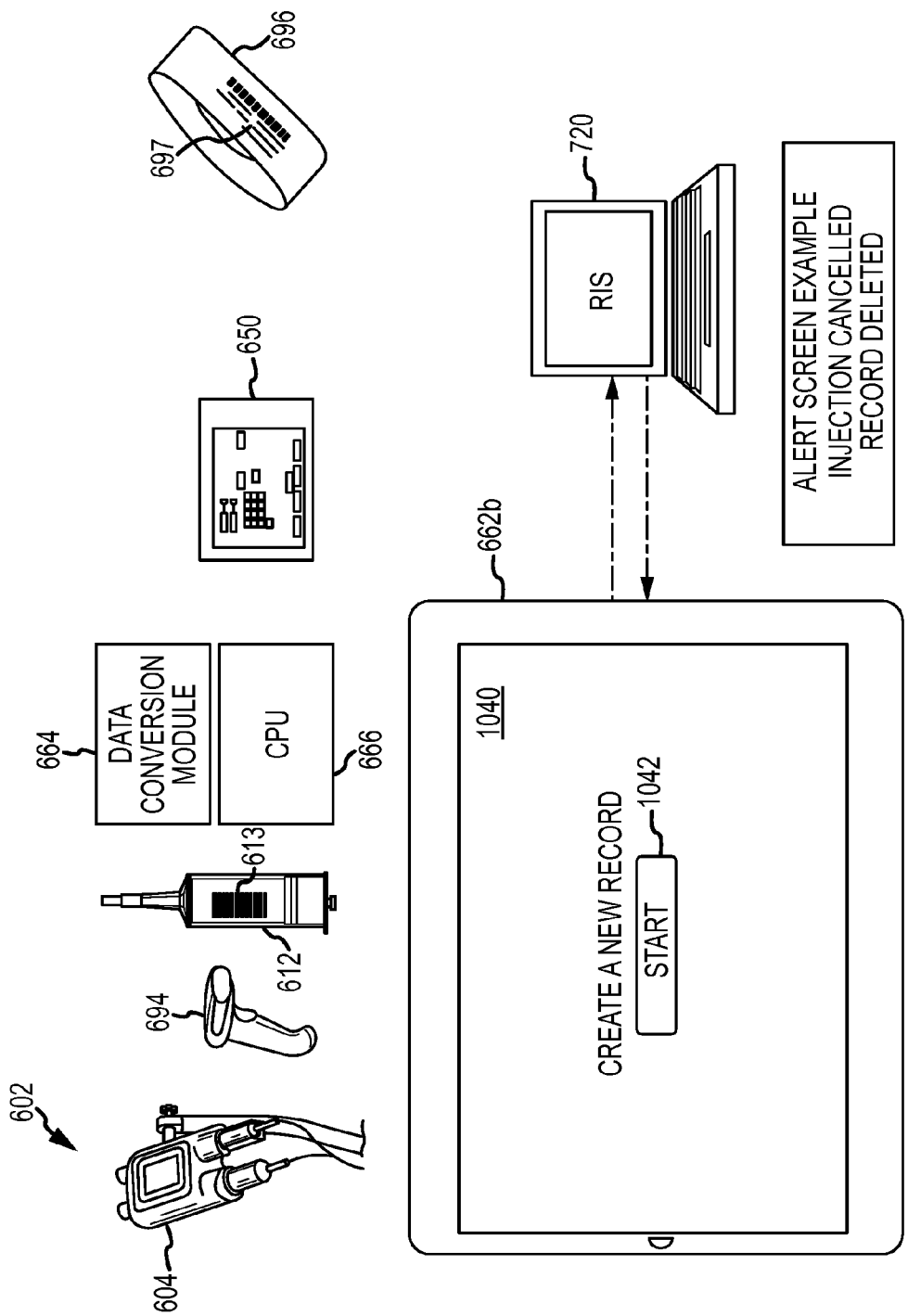
FIG. 34 is one embodiment of a create new record screen that may be used by an injection data management system or module having data format conversion capabilities.

Step 942 of the data management protocol 930 of FIG. 26 is directed to assessing patient data that has been loaded into the injection data management system 660*d*. One of the assessments that may be undertaken pursuant to step 942 is an assessment of the patient's renal function in accordance with the foregoing. The patient's renal function may be compared with a renal function threshold. In the event that the patient's renal function does not comply with the renal function threshold, the contrast media injector system 602 and/or the injection data management system 660*d* may be configured to provide two options. One option would be to allow the injection to proceed. In this regard, FIG. 33 presents one embodiment of a GFR or renal function alert screen 1030 for the injection data management system 660*d*, and which could be displayed if an injection is going to proceed, notwithstanding the patient's renal function failing to comply with a renal function threshold. The injection data management system 660*d* may be configured to require a user to identify the reason or rationale for proceeding in this type of instance, and this data may be retained in the corresponding injection history 649. The GFR alert screen 1030 provides four representative alert override options 1032. Other alert override options may be utilized. When a user activates one of the alert override options 1032, the corresponding injection history 649 is updated to include data that is indicative of the reason that the renal function alert was overridden.

Another option if the patient's renal function fails to comply with the renal function threshold is to not allow the injection of the patient to proceed. In this case, the injection data management system 660*d* may be configured to delete the correspondent injection history 649 from its data storage system 622. The injection data management system 660*d* may be configured to then transition to a "create new record" screen 1050 that is presented in FIG. 34. This create new record screen 1050 may be used to add a record 782 or injection history 649 to the data structure 780 stored on the data storage system 622 of the injection data management system 660*d* in this or any other instance. For instance and as noted above, the create new record screen 1040 could be generated in response to activation of the create order button 982 on the main screen 980 of FIG. 29.

Figure 35:
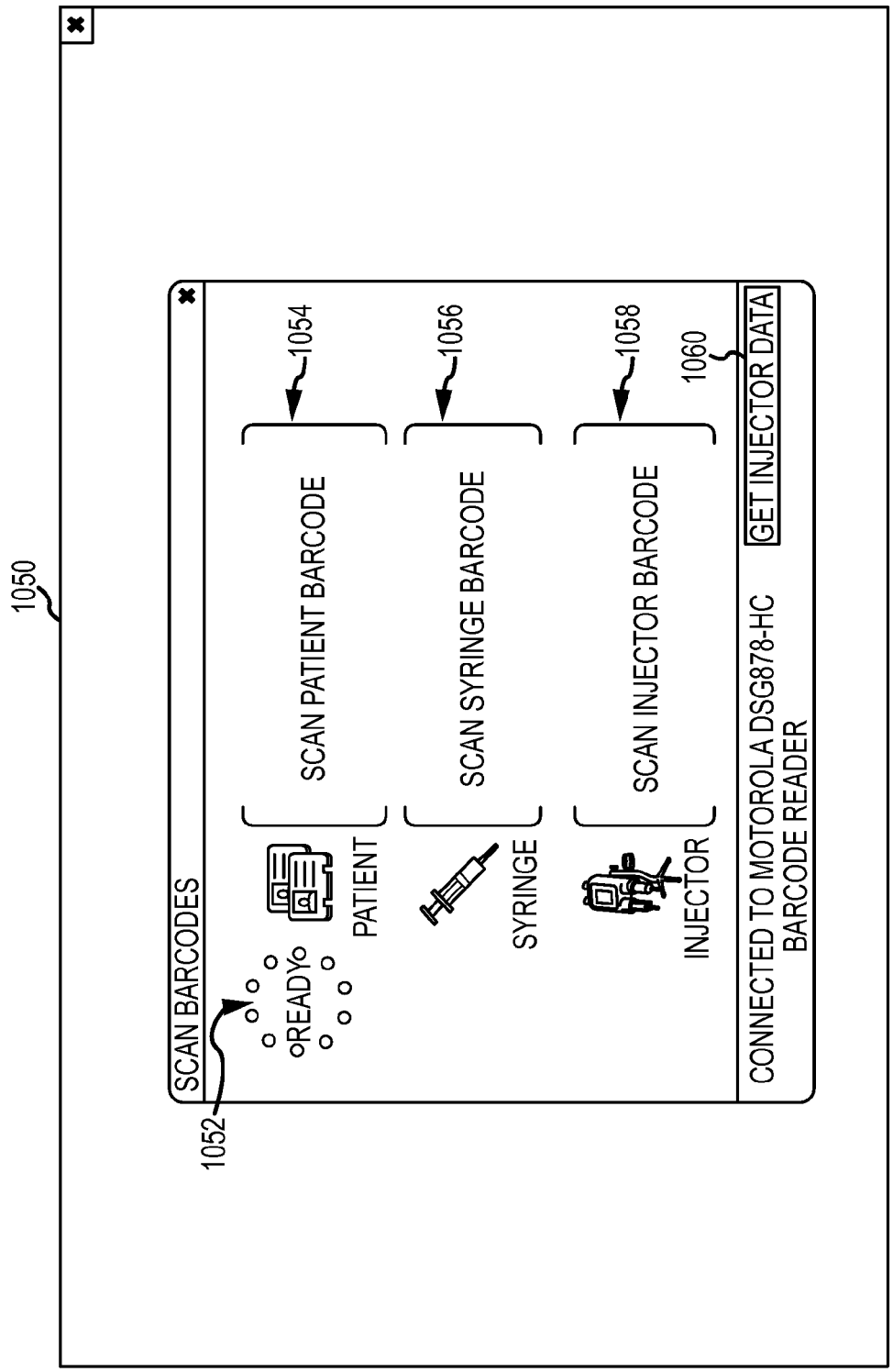
FIG. 35 is one embodiment of a data acquisition screen that may be used by an injection data management system or module having data format conversion capabilities.

FIG. 35 presents one embodiment of a "data scan" or more generally an "acquire data" screen 1050 for the injection data management system 660*d*. The acquire data screen 1050 may include a status icon 1052 (for indicating when the injection data management system 660*d* is ready to receive various types of data). An "acquire patient data" prompt 1054 may be presented on the acquire data screen 1050 (e.g., relation to inputting patient data (e.g., for fields 784-810 of data structure 780 discussed above in relation to FIGS. 23A-D) to the injection data management system 660*b*). An "acquire contrast media data" prompt 1056 may be presented on the acquire data screen 1050 (e.g., in relation to inputting contrast media data (e.g., for fields 818-824 and fields 831-836 of data structure 780 discussed above in relation to FIGS. 23A-D) to the injection data management system 660*d*). An "acquire injector system 602 ID" prompt 1058 may be presented on the acquire data screen 1050 (e.g., in relation to inputting an ID pertaining to the contrast media injector system 602, pertaining to its corresponding data conversion module 664, or both). A status icon 1052 could be displayed to each of the prompts 1054, 1056, and 1058 (e.g., an indicator of one state when the module 660*d* is ready to acquire the associated data, and an indicator in another when this data has actually been acquired).

The acquire data screen 1050 of FIG. 35 may also include a "get injection data" button 1060. Activation of the get injection data button 106 may be used to acquire contrast injection data from the contrast media injector system 602. However, the contrast media injector system 602 could also be configured to automatically push contrast injection data to the injection data management system 660*d*.

Figure 36:
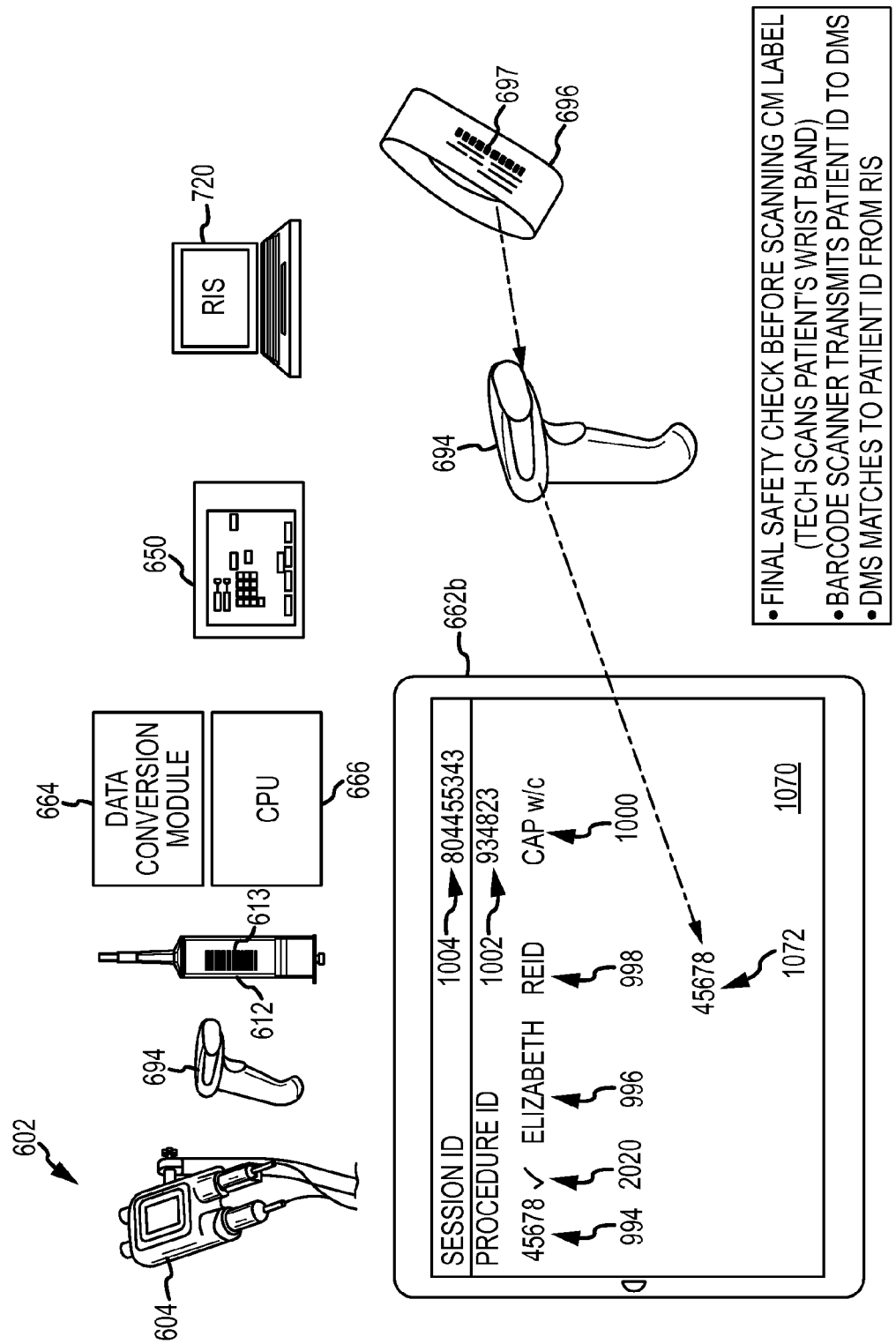
FIG. 36 is one embodiment of a patient ID validation screen that may be used by an injection data management system or module having data format conversion capabilities.

FIG. 36 presents one embodiment of a patient ID validation screen 1070 for the injection data management system 660*d*. In the illustrated embodiment, the patient ID 994 was loaded into the injection data management system 660*d* from the RIS 720. The injection data management system 660*d* may be configured to confirm or validate this patient ID 994 before allowing an injection to proceed with respect to this patient. In one embodiment, the barcode scanner 694 (or other appropriate data reader) may be used to scan a barcode 697 on a wristband 696 of the patient to be injected. This barcode 697 may include a patient ID 1072, and once scanned by the barcode scanner 694 the scanned patient ID 172 may be displayed on the patient ID validation screen 1070. If the scanned patient ID 1072 matches the patient ID 994 (again, retrieved from the RIS 720 in the illustrated embodiment), an appropriate validation indicator 2020 may be displayed next to the patient ID 994, and the injection may be allowed to proceed. If the scanned patient ID 1072 does not match the patient ID 994, the injection data management system 660*d* may be configured to not allow the injection of the patient (using the contrast media injector system 602) to proceed.

Figure 37:
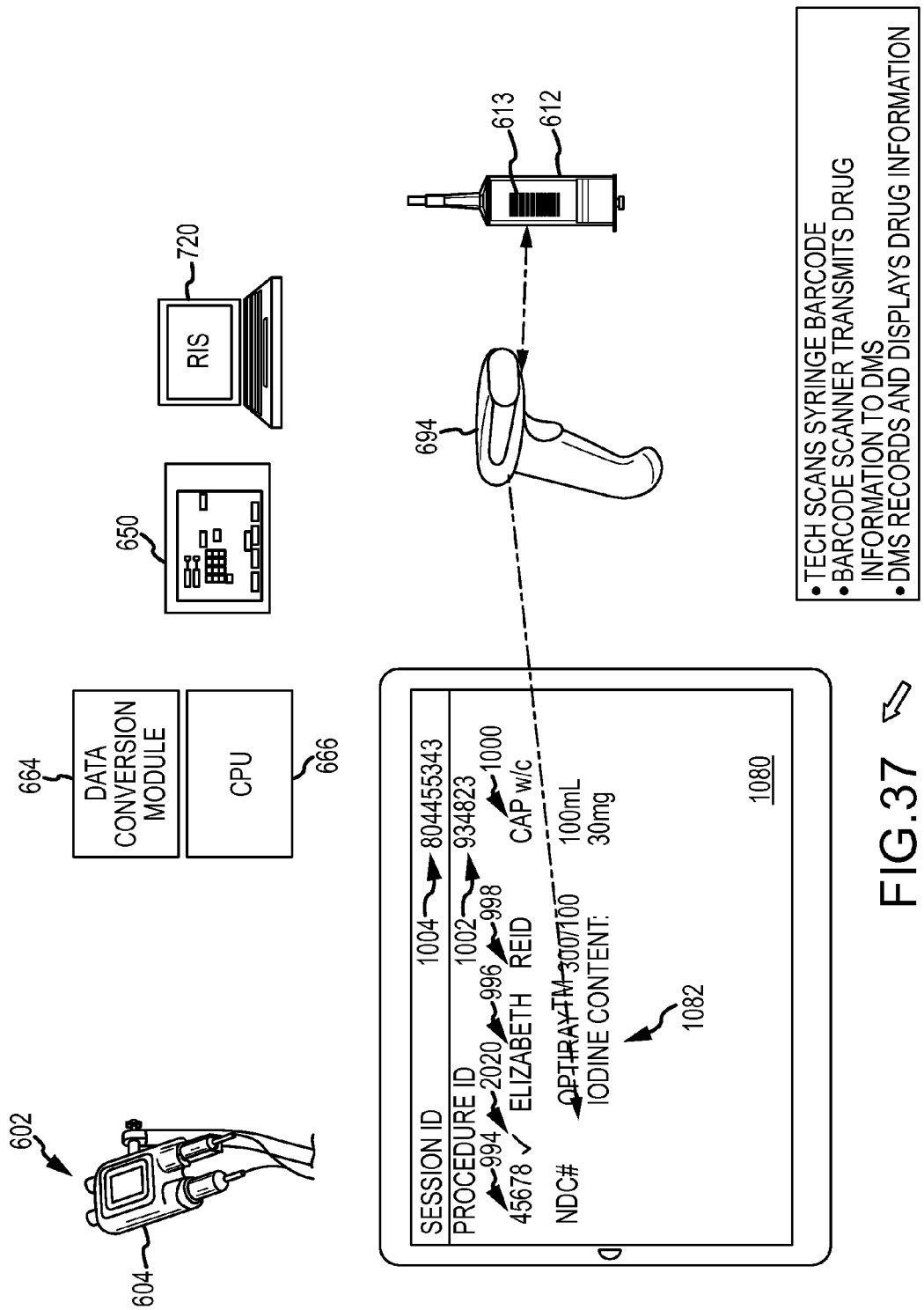
FIG. 37 is one embodiment of a contrast media data screen that may be used by an injection data management system or module having data format conversion capabilities.

FIG. 37 presents one embodiment of a scanned contrast media data screen 1080 for the injection data management system 660*d*. As discussed, contrast media data (e.g., for fields 818-824 and fields 831-836 of data structure 780 discussed above in relation to FIGS. 23A-D) may be stored on a data storage device 613 (e.g., a barcode) incorporated by the syringe 612. The barcode scanner 694 (or any other appropriate data reader) may be used to scan the data storage device 613 on the syringe 612 to input contrast media data to the injection data management system 660*d*.

Figure 38:
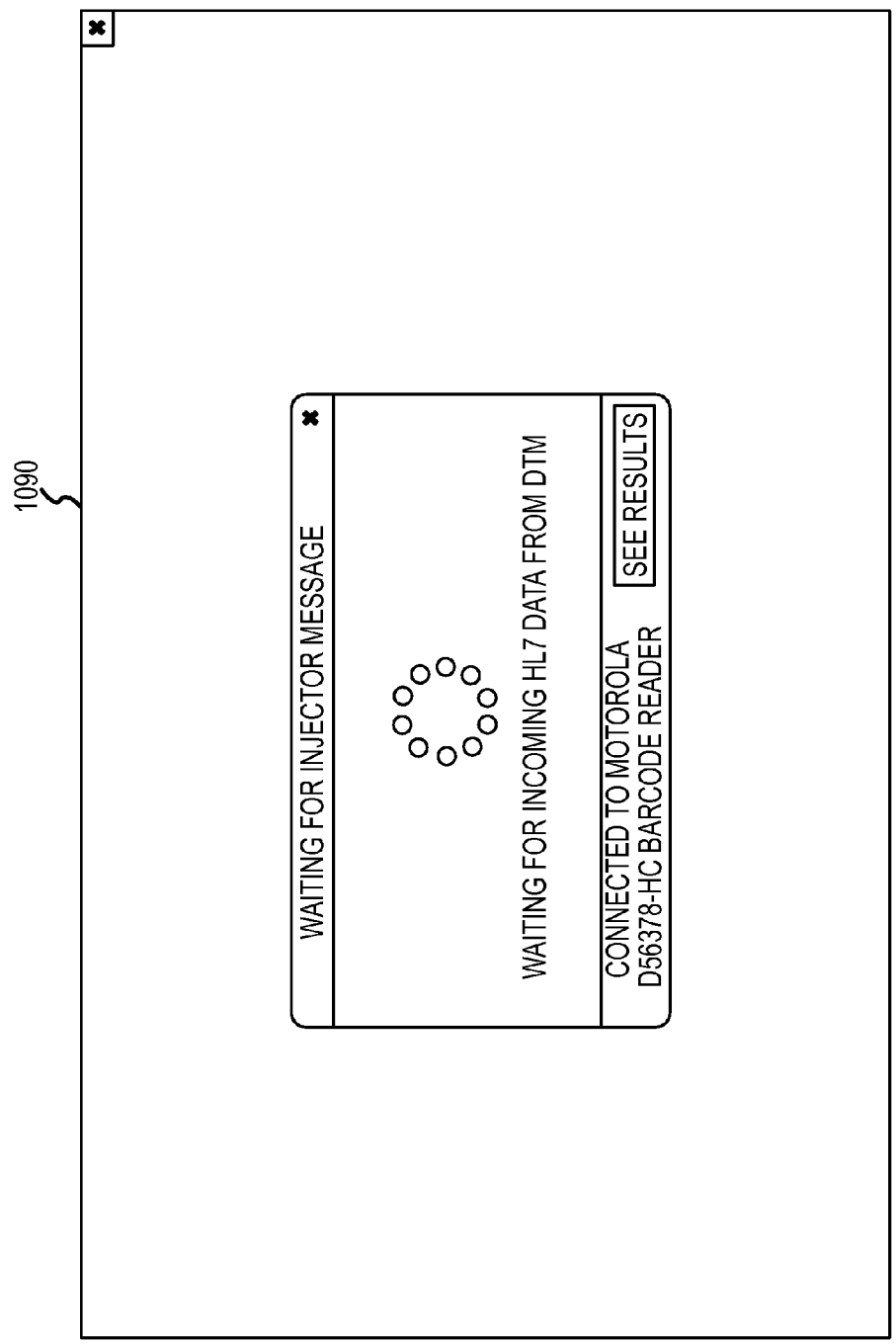
FIG. 38 is one embodiment of a contrast injection data status screen that may be used by an injection data management system or module having data format conversion capabilities.

FIG. 38 presents one embodiment of the contrast injection data status screen 1090 for the injection data management system 660*d*. This screen 1090 may be presented on one or more displays 662*b* of the injection data management system 660*d* to indicate when the injection data management system 660*b* is awaiting contrast injection data (e.g., programmed/prescribed contrast injection data, such as for fields 812-816 of data structure 780 discussed above in relation to FIGS. 23A-D; administered/achieved contrast injection data, such as for fields 826-830 of data structure 780 discussed above in relation to FIGS. 23A-D) from the contrast media injector system 602.

Figure 39:
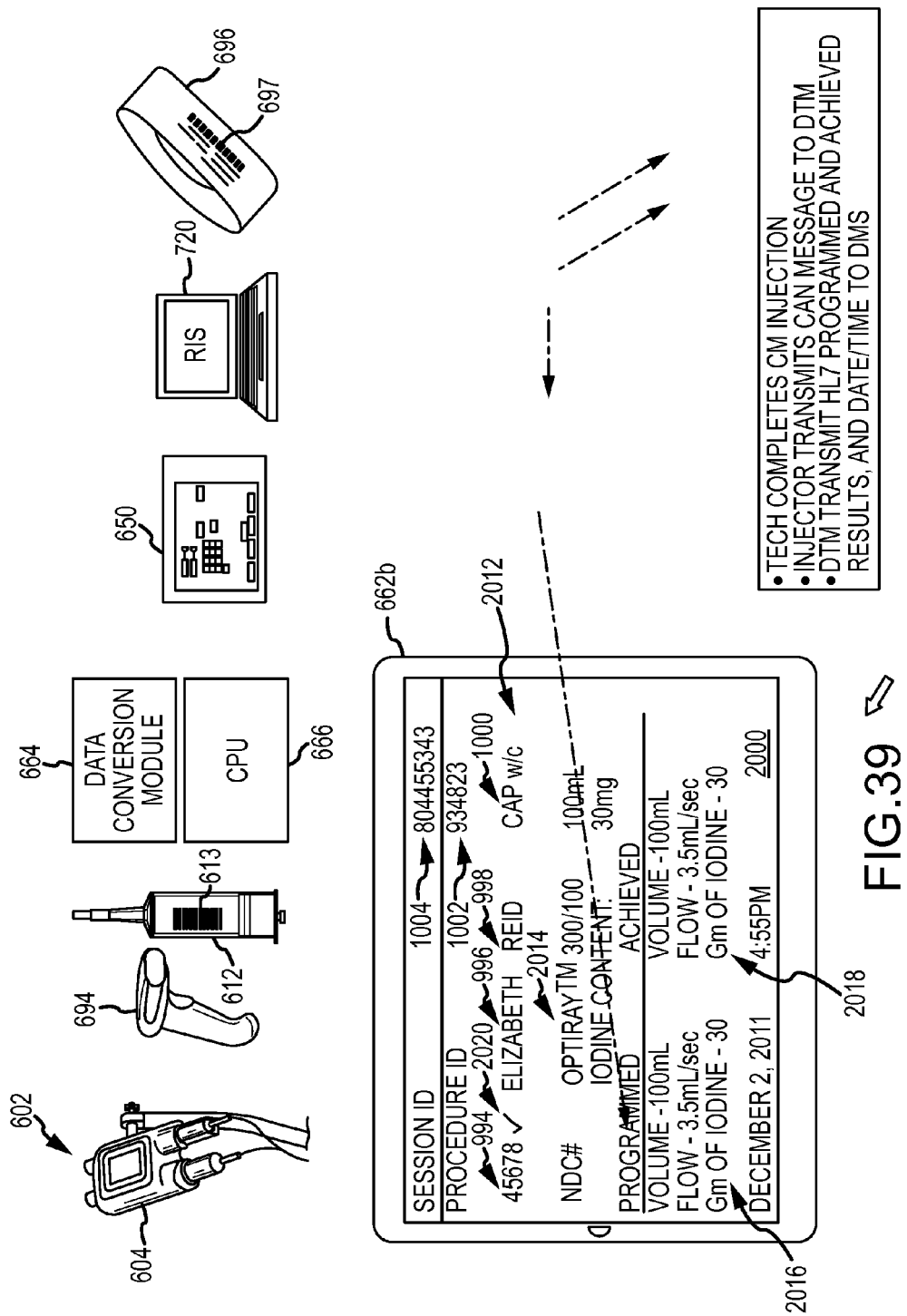
FIG. 39 is one embodiment of a current results screen that may be used by an injection data management system or module having data format conversion capabilities.

FIG. 39 presents one embodiment of a current results screen 2000 for the injection data management system 660*d*. This current results screen 2030 may be presented on one or more displays 662*b* of the injection data management system 660*d* during an injection. At least some patient data 2012 (e.g., from fields 784-810 of data structure 780 discussed above in relation to FIGS. 23A-D) and at least some contrast media data 2014 (e.g., from fields 818-824 and fields 831-836 of data structure 780 discussed above in relation to FIGS. 23A-D) may be displayed on the current results screen 2000. The session ID 1004, procedure ID 1002, and the current date and time may also be displayed on the results screen 2000. In addition, at least some of the programmed/prescribed contrast injection data 2016 (e.g., from/for fields 812-816 of data structure 780 discussed above in relation to FIGS. 23A-D), and at least some administered/achieved contrast injection data 2018 (e.g., from/for fields 826-830 of data structure 780 discussed above in relation to FIGS. 23A-D) for the current phase of the injection procedure being executed may be presented on the current results screen 2000 as well.

FIG. 40 presents one embodiment of a results screen 2030 for the injection data management system 660*d*. This results screen 2030 may be presented on one or more displays 662*b* of the injection data management system 660*d* to display one or more data categories relating to a completed injection. At least some patient data 2032 (e.g., from fields 784-810 of data structure 780 discussed above in relation to FIGS. 23A-D), at least some contrast media data 2034 (e.g., from fields 818-824 and fields 831-836 of data structure 780 discussed above in relation to FIGS. 23A-D), at least some programmed/prescribed contrast injection data 2036 (e.g., from fields 812-816 of data structure 780 discussed above in relation to FIGS. 23A-D), and at least some administered/achieved contrast injection data 2038 (e.g., from fields 826-830 of data structure 780 discussed above in relation to FIGS. 23A-D) may be simultaneously presented on the results screen 2030.

Figure 41:
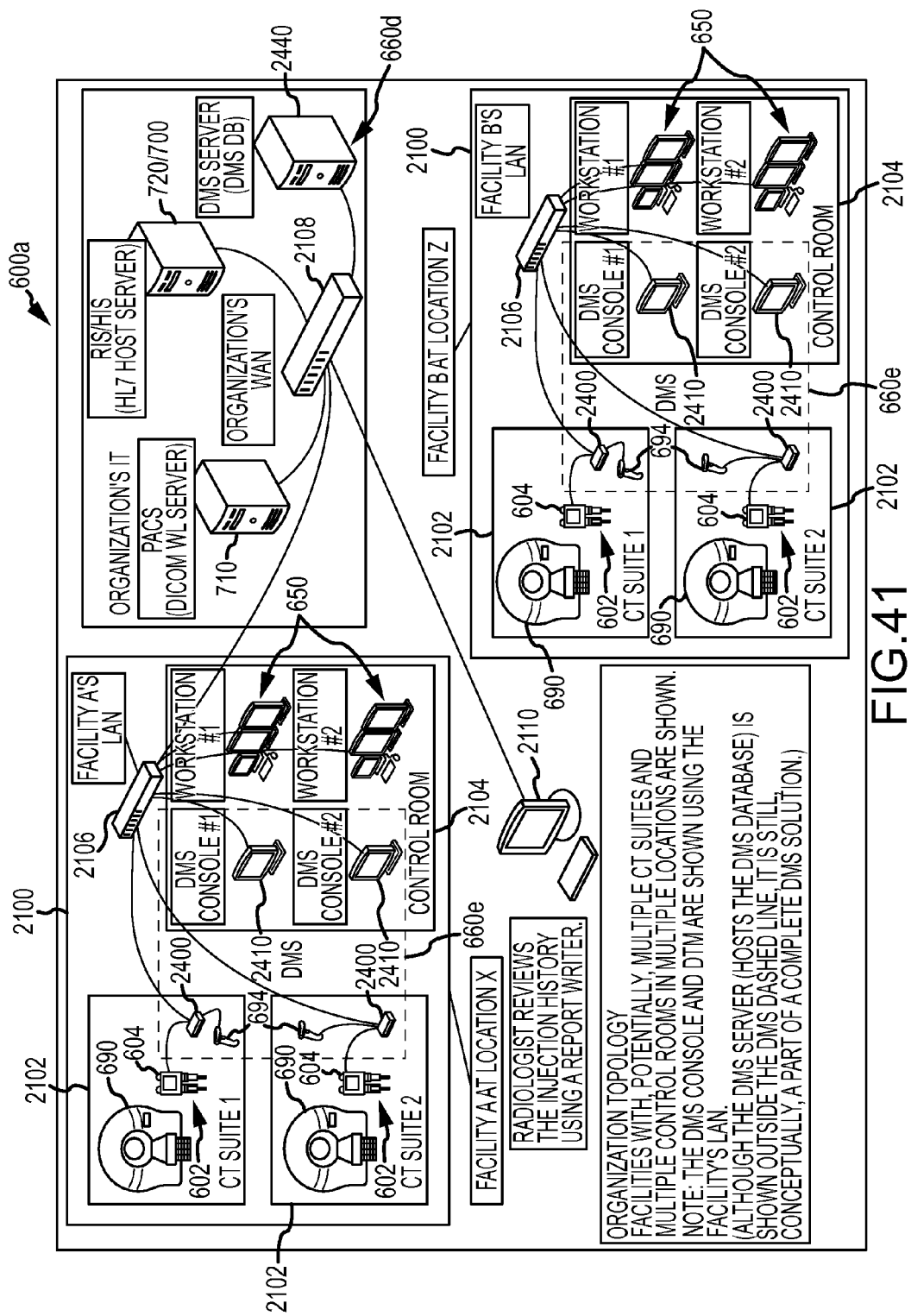
FIG. 41 is another embodiment of a medical system having an injection data management system or module having data format conversion or translation capabilities.

FIG. 41 presents a variation of the medical system 600 of FIG. 18, and is in the form of a medical system 600*a*. Unless otherwise noted to the contrary, the various features of the medical system 600 of FIG. 18 may be utilized by the medical system 600*a* of FIG. 41 (and vice versa). Generally, the medical system 600*a* of FIG. 41 includes a data management system 660*e* that is incorporated on a network, in a networked environment, or in a networked configuration with various other sub-systems of the medical system 600*a*.

The medical system 600*a* of FIG. 41 may include one or more medical facilities 2100 that are at different locations, including at different locations within the same city or in different cities. Any appropriate number of medical facilities 2100 may be part of the medical system 600*a*. Each medical facility 2100 utilizes a local area network 2106 for accommodating communications between various sub-systems within the given medical facility 2100. The local area network 2106 of each medical facility 2100 is also part of a wide area network 2108 for the medical system 600*a*.

Each medical facility 2100 may include one or more imaging suites 2102 (e.g., in accordance with the imaging room 420 discussed above in relation to FIG. 11). Any appropriate number of imaging suites 2102 may be located within a given medical facility 2100. Each imaging suite 2102 includes an imaging system 690 (e.g., a CT scanner) and at least part of a contrast media injector system 602 (e.g., a powerhead 604). Appropriate shielding may be provided for each imaging suite 2102.

The medical facility 2100 includes one or more control rooms 2104 (e.g., in accordance with the control room 402 discussed above in relation to FIG. 11). A given control room 2104 may be located adjacent to one or more imaging suites 2102, with appropriate shielding being disposed between a given imaging suite 2102 and its corresponding control room 2104. A remote console 650 (e.g., in accordance with the foregoing discussion) for one or more contrast media injector systems 602 may be located in each control room 2104. A given injector system remote console 650 may be dedicated to a single contrast media injector system 602. As such, one or more injector system remote consoles 650 may be located in each control room 2104 (two in the illustrated embodiment—one for each of the associated imaging suites 2102/contrast media injector systems 602).

The medical system 600*a* presented in FIG. 41 is illustrated as incorporating an injection data management system 660*e* that is least generally in accordance with the foregoing injection data management systems. The data management system 660*e* may utilize a data conversion or translation module 2400 for each contrast media injector system 602. The injection head or powerhead 604 of a given contrast media injector system 602 may communicate with its corresponding data translation module 2400 over an appropriate communication link on the local area network 2106 of the corresponding medical facility 2100. Data acquired by a barcode scanner 694 of the data management system 600*e* may be communicated to the contrast media injector system 602, which may relay the same to its corresponding data translation module 2400. Alternatively, data acquired by a barcode scanner 694 may be communicated directly to the corresponding data translation module 2400. In accordance with the foregoing discussion, a given data translation module 2400 may also communicate with the imaging system 690 that is associated with its corresponding contrast media injector system 602 (optional).

Each data translation module 2400 may communicate with its corresponding local area network 2106 over an appropriate communication link. In this regard, data from a contrast media injector system 602 may be transmitted to its corresponding data translation module 2400 over the local area network 2106. This data ultimately may be transmitted to one or more medical sub-systems within the corresponding medical facility 2100 over the local area network 2106, ultimately may be transmitted to a data management system (DMS) server 2440 over the wide area network 2108 (which could then make this data available to other medical facilities 2100 of the medical system 600*a*, although not required), or both. Generally, the DMS server 2440 is part of the data management system 660*e*, and may at least provide the function of the data processing unit 666 addressed above for multiple data translation modules 2400.

The data management system 660*e* provides a dedicated DMS console 2410 for each data translation module 2400. Stated another way and for the case of the medical system 600*a* of FIG. 41, the data management system 660*e* utilizes a single. DMS console 2410 for each contrast media injector system 602. Each DMS console 2410 may be disposed at any appropriate location. In the illustrated embodiment, each DMS console 2410 is located in the control room 2104 of its corresponding data translation module 2400/contrast media injector system 602.

Each DMS console 2410 of the data management system 660e may be used in relation to the generation of a DMS patient record 2420 on an injection procedure for a patient (discussed below in relation to FIG. 41B, but where one or more medical fluids may be injected into the patient, including where each phase of an injection protocol may provide for the injection of a single medical fluid into the patient or the simultaneous injection of multiple medical fluids into the patient). DMS patient records 2420 could also be reviewed on a given DMS console 2410. Generally, data from a data translation module 2400 relating to an injection of a patient may be transmitted to and stored on its corresponding DMS console 2410. At some point in time thereafter, the DMS console 2410 may thereafter transmit DMS patient records 2420 to the DMS server 2440. The data management system 660e may include one or more workstations 2110 on one or more of the local area networks 2106 of the medical system 600a, on the wide area network 2108 for the medical system 600a, or both. A user may access/review DMS patient records 2420 that are being stored on the DMS server 2440, and may generate/view any appropriate reports regarding one or more of the DMS patient records 2420 through such a workstation 2110.

The medical system 600a of FIG. 41 also shows a PACS 710 and a RIS 720/HIS 700, and which may each communicate with the DMS server 2440 over the wide area network 2108 of the medical system 600a. The medical system 600a could also utilize other components shown in FIG. 18A and as noted above. Although the medical system 600a is shown as having a PACS 710 and RIS 720/HIS 700 that are shared by multiple medical facilities 2100, a given medical facility 2100 could also have a designated PACS 710, a designated RIS 720, a designated HIS 700, or could share one or more of these medical sub-systems with one or more other medical facilities 2100.

Figure 41A:
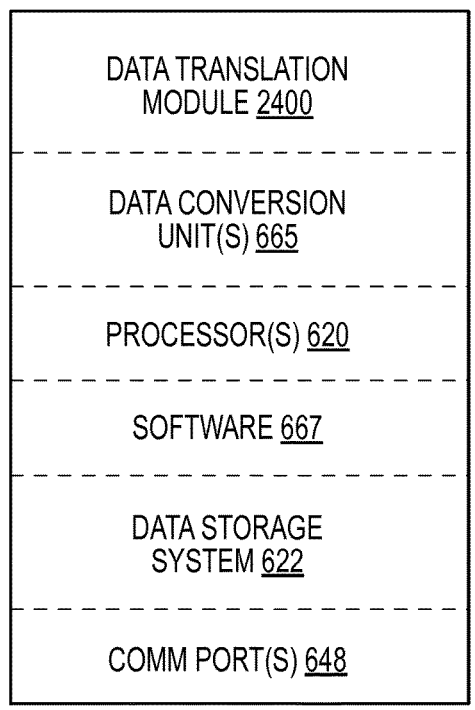
FIG. 41A is a schematic of one configuration for a data conversion or translation module used by the injection data management system of FIG. 41.

FIG. 41A presents a representative embodiment for a data translation module for the data management system 660e (a data conversion/translation module 664 also having been discussed above in relation to the medical system 600a of FIG. 41). Generally, each data translation module 2400 may be configured to convert or translate data from at least one format into at least one other format (e.g., to convert CAN-compliant data into an HL-7-compliant format, to convert or translate CAN-compliant data into a PACS-compliant or DICOM-compliant format, to convert or translate data from one CAN-compliant format into a different CAN-compliant format). Each data translation module 2400 may be configured: 1) to translate an injection protocol to be used/being used by the corresponding contrast media injector system 602 to inject one or more medical fluids into a patient (e.g., injection data 2424 discussed below in relation to FIG. 41O), to translate the achieved values from the execution of an injection protocol by the corresponding contrast media injector system 602 (e.g., injection data 2424), to translate injection media data acquired by the data management system 660e (e.g., contrast media data 2426 and/or saline media data 2428 discussed below in relation to FIG. 41O), and to transmit such data to its corresponding DMS console 2410; 2) to notify a user of the data management system 660e when communication has been lost with its corresponding contrast media injector system 602 (e.g., by causing an appropriate message to be displayed on the DMS console 2410 associated with the data translation module 2400); 3) to notify the DMS console 2410 when the data translation module 2400 is unable to report injection data (e.g., injection data 2424); and 4) to communicate with its corresponding contrast media injector system 602 to acquire the time and date from its internal clock for storage with a corresponding DMS patient record 2420.

The data translation module 2400 may include one or more data conversion units 665 (e.g., any of the data conversion units discussed above, including those addressed in relation to FIGS. 19 and 20). Any multiple data conversion unit 665 configuration for the data translation module 2400 may utilize any appropriate architecture, including the architectures presented by FIGS. 19 and 20. The data translation module 2400 may further include one or more processors 620, software 667, at least part of the data storage system 622 for the data management system 660e, and one or more communication ports 648, all in accordance with the discussion presented above.

Each data translation module 2400 of the data management system 660e may be characterized as a self-contained, embedded system that is dedicated to the translation of internal CAN messages of its corresponding contrast media injector system 602 (e.g., to convert a communication or command from one data format to a different data format), and communicating these translations to its corresponding DMS console 2410 over the local area network 2106. Each data translation module 2400 may also be characterized as being responsible for the translation of (including by monitoring CAN messages that are internal to the contrast media injector system 602): 1) an injection protocol being used by its corresponding contrast media injector system 602 (e.g., injection data 2424); 2) values achieved by the contrast media injector system 602 in executing an injection protocol to inject one or more medical fluids into a patient, including sequential and/or simultaneous injections using multiple injection media (e.g., injection data 2424); 3) contrast media data regarding contrast media to be used by its corresponding contrast media injector system 602 in the execution of an injection protocol (e.g., contrast media data 2426); and 4) saline data regarding saline to be used by its corresponding contrast media injector system 602 in the execution of an injection protocol (e.g., saline media data 2428).

Data that is acquired by the data translation module 2400 may be stored locally on its data storage system 622, and may be transmitted to its corresponding DMS console 2410 on any appropriate basis. In one embodiment, the data translation module 2400 notifies its corresponding DMS console 2410 when an injection of a patient has been completed by its corresponding contrast media injector system 602. This notification may be in the form of the data translation module 2400 sending the injection data (e.g., injection data 2424) to its corresponding DMS console 2410, including only after completion of the injection. The data management system 660e may be configured so that injection data (e.g., injection data 2424) is not sent by a given data translation module 2400 to its corresponding DMS console 2410 upon completion of a drip injection by its corresponding contrast media injector system 602, upon completion of a patency check injection by its corresponding contrast media injector system 602, or both.

Figure 41B:
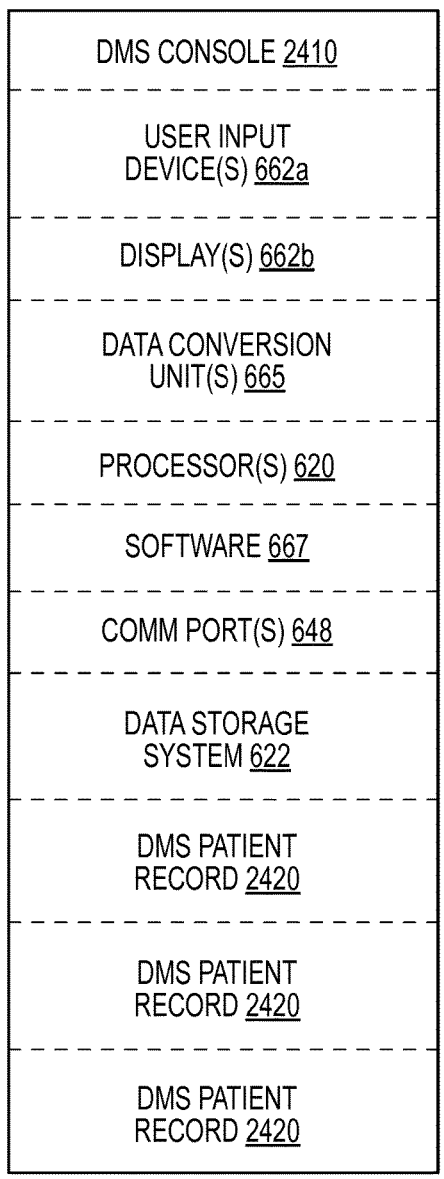
FIG. 41B is a schematic of one configuration for a DMS console used by the injection data management system of FIG. 41.

FIG. 41B presents a representative embodiment of a DMS console 2410 for the data management system 660e (discussed above in relation to the medical system 600a of FIG. 41), and which may use an operating system that supports multitasking. As noted above, the data management system 660e may be configured such that each data translation module 2400 has a dedicated DMS console 2410 (e.g., each data translation module 2400 may communicate with a single DMS console 2410, and each DMS console 2410 may communicate with a single data translation module 2400). Generally, each DMS console 2410 may be characterized as being a self-contained, embedded system that is dedicated to providing a user interface for at least its corresponding portion of the data management system 660e, for facilitating the management of injection data 2424, contrast media data 2426, saline media data 2428, and patient data 2430 (again, discussed below in relation FIG. 41C), for displaying various data to a user of the data management system 660e, and the like. In this regard, each DMS console 2410 includes one or more user input devices 662a of the above-described type (including without limitation touch screen functionality) and one or more displays 662b of the above-described type.

Each DMS console 2410 may be of any appropriate configuration, for instance including one or more processors 620, software 667, at least part of the data storage system 622 for the data management system 660e, and one or more communication ports 648, all in accordance with the discussion presented above. The DMS console 2410 could also include one or more data conversion units 665 (e.g., any of the data conversion units discussed above, including those addressed in relation to FIGS. 19 and 20), although the DMS console 2410 could be configured so as to not have any data conversion functionality. Any multiple data conversion unit 665 configuration for the DMS console 2410 may utilize any appropriate architecture, including the architectures presented above in relation to FIGS. 19 and 20. In one embodiment, all data conversion/translation functionality of the data management system 660e resides only in the various data translation modules 2400.

Continuing to refer to FIG. 41B, each DMS console 2410 is configured to store one or more DMS patient records 2420 on its corresponding portion of the data storage system 622 for the data management system 660e. Each DMS console 2410 may be configured to compile a DMS patient record 2420 at least from data received from its corresponding data translation module 2400. In one embodiment, each DMS console 2410 is configured to be able to store only a predetermined number of patient records 2420 (e.g., 24 DMS patient records 2420). DMS patient records 2420 may be transmitted from a given DMS console 2410 to the DMS server 2440 on any appropriate basis (e.g., periodically; on a programmed basis; upon request).

Other functionality may be associated with the DMS console 2410. The DMS console 2410 may be used to monitor the state of its corresponding data translation module 2400. A message may be presented on the DMS console 2410 when its corresponding data translation module 2400 becomes inactive, as well as when its corresponding data translation module 2400 is unable to report injection data 2424. A DICOM worklist may be retrieved (e.g., from the RIS 720 and/or PACS 710) through the DMS console 2410 (e.g., in response to user input to the DMS console 2410). The DMS console 2410 may be configured to acquire the time and date from the internal clock of the DMS server 2440 for purposes of the storage of a corresponding DMS patient record 2420 (e.g., associated with the time/date of creation of the DMS patient record 2420). In the event of a loss of connectivity between the DMS console 2410 and the DMS server 2440 during the transmission of queried DMS patient records 2420 from the DMS console 2410 to the DMS server 2440, the DMS console 2410 may be configured to send any remaining queried DMS patient records 2420 to the DMS server 2440 when network connectivity is restored.

Figure 41C:
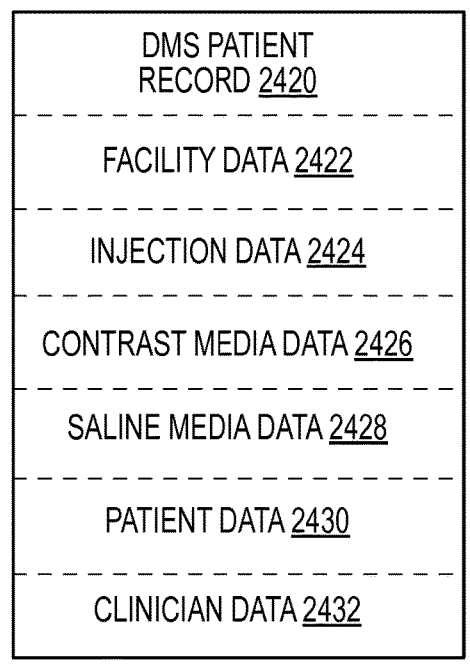
FIG. 41C is a schematic of one configuration of a DMS patient record that may be stored on the injection data management system of FIG. 41.

FIG. 41C presents a representative DMS patient record 2420. A DMS patient record 2420 may be at least generally in accordance with the above-discussed injection history 649, and in any case may include an identification of the contrast media injector system 602 that was used for the procedure associated with the data contained in the DMS patient record 2420, an identification of the data translation module 2400 and/or DMS console 2410 that was used to generate the DMS patient record 2420 (and which is dedicated to a particular contrast media injector system 602), and the like. Each DMS patient record 2420 may also include the date and time of the completion of the corresponding injection based on the clock from the corresponding contrast media injector system 602, may include the date and time of the creation of the DMS patient record 2420 by the DMS console 2410 based on the clock of the DMS server 2440, or both.

Each DMS patient record 2420 may include facility data 2422 (e.g., organization name, facility name, facility address, modality control room identifier, modality identifier), injection data 2424 (e.g., programmed injection data, discussed above, and such as protocol name, injection delay, scan delay, pressure limit, phase parameters, phase number, phase type (Side A of the contrast media injector system 602 (e.g., associated with one syringe 612 installed on the powerhead 604), Side B of the contrast media injector system 602 (e.g., associated with another syringe 612 installed on the same powerhead 604), Simultaneous Injection (e.g., concurrent operation of Side A and Side B of the contrast media injector system 602), OptiBolus, Timing Bolus); actual/administered injection data or "achieved results", discussed above, such as injection delay, scan delay, peak pressure, phase parameters, phase number, phase type (Side A, Side B, Simultaneous Injection, OptiBolus, Timing Bolus), volume, flow rate, phase delay; contrast media data 2426 (e.g., contrast media data 2014 discussed above, such as media type, drug or product name (commercial name), package type (bottle or syringe), syringe size, contrast media volume, barcode, iodine concentration, manufacture date, expiration date, manufacturers lot number); saline media data 2428 (media type, drug or product name (commercial name), package type (bottle or syringe), syringe size, manufacture date, expiration date, manufacturer's lot identifier); patient data 2430 (e.g., patient data 2012 discussed above, such as diagnostic procedure date, ICD-9 Code, patient ID, patient name, patient age, patient sex, patient weight, patient GFR, known patient allergies, current prescribed medications, known patient iodine load, referring physician, referring physician ID, procedure location, modality, medical order ID, diagnostic procedure name, prescribed contrast media concentration, prescribed contrast media flow rate); and clinician data 2432 (clinician name, clinician employment identifier).

Figure 41D:
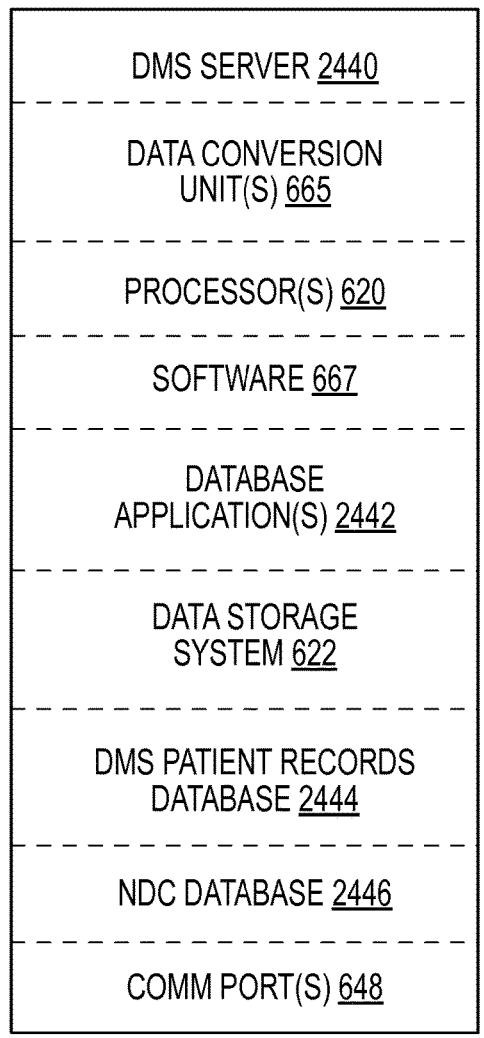
FIG. 41D is a schematic of one configuration for a DMS server used by the injection data management system of FIG. 41.

FIG. 41D presents a representative embodiment for the DMS server 2440 of the data management system 660e (discussed above in relation to the medical system 600a of FIG. 41). The DMS server 2440 may be of any appropriate configuration, for instance including one or more processors 620, software 667, at least part of the data storage system 622 for the data management system 660e, and one or more communication ports 648, all in accordance with the discussion presented above. The OMS server 2440 could also include one or more data conversion units 665 (e.g., any of the data conversion units discussed above in relation to FIGS. 19 and 20, for instance to convert data stored in a DMS patient record 2420 into an HL-7-compliant format for transmission to the HIS 700), although the DMS server 2440 could be configured so as to not have any data conversion functionality. Any multiple data conversion unit 665 configuration for the DMS server 2440 may utilize any appropriate architecture, including the architectures presented above in relation to FIGS. 19 and 20.

The DMS server 2440 may include a national drug code or NDC database 2446 within its corresponding portion of the data storage system 622 for the data management system 660e. The DMS server 2440 also includes a DMS patient records database 2444 within its corresponding portion of the data storage system 622. DMS patient records 2420 from one or more DMS consoles 2410 may be stored within the DMS patient records database 2444. Typically, multiple DMS patient records 2420 from multiple DMS consoles 2410 will be stored on the DMS server 2440. In one embodiment, the DMS server 2440 is configured to store at least a predetermined number of DMS patient records 2424 from each DMS console 2410/data translation module 2400 pair that is part of the data management system 660e.

The DMS server 2440 may include one or more database applications 2442 for use in conjunction with the DMS patient records database 2444 and/or the NDC database 2446. The DMS server 2440 may be configured: 1) such that only DMS patient records 2420 with a corresponding patient ID are transmitted to the HIS 700; 2) to disable transmission of DMS patient records 2420 to the HIS 700; 3) to query a DICOM worklist from the PACS 710 and/or RIS 720; and 4) to transmit DMS patient records 2420 to the HIS 700 on any appropriate basis (e.g., periodically; on a programmed basis; as requested). In the event of a loss of connectivity between the DMS server 2440 and the HIS 700 during the transmission of queried DMS patient records 2420 from the DMS server 2440 to the HIS 700, the DMS server 2440 may be configured to send any remaining queried DMS patient records 2420 to the HIS 700 when network connectivity is restored.

Figure 42:
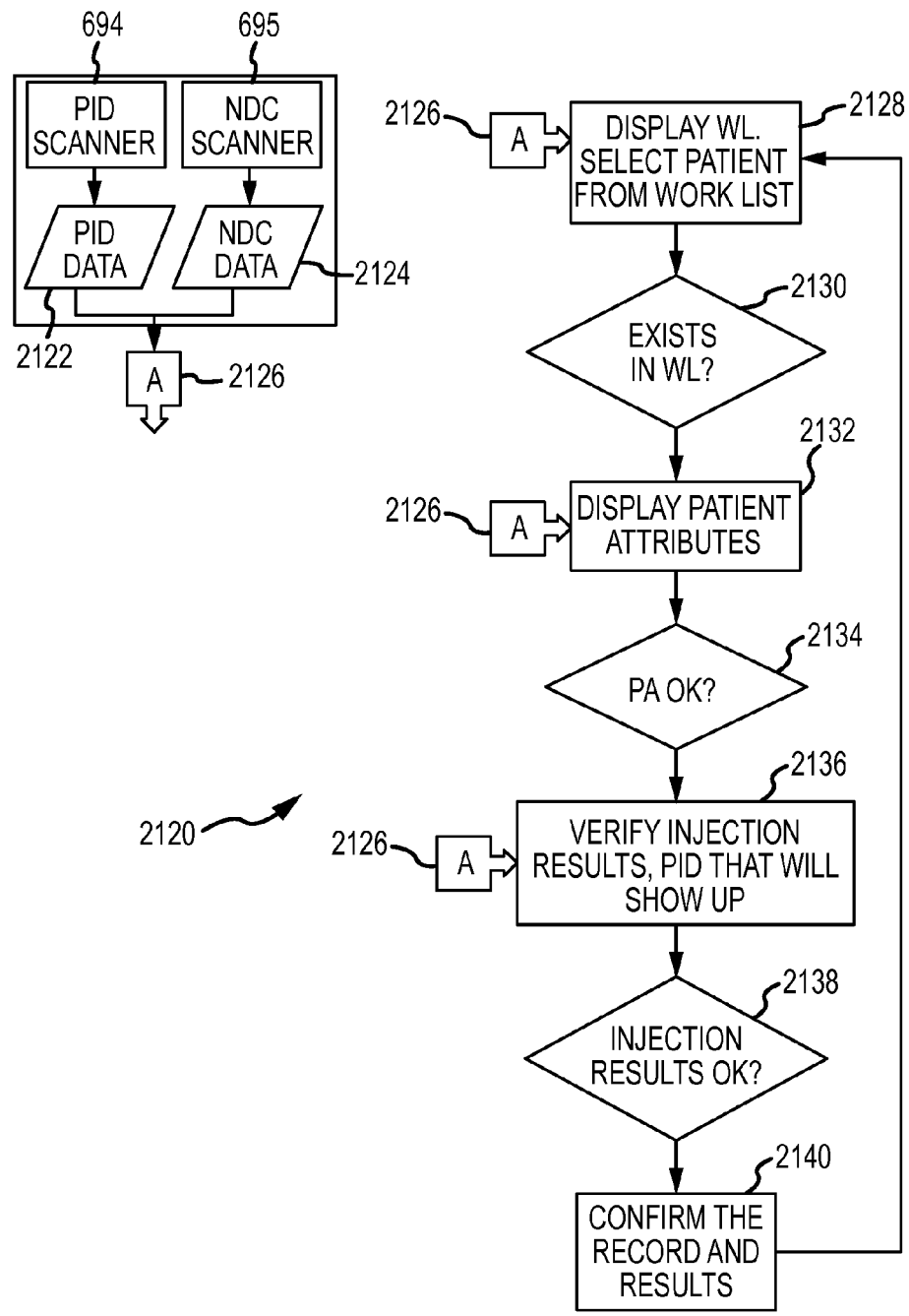
FIG. 42 is another embodiment of a data management protocol that may be used by an injection data management system or module having data format conversion capabilities.

FIG. 42 presents another embodiment of a data management protocol that may be used by a data management system, and that is identified by reference numeral 2120 in FIG. 42. Although the data management protocol 2120 will be described in relation to the data management system 660e of FIG. 41, it should be appreciated that the data management protocol 2120 may be used/adapted for use by any of the data management systems described herein (e.g., data management systems 660, 660a, 660b, 660c, and 660d). It should also be appreciated that the discussion of the data management protocol 2120 will be in relation to a contrast media injector system 602 and its corresponding data translation module 2400 and DMS console 2410. However, the same data management protocol 2120 may be executed in relation to each contrast media injector system 602 of the medical system 600a, along with their corresponding data translation module 2400 and DMS console 2410.

Patient identification information may be acquired in any appropriate manner for purposes of the data management protocol 2120 (step 2122), for instance using a barcode scanner 694 to read a data storage device 697 incorporated by a wristband 696 worn by the patient that is to undergo an injection procedure. The barcode scanner 694 could communicate patient ID data directly to the corresponding data translation module 2400, or the barcode scanner 694 could communicate the patient ID data to the contrast media injector system 602, which could then relay the patient ID data to the corresponding data translation module 2400. Patient ID data could also be input to the data management system 660e using the DMS console 2410 associated with the contrast media injector system 602 that will be used to inject the patient. In any case, patient ID data may be stored on the corresponding data translation module 2400 and/or on the DMS console 2410 (after being transmitted from the data translation module 2400).

Contrast media, alone or in combination with saline, will typically be injected into a patient (generally, "injection media") in conjunction with the execution of the data management protocol 2120 of FIG. 42, although other injectable medical fluids may be appropriate for use in conjunction with the data management protocol 2120. Data on each injection media may be acquired in any appropriate manner (step 2124) for purposes of the data management protocol 2120. For instance, a scanner 695 may be used to read contrast media data 2426 stored on a data storage device 613 associated with a syringe 612 to be used by the contrast media injector system 602, to read saline media data 2428 stored on a data storage device 613 associated with a syringe 612 to be used by the contrast media injector system 602, or both. As discussed above, a barcode scanner 694 from the data management system 660e could also be used to acquire injection media data, as could an appropriate reader incorporated by the contrast media injector system 602 itself (e.g., in accordance with the discussion of FIGS. 7-10, such as an RF reader). The injection media data from step 2124 may be stored on the corresponding data translation module 2400, but is ultimately transmitted to the corresponding DMS console 2410. The injection media data acquired pursuant to step 2124 may also be displayed on the DMS console 2410 at the time of acquisition. Although the patient identification data (step 2122) and the injection media data (step 2124) are each characterized as an input 2126 on the flowchart of FIG. 42, each may be independently acquired (at the same time or a different time) and transmitted (at the same time or a different time) to the data translation module 2400 and/or the DMS console 2410.

The DMS console 2410, to be used in conjunction with an injection of a patient, may retrieve a worklist from the PACS 710 or the RIS 720 (e.g., worklist 992 discussed above in relation to FIG. 30; worklist 2232 discussed below in relation to FIG. 45B). Step 2128 of the data management protocol 2120 of FIG. 42 is directed toward selecting a patient from the worklist that may be displayed on the DMS console 2410. This selection may be made using the DMS console 2410 (e.g., through a user input device 662a). A determination may be made as to whether the patient is identified on the worklist (step 2130). The patient identification information (step 2122) could be used by the data management protocol 2120 to automatically identify/select the patient on the worklist (step 2128), or the selection of the patient from the worklist (step 2128) could be in response to user input through the DMS console 2410. Assuming that the patient is indeed on the worklist (step 2128), the data management protocol 2120 proceeds from step 2130 to step 2132.

It should be appreciated that the data management protocol 2120 could be supplemented to allow for manual entry of a patient in the manner discussed below in relation to the data management protocol 2150 of FIGS. 43A and 43B. It should also be appreciated that the selection of the patient from the worklist through a user input device 662a of the DMS console 2410 (step 2128) could be compared with the acquired patient ID data (step 2122) to confirm that there is in fact a match, all in conjunction with step 2130 of the protocol 2120. If the patient ID data (step 2122) does not match the patient selected from the worklist (step 2128) in this case, the data management protocol 2120 could be configured to present a patient ID error window 2330 on the DMS console 2410, as will be discussed below in relation to FIG. 45C.

Patient data 2430 may be displayed on the DMS console 2410 through execution of step 2132 of the data management protocol 2120 of FIG. 42. For instance, the patient identification information (step 2122) and/or the selection of the patient from the worklist (step 2128) may be used to retrieve patient data 2430 for purposes of step 2132. Patient data 2430 may be provided to the data management system 660e in any appropriate manner for purposes of step 2132. For instance, the patient ID provided pursuant to step 2122 may be used by the data management system 660e to retrieve corresponding patient data 2430 from a medical sub-system 735 that is operatively interconnected with the data management system 660e (e.g., from the worklist associated with steps 2128 and 2130; from the HIS 700), and which would then transmit this data to the data management system 660e. The contrast media data 2426 and/or saline media data 2428 that was acquired pursuant to step 2124 could also be displayed for purposes of step 2132, as well as the corresponding programmed injection data (which could be retrieved from the worklist—see step 2128; which could be provided by the contrast media injector system 602 to the data translation module 2400, which could then transmit this data to the DMS console 2410). In any case, the data management protocol 2120 may be configured to request user input (step 2134) regarding the validity of the patient data 2430 that is being displayed pursuant to step 2132 (e.g., requiring a user to confirm that the information displayed pursuant to step 2132 is appropriate for purposes of proceeding with an actual injection of the associated patient).

The injection of the patient with contrast media, alone or in combination with saline, takes place between steps 2134 and 2136 of the data management protocol 2120 of FIG. 42. The injection data 2424 may be stored on the data translation module 2400 (and as discussed above, may be translated or converted from one data format to another as well). Upon completion of the injection procedure on the patient: 1) the data translation module 2400 notifies the DMS console 2410 regarding the same; and 2) the data translation module 2400 sends the injection data 2424 to the DMS console 2410. It should be appreciated that the notification by the data translation module 2400 (regarding completion of the injection) could be simply in the form of the data translation module 2400 sending the injection data 2424 to the DMS console 2410.

Upon completion of the injection of the patient with at least contrast media, step 2136 of the data management protocol 2120 of FIG. 42 may be configured to display the injection results (e.g., administered or actual contrast/saline injection data, as discussed above, for instance at least part of the injection data 2424), for instance on the DMS console 2410, as well as possibly the identification of the patient (more generally, at least some patient data 2430). Verification of the injection results (and possibly proper patient identification) could be required pursuant to step 2138 (e.g., requiring user input to the data management system 660e (e.g., through the DMS console 2410) to verify the validity of the injection results and/or patient identification). In the event that the injection results are verified, the data management protocol 2120 proceeds from step 2138 to step 2140, where the patient data 2430, the contrast media data 2426, any saline media data 2428, and the injection data 2424 (e.g., the actual/administered injection data, and possibly the programmed injection data) may be stored as a DMS patient record 2420 on the DMS console 2410.

Figure 43A:
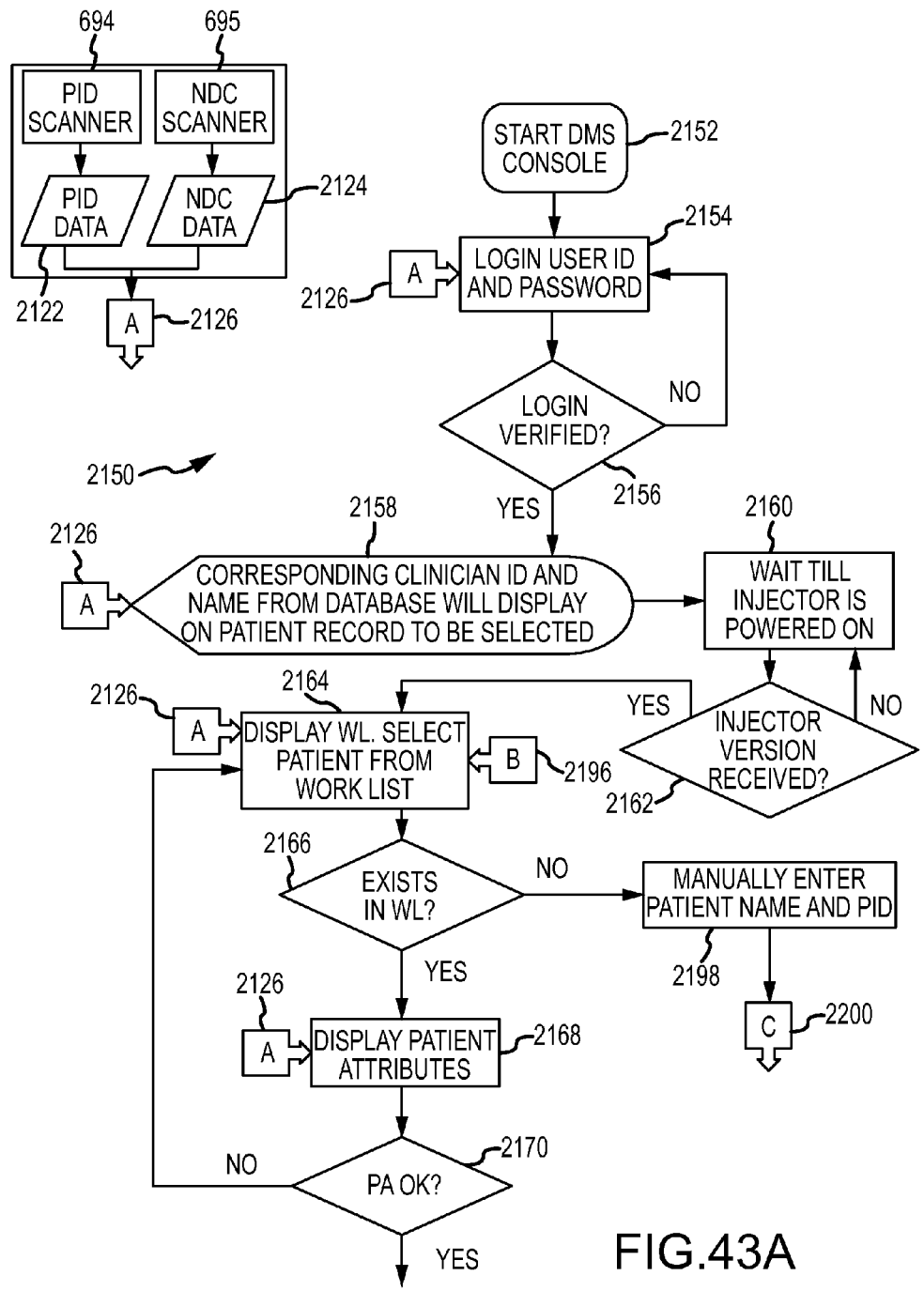
FIGS. 43A and 43B is another embodiment of a data management protocol that may be used by an injection data management system or module having data format conversion capabilities.
Figure 43B:
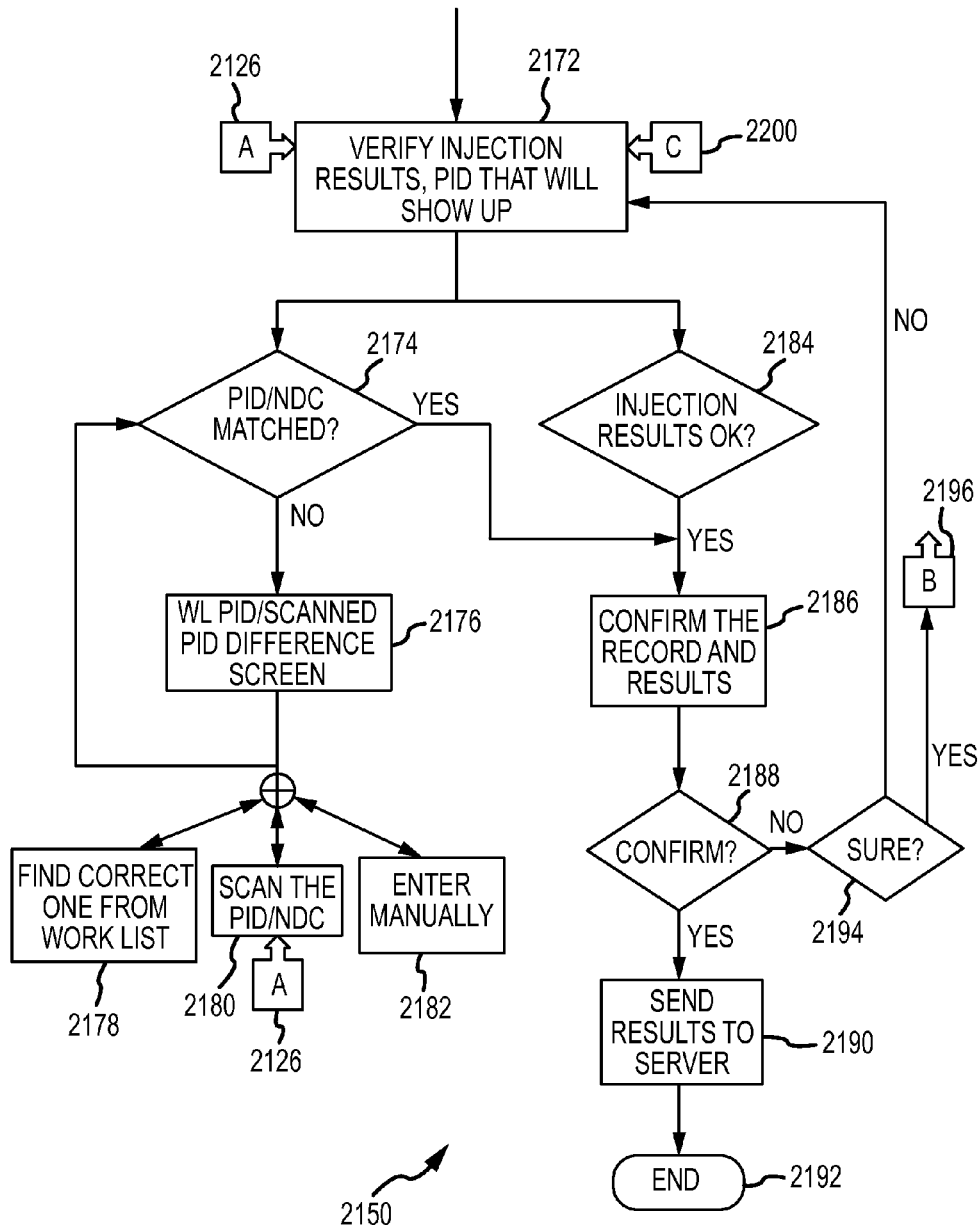

FIGS. 43A and 43B present another embodiment of a data management protocol that may be used by a data management system as described herein, and that is identified by reference numeral 2150 in FIGS. 43A and 43B (FIGS. 43A and 43B defining different portions of a single, common flowchart). Although the data management protocol 2150 will be described in relation to the data management system 660e of FIG. 41, it should be appreciated that the data management protocol 2150 may be used by/adapted for use by any of the injection data management systems described herein (e.g., data management systems 660, 660a, 660b, 660c, and 660d). It should also be appreciated that the discussion of the data management protocol 2150 will be in relation to a contrast media injector system 602, along with its corresponding data translation module 2400 and DMS console 2410. However, the same data management protocol 2150 may be executed in relation to each contrast media injector system 602 of the medical system 600a, along with its corresponding data translation module 2400 and DMS console 2410. Finally, the discussion presented below is of course applicable to any corresponding steps of the data management protocol 2120 of FIG. 42, and vice versa.

Patient identification information may be acquired in any appropriate manner for purposes of the data management protocol 2150 (step 2122), for instance in accordance with the discussion of the data management protocol 2120 of FIG. 42 presented above (e.g., using the barcode scanner 694 to scan the wristband 696 of the patient to be injected). Similarly, injection media data may be acquired in any appropriate manner (step 2124, for instance contrast media data 2426 and saline media data 2428), for instance in accordance with the discussion of the data management protocol 2120 of FIG. 42 presented above (e.g., using an appropriate reader (e.g., barcode scanner 694; using an RFID reader incorporated by the contrast media injector system 602) to scan a data storage device 613 associated with the syringe(s) 612 (or other medical fluid container) to be used in the injection of the patient). Step 2124 may be executed at any appropriate time, except during the actual injection of the patient. Acquired injection media data may be displayed on the DMS console 2410. The data translation module 2400 may translate this injection media data as required (e.g., from one data format to a different data format). In any case and for the flowchart shown in FIGS. 43A and 43B, the patient ID data (step 2122) and the injection media data (step 2124) again are each characterized as defining an input 2126.

Step 2152 of the data management protocol 2150 of FIGS. 43A and 43B may be used to start the data management protocol 2150 using the DMS console 2410 of the data management system 660e. A user may be required to enter both a user ID and a password pursuant to step 2154 (e.g., clinician data 2432). If at least one of the user ID and password from step 2154 is incorrect, the data management protocol 2150 proceeds from step 2156 back to step 2154. Otherwise, when the user ID and password from step 2154 have been verified by step 2156, the data management protocol 2150 proceeds to step 2158, which notes that the information provided through execution of step 2154 (e.g., clinician data 2432) will be appended to the DMS patient record 2420 that may be generated upon completion of the data management protocol 2150. It should be appreciated that the facility data 2422 could be automatically appended to the DMS patient record 2420 as well based upon, for instance, an association of the contrast media injector system 602 with a particular medical facility 2100 and/or imaging suite 2102.

Step 2160 of the data management protocol 2150 may assess if the contrast media injector system 602 for the injection of the patient is in a "powered on" state or condition. Once the contrast media injector system 602 is in a powered on state or condition and identified as such by the protocol 2150, the protocol 2150 proceeds from step 2160 to step 2162. Here, the data management protocol 2150 may be configured to confirm that the contrast media injector system 602 includes the proper software updates. Although step 2162 may be optional, the illustrated configuration of the data management protocol 2150 does not allow a DMS patient record 2420 to be created unless the contrast media injector system 602 is in fact utilizing a current software version.

The DMS console 2410 of the data management system 660e, to be used in conjunction with an injection of a patient, may retrieve a worklist (e.g., a DICOM worklist) from the RIS 720 (or possibly the PACS 710) (e.g., worklist 992 discussed above in relation to FIG. 30; worklist 2232 discussed below in relation to FIG. 45B). Step 2164 of the data management protocol 2150 of FIG. 43A is directed toward selecting a patient from the worklist that may be displayed on the DMS console 2410. This selection may be in response to user input to the DMS console 2410 (e.g., through a user input device(s) 662a). Alternatively, the identification of the patient on the worklist for purposes of step 2164 may be done automatically in response to patient ID data acquired through execution of step 2122 (although the data management system 660e may be configured to still require user input to the DMS console 2410 to select a patient that was automatically identified on the worklist in the noted manner).

It may be that a given patient is not on the worklist (step 2164) for one reason or another (e.g., an emergency patient). In this case, the data management protocol 2150 may be configured to proceed from step 2166 to step 2198 to allow at least certain patient data 2430 (e.g., patient name and patient ID) to be manually entered through execution of step 2198 (e.g., through user input to the DMS console 2410). This information collectively defines an input 2200, which is directed to step 2172 of the data management protocol 2150 discussed below.

In the event that the patient is on the displayed worklist and is selected (step 2164), the data management protocol 2150 proceeds from step 2164 to step 2166. At least some patient data 2430 may be displayed on the DMS console 2410 through execution of step 2168 of the data management protocol 2150 of FIG. 43A. For instance, patient identification information (step 2122) and/or the selection of the patient from the worklist (step 2164) may be used to retrieve patient data 2430 for purposes of step 2168. Patient data 2430 may be provided to the data management system 660e in any appropriate manner for purposes of step 2168. For instance, the patient ID provided pursuant to step 2122 may be used by the data management system 660e to retrieve corresponding patient data 2430 from a medical sub-system 735 that is operatively interconnected with the data management system 660e (e.g., the HIS 700), and which would then transmit this data to the data management system 660e. Patient data 2430 could also be retrieved by the data management system 660e from the worklist associated with steps 2164 and 2166.

The contrast media data 2426 and/or saline media data 2428 that was acquired pursuant to step 2124 of the protocol 2150 could also be displayed for purposes of step 2168 of the data management protocol 2150, as well as the corresponding programmed injection data (which could be retrieved from the worklist—see step 2164; which could be provided by the contrast media injector system 602 to the data translation module 2400, which could then transmit this data to the DMS console 2410). In any case, the data management protocol 2150 may be configured to request user input (step 2170) regarding the validity of the patient data 2430 that is displayed pursuant to step 2168 (e.g., requiring a user to confirm that the information displayed pursuant to step 2168 is appropriate for purposes of proceeding with an actual injection of the selected patient).

The data management system 660e may be configured to provide additional functionality in relation to steps 2168 and 2170 of the data management protocol 2150, for instance through the DMS console 2410. A user may be allowed to select a subset of the patient data 2430 (being displayed by step 2168) for further review. A user may be able to provide input to and change one or more tolerances associated with this subset of patient data 2430. A user may be allowed to compare current tolerances associated with this subset of patient data 2430 to historical tolerances for the same patient (e.g., a tolerance from a prior injection). A notification or alert may be provided on the DMS console 2410 when the selected subset of patient data is not within a specified tolerance.

The injection of the patient with contrast media, alone or in combination with saline, takes place between steps 2170 and 2172 of the data management protocol 2150 of FIGS. 43A and 43B. An "injection in progress" status may be displayed on the DMS console 2410 throughout the injection of the patient. In any case, injection data 2424 that is generated in relation to this injection may be translated by the data translation module 2400 (e.g., from one data format to another data format). This injection data 2424 may be stored on the data translation module 2400. Upon completion of the injection procedure on the patient: 1) the data translation module 2400 may notify the DMS console 2410 regarding the same; and 2) the data translation module 2400 may transmit the injection data 2424 to the DMS console 2410. It should be appreciated that the notification by the data translation module 2400 (regarding completion of the injection) could be simply in the form of the data translation module 2400 actually sending the injection data 2424 to the DMS console 2410. If the data translation module 2400 is unable to transmit the injection data 2424 to the DMS console 2410, it may be configured to notify the DMS console 2410 to this effect. It should be appreciated that the data translation module 2400 may retrieve the time and date from the internal clock of the contrast media injector system 602 at the completion of the injection for inclusion with the DMS patient record 2420 (e.g., as being indicative of the time and date that the injection procedure was completed).

Upon completion of the injection of the patient with contrast media, the data translation module 2400 may send the injection data 2424 to the DMS console 2410. Step 2172 of the data management protocol 2150 of FIGS. 43A and 43B may be configured to display the injection results (e.g., administered or actual contrast injection data, as discussed above; injection data 2424), for instance on the DMS console 2410, as well as possibly the identification of the patient (more generally, at least some patient data 2430). Step 2172 may also require verification of the injection results. Part of this verification may be directed to determining if there is a match between the patient ID data (step 2122) and the patient that was selected from the worklist (step 2164), as noted by step 2174. Step 2174 may be configured to compare the patient ID data (step 2122) with patient ID data that may be stored on the medical fluid container (e.g., syringe 612) that was scanned pursuant to step 2124 of the protocol 2150. Step 2174 of the protocol 2150 may be configured to determine if there is a match between the patient ID data (step 2122) and the patient that was selected from the worklist (step 2164). The protocol 2150 could require a "match" between at least one of these comparisons, or may require a "match" for each of these comparisons.

If the data management protocol 2150 determines that there is not a "match" regarding the identification of the patient (step 2174), the data management protocol 2150 proceeds from step 2174 to step 2176 where a user of the data management system 660e is notified of the situation (e.g., via a patient ID error window 2330 presented on the DMS console 2410, and as discussed below in relation to FIG. 45C). A number of options may be undertaken in conjunction with step 2176 of the protocol 2150. For instance, the correct patient may be identified from the worklist (step 2178) on the DMS console 2410. Step 2122 (patient ID data acquisition) may be repeated pursuant to step 2180. The identity of the patient could also be manually entered pursuant to step 2182, for instance through user input to the corresponding DMS console 2410. Thereafter, the match assessment between the patient identification information and the contrast media data may be repeated through execution of step 2174. It should be appreciated that the "mismatch" regarding the patient identification addressed herein does not pertain to the injection (i.e., it is not directed to the situation where the wrong patient was subjected to an injection), but simply to the generation of a DMS patient record 2420 to be stored on the data management system 660e.

Another verification provided by execution of the data management protocol 2150 is with regard to the injection results (e.g., injection data 2424), and which may be undertaken through execution of step 2184 (e.g., requiring user input to the injection data management system 660e to verify the validity of the injection results, for instance by providing user input through the DMS console 2410). In the event that there is an appropriate "match" for purposes of step 2174, and if the injection results have been verified (step 2184), the data management protocol 2150 proceeds to step 2186. Step 2186 is directed to confirmation of the patient data 2430, the contrast media data 2426, saline media data 2428, and the injection data 2424 (e.g., at least the actual/administered contrast injection data, but possibly also the programmed contrast injection data), and this confirmation may be made via user input to the DMS console 2410. At any time prior to providing this confirmation (except during execution of the injection), the data management system 660 may be configured to allow for re-entry of any data that has been input to the data management system 660e (e.g., via user input to the DMS console 2410).

The data management protocol 2150 may be configured to give the user the option (e.g., on the DMS console 2410) to store the patient data 2430, the contrast media data 2426, the saline media data 2428, and the injection data 2424, along with the corresponding facility data 2422 and clinician data 2432, as a DMS patient record 2420. Confirmation by the user to proceed (e.g., via user input to the DMS console 2410 for purposes of step 2188) may provide control to step 2190 of the data management protocol 2150. Step 2190 may initially be directed to storing the DMS patient record 2420 on the data management system 660e. Again, each DMS patient record 2420 relates to a single injection procedure on a single patient, and may be compiled by and stored on the DMS console 2410. The DMS console 2410 may be configured to query the DMS server 2440 to acquire the time and date from the internal clock of the DMS server 2440 for inclusion with the DMA patient record 2420 (the time/date associated with the creation of the DMS patient record 2420). At some point in time, the DMS console 2410 may thereafter transmit one or more DMS patient records 2420 to the DMS server 2440, after which the data management protocol 2150 may be terminated through execution of step 2192. DMS patient records 2420 may be transmitted from the DMS console 2410 to the DMS server 2440 on any appropriate basis.

Not all executions of the data management protocol 2150 will necessarily result in the generation of a DMS patient record 2420 on the data management system 660e. For instance, if a user elected (through user input to the DMS console 2410) to not confirm that a DMS patient record 2420 should be stored on the data management system 660e at step 2188 of the protocol 2150, the protocol 2150 may be configured to require reconfirmation (step 2194, which may result in generation of a cancel injection window 2420 on the DMS console 2410, discussed below in relation to FIG. 45H). Reconfirmation by the user of the data management system 660e that a DMS patient record 2420 is not to be retained causes the data management protocol 2150 to proceed from step 2194 back to step 2164 for repetition in accordance with the foregoing (e.g., for creation of a DMS patient record 2420 for another patient and/or injection without saving the current DMS patient record 2420 on the DMS console 2410). Otherwise, the data management protocol 2150 is configured to proceed from step 2194 back to step 2172 for repetition in accordance with the foregoing. If a DMS patient record 2420 is not confirmed in accordance with the data management protocol 2150, it is not saved for future reference.

Figure 44:
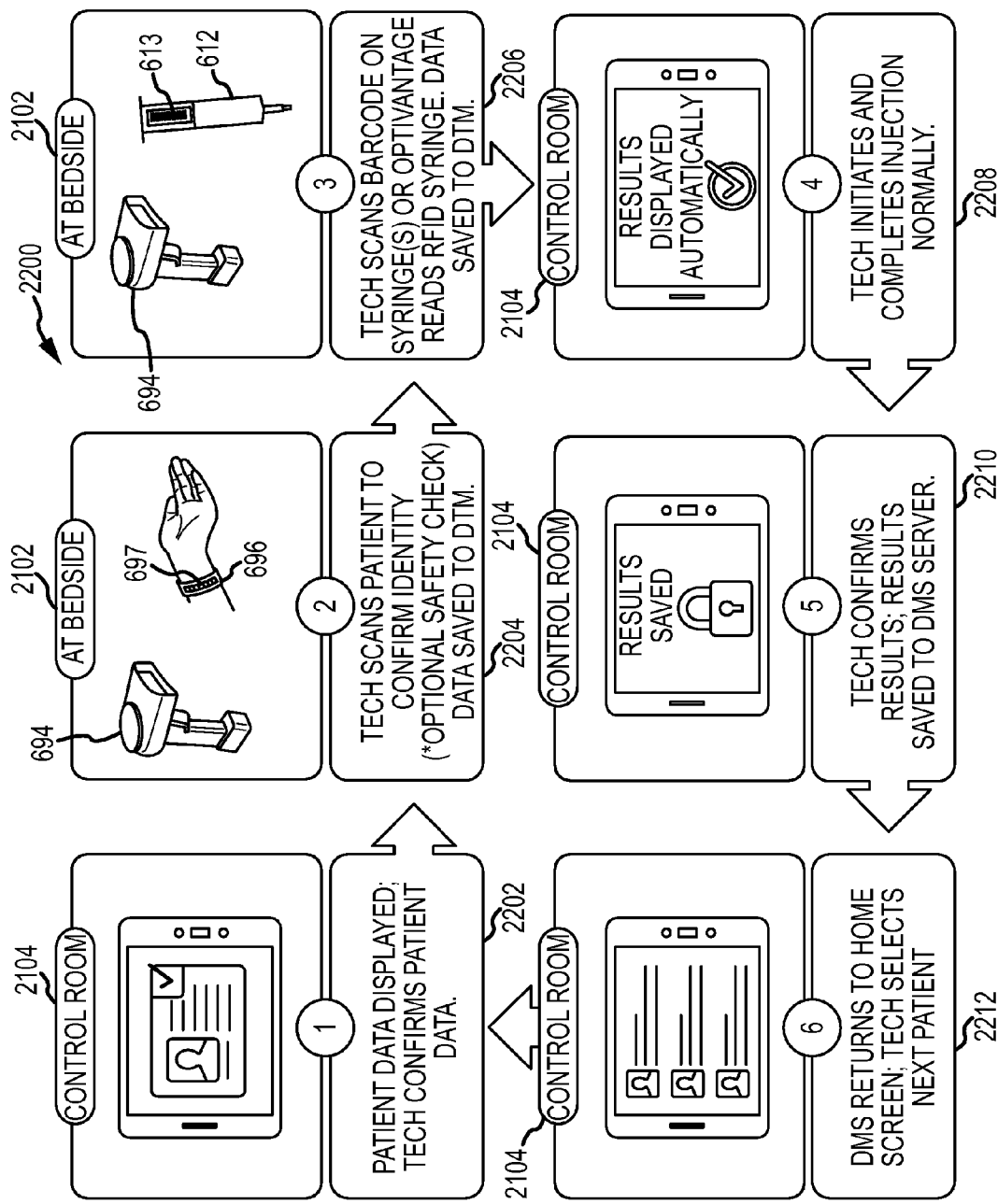
FIG. 44 is another embodiment of a data management protocol that may be used by an injection data management system or module having data format conversion capabilities.

Another embodiment of a data management protocol is illustrated in FIG. 44 and is identified by reference numeral 2200. The data management protocol 2200 may be integrated with and/or adapted for use by other data management protocols described herein, for instance the data management protocol 2120 of FIG. 42 and the data management protocol 2150 of FIGS. 43A and 43B. The data management protocol 2200 will be discussed in relation to the data management system 660e of FIG. 41, but may be utilized by any of the data management systems addressed herein.

At least some patient data 2430 or attributes may be displayed in conjunction with the data management protocol 2200 of FIG. 44, for instance on a DMS console 2410 in a control room 2104 (step 2202). Step 2202 could be executed in response to selection of a patient from a worklist (e.g., steps 2130 and 2132 of the data management protocol 2120 of FIG. 42; steps 2164, 2166, and 2168 of the data management protocol 2150 of FIGS. 43A and 43B). A technician, clinician, or user of the injection data management system 660e may confirm this patient data 2430 in conjunction with step 2202 (e.g., step 2134 of the data management protocol 2120 of FIG. 42; step 2170 of the data management protocol 2150 of FIGS. 43A and 43B).

Patient identification information may be acquired pursuant to step 2204 of the data management protocol 2200 of FIG. 44 (e.g., within the imaging suite 2102; e.g., corresponding to step 2122 of the data management protocol 2120 of FIG. 42 and the data management protocol 2150 of FIGS. 43A and 43B). For instance, a barcode scanner 694 or other appropriate reader of the injection data management system 660e may be used to read data stored on a data storage device 697 incorporated by a patient wristband 696. The patient identification information that is acquired pursuant to step 2204 may be compared with the patient data that is displayed in conjunction with step 2202 (e.g., patient data 2430) for purposes of confirming the identity of the patient. Confirmation that the patient identification information (step 2204) corresponds with the patient data (step 2202) may result in the saving of the patient identification information to the data translation module 2400 and/or the DMS console 2410 of the injection data management system 660e in conjunction with step 2204.

Contrast media data 2426 and saline media data 2428 (if being used in the injection of the patient) may be acquired pursuant to step 2206 of the data management protocol 2200 of FIG. 44 (e.g., within an imaging suite 2102; e.g., corresponding with step 2124 of the data management protocol 2120 of FIG. 42 and of the data management protocol 2150 of FIGS. 43A and 43B). For instance, a barcode scanner 694 or other appropriate reader for/associated with the injection data management system 660e may be used to read data stored on a data storage device 613 associated with a syringe(s) 612 or other medical fluid container that is to be used in the injection of the patient. This contrast media data 2426 and any saline media data 2428 may be saved to the corresponding data translation module 2400 and/or DMS console 2410 of the injection data management system 660e in conjunction with step 2206.

The injection of the patient (e.g., within an imaging suite 2102) using a contrast media injector system 602 is undertaken, and is depicted by step 2208 of the data management protocol 2200 of FIG. 44. The technician or clinician may control the operation of the contrast media injector system 602 from within the control room 2104 as addressed herein (e.g., via a remote console 650 for the contrast media injector system 602). Data on the injection may be displayed on the DMS console 2410, as noted by step 2208 (e.g., current injection data 2426 may be displayed on the DMS console 2410). The injection results (e.g., injection data 2424) may be confirmed and saved to the injection data management system 660e (e.g., to the corresponding DMS console 2410) pursuant to step 2210 (e.g. corresponding to steps 2138 and 2140 of the data management protocol 2120 of FIG. 42; corresponding to steps 2184, 2186, 2188, and 2190 of the data management protocol 2150 of FIGS. 43A and 43B). The data management protocol 2200 may conclude pursuant to step 2212, for instance by the injection data management system 660e returning to a home screen for repetition in accordance with the foregoing.

FIGS. 45A-45H present various screens that may be generated on a user interface of any of the injection data management systems and any of the data management protocols addressed herein, but will be addressed in relation to the data management system 660e of FIG. 41, the medical system 600a of FIG. 41, and the data management protocol 2150 of FIGS. 43A and 43B. It should be appreciated that each of the screens that may be presented on a DMS console 2410 of the data management system 660e may include any appropriate features for navigating within a given screen, for accessing any appropriate functionality presented on the screen, for accessing other screens, and the like.

FIG. 45A is an embodiment of a login screen 2220 that may be presented on a DMS console 2410 of the data management system 660e. This login screen 2220 may include a prompt 2222 to enter identification information for the contrast media injector system 602 to be used in conjunction with the injection of a patient and/or generation of a DMS patient record 2420 (e.g., an injector ID prompt 2222). The login screen 2220 may also present a password prompt 2224 (e.g., a password associated with the contrast media injector system 602; a password associated with accessing the injection data management system 660e). An injector ID may be entered at the injector ID prompt 2222, a password may be entered at the password prompt 2224, and a login button 2226 may be activated to gain access to the data management system 660e.

Figure 45B:
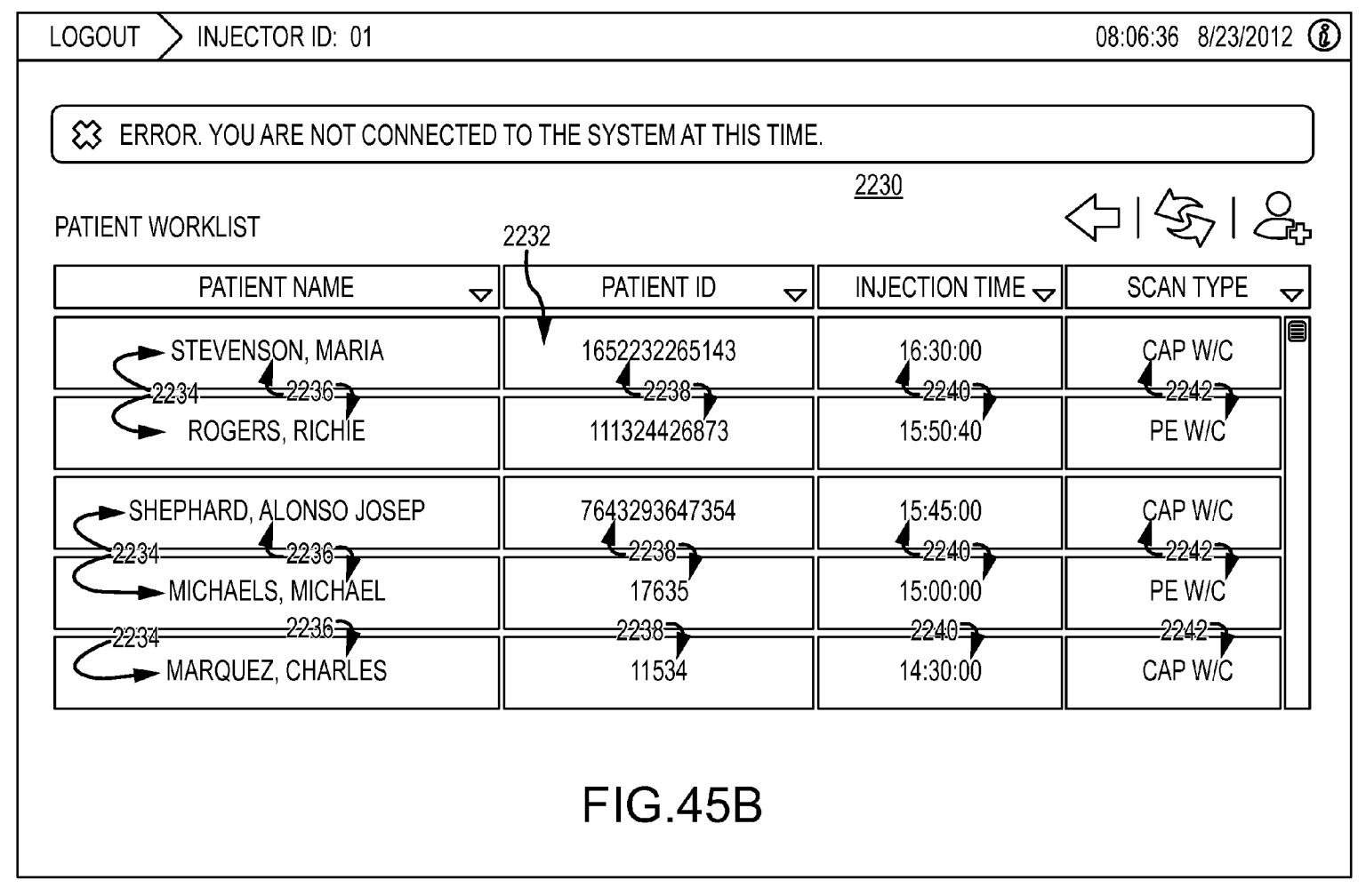

FIG. 45B is an embodiment of a worklist screen 2230 that may be presented on a DMS console 2410 of the data management system 660e. A worklist 2232 may be presented on the worklist screen 2230 (step 2164 of the data management protocol 2150 of FIGS. 43A and 423B). The worklist 2232 includes what may be characterized as a plurality of worklist entries 2234. Each worklist entry 2234 presents patient name data 2236, patient ID data 2238, injection time data 2240 (e.g., the time that has been scheduled for the injection of the associated patient), and scan/procedure type data 2242.

Figure 45C:
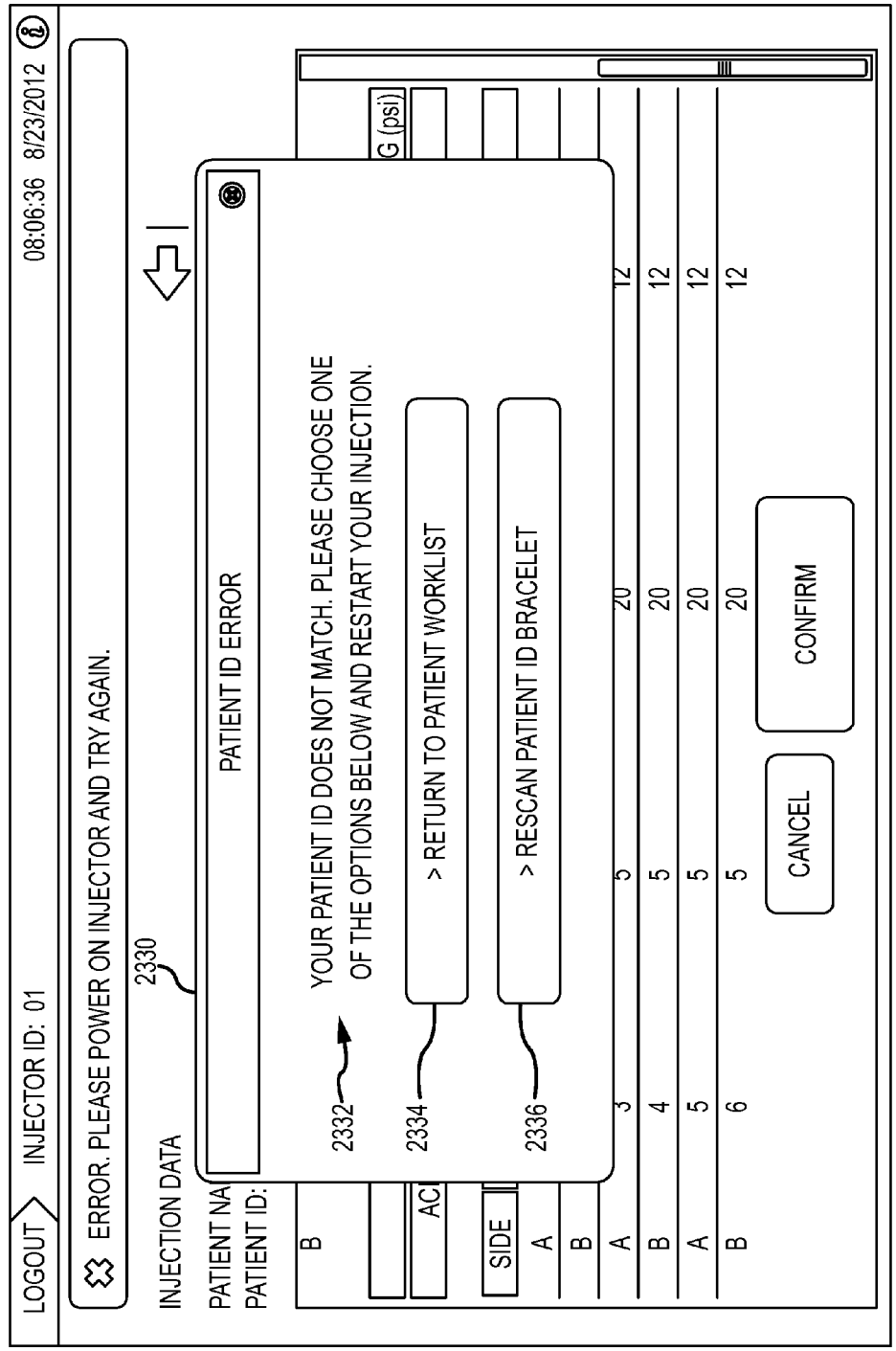
FIG. 45C is one embodiment of a patient ID error window that may be used by an injection data management system or module having data format conversion capabilities.

FIG. 45C is an embodiment of a patient ID error screen 2330 that may be presented on a DMS console 2410 of the data management system 660e. In the illustrated embodiment, the patient ID error screen 2330 is actually in the form of a patient ID error window 2330 that is superimposed over the worklist screen 2230. In any case, the patient ID error screen 2330 presents an error message 2332 regarding the patient identification. For instance, the patient ID error screen 2330 could be presented when the patient that was selected from the worklist 2232 (step 2164 of the data management protocol 2150 of FIGS. 43A and 43B) does not match the patient ID data that was separately acquired (e.g., from execution of step 2122 of the data management protocol 2150 of FIGS. 43A and 43B). The patient ID error screen 2330 may present a number of options to address the mismatch of patient ID information. For instance, the patient ID error screen 2330 may include a button 2334 that will return the injection data management system 660e to the worklist screen 2230 (FIG. 45B). The patient ID error screen 2330 may include a button 2336 that is directed to re-acquiring patient ID data (e.g., direct the technician/clinician to re-execute step 2122 of the data management protocol 2150 of FIGS. 43A and 43B).

Figure 45D:
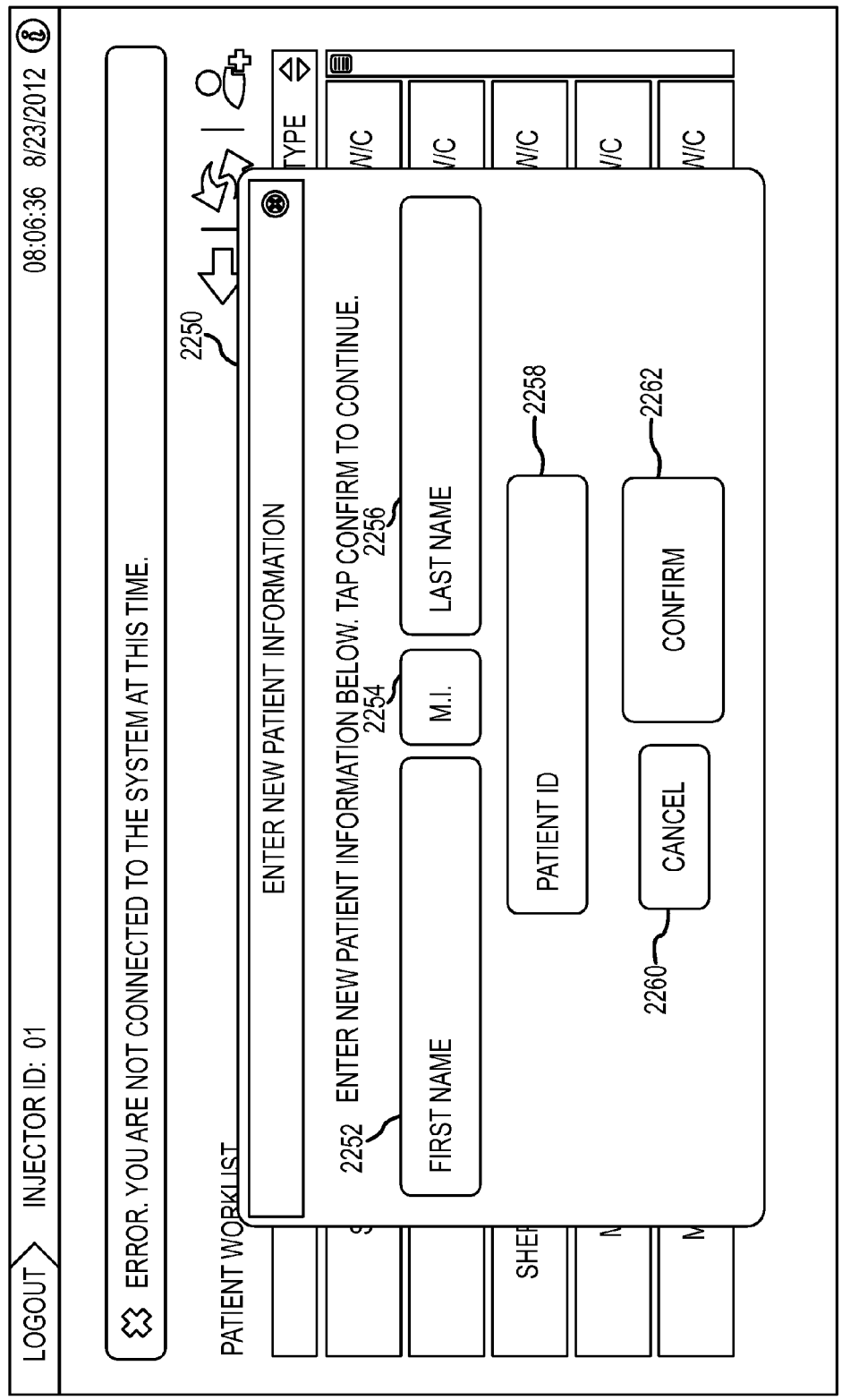
FIG. 45D is one embodiment of a new patient entry screen that may be used by an injection data management system or module having data format conversion capabilities.

FIG. 45D is an embodiment of a new patient entry screen 2250 that may be presented on a DMS console 2410 of the data management system 660e, for instance for purposes of step 2198 of the data management protocol 2150 of FIGS. 43A and 43B (e.g., for the case where a patient is not included on the worklist 2232). In the illustrated embodiment, the new patient entry screen 2250 is actually in the form of a new patient entry window 2250 that is superimposed over the worklist screen 2230 (FIG. 45B). In any case, the new patient entry screen 2250 presents a first name prompt 2252, a middle initial prompt 2254, a last name prompt 2256, and a patient ID prompt 2258 for receiving corresponding data on the new patient.

FIG. 45E is an embodiment of a patient attributes screen 2270 that may be presented on a DMS console 2410 of the injection data management system 660e, for instance for purposes of step 2168 of the data management protocol 2150 of FIGS. 43A and 43B. The patient attributes screen 2270 may present patient name data 2234 and patient ID data 2236. An attributes listing 2272, associated with the noted patient, may also be presented on the patient attributes screen 2272. This attributes listing 2272 includes a plurality of attribute entries 2273. Each attribute entry 2273 may include attribute ID data 2274 (e.g., the name of a particular patient attribute), an attribute value 2276, and any associated attribute threshold 2278. A confirm button 2279 may also be presented on the patient attributes screen 2270, for instance for purposes of step 2170 of the data management protocol 2150 of FIGS. 43A and 43B.

FIG. 45F is an embodiment of a programmed injection data screen 2280 that may be presented on a DMS console 2410 of the data management system 660e. The programmed injection data screen 2280 may present patient name data 2234 and patient ID data 2236. The programmed injection data screen 2280 may present syringe/contrast media data 2282 (e.g., in association with step 2124 of the data management protocol 2150 of FIGS. 43A and 43B). Multiple fluids may be used in the execution of an injection protocol in conjunction with the patient presented on the programmed injection data screen 2280. In this regard, the syringe/medical fluid data 2282 may include one or more syringe/medical fluid entries 2284. Each syringe/medical fluid entry 2284 may include: side data 2286 (e.g., identifying the corresponding portion of the contrast media injector system 602 that will use the syringe or medical fluid container associated with the syringe/medical fluid entry 2284—"A" and "B" defining the two heads of a dual-head injector system); NDC data 2288 (e.g., the associated national drug code); fluid type data 2290 (e.g., identifying the type of medical fluid); fluid name data 2292 (e.g., the commercial name of the associated medical fluid); concentration data 2294; volume data 2296 (e.g., the volume of the associated medical fluid); and package type data 2298 (e.g. identifying the type of container being used for the associated medical fluid).

The programmed injection data screen 2280 of FIG. 45F may also present the programmed injection data 2300 associated with the patient. The programmed injection data 2300 may include inject delay data 2310, scan delay data 2312, and peak pressure data 2314 that is to be used in the execution of the injection protocol. The programmed injection data 2300 may also pertain to an injection protocol, which may include any appropriate number of phases, where each phase is identified by phase data 2302. In this regard, and for each phase of the injection protocol, the programmed injection data 2300 may also include: side data 2284 (e.g., identifying the type of medical fluid to be injected in the corresponding phase); injection flow rate data 2304 (e.g., the flow rate to be used in the execution of the corresponding phase); injection volume data 2306 (e.g., the volume of medical fluid to be injected in the execution of the corresponding phase); and phase delay data 2308 (e.g., the amount of time before the phase in executed, in relation to the preceding event of the injection protocol).

Figure 45G:
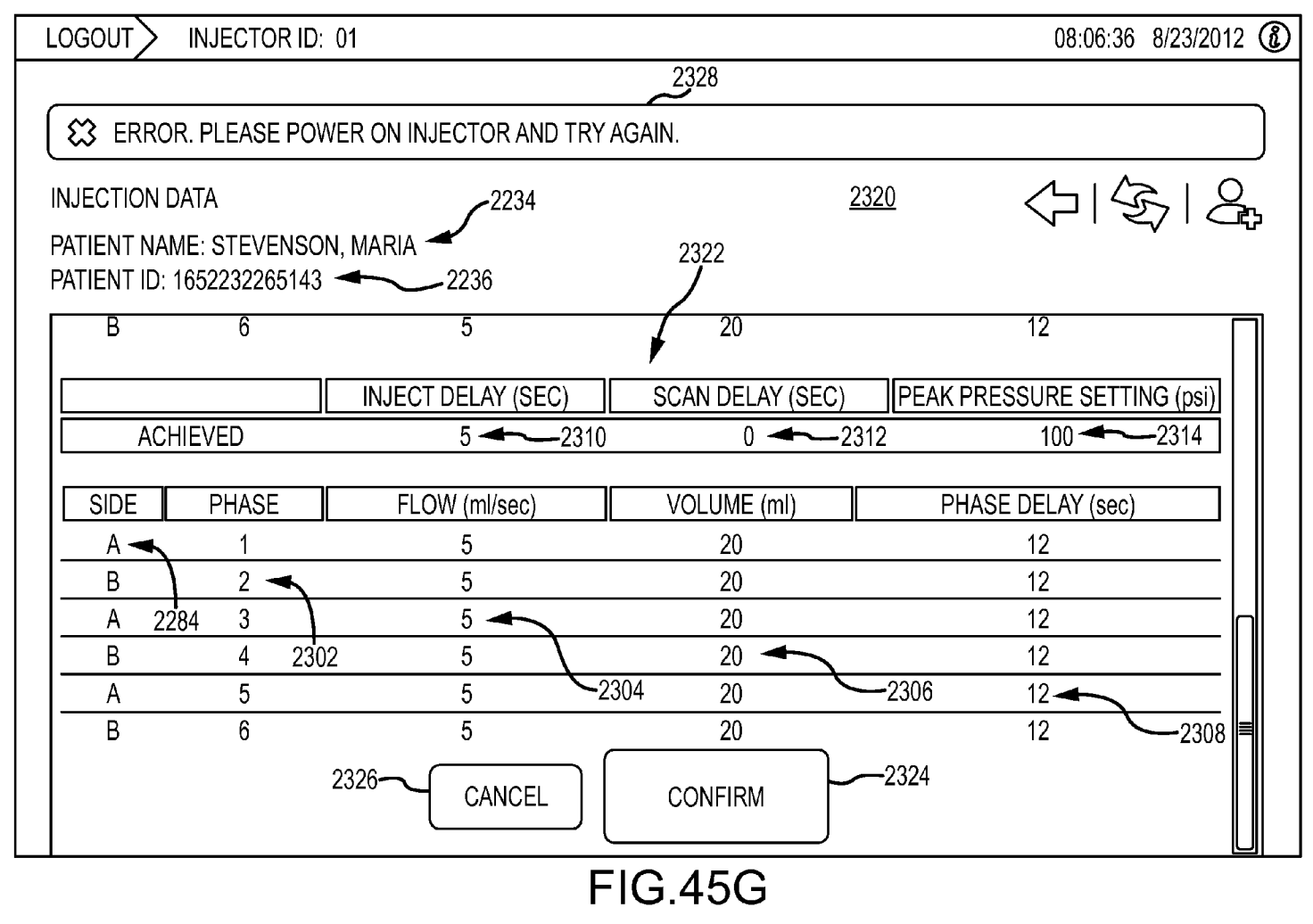

FIG. 45G is an embodiment of an administered injection data or achieved results screen 2320 that may be presented on a DMS console 2410 of the injection data management system 660e. Initially, an error message 2328 is being displayed on the achieved results screen 2320. Any appropriate error message 2328 may be displayed on any of the screens discussed herein, as well as on any screen presented on the DMS console 2410.

The administered injection data screen 2320 of FIG. 45G may present patient name data 2234 and patient ID data 2236. The administered injection data screen 2320 may also present the administered or achieved injection data 2300 associated with the completion of the injection of the associated patient. The administered injection data 2322 may include inject delay data 2310, scan delay data 2312, and peak pressure data 2314 that was used in the execution of the injection protocol. For each phase of the injection protocol (represented by phase data 2302) that was executed on the patient, the administered injection data 2300 may also include: side data 2284 (e.g., identifying the type of medical fluid that was actually injected in the corresponding phase); injection flow rate data 2304 (e.g., the flow rate that was actually realized in the execution of the corresponding phase); injection volume data 2306 (e.g., the volume of medical fluid that was actually injected in the execution of the corresponding phase); and phase delay data 2308 (e.g., the amount of time before the phase was executed, in relation to the preceding event of the injection protocol).

Figure 45H:
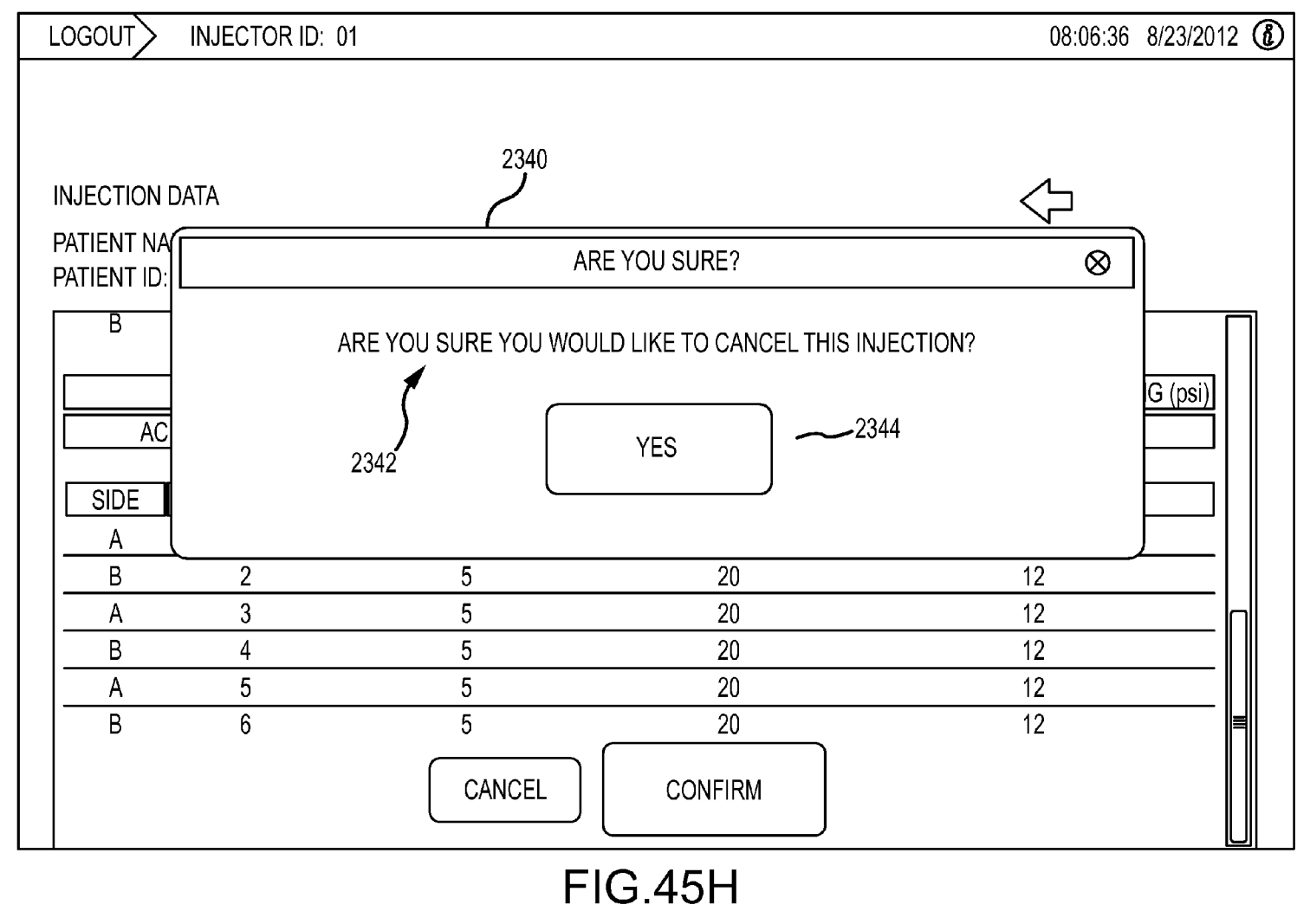

The administered injection data screen 2320 may include a confirm button 2324, along with a cancel button 2326. As discussed above in relation to the data management protocol 2150 of FIGS. 43A and 43B, a user of the injection data management system 660e may be provided with the option to save the patient data, the contrast media data, the programmed contrast injection data, and the actual/administered contrast injection data as a DMS patient record 2420 on the injection data management system 660e (e.g., a DMS patient record 2420 need not be automatically saved to the injection data management system 660e). In this case, a user may actuate the confirm button 2324 to save this data as a DMS patient record 2420 on the data management system 660e (e.g., steps 2186, 2188, and 2190 of the data management protocol 2150 of FIGS. 43A and 43B). Again, a user of the injection data management system 660e may also be provided with the option to disregard or "not save" the patient data, the contrast media data, the programmed contrast injection data, and the actual/administered contrast injection data as a DMS patient record 2420 on the injection data management system 660e. In this case, a user may actuate the cancel button 2326 on the administered injection data screen 2320 (e.g., steps 2186, 2188, 2194, and 2196 of the data management protocol 2150 of FIGS. 43A and 43B). In order to reduce the potential of an inadvertent election to not save the noted data as a DMS patient record 2420, actuation of the cancel button 2326 on the administered injection data screen 2320 may produce the cancel injection screen 2340, which may be in the form of a window that is superimposed over the administered injection data screen 2320 (FIG. 45H). In any case, the cancel injection screen 2340 of FIG. 45H (e.g., step 2194 of the data management protocol 2150 of FIGS. 43A and 43B) may include a cancellation message 2342, along with a "confirm cancellation" or "yes" button 2344. The cancel injection screen 2340 could also include a "reject cancellation" or "no" button, or closing the cancel injection screen 2340 could return the control to the administered injection data screen 2320 of FIG. 45G.

Any of the modules, protocols, logic, or the like addressed herein may be implemented in any appropriate manner, including without limitation in any appropriate software, firmware, or hardware, using one or more platforms, using one or more processors, using memory of any appropriate type, using any single computer of any appropriate type or multiple computers of any appropriate type and interconnected in any appropriate manner, or any combination thereof. These modules, protocols, logic, or the like may be implemented at any single location or at multiple locations that are interconnected in any appropriate manner (e.g., via any type of network).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A medical system comprising:
a network;
a first facility;
a plurality of imaging suites comprising first and second imaging suites, wherein said first facility comprises said first and second imaging suites, wherein each said imaging suite comprises an imaging system;
a separate contrast media injector system associated with each said imaging suite, wherein each said contrast media injector system is on said network, wherein each said contrast media injector system comprises an injection head, and wherein said injection head for each said contrast media injector system is located within its corresponding said imaging suite;
a plurality of control rooms, wherein each said control room is associated with at least one said imaging suite;
a first medical information system on said network; and
an injection data management system comprising:
a separate data translation module and a separate data management system (DMS) console for each said contrast media injector system such that each said contrast media injector system has a dedicated said data translation module and a dedicated said DMS console, wherein each said DMS console comprises at least one user input device and at least one display; and
a data management system (DMS) server;
wherein said data translation module and said DMS console for each said contrast media injector system, as well as said DMS server, are all on said network;
wherein each said data translation module receives injection data from its corresponding said contrast media injector system, and comprises a first data conversion unit to convert at least some of said injection data from a first data format to a second data format, and wherein each said data translation module is configured to send said injection data, in said second format, to its corresponding said DMS console;
wherein each said DMS console is configured to compile, based at least in part on injection data received from its corresponding said contrast media injector system, a data management system (DMS) patient record pertaining to a single injection procedure on a single patient using at least one medical fluid and its corresponding said contrast media injector system, wherein said DMS console is further configured to store a plurality of said DMS patient records generated from execution of a plurality of injection procedures by its corresponding said contrast media injector system, and wherein each said DMS console is configured to transmit selected said DMS patient records, that are currently stored on said DMS console, to said DMS server; and
wherein said DMS server comprises a DMS records database comprising a plurality of DMS patient records received from each said DMS console; and
wherein said DMS server is configured to transmit selected said DMS patient records, that are currently stored on said DMS server, to said first medical information system.

2. The medical system of claim 1, wherein said network comprises at least one local area network and a wide area network, wherein each said contrast media injector system, along with its corresponding said data translation module and said DMS console, are on said local area network, and wherein said DMS server is on said wide area network.

3. The medical system of claim 1, wherein each said contrast media injector system comprises a remote console that is located within a corresponding said control room for its corresponding said imaging suite, wherein said DMS console for each said contrast media injector system is located within the corresponding control room for said imaging suite, and wherein said remote console for each said contrast media injector system comprises a remote console display and a remote console user input device and furthermore accommodates programming of injection parameters for its corresponding contrast media injector system.

4. The medical system of claim 1, wherein said data translation module for each said contrast media injector system is located within the corresponding said imaging suite, and wherein said DMS console for each said contrast media injector system is located within the corresponding said control room for the corresponding said imaging suite.

5. The medical system of claim 1, wherein said data translation module for each said contrast media injector system is configured to send said injection data to its corresponding said DMS console only after completion of a corresponding injection procedure on a patient.

6. The medical system of claim 1, wherein each said DMS patient record comprises patient data, injection media data, and said injection data.

7. The medical system of claim 6, wherein said injection media data comprises contrast media data.

8. The medical system of claim 7, wherein said injection media data comprises saline media data.

9. The medical system of claim 6, wherein said patient data is acquired by said injection data management system from said first medical information system, and wherein said first medical information system is a hospital information system.

10. The medical system of claim 6, further comprising:
a second medical information system on said network, wherein said patient data is acquired by said injection data management system from said second medical information system, and wherein said second medical system is a radiology/radiological information system (RIS).

11. The medical system of claim 6, wherein said injection data management system is configured to retrieve a patient worklist, and wherein said patient data is retrieved from said patient worklist by said DMS console.

12. The medical system of claim 11, wherein said patient worklist is a DICOM patient worklist.

13. The medical system of claim 6, further comprising:
a separate first data reader for each said contrast media injector system, wherein said first data reader communicates with said data translation module of the corresponding said contrast media injector system without having to first pass through the corresponding said contrast media injector system.

14. The medical system of claim 13, further comprising:
a patient data storage device associated with a patient and comprising first patient ID data, wherein a corresponding said first data reader is operable to read said first patient ID data from said patient data storage device and transmit said first patient ID data to the corresponding said data translation module.

15. The medical system of claim 14, wherein said injection data management system comprises patient ID validation logic.

16. The medical system of claim 15, wherein said patient ID validation logic compares said first patient ID data with second patient ID data acquired from a separate data source.

17. The medical system of claim 16, wherein said second patient ID is part of said patient data.

18. The medical system of claim 13, wherein each said contrast media injector system comprises a first injection media container comprising a first data storage device, wherein said injection media data pertains to injection media within said first injection media container and is stored on said first data storage device of said first injection media container, wherein said first data reader for each said contrast media injector system retrieves said injection data from said first data storage device of the corresponding said first injection media container, and wherein said injection media data is transmitted to the corresponding said data translation module.

19. The medical system of claim 13, wherein each said contrast media injector system comprises a second data reader, wherein each said contrast media injector system comprises a first injection media container comprising a first data storage device, wherein said injection media data pertains to injection media within said first injection media container and is stored on said first data storage device of said first injection media container, wherein said second data reader of each said contrast media injector system retrieves said injection data from said first data storage device of the corresponding said first injection media container, and wherein said injection media data is transmitted to the corresponding said data translation module.

20. The medical system of claim 19, wherein said second data reader comprises an RF reader, and wherein said first data storage device of said first injection media container comprises an RF data tag.

21. The medical system of claim 20, wherein each said contrast media injector system comprises a syringe mount, which in turn comprises said RF reader.

22. The medical system of claim 1, wherein said first data format is a CAN-compliant format and said second data format is a non-CAN-compliant format.

23. The medical system of claim 1, wherein said data translation module for each said contrast media injector system comprises a second data conversion unit that converts data from one data format to a different data format.

24. The medical system of claim 23, wherein said second data format is an HL-7-compliant data format, and wherein said second data conversion unit of each said data translation module converts data into a DICOM-compliant data format.

* * * * *